(12) United States Patent
Liu et al.

(10) Patent No.: US 7,384,970 B2
(45) Date of Patent: Jun. 10, 2008

(54) INHIBITORS OF CATHEPSIN S

(75) Inventors: Hong Liu, San Diego, CA (US); Phil Alper, Poway, CA (US); Arnab Chatterjee, Encinitas, CA (US); David Tully, San Diego, CA (US); Badry Bursulaya, San Diego, CA (US); David Woodmansee, San Diego, CA (US); Robert Epple, San Diego, CA (US); Jennifer Leslie Harris, San Diego, CA (US); Jun Li, San Diego, CA (US)

(73) Assignee: IRM LLC, Hamilton (BM)

( * ) Notice: Subject to any disclaimer, the term of this patent is extended or adjusted under 35 U.S.C. 154(b) by 480 days.

(21) Appl. No.: 10/807,613

(22) Filed: Mar. 23, 2004

(65) Prior Publication Data

US 2004/0248887 A1  Dec. 9, 2004

Related U.S. Application Data

(60) Provisional application No. 60/457,848, filed on Mar. 24, 2003.

(51) Int. Cl.
*A61K 31/4045* (2006.01)
*C07D 209/08* (2006.01)

(52) U.S. Cl. .................. 514/415; 548/491
(58) Field of Classification Search .......... 514/415; 548/491
See application file for complete search history.

(56) References Cited

U.S. PATENT DOCUMENTS

| 4,499,295 A | 2/1985 | Mueller et al. |
| 5,370,879 A | 12/1994 | Masterson et al. |
| 5,374,623 A | 12/1994 | Zimmerman et al. |
| 5,574,064 A | 11/1996 | Shibata et al. |
| 5,691,368 A | 11/1997 | Peet et al. |
| 5,723,469 A | 3/1998 | Shibata et al. |
| 5,849,711 A | 12/1998 | Tung et al. |
| 5,858,982 A | 1/1999 | Tung et al. |
| 5,916,887 A | 6/1999 | Singh et al. |
| 5,998,470 A | 12/1999 | Halbert et al. |
| 6,004,933 A | 12/1999 | Spruce et al. |
| 6,030,946 A | 2/2000 | Klaus et al. |
| 6,057,362 A | 5/2000 | Yamashita |
| 6,232,342 B1 | 5/2001 | Carr et al. |
| 6,274,336 B1 | 8/2001 | Abdel-Meguid et al. |
| 6,331,542 B1 | 12/2001 | Carr et al. |
| 6,353,017 B1 | 3/2002 | Altmann et al. |
| 6,369,077 B1 | 4/2002 | Marquis et al. |
| 6,395,897 B1 | 5/2002 | Cywin et al. |
| 6,420,364 B1 | 7/2002 | Emmanuel et al. |
| 6,455,502 B1 | 9/2002 | Bryant et al. |
| 2002/0086070 A1 | 7/2002 | Kuhrts |
| 2002/0119196 A1 | 8/2002 | Parikh et al. |

FOREIGN PATENT DOCUMENTS

| WO | WO 98/00171 A2 | 1/1998 |
| WO | WO 98/50534 A1 | 11/1998 |
| WO | WO 00/48993 A1 | 8/2000 |
| WO | WO 00/51998 A1 | 9/2000 |
| WO | WO 01/09110 A1 | 2/2001 |
| WO | WO 01/19816 A1 | 3/2001 |
| WO | WO 02/14314 A2 | 2/2002 |
| WO | WO 02/14317 A2 | 2/2002 |
| WO | WO 02/14315 A2 | 3/2002 |
| WO | WO 02/051983 A2 | 7/2002 |
| WO | WO 02/069901 A2 | 9/2002 |
| WO | WO 02/070517 A2 | 9/2002 |
| WO | WO 02/070519 A1 | 9/2002 |
| WO | WO 03/013518 A1 | 2/2003 |
| WO | WO 03/020287 A2 | 3/2003 |

OTHER PUBLICATIONS

Bania, J. et al.: "Human cathepsin S, but not cathepsin L, degrades efficiently MHC class II-associated Invariant chain In nonprofessional APCs" PNAS; vol. 100, No. 11; pp. 6664-6669 (May 27, 2003).

*Primary Examiner*—Rebecca Anderson
(74) *Attorney, Agent, or Firm*—Emily Tongco Wu; Genomics Institute of the Novartis Research Foundation

(57) ABSTRACT

The present invention provides compounds, compositions and methods for the selective inhibition of cathepsin S. In a preferred aspect, cathepsin S is selectively inhibited in the presence of at least one other cathepsin isozyme. The present invention also provides methods for treating a disease state in a subject by selectively inhibiting cathepsin S.

15 Claims, 1 Drawing Sheet

INHIBITORS OF CATHEPSIN S

CROSS-REFERENCES TO RELATED APPLICATIONS

This application claims priority to U.S. Provisional Patent Application No. 60/457,848, filed Mar. 24, 2003, the teachings of which are hereby incorporated by reference in their entirety.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, *J Biol Chem* 1997, 272(13), 8109-12; Saftig, P., E. Hunziker, et al., *Adv Exp Med Biol* 2000+ADs 2000, 477, 293-303; Saftig, P., E. Hunziker, et al., *Proc Natl Acad Sci USA* 1998, 95(23), 13453-8), periodontal diseases, Paget's disease, atherosclerosis (Jormsjo, S., D. M. Wuttge, et al., *Am J Pathol* 2002 161(3), 939-45), multiple sclerosis (Beck, H., G. Schwarz, et al., *Eur J Immunol* 2001, 31(12), 3726-36), rheumatoid arthritis (Nakagawa, T. Y., W. H. Brissette, et al., *Immunity* 1999, 10(2), 207-17; Hou, W. S., Z. Li, et al., *Am J Pathol* 2001, 159(6), 2167-77), juvenile onset diabetes, lupus, asthma (Cimerman, N., P. M. Brguljan, et al., *Pflugers Arch* 2001, 442 (6 Suppl 1), R204-6), tissue rejection, Alzheimer's disease (Lernere, C. A., J. S. Munger, et al., *Am J Pathol* 1995, 146(4), 848-60), Parkinson's disease (Liu, Y., L. Fallon, et al., *Cell* 2002, 111(2), 209-18), neuronal degeneration, shock (Jaeschke, H., M. A. Fisher, et al., *J Immunol* 1998, 160(7), 3480-6), cancer (Fernandez, P. L., X. Farre, et al., *Int J Cancer* 2001, 95(1), 51-5), malaria (Malhotra, P., P. V. Dasaradhi, et al., *Mol Microbiol* 2002, 45(5), 1245-54), Chagas (Eakin, A. E., A. A. Mills, et al., *J Biol Chem* 1992, 267(11), 7411-20), leishmaniasis, shistosomiasis, and African trypanosomiasis (Caffrey, C. R., S. Scory, et al., *Curr Drug Targets* 2000, 1(2), 155-62; Lalmanach, G., A. Boulange, et al., *Biol Chem* 2002, 383(5), 739-49).

Cathepsins are a subclass of cysteine protease that belong to the enzyme classification EC 3.4.22 (Barrett, A. J., N. D. Rawlings, et al., *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281-94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al., *Immunity* 1999, 10(2) 197-206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al., *J Biol Chem* 1996, 271(4), 2126-32). There is a need in the art for compounds and methods that selectively inhibit specific cysteine proteases for treating several pathogenic disorders in mammals. The present invention satisfies these and other needs.

BRIEF SUMMARY OF THE INVENTION

The present invention provides compounds, compositions and methods for the selective inhibition of cathepsin S. The compounds of the present invention are selective for cathepsin S in the presence of other cathepsin isozymes (e.g. cathepsin K). The present invention also provides methods for treating a disease state in a subject by selectively inhibiting cathepsin S in the presence of other cathepsin isozymes.

As such, in one embodiment, the present invention provides a compound of Formula I:

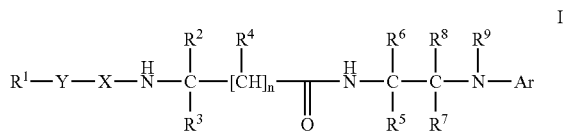

or a pharmaceutically acceptable salt or prodrug thereof, wherein:

$R^1$ is a member selected from the group of H, $C_6$-$C_{10}$ aryl substituted with 0-3 $R^{1a}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$, a $C_3$-$C_8$ cycloalkyl substituted with 0-2 $R^{1b}$, wherein said $C_3$-$C_8$ cycloalkyl is saturated or unsaturated; and a $C_3$-$C_8$ heterocycle containing 1 to 2 heteroatoms each independently a member selected from the group consisting of N, O and S, wherein said heterocycle is substituted with 0-2 $R^{1c}$ and is saturated or unsaturated;

each $R^{1a}$ is independently a member selected from the group of H, $C_1$-$C_3$ perfluoroalkyl, $C_3$-$C_7$ cycloalkyl, F, Cl, Br, CN, $NO_2$, $OR^{10}$, $SCH_3$, $S(=O)CH_3$, $S(=O)_2R^{10}$, $NR^{11}R^{12}$, acetyl, $C(=O)OR^{13}$, $C(=O)NR^{13}R^{14}$, $S(=O)_2NR^{13}R^{14}$, phenyl substituted with 0-3 $R^{15}$, a 5- to 6-membered monocyclic heteroaryl containing 1 to 4 heteroatoms each independently a member selected from the group of N, O and S, wherein said heteroaryl is substituted with 0-2 $R^{15}$, a $C_3$-$C_8$ heterocycle containing 1 to 2 heteroatoms each independently a member selected from the group of N, O and S, wherein said heterocycle is substituted with 0-2 $R^{1c}$ and is saturated or unsaturated, and a $C_1$-$C_4$ alkyl substituted with 0-2 $R^{16}$;

each $R^{1b}$ is independently a member selected from the group of H, OH, F, Cl, acetyl, =O, $C_1$-$C_6$ alkyl, $C_1$-$C_6$ alkoxy, $CF_3$ and $OCF_3$;

each $R^{1c}$ is independently a member selected from the group of H, OH, F, Cl, =O, $C_1$-$C_6$ alkyl substituted with 0-2 $R^{16}$, $C_1$-$C_6$ alkoxy, $CF_3$, $OCF_3$, $C(=O)R^{10}$, $S(=O)_2R^{10}$, tBoc, Cbz; phenyl substituted with 0-3 $R^{15}$; a 5- to 6-membered monocyclic heteroaryl containing 1 to 4 heteroatoms each independently a member selected from the group of N, O and S, wherein said heteroaryl is substituted with 0-2 $R^{15}$;

$R^2$ is a member selected from the group of a phenyl substituted with 0-3 $R^{15}$, a 5- to 6-membered monocyclic heteroaryl containing 1 to 4 heteroatoms each independently a member selected from the group of N, O and S, wherein said heteroaryl is substituted with 0-2 $R^{15}$, a $C_1$-$C_6$ alkyl substituted with 0-2 $R^{2a}$, wherein said $C_1$-$C_6$ alkyl optionally contains a heteroatom selected from the group of —O—, —S—, and —S(=O)_2—, a $C_2$-$C_6$ alkenyl, a $C_2$-$C_6$ alkynyl, a $C_3$-$C_7$ cycloalkyl substituted with 0-2 $R^{19}$, wherein said $C_3$-$C_7$ cycloalkyl optionally contains a heteroatom selected from —O—, —S—, and —S(=O)$_2$—, and a $C_7$-$C_{11}$ bicycloalkyl substituted with 0-2 $R^{19}$;

each $R^{2a}$ is independently a member selected from the group of a $C_6$-$C_{10}$ aryl substituted with 0-3 $R^{15}$, a 5- to 6-membered monocyclic or 8- to 10-membered bicyclic heteroaryl containing 1 to 4 heteroatoms each independently a member selected from the group of N, O and S, wherein said heteroaryl is substituted with 0-3 $R^{15}$, a $C_3$-$C_8$ cycloalkyl substituted with 0-2 $R^{19}$, and a $C_7$-$C_{11}$ bicycloalkyl substituted with 0-2 $R^{19}$;

$R^3$ is a member selected from the group of H and $C_1$-$C_4$ alkyl;

subscript n is 0 or 1;

$R^4$ is a member selected from the group of H and $C_1$-$C_6$ alkyl;

alternatively, $R^2$ and $R^4$ are taken together to form a $C_5$-$C_7$ cycloalkyl substituted with 0-2 $R^{19}$;

$R^5$ is a member selected from the group of H, $C_3$-$C_7$ cycloalkyl, $C_2$-$C_6$ alkenyl, $C_2$-$C_6$ alkyne, phenyl substituted with 0-2 $R^{15}$; 5- to 6-membered heteroaryl containing 1 to 4 heteroatoms each independently a member selected from the group of N, O and S, wherein said heteroaryl is substituted with 0-2 $R^{15}$, a $C_1$-$C_6$ alkyl substituted with 0-2 $R^{18}$, wherein said $C_1$-$C_6$ alkyl optionally contains a heteroatom selected from the group of —O—, —S—, —S(=O)—, —S(=O)$_2$— and —NR$^{17}$—;

Y is a member independently selected from the group of a bond and —(CR$^{20}$R$^{21}$)$_m$—W—(CR$^{22}$R$^{23}$)$_p$—;

subscript p is 1 or 2;

subscript m is 0 or 1;

W is a member independently selected from the group of a bond, —O—, —S—, —S(=O)—, —S(=O)$_2$— and —NR$^{12}$—;

X is selected from the group of —C(=O)—, —OC(=O)—, —NR$^{24}$C(=O)— and —S(=O)$_2$—;

each of $R^6$, $R^7$, $R^8$ and $R^9$ is independently a member selected from the group of H and $C_1$-$C_4$ alkyl;

alternatively, $R^5$ and $R^7$ are taken together to form a $C_5$-$C_7$ cycloalkyl substituted with 0-2 $R^{19}$;

alternatively, $R^5$ and $R^9$ are taken together to form a 6-7 membered heterocyclic ring containing 1-2 heteroatoms each independently a member selected from the group of N, O and S;

Ar is a member selected from the group of phenyl substituted with 0-3 $R^{29}$, and 5- to 6-membered heteroaryl containing 1 to 4 heteroatoms each independently a member selected from the group of N, O and S, wherein said heteroaryl is substituted with 0-3 $R^{29}$;

each $R^{10}$ is independently a member selected from the group of H, $C_3$-$C_7$ cycloalkyl, a $C_1$-$C_3$ perfluoroalkyl, a $C_1$-$C_4$ alkyl substituted with 0-1 $R^{25}$, a phenyl substituted with 0-3 $R^{15}$; a 5- to 6-membered heteroaryl containing 1 to 4 heteroatoms each independently a member selected from the group of N, O and S, wherein said heteroaryl is substituted with 0-2 $R^{15}$, and a $C_3$-$C_8$ heterocycle containing 1 to 2 heteroatoms each independently a member selected from the group of N, O and S, wherein said heterocycle is substituted with 0-2 $R^{1c}$;

each $R^{11}$ is independently a member selected from the group of H, $^t$BOC, Cbz, $C_3$-$C_8$ cycloalkyl, ($C_1$-$C_6$ alkyl)-C(=O)—, ($C_1$-$C_6$ alkyl)-S(=O)$_2$— and a $C_1$-$C_6$ alkyl;

each of $R^{12}$, $R^{13}$ and $R^{14}$ is independently a member selected from the group of H and $C_1$-$C_4$ alkyl;

alternatively, $R^{13}$ and $R^{14}$ on the same N atom are taken together to form a $C_5$-$C_7$ heterocycle containing 1-2 heteroatoms each independently a member selected from the group of N, O and S;

each $R^{15}$ is independently a member selected from the group of H, OH, F, Cl, Br, I, CN, NO$_2$, COOR$^{13}$, C(=O)NR$^{13}$R$^{14}$, S(=O)$_2$NR$^{13}$R$^{14}$, acetyl, —SCH$_3$, —S(=O)CH$_3$, —S(=O)$_2$CH$_3$, NR$^{26}$R$^{27}$, $C_1$-$C_6$ alkoxy, $C_1$-$C_3$ perfluoroalkyl, $C_1$-$C_3$ perfluoroalkoxy and a $C_1$-$C_6$ alkyl;

each $R^{16}$ is independently a member selected from the group of H, OH, COOR$^{13}$, C(=O)NR$^{13}$R$^{14}$, S(=O)$_2$NR$^{13}$R$^{14}$, acetyl, —SCH$_3$, —S(=O)CH$_3$, —S(=O)$_2$CH$_3$, $C_1$-$C_6$ alkoxy, NR$^{26}$R$^{27}$, a phenyl substituted with 0-3 $R^{15}$, a 5- to 6-membered heteroaryl containing 1 to 4 heteroatoms each independently a member selected from the group of N, O and S, wherein said heteroaryl is substituted with 0-3 $R^{15}$, and a $C_3$-$C_8$ heterocycle containing 1 to 2 heteroatoms each independently a member selected from the group of N, O and S, wherein said heterocycle is substituted with 0-2 $R^{15}$ and is saturated or unsaturated;

$R^{17}$ is a member selected from the group of H and $C_1$-$C_4$ alkyl;

each $R^{18}$ is independently a member selected from the group of H, OH, F, Cl, CN, NO$_2$, C(=O)OR$^{30}$, C(=O)NR$^{13}$R$^{14}$, NR$^{11}$R$^{12}$, a $C_1$-$C_3$ perfluoroalkyl, a $C_1$-$C_3$ perfluoroalkoxy, a phenyl substituted with 0-3 $R^{15}$, a 5- to 6-membered heteroaryl containing 1 to 4 heteroatoms each independently a member selected from the group of N, O and S, wherein said heteroaryl is substituted with 0-3 $R^{15}$, a $C_3$-$C_8$ heterocycle containing 1 to 2 heteroatoms each independently a member selected from the group of N, O and S, wherein said heterocycle is substituted with 0-2 $R^{15}$ and is saturated or unsaturated; and $C_3$-$C_8$ cycloalkyl;

each $R^{19}$ is a independently a member selected from the group of $C_1$-$C_4$ alkyl, F, Cl and $C_1$-$C_4$ alkoxy, CF$_3$ and OCF$_3$;

alternatively, two $R^{19}$ on the same carbon may be combined to form $C_3$-$C_6$ cycloalkyl;

each of $R^{20}$, $R^{21}$, $R^{22}$ and $R^{23}$ is independently a member selected from the group of a bond, H, F, OH, $C_1$-$C_4$ alkyl, and $C_1$-$C_3$ alkylhydroxy;

alternatively, $R^{20}$ and $R^{21}$ or $R^{22}$ and $R^{23}$ are taken together to form a $C_3$-$C_6$ cycloalkyl;

$R^{24}$ is a member selected from the group of H and $C_1$-$C_4$ alkyl;

each $R^{25}$ is independently a member selected from the group of H, $C_3$-$C_7$ cycloalkyl, a phenyl substituted with 0-3 $R^{15}$ and a 5- to 6-membered heteroaryl containing 1 to 4 heteroatoms each independently a member selected from the group of N, O and S, wherein said 5- to 6-membered heteroaryl is substituted with 0-2 $R^{15}$;

each $R^{26}$ is independently a member selected from the group of H, $C_1$-$C_4$ alkyl, ($C_1$-$C_4$ alkyl)-C(=O)— and ($C_1$-$C_4$ alkyl)-S(=O)$_2$—;

each $R^{27}$ is independently a member selected from the group of H and $C_1$-$C_4$ alkyl;

alternatively, $R^{26}$ and $R^{27}$ on the same N atom are taken together to form a $C_5$-$C_7$ heterocycle containing 1-2 heteroatoms each independently a member selected from the group of N, O and S;

each $R^{28}$ is independently a member selected from the group of H, a $C_1$-$C_6$ alkyl, $C_3$-$C_9$ cycloalkyl, a phenyl substituted with 0-3 $R^{15}$, a benzyl substituted with 0-2 $R^{15}$;

each $R^{29}$ is independently a member selected from the group of H, F, Cl, Br, I, CN, $NO_2$, $OR^{28}$, $SR^{28}$, $S(=O)R^{28}$, $S(=O)_2R^{28}$, $S(=O)_2NR^{13}R^{14}$, $NR^{26}R^{27}$, acetyl, $C(=O)NR^{13}R^{14}$, $C(=O)OR^{13}$, $C_1$-$C_6$alkyl, $OCHF_2$, $SCF_3$, $OCF_3$, —$C(=NH)NH_2$, and 5- to 6-membered heteroaryl containing 1 to 4 heteroatoms each independently a member selected from the group of N, O and S; alternatively, two $R^{29}$ substituted on adjacent atoms may be combined to form a 5 to 6 membered heterocyclic fused radical, wherein said 5 to 6 membered heterocyclic fused radical comprise 1 or 2 heteroatom(s) selected from O, S and N; wherein said 5 to 6 membered heterocyclic fused radical is substituted with 0-1 oxo;

alternatively, $R^{29}$ and $R^9$ are taken together to form a 5- to 7-membered fused heterocyclic ring containing 1-2 heteroatom(s) each independently a member selected from the group of N, O and S; wherein said 5 to 7 membered fused heterocyclic ring is substituted with 0-2 $R^{19}$;

each $R^{30}$ is independently a member selected from the group of H, $C_3$-$C_7$ cycloalkyl, $C_1$-$C_4$ alkyl substituted with 0-1 $R^{25}$, a phenyl substituted with 0-3 $R^{15}$, and a 5- to 6-membered heteroaryl containing 1 to 4 heteroatoms each independently a member selected from the group of N, O and S, wherein said heteroaryl is substituted with 0-3 $R^{15}$; and with the proviso that $R^3$, $R^4$, $R^5$, $R^6$, $R^7$, $R^8$, and $R^9$ are not all hydrogen.

In a second aspect, the present invention provides a pharmaceutical composition comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

These and other aspects, objects and embodiments will become more apparent when read with the accompanying figure and detailed description which follows.

DETAILED DESCRIPTION OF THE INVENTION

I. Definitions

Figure 1:
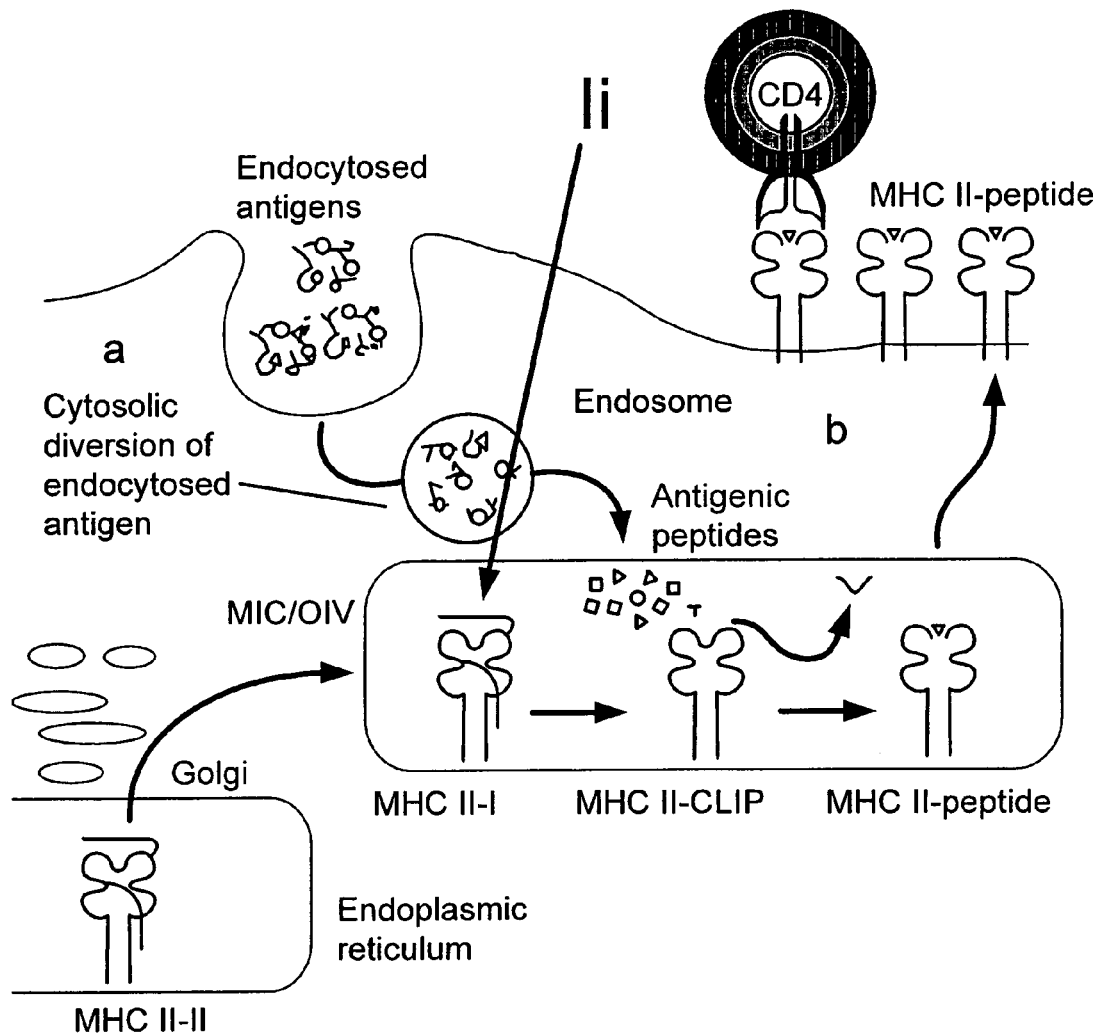
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

| | |
|---|---|
| Ac | acetyl |
| Bn | benzyl |
| Boc | t-butoxycarbonyl |
| Cbz or Z | benzyloxycarbonyl |

-continued

| | |
|---|---|
| DCC | N,N'-dicyclohexylcarbodiimide |
| DCM | dichoromethane |
| DIBAL | diisobutylaluminum hydride |
| DIC | N,N'-diisopropylcarbodiimide |
| DIEA or DIPEA | diisopropylethylamine |
| DMAP | 4-(dimethylamino)pyridine |
| DMF | dimethylformamide |
| DMSO | dimethyl sulfoxide |
| EDC or EDCI | 1-ethyl-3-(dimethylaminopropyl)-carbodiimide |
| Fmoc | 9-fluorenylmethoxycarbonyl |
| HATU | O-(7-azabenzoatriazol-1-yl)-N,N,N',N'-tetramethyluronium hexafluorophosphate |
| HOBt | 1-hydroxybenzotriazole |
| KHMDS | potassium hexamethyldisilazide |
| LAH | lithium aluminum hydride |
| LDA | lithium diisopropylamide |
| LHMDS | lithium hexamethyldisilazide |
| m-CPBA | m-chloroperbenzoic acid |
| MW | microwave |
| NaHMDS | sodium hexamethyldisilazide |
| PCC | pyridinium chlorochromate |
| PDC | pyridinium dichromate |
| PG | protecting group |
| PTSA | p-toluenesulfonic acid |
| Py | pyridine |
| RT or rt | room temperature |
| TEA | triethylamine |
| Tf | trifluoromethanesulfonyl |
| TFA | trifluoroacetic acid |
| THF | tetrahydrofuran |
| Tol | p-tolyl |
| TPAP | tetrapropylammonium perruthenate |

The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

An alkyl group is branched or unbranched and contains 1 to 7 carbon atoms, preferably 1-4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2-4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2-4 carbon atoms, e.g. as acetylenyl, propynyl, isoprpropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, or optionally substituted amino-oxy or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7.

An alkoxy (or alkyloxy) group preferably contains 1-7 carbon atoms, more preferably 1-6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as Rare, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, pyridyl N-oxide, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl). Tetrazolyl is preferably 5-tetrazolyl.

Preferably, heteroaryl is pyridyl, pyridyl N-oxide, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl.

Bicycloalkyl represents a saturated bicyclic ring group of 7-15 carbon atoms. Exemplary bicycloalkyl rings include [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth, optionally substituted by alkyl.

Amino can be optionally substituted by, e.g., alkyl.

Carbocyclic represents a saturated or partially unsaturated cyclic hydrocarbon with to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2 heteroatoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W.H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{aPP}$ using described methods (Kuzmic, P., K. C. Elrod, et al., *Anal Biochem* 2000, 286(1), 45-50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$, for competitive inhibitors by using the following relationship:

$$K_i = \frac{K_i^{app}}{1 + [S]/K_m}.$$

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

"Prodrug" refers to the compounds of this invention which may be modified by appending appropriate functionalities to enhance selective biological properties. Such modifications are known in the art and include those which increase penetration into a given biological compartment (e.g. central nervous system), increase oral bioavailability, increase solubility to allow administration by injection, alter metabolism and alter rate and/or route of excretion. In addition, the compounds may be altered to prodrug form such that the desired compound is created in the body of the patient as the result of the action of metabolic or other biochemical processes on the prodrug.

It will be apparent to one skilled in the art that certain compounds of this invention may exist in tautomeric forms or hydrated forms, all such forms of the compounds being within the scope of the invention.

Structures depicted herein are also meant to include compounds that differ only in the presence of isotopically enriched atoms. For example, compounds having the present structures except for the replacement of a hydrogen by a deuterium are expressly included in the present invention.

II. General

Cathepsin S is a cysteine protease that has been associated with several normal and disease processes in mammals. Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme (e.g. cathepsin K).

III. Compounds

A. Preparation of Compounds

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

Compounds of the present invention can be made via the route shown in Scheme 1.

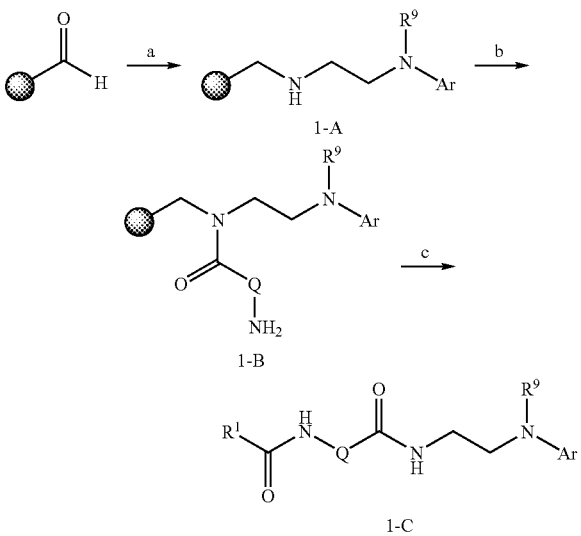

a) i) $NH_2CH_2CH_2NR^9Ar$, AcOH, DMF, rt;
ii) $NaHB(OAc)_3$, DMF;
b) i) $FmocHNQCO_2H$, HOBt, DIC, DMF, rt;
ii) 20% piperidine in DMF;
c) i) $R^1CO_2H$, HOBt, DIC, DMF, rt;
ii) $TFA/DCM/H_2O$.

Polystyrene aldehyde (PAL) resin was reductively aminated with a monoaryl diamine ($NH_2CH_2CH_2NR^9Ar$) which was made as per literature protocol [Altman, E.; Renaud, J.; Green, J.; Farley, D.; Cutting, B; Jahnke W. *J Med. Chem.* 2002, 45, 2352-54 and references cited therein] to obtain the resin 1-A (Scheme 1). This material was acylated with an N-protected amino acid using standard conditions [as described in A. R. Chamberlin, *Chem. Rev.* 1997, 97, 2243-66; M. Bodanszky et al. *The Practice of Peptide Synthesis* 2$^{nd}$, Springer-Verlag, 1984] and the product was then deprotected with piperidine to furnish 1-B. After acylation with $R^1CO_2H$ under standard amide coupling condition, cleavage from resin using TFA furnished 1-C. In scheme 1, Q is defined as —CR²R³—.

Compounds of the present invention can be made via the route shown in Scheme 2.

Scheme 2

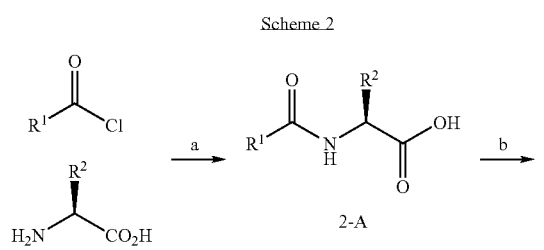

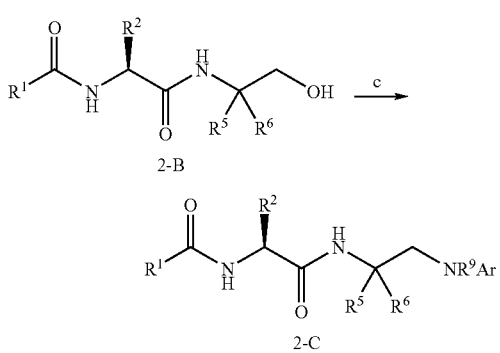

a) 1M NaOH; [EDC, HOBt, DCM or DMF, then ethanolamine (5 eq.) in DMF or DCM] or [PyBOP—Cl (1.0 eq.), TEA (1.0 eq.), NH₂CHR⁵R⁶CH₂OH in DCM followed by TEA in DCM];
b) i) Dess-Martin periodinane, DCM; ii) NHR⁹Ar, NaCNBH₃, AcOH, MeOH A conjugate 2-A (Scheme 2) was synthesized by Schotten-Bauman reaction of an acyl chloride with the appropriate amino acid in 1 M NaOH. The intermediate 2-B was synthesized by acylating NH₂CR⁵R⁶CH₂OH with 2-A using standard conditions. The alcohol 2-B was then oxidized. The resulting aldehyde was reacted with an aromatic amine in methanol in the presence of acetic acid and NaCNBH₃ to give product 2-C.

The arylaminoethylamines 3-A (Scheme 3) used in the present invention can be prepared by a decarboxylative ring opening of oxazolidin-2-one with an aromatic amine as described in E. Altman et al *J. Med. Chem.* 2002, 45, 2352-54 and references cited therein.

Scheme 3

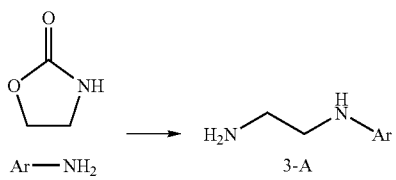

Mono-arylated diamine intermediates used in the present invention can be made via the route described in Scheme 4.

Scheme 4

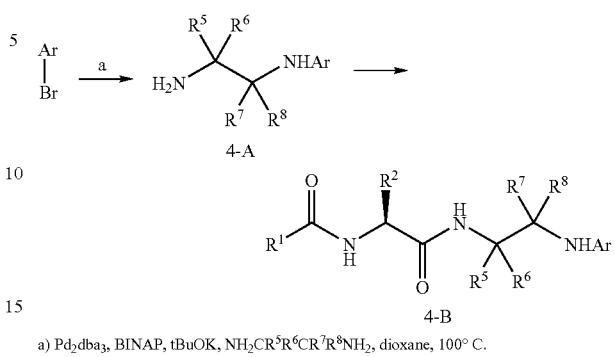

a) Pd₂dba₃, BINAP, tBuOK, NH₂CR⁵R⁶CR⁷R⁸NH₂, dioxane, 100° C.

An aryl bromide (or iodide) was reacted with a diamine using a Pd-BINAP catalyst and tBuOK as base (Frost, C. G.; Mendonga, P. *Tetrahedron: Asymmetry* 1999, 10, 1831-4 and references cited therein). Intermediate 4-A (scheme 4) can be coupled to an amino acid conjugate under standard condition to yield 4-B.

Another synthetic route to compounds of the present invention of general formula (I), in which R⁵ and/or R⁶≠H, is described in Scheme 5.

Scheme 5

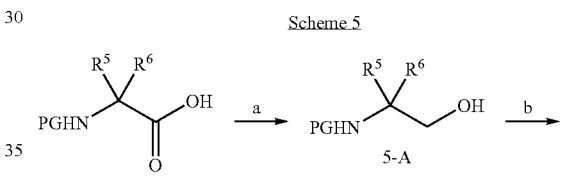

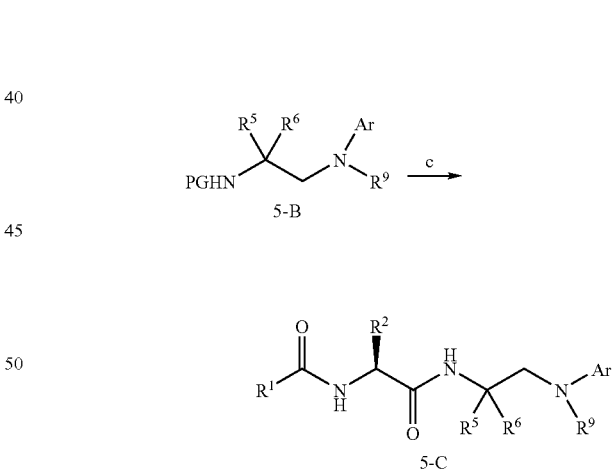

a) [BH₃•THF, THF 0° C.] or [i) TEA, i-butyl-chloroformate, THF, 0° C.; ii) NaBH₄, H₂O, 0° C. to RT];
b) i) Dess-Martin periodinane, DCM; ii) NHR⁹Ar, NaCNBH₃, AcOH, MeOH;
c) i) removal of PG; ii) amide coupling condition.

A N-protected amino acid can be reduced using either the BH₃ method or NaBH₄ reduction of the corresponding mixed anhydride [see R. C. Larock *A guide to functional group preparations* pp. 548-552, Wiley-VCH, 1989] to obtain 5-A (Scheme 5). One can then oxidize the alcohol to the aldehyde and reductively aminate the resulting aldehyde with an amine to afford 5-B. This intermediate can then be deprotected using the appropriate reagents for the PG, such as TFA for Boc, and the resulting amine can be acylated to give access to 5-C.

To access compounds of the present invention with cyclic diamines incorporated, the protocol illustrated in Scheme 6 can be used.

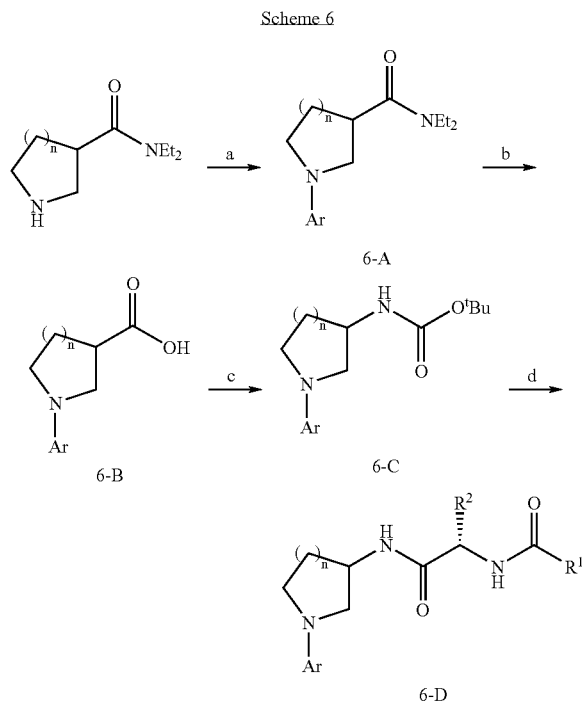

Scheme 6 a) Ar—Br, Pd$_2$dba$_3$, 2-(di-t-Buphosphino)biphenyl, tBuOK, dioxane, heat;
b) 6M HCl, reflux;
c) Diphenylphosphoryl azide, Et$_3$N, $^t$BuOH, heat;
d) i) HCl, MeOH; ii) standard amide coupling condition.

An amide derivative of a cyclic amino acid can be N-arylated under Pd catalysis to afford 6-A (Scheme 6). This intermediate can then be hydrolyzed using strong acid such as 6 M HCl at elevated temperature for an extended period of time to furnish 6-B. This acid can then be degraded via Curtius rearrangement using DPPA in an t-BuOH solvent to obtain the carbamate 6-C. After the removal of the Boc protecting group, the intermediate can be coupled with an amino acid conjugate under standard condition to afford 6-D.

Synthetic approaches to indolines used in this invention are widely describe in the literature and well know to one skilled in the art. The typical methods are illustrated, but are not limited to, in the following references. See: (a) G. W. Gribble et al *Synthesis* 1977, 859; (b) A. Smith et al *Chem. Commun.* 1965, 427; (c) G. W. Gribble et al *J. Am. Chem. Soc.* 1974, 96, 7812; (d) J. G. Berger *Synthesis* 1974, 508; (e) L. J. Dolby et al *J. Heterocycl. Chem.* 1966, 3, 124; (f) W. A. Remers at al *J. Org. Chem.* 1971, 36, 279; (g) S. O'Brien et al *J. Chem. Soc.* 1960, 4609; (h) Y. Kikugawa et al *Synthesis* 1978, 477.

Synthetic approaches to non-commercially available α- and β-amino acids used in the present invention are widely described in the literature. The typical methods are illustrated in the following references. See: (a) D. J. Ager et al. *Current opinion in drug discovery & development* 2001, 4, 800-807; (b) R. O. Duthaler *Tetrahedron* 1994, 50, 1539-1650; (c) M. J. O'Donnell *Aldrichimica Acta* 2001, 34, 3-15; (d) K. B. Sharpless et al. *J. Am. Chem. Soc.* 1998, 120, 1207-17; (e) E. Juaristi et al. *Aldrichimica Acta* 1994, 27, 3-11; (f) D. C. Cole *Tetrahedron* 1994, 50, 9517-9582, and references cited therein.

Compounds of the present invention in which, for example, $R^1$ is furanyl or thienyl; and $R^{1a}$ is phenyl or 5- to 6-membered heteroaryl substituted with 0-2 $R^{15}$, are prepared (a) by Suzuki coupling (N. Miyaura et al. *Synth. Commun.* 1981, 11(7), 513-19; A. Suzuki et al. *Chem. Rev.* 1995, 95, 2457-2483) of appropriate phenyl- or heteroaryl-boronic acid with bromofurancarboxylic acid or bromothiophenecarboxylic acid; (b) according to Bartoli, J. et. al. *J. Med. Chem.* 1998, 41, 1855-1868; Holzer, W. et al. *J. Hetcycl. Chem.* 1993, 30(4), 865-872; Molteni, G. et al. *New J. Chem.* 2002, 26(10), 1340-1345; Seigo I. et al. *Bioorg. Med. Chem.* 2001, 11(7), 879-882, when $R^{1a}$ is pyrazolyl; and $R^{1a}$ is phenyl or 5- to 6-membered heteroaryl substituted with 0-2 $R^{15}$ (c) according to Evans, D. L. et. al. *J. Org. Chem.* 1979, 44, 497; Takeuchi, K. et. al. *J. Med. Chem.* 1998, 41, 5362-5374; Dondoni, A. et al. *J. Org. Chem.* 1987, 52(15), 3413-3420; Millan, D. S. et al. *Tetrahedron* 2000, 56(5), 811-816; Duarte, M. P. et al. *Tetrahedron Lett.* 2000, 41(39), 7433-7435, when $R^1$ is oxazolyl; and $R^{1a}$ is phenyl or 5- to 6-membered heteroaryl substituted with 0-2 $R^{15}$; (d) according to Bartroli, J. et al. *J. Med. Chem.* 1998, 41(11), 1855-1868; Wright, S. W. et al *J. Med. Chem.* 2002, 45(18), 3865-3877; Janusz, J. M. et al. *J. Med. Chem.* 1998, 41(18), 3515-3529; Tanaka, C. et al. *Chem. Pharm. Bulletin* 1982, 30(11), 4195-8, when $R^1$ is thiazolyl; and $R^{1a}$ is phenyl or 5- to 6-membered heteroaryl substituted with 0-2 $R^{15}$; (e) Liu, G. et al. *J. Med. Chem.* 2003, 46(20), 4232-5; Hamper, B. C. et al. *J. HeterocycL Chem.* 2003, 40(4), 575-583, when $R^1$ is isoxazolyl; and $R^{1a}$ is phenyl or 5- to 6-membered heteroaryl substituted with 0-2 $R^{15}$; (f) Bartroli, J. et al. *J. Med. Chem.* 1998, 41(11), 1855-1868, when $R^1$ is 1,3,4-oxadiazolyl; and $R^{1a}$ is phenyl or 5- to 6-membered heteroaryl substituted with 0-2 $R^{15}$.

B. Preferred Compounds

In one aspect, preferred compounds of the present invention have formula Ia:

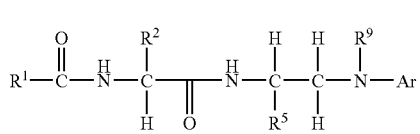

Ia wherein:
$R^1$ is a 5- to 6-membered heteroaryl containing 1 to 4 heteroatoms each independently a member selected from the group consisting of N, O and S, wherein said heteroaryl is substituted with 1 $R^{1a}$;

$R^{1a}$ is independently a member selected from the group consisting of phenyl substituted with 0-2 $R^{15}$, and a 5- to 6-membered monocyclic heteroaryl containing 1 to 4 heteroatoms each independently a member selected from the group consisting of N, O and S, wherein said heteroaryl is substituted with 0-2 $R^{15}$;

$R^2$ is a member selected from the group consisting of a phenyl substituted with 0-3 $R^{15}$, a 5- to 6-membered monocyclic heteroaryl containing 1 to 4 heteroatoms each independently a member selected from the group consisting of N, O and S, wherein said heteroaryl is substituted with 0-2 $R^{15}$, a $C_1$-$C_6$ alkyl, a $C_1$-$C_3$ alkyl substituted with 1$R^{2a}$, and a $C_3$-$C_7$ cycloalkyl substituted with 0-2 $R^{19}$;

each $R^{2a}$ is independently a member selected from the group consisting of a $C_6$-$C_{10}$ aryl substituted with 0-3 $R^{15}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{15}$, a $C_3$-$C_8$ cycloalkyl substituted with 0-2 $R^{19}$ and a $C_7$-$C_{11}$ bicycloalkyl substituted with 0-2 $R^{19}$; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 $R^{19}$.

Alternatively, in another aspect, preferred compounds of the present invention have formula Ia wherein:

$R^1$ is a member selected from the group consisting of a $C_3$-$C_8$ cycloalkyl substituted with 0-2 $R^{1b}$, wherein said $C_3$-$C_8$ cycloalkyl is saturated or unsaturated and a $C_4$-$C_7$ heterocycle containing 1 to 2 heteroatoms each independently a member selected from the group consisting of N, O and S, wherein said heterocycle is substituted with 0-2 $R^{1c}$ and is saturated or unsaturated;

$R^2$ is a member selected from the group consisting of a phenyl substituted with 0-3 $R^{15}$, a 5- to 6-membered monocyclic heteroaryl containing 1 to 4 heteroatoms each independently a member selected from the group consisting of N, O and S, wherein said heteroaryl is substituted with 0-2 $R^{15}$, a $C_1$-$C_6$ alkyl substituted with 0-2 $R^{2a}$, and a $C_3$-$C_7$ cycloalkyl substituted with 0-2 $R^{19}$; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2$R^{19}$.

In still another aspect, preferred compounds of the present invention have formula Ia wherein:

$R^1$ is a member selected from the group consisting of $C_6$-$C_{10}$ aryl substituted with 0-3 $R^{1a}$, and a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$;

each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, $S(=O)CH_3$, $S(=O)_2R^{10}$, $NR^{11}$, $R^{12}$, acetyl, $C(=O)OR^{13}$, $C(=O)NR^{13}R^{14}$, $S(=O)_2NR^{13}R^{14}$, phenyl substituted with 0-3 $R^{15}$; and a $C_1$-$C_4$ alkyl substituted with 0-2 $R^{16}$;

$R^2$ is a member selected from the group consisting of a phenyl substituted with 0-3 $R^{15}$; a 5- to 6-membered monocyclic heteroaryl containing 1 to 4 heteroatoms each independently a member selected from the group consisting of N, O and S, wherein said heteroaryl is substituted with 0-2 $R^{15}$, a $C_1$-$C_6$ alkyl, a $C_1$-$C_2$ alkyl substituted with $1R^{2a}$; a $C_3$-$C_7$ cycloalkyl substituted with 0-2 $R^{19}$.

each $R^{2a}$ is independently a member selected from the group consisting of a $C_6$-$C_{10}$ aryl substituted with 0-3 $R^{15}$; a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{15}$; a $C_3$-$C_8$ cycloalkyl substituted with 0-2 $R^{19}$; and a $C_7$—Cl, bicycloalkyl substituted with 0-2 $R^{19}$; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 $R^{19}$.

In another aspect, preferred compounds of the present invention have formula Ib:

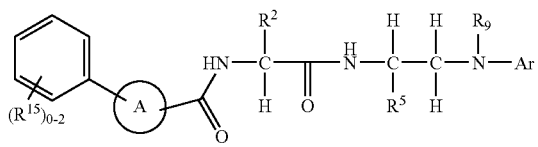

wherein:

each $R^5$, if present, is independently a member selected from the group consisting of OH, F, Cl, Br, I, CN, $NO_2$, $COOR^{13}$, $C(=O)NR^{13}R^{14}$, $S(=O)_2NR^{13}R^{14}$, acetyl, $-SCH_3$, $-S(=O)CH_3$, $-S(=O)_2CH_3$, $NR^{26}R^{27}$, $C_1$-$C_6$ alkoxy, $C_1$-$C_3$ perfluoroalkyl, $C_1$-$C_3$ perfluoroalkoxy and a $C_1$-$C_6$ alkyl; and A is a 5-membered heteroaryl selected from the group consisting of furanylene, thienylene, thiazolylene, oxadiazolylene, isoxazolylene, tetrazolylene, and oxazolylene.

In another aspect, preferred compounds of the present invention have formula Ic:

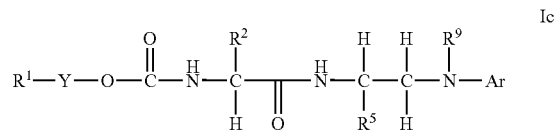

wherein:

$R^1$ is a member selected from the group consisting of tBu, phenyl substituted with 0-2 $R^{15}$, a 5- to 6-membered heteroaryl containing 1 to 4 heteroatoms each independently a member selected from the group consisting of N, O and S, wherein said heteroaryl is substituted with 0-2 $R^{15}$, and a $C_4$-$C_7$ heterocycle containing 1 to 2 heteroatoms each independently a member selected from the group consisting of N, O and S, wherein said heterocycle is substituted with 0-2 $R^{1c}$;

each $R^{1c}$ is independently a member selected from the group consisting of H, OH, F, Cl, =O, $C_1$-$C_6$ alkyl substituted with 0-2 $R^{16}$, a $C_1$-$C_6$ alkoxy, $CF_3$, $OCF_3$, $C(=O)R^{10}$, $S(=O)_2R^{10}$, tBoc, Cbz, phenyl substituted with 0-3 $R^{15}$, and a 5- to 6-membered monocyclic heteroaryl containing 1 to 4 heteroatoms each independently a member selected from the group consisting of N, O and S, wherein said heteroaryl is substituted with 0-2 $R^{15}$;

Y is a member independently selected from the group consisting of a bond and $-(CR^{20}R^{21})_m-W-(CR^{22}R^{23})_p-$, wherein m is 0, W is a bond, and $R^{22}R^{23}$ are both H;

$R^2$ is a member selected from the group consisting of a phenyl substituted with 0-3 $R^{15}$, a 5- to 6-membered monocyclic heteroaryl containing 1 to 4 heteroatoms each independently a member selected from the group consisting of N, O and S, wherein said heteroaryl is substituted with 0-2 $R^5$, a $C_1$-$C_6$ alkyl, a $C_1$-$C_3$ alkyl substituted with l$R^{2a}$, and a $C_3$-$C_7$ cycloalkyl substituted with 0-2 $R^{19}$;

each $R^{2a}$ is independently a member selected from the group consisting of a $C_6$-$C_{10}$ aryl substituted with 0-3 $R^{15}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^5$, a $C_3$-$C_8$ cycloakyl substituted with 0-2 $R^{19}$, and a $C_7$-$C_{11}$ bicycloalkyl substituted with 0-2 $R^{19}$; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2$R^{19}$.

In yet another aspect, preferred compounds of the present invention have formula Id:

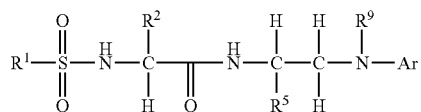

Id wherein:
$R^1$ is a member selected from the group consisting of methyl, benzyl, $C_6$-$C_{10}$ aryl substituted with 0-3 $R^{1a}$, and a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$;

each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, $S(=O)CH_3$, $S(=O)_2R^{10}$, $NR^{11}R^{12}$, acetyl, $C(=O)OR^{13}$, $C(=O)NR^{13}R^{14}$, $S(=O)_2NR^{13}R^{14}$, phenyl substituted with 0-3 $R^{15}$, a 5- to 6-membered monocyclic heteroaryl containing 1 to 4 heteroatoms each independently a member selected from the group consisting of N, O and S, wherein said heteroaryl is substituted with 0-2 $R^{15}$; and a $C_1$-$C_4$ alkyl; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 $R^{19}$.

In still yet another aspect, preferred compounds of the present invention have formula Ie:

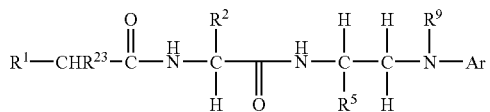

Ie wherein:
$R^1$ is a member selected from the group consisting of a $C_6$-$C_{10}$ aryl substituted with 0-3 $R^{1a}$, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1a}$;

each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, $S(=O)CH_3$, $S(=O)_2R^{10}$, $NR^{11}R^{12}$, acetyl, $C(=O)OR^{13}$, $C(=O)NR^{13}R^{14}$, $S(=O)_2NR^{13}R^{14}$, phenyl substituted with 0-3 $R^{15}$, a 5- to 6-membered monocyclic heteroaryl containing 1 to 4 heteroatoms each independently a member selected from the group consisting of N, O and S, wherein said heteroaryl is substituted with 0-2 $R^{15}$, a $C_3$-$C_8$ heterocycle containing 1 to 2 heteroatoms each independently a member selected from the group consisting of N, O and S, wherein said heterocycle is substituted with 0-2 $R^{1c}$ and is saturated or unsaturated, and a $C_1$-$C_4$ alkyl substituted with 0-2 $R^{16}$; and Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 $R^{19}$.

In yet another aspect, preferred compounds of the present invention have formula If:

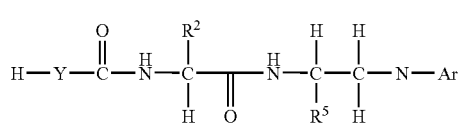

If wherein:
Y is a member selected from the group consisting of a bond and $-(CR^{20}R^{21})_m-W-(CR^{22}R^{23})_p-$;
subscript p is the integer 1 or 2;
subscript m is 0 or 1;
W is a oxygen; and
Ar is phenyl substituted with 0-3 $R^{29}$, or alternatively, $R^{29}$ and $R^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 $R^{19}$.

In another aspect, preferred compounds of the present invention have formula Ig:

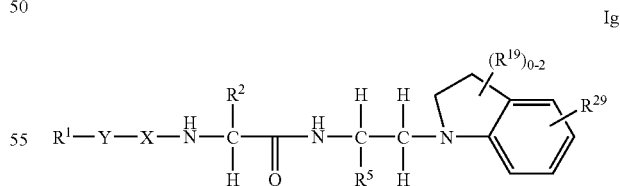

Ig wherein:
$R^5$ is a member selected from the group consisting of H, $C_3$-$C_7$ cycloalkyl, $C_2$-$C_6$ alkenyl, $C_2$-$C_6$ alkyne, phenyl substituted with 0-2 $R^{15}$; 5- to 6-membered heteroaryl containing 1 to 4 heteroatoms each independently a member selected from the group consisting of N, O and S, wherein said heteroaryl is substituted with 0-2 $R^{15}$, a $C_1$-$C_6$ alkyl substituted with 0-2 $R^{15}$, wherein said $C_1$-$C_6$ alkyl optionally contains a heteroatom selected from the group consisting of —O—, —S—, —S(=O)—, —S(=O)$_2$— and —NR$^{17}$—.

In another aspect, preferred compounds of the present invention have formula Ih:

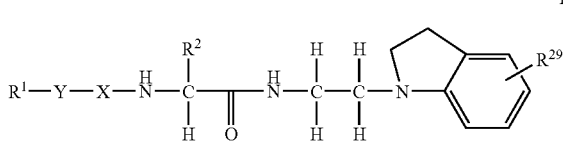

Ih

In another aspect, the present invention provides compounds wherein R$^9$ is H; and Ar is phenyl substituted with 0-3 R$^{29}$, or alternatively, R$^{29}$ and R$^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 R$^{19}$.

In another aspect, compounds of formula I wherein R$^5$ and R$^7$ are taken together to form a C$_5$-C$_7$ cycloalkyl substituted with 0-2 R$^{19}$; and Ar is phenyl substituted with 0-3 R$^{29}$, or alternatively, R$^{29}$ and R$^9$ are taken together to form a 5- to 7-membered fused heterocyclic ring containing 1-2 heteroatom(s) each independently a member selected from the group consisting of N, O and S; wherein said 5- to 7-membered fused heterocyclic ring is substituted with 0-2 R$^{19}$ are preferred.

In one aspect, with respect to formulae Ia, Ib Ic, Id, and Ie, compounds wherein:

R$^2$ is a member selected from the group consisting of a C$_1$-C$_2$ alkyl substituted with 1 R$^{2a}$, and C$_1$-C$_6$ alkyl;

each R$^{2a}$ is independently a member selected from the group consisting of a phenyl substituted with 0-3 R$^{15}$, and a C$_3$-C$_8$ cycloalkyl substituted with 0-2 R$^{19}$;

R$^5$ is a member selected from the group consisting of H, C$_3$-C$_7$ cycloalkyl; a C$_1$-C$_6$ alkyl substituted with 0-1 R$^{18}$, wherein said C$_1$-C$_6$ alkyl optionally contains a heteroatom selected from the group consisting of —O—, —S—, —S(=O)—, —S(=O)$_2$— and —NR$^{17}$—; and each R$^{18}$ is independently a member selected from the group consisting of H, OH, F, Cl, CN, C(=O)OR$^{30}$, C(=O)NR$^{13}$R$^{14}$, NR$^{11}$R$^{12}$, a phenyl substituted with 0-3 R$^{15}$, a C$_3$-C$_8$ heterocycle containing 1 to 2 heteroatoms each independently a member selected from the group consisting of N, O and S, wherein said heterocycle is substituted with 0-2 R$^{15}$ and is saturated or unsaturated; and C$_3$-C$_8$ cycloalkyl are preferred.

In formulae Ia, Ib, Ic, Id, and Ie, in one aspect, R$^{29}$ and R$^9$ are taken together to form a 5- to 7-membered fused heterocyclic ring containing 1-2 heteroatom(s) each independently a member selected from the group consisting of N, O and S; wherein the 5- to 7-membered fused heterocyclic ring is substituted with 0-2 R$^{19}$. The heterocyclic ring is fused with the Ar portion, such that the total number of ring atoms within these fused systems is between 8-11 (e.g. 8, 9, 10 and 11 ring atoms). Within this embodiment, in one preferred aspect, compounds have the following indoline structure:

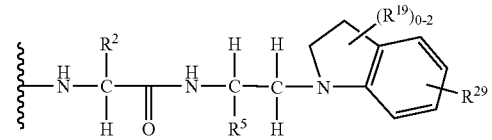

The compounds set forth below in Table I are especially preferred compounds of the invention.

TABLE I

1. N-{cis-2-[2-(4-Methoxy-phenylamino)-ethylcarbamoyl]-cyclohexyl}-3-methyl-benzamide;
2. 5-(3-Trifluoromethyl-phenyl)-furan-2-carboxylic acid (S)-{2-cyclohexyl-1-[2-(5-fluoro-2,3-dihydro-indol-1-yl)-ethylcarbamoyl]-ethyl}-amide;
3. (S)-N-{1-[2-(5-Fluoro-2,3-dihydro-indol-1-yl)-ethylcarbamoyl]-3-methyl-butyl}-3-methyl-benzamide;
4. N-(S)-{2-cyclohexyl-1-[2-(5-fluoro-2,3-dihydro-indol-1-yl)-ethylcarbamoyl]-ethyl}-4-phenoxy-benzamide;
5. 1-Benzoyl-piperidine-4-carboxylic acid (S)-{2-cyclohexyl-1-[2-(5-fluoro-2,3-dihydro-indol-1-yl)-ethylcarbamoyl]-ethyl}-amide;
6. (S)-3-Cyclohexyl-N-[2-(5-fluoro-2,3-dihydro-indol-1-yl)-ethyl]-2-[2-(4-methoxy-phenyl)-acetylamino]-propionamide;
7. (S)-N-{1-[2-(5-Chloro-2,3-dihydro-indol-1-yl)-ethylcarbamoyl]-3-methyl-butyl}-3-methyl-benzamide;
8. (S)-N-{3-Cyclohexyl-1-[2-(7-methoxy-2,3-dihydro-indol-1-yl)-ethylcarbamoyl]-propyl}-3-methoxy-benzamide;
9. Furan-2-carboxylic acid (S)-{2-cyclohexyl-1-[2-(5-fluoro-2,3-dihydro-indol-1-yl)-ethylcarbamoyl]-ethyl}-amide;
10. (S)-N-{3-Cyclohexyl-1-[2-(6-fluoro-2,3-dihydro-indol-1-yl)-ethylcarbamoyl]-propyl}-3-methoxy-benzamide;
11. (S)-N-{3-Cyclohexyl-1-[2-(7-fluoro-2,3-dihydro-indol-1-yl)-ethylcarbamoyl]-propyl}-3-methoxy-benzamide;
12. (S)-N-{3-Cyclohexyl-1-[2-(5-cyano-2,3-dihydro-indol-1-yl)-ethylcarbamoyl]-propyl}-3-methoxy-benzamide;
13. Furan-3-carboxylic acid (S)-{2-cyclohexyl-1-[2-(5-fluoro-2,3-dihydro-indol-1-yl)-ethylcarbamoyl]-ethyl}-amide;
14. Cyclopropanecarboxylic acid (S)-{2-cyclohexyl-1-[2-(5-fluoro-2,3-dihydro-indol-1-yl)-ethylcarbamoyl]-ethyl}-amide;
15. (S)-N-{3-Cyclohexyl-1-[2-(4-methoxy-2,3-dihydro-indol-1-yl)-ethylcarbamoyl]-propyl}-3-methoxy-benzamide;
16. (S)-N-{3-Cyclohexyl-1-[2-(5-methoxy-2,3-dihydro-indol-1-yl)-ethylcarbamoyl]-propyl}-3-methoxy-benzamide;

TABLE I-continued 17. 1-(4-Chloro-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;
18. (S)-N-{3-Cyclohexyl-1-[2-(5-fluoro-2,3-dihydro-indol-1-yl)-ethylcarbamoyl]-propyl}-3-methoxy-benzamide;
19. (S)-N-{3-Cyclohexyl-1-[2-(5-benzyloxy-2,3-dihydro-indol-1-yl)-ethylcarbamoyl]-propyl}-3-methoxy-benzamide;
20. N-{1-(S)-[2-(4-Methoxy-phenylamino)-propylcarbamoyl]-3-methyl-butyl}-3-methyl-benzamide;
21. N-{1-(S)-[2-(4-Methoxy-phenylamino)-1-methyl-ethylcarbamoyl]-3-methyl-butyl}-3-methyl-benzamide;
22. N-(1-(S)-[2-(4-Methoxy-phenylamino)-1-(S)-methyl-ethylcarbamoyl]-3-methyl-butyl}-3-methyl-benzamide;
23. N-{1-(S)-[2-(4-Methoxy-phenylamino)-1-(R)-methyl-ethylcarbamoyl]-3-methyl-butyl}-3-methyl-benzamide;
24. 1H-Indole-2-carboxylic acid {3-cyclohexyl-(1S)-[2-(4-methoxy-phenylamino)-(1S)-methyl-ethylcarbamoyl]-propyl}-amide;
25. 1H-Indole-2-carboxylic acid {3-cyclohexyl-(1S)-[2-(4-methoxy-phenylamino)-(1R)-methyl-ethylcarbamoyl]-propyl}-amide;
26. N-{2-Cyclohexyl-(1S)-[2-(4-methoxy-phenylamino)-(1R)-methyl-ethylcarbamoyl]-ethyl }-3-methoxy-benzamide;
27. 5-(3-Trifluoromethyl-phenyl)-furan-2-carboxylic acid {3-cyclohexyl-(1S)-[2-(4-methoxy-phenylamino)-(1S)-methyl-ethylcarbamoyl]-propyl}-amide;
28. N-{(1S)-[2-(5-Fluoro-2,3-dihydro-indol-1-yl)-1,1-dimethyl-ethylcarbamoyl]-2-phenyl-ethyl}-3-methyl-benzamide;
29. Tetrahydrofuran-2-(S)-carboxylic acid {2-cyclohexyl-1-(S)-[1-(S)-methyl-2-(4-trifluoromethoxy-phenylamino)-ethylcarbamoyl]-ethyl}-amide;
30. Tetrahydrofuran-2-(R)-carboxylic acid {2-cyclohexyl-1-(S)-[1-(S)-methyl-2-(4-trifluoromethoxy-phenylamino)-ethylcarbamoyl]-ethyl}-amide;
31. N-{1-(S)-[1-(4-Methoxy-phenyl)-piperidin-3-(S)-ylcarbamoyl]-3-methyl-butyl}-3-methyl-benzamide;
32. N-{1-(S)-[1-(4-Methoxy-phenyl)-piperidin-3-(R)-ylcarbamoyl]-3-methyl-butyl }-3-methyl-benzamide;
33. N-{1-(S)-[cis-2-(4-Methoxy-phenylamino)-cyclohexylcarbamoyl]-3-methyl-butyl}-3-methyl-benzamide;
34. N-{1-(S)-[trans-2-(4-Methoxy-phenylamino)-cyclohexylcarbamoyl]-3-methyl-butyl }-3-methyl-benzamide;
35. N-{1-(S)-[1-(R)-Benzyloxymethyl-2-(4-methoxy-phenylamino)-ethylcarbamoyl]-3-methyl-butyl}-3-methyl-benzamide;
36. N-(S)-{[1-(R)-Benzyloxymethyl-2-(5-fluoro-2,3-dihydro-indol-1-yl)-ethylcarbamoyl]-phenyl-methyl}-3-methoxy-benzamide;
37. N-[1-(S)-[1-(R)-Benzyloxymethyl-2-(5-fluoro-2,3-dihydro-indol-1-yl)-ethylcarbamoyl]-2-(4-fluoro-phenyl)-ethyl]-3-methoxy-benzamide;
38. N-{1-(S)-[(2-Benzyloxy-1-(R)-(5-fluoro-2,3-dihydro-indol-1-ylmethyl)-ethylcarbamoyl]-3-cyclohexyl-propyl}-3-methoxy-benzamide;
39. N-{3-Cyclohexyl-1-(S)-[2-(5-fluoro-2,3-dihydro-indol-1-yl)-1-(R)-hydroxymethyl-ethylcarbamoyl]-propyl}-3-methoxy-benzamide;
40. N-{3-Cyclohexyl-1-(R)-[(S)-2-(5-fluoro-2,3-dihydro-indol-1-yl)-1-(R)-hydroxymethyl-ethylcarbamoyl]-propyl}-3-methoxy-benzamide;
41. 1H-Indole-2-carboxylic acid {(1S)-[2-benzyloxy-(1R)-(5-fluoro-2,3-dihydro-indol-1-ylmethyl)-ethylcarbamoyl]-3-cyclohexyl-propyl}-amide;
42. (S,S)-5-(5-Fluoro-2,3-dihydro-indol-1-yl)-4-[4-methyl-2-(3-methyl-benzoylamino)-pentanoylamino]-pentanoic acid benzyl ester;
43. (S,S)-5-(5-Fluoro-2,3-dihydro-indol-1-yl)-4-[4-methyl-2-(3 -methyl-benzoylamino)-pentanoylamino]-pentanoic acid;
44. (S,S)-N-{1-[3-Carbamoyl-1-(5-fluoro-2,3-dihydro-indol-1-ylmethyl)-propylcarbamoyl]-3-methyl-butyl}-3-methyl-benzamide;
45. (S,S)-N-{1-[1-(5-Fluoro-2,3-dihydro-indol-1-ylmethyl)-3-ureido-propylcarbamoyl]-3-methyl-butyl}-3-methyl-benzamide;
46. (S,S)-3-[4-Cyclohexyl-2-(3-methoxy-benzoylamino)-butyrylamino]-4-(5-fluoro-2,3-dihydro-indol-1-yl)-butyric acid benzyl ester;
47. (S,S)-3-[4-Cyclohexyl-2-(3-methoxy-benzoylamino)-butyrylamino]-4-(5-fluoro-2,3-dihydro-indol-1-yl)-butyric acid;
48. (S,S)-N-{1-[1-Benzyl-2-(5-fluoro-2,3-dihydro-indol-1-yl)-ethylcarbamoyl]-3-cyclohexyl-propyl}-3-methoxy-benzamide;
49. (S,S)-N-{3-Cyclohexyl-1-[1-(5-fluoro-2,3-dihydro-indol-1-ylmethyl)-3-methyl-butylcarbamoyl]-propyl}-3-methoxy-benzamide;
50. (S,S)-N-{3-Cyclohexyl-1-[1-(5-fluoro-2,3-dihydro-indol-1-ylmethyl)-2-methyl-propylcarbamoyl]-propyl}-3-methoxy-benzamide;
51. (S,S)-N-{3-Cyclohexyl-1-[2-(5-fluoro-2,3-dihydro-indol-1-yl)-1-phenyl-ethylcarbamoyl]-propyl}-3-methoxy-benzamide;
52. (S,S)-N-{3-Cyclohexyl-1-[1-(5-fluoro-2,3-dihydro-indol-1-ylmethyl)-3-morpholin-4-yl-propylcarbamoyl]-propyl}-3-methoxy-benzamide;
53. N-{1-(S)-[2-(R)-Benzyloxy-1-(R)-(5-fluoro-2,3-dihydro-indol-1-ylmethyl)-propylcarbamoyl]-3-cyclohexyl-propyl}-3-methoxy-benzamide;
54. N-{1-(R)-[1-(R)-Benzylsulfanylmethyl-2-(5-fluoro-2,3-dihydro-indol-1-yl)-ethylcarbamoyl]-3-cyclohexyl-propyl}-3-methoxy-benzamide;
55. (S,S)-[5-[4-Cyclohexyl-2-(3-methoxy-benzoylamino)-butyrylamino]-6-(5-fluoro-2,3-dihydro-indol-1-yl)-hexyl]-carbamic acid benzyl ester;

TABLE I-continued 56. 1-(6-Chloro-pyridazin-3-yl)-piperidine-4-carboxylic acid (S)-{2-cyclohexyl-1-[2-(5-fluoro-2,3-dihydro-indol-1-yl)-ethylcarbamoyl]-ethyl}-amide;
57. 1-(4-Methoxy-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;
58. 1-Benzenesulfonyl-piperidine-4-carboxylic acid (S)-{2-cyclohexyl-1-[2-(5-fluoro-2,3-dihydro-indol-1-yl)-ethylcarbamoyl]-ethyl}-amide;
59. N-{2-cyclohexyl-1-(S)-[2-(5-fluoro-2,3-dihydro-indol-1-yl)-ethylcarbamoyl]-ethyl}-2-(2-fluoro-biphenyl-4-yl)-propionamide;
60. N-{2-cyclohexyl-1-(S)-[2-(5-fluoro-2,3-dihydro-indol-1-yl)-ethylcarbamoyl]-ethyl}-2-p-tolyl-propionamide;
61. N-{2-cyclohexyl-1-(S)-[2-(5-fluoro-2,3-dihydro-indol-1-yl)-ethylcarbamoyl]-ethyl}-2-o-tolyl-propionamide;
62. N-{2-cyclohexyl-1-(S)-[2-(5-fluoro-2,3-dihydro-indol-1-yl)-ethylcarbamoyl]-ethyl}-2-(4-fluoro-phenyl)-propionamide;
63. 1-Methyl-i H-imidazole-4-carboxylic acid (S)-{2-cyclohexyl-1-[2-(5-fluoro-2,3-dihydro-indol-1-yl)-ethylcarbamoyl]-ethyl}-amide;
64. 2-(4-Chloro-phenyl)-N-{2-cyclohexyl-1-(S)-[2-(5-fluoro-2,3-dihydro-indol-1-yl)-ethylcarbamoyl]-ethyl}-propionamide;
65. 1-Benzyl-5-oxo-pyrrolidine-3-carboxylic acid (S)-{2-cyclohexyl-1-[2-(5-fluoro-2,3-dihydro-indol-1 -yl)-ethylcarbamoyl]-ethyl}-amide;
66. 1-(4-Fluoro-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;
67. N-(S)-{2-cyclohexyl-1-[2-(5-fluoro-2,3-dihydro-indol-1-yl)-ethylcarbamoyl]-ethyl}-4-(piperidin-4-yloxy)-benzamide;
68. N-(S)-{2-cyclohexyl-1-[2-(5-fluoro-2,3-dihydro-indol-1-yl)-ethylcarbamoyl]-ethyl}-4-(1-methanesulfonyl-piperidin-4-yloxy)-benzamide;
69. 4-(1-Acetyl-piperidin-4-yloxy)-N-(S)-{2-cyclohexyl-1-[2-(5-fluoro-2,3-dihydro-indol-1-yl)-ethylcarbamoyl]-ethyl}-benzamide;
70. N-{2-cyclohexyl-1-(S)-[2-(5-fluoro-2,3-dihydro-indol-1-yl)-ethylcarbamoyl]-ethyl}-2-(R)-phenyl-propionamide;
71. N-(S)-{2-cyclohexyl-1-[2-(5-fluoro-2,3-dihydro-indol-1-yl)-ethylcarbamoyl]-ethyl}-3-methyl-benzamide;
72. 5-Methanesulfonyl-thiophene-2-carboxylic acid (S)-{2-cyclohexyl-1-[2-(5-fluoro-2,3-dihydro-indol-1-yl)-ethylcarbamoyl]-ethyl}-amide;
73. 5-Oxo-1-thiophen-2-ylmethyl-pyrrolidine-3-carboxylic acid (S)-{2-cyclohexyl-1-[2-(5-fluoro-2,3-dihydro-indol-1-yl)-ethylcarbamoyl]-ethyl}-amide;
74. 1-Furan-2-ylmethyl-5-oxo-pyrrolidine-3-carboxylic acid (S)-{2-cyclohexyl-1-[2-(5-fluoro-2,3-dihydro-indol-1-yl)-ethylcarbamoyl]-ethyl}-amide;
75. 5-Phenyl-furan-2-carboxylic acid (S)-{2-cyclohexyl-1-[2-(5-fluoro-2,3-dihydro-indol-1-yl)-ethylcarbamoyl]-ethyl}-amide;
76. 2-Phenyl-thiazole-4-carboxylic acid (S)-{2-cyclohexyl-1-[2-(5-fluoro-2,3-dihydro-indol-1-yl)-ethylcarbamoyl]-ethyl}-amide;
77. 1-Methanesulfonyl-piperidine-4-carboxylic acid (S)-{2-cyclohexyl-1-[2-(5-fluoro-2,3-dihydro-indol-1-yl)-ethylcarbamoyl]-ethyl}-amide;
78. 5-Methyl-2-trifluoromethyl-furan-3-carboxylic acid (S)-{2-cyclohexyl-1-[2-(5-fluoro-2,3-dihydro-indol-1-yl)-ethylcarbamoyl]-ethyl}-amide;
79. N-(S)-{2-cyclohexyl-1-[2-(5-fluoro-2,3-dihydro-indol-1-yl)-ethylcarbamoyl]-ethyl}-4-(methanesulfonylamino-methyl)-benzamide;
80. N-(S)-{2-cyclohexyl-1-[2-(5-fluoro-2,3-dihydro-indol-1-yl)-ethylcarbamoyl]-ethyl}-3-methanesulfonyl-benzamide;
81. N-(S)-{2-cyclohexyl-1-[2-(5-fluoro-2,3-dihydro-indol-1-yl)-ethylcarbamoyl]-ethyl}-4-methanesulfonylamino-benzamide;
82. 5-Phenyl-thiophene-2-carboxylic acid (S)-{2-cyclohexyl-1-[2-(5-fluoro-2,3-dihydro-indol-1-yl)-ethylcarbamoyl]-ethyl}-amide;
83. 5-(3-Fluoro-phenyl)-furan-2-carboxylic acid {2-cyclohexyl-1-(S)-[1-(S)-methyl-2-(4-trifluoromethoxy-phenylamino)-ethylcarbamoyl]-ethyl}-amide;
84. 5-(3-Fluoro-phenyl)-furan-2-carboxylic acid {2-cyclohexyl-1-(S)-[2-(4-difluoromethoxy-phenylamino)-1-(S)-methylethylcarbamoyl]-ethyl}-amide;
85. 5-(3-Fluoro-phenyl)-furan-2-carboxylic acid {1-(S)-[2-(benzo[1,3]dioxol-5-ylamino)-1-(S)-methyl-ethylcarbamoyl]-2-cyclohexyl-ethyl}-amide;
86. 5-(3-Fluoro-phenyl)-furan-2-carboxylic acid {2-cyclohexyl-1-(S)-[2-(4-methoxy-phenylamino)-1-(S)-methyl-ethylcarbamoyl]-ethyl}-amide;
87. 5-(3-Fluoro-phenyl)-furan-2-carboxylic acid {2-cyclohexyl-1-(S)-[2-(3,5-difluoro-phenylamino)-1-(S)-methyl-ethylcarbamoyl]-ethyl}-amide;
88. 5-(3-Fluoro-phenyl)-furan-2-carboxylic acid {2-cyclohexyl-1-(S)-[2-(3-methanesulfonyl-phenylamino)-1-(S)-methyl-ethylcarbamoyl]-ethyl}-amide;
89. 5-(3-Fluoro-phenyl)-furan-2-carboxylic acid {2-cyclohexyl-1-(S)-[2-(4-methanesulfonyl-phenylamino)-1-(S)-methyl-ethylcarbamoyl]-ethyl}-amide;
90. 5-(3-Fluoro-phenyl)-furan-2-carboxylic acid {2-cyclohexyl-1-(S)-[2-(2,3-difluoro-phenylamino)-1-(S)-methyl-ethylcarbamoyl]-ethyl}-amide;
91. 5-(3-Fluoro-phenyl)-furan-2-carboxylic acid {2-cyclohexyl-1-(S)-[2-(2,5-difluoro-phenylamino)-1-(S)-methyl-ethylcarbamoyl]-ethyl}-amide;
92. 5-(3-Fluoro-phenyl)-furan-2-carboxylic acid {2-cyclohexyl-1-(S)-[2-(2,6-difluoro-phenylamino)-1-(S)-methyl-ethylcarbamoyl]-ethyl}-amide;
93. 5-(3-Fluoro-phenyl)-furan-2-carboxylic acid {1-(S)-[2-(4-cyano-phenylamino)-1-(S)-methyl-ethylcarbamoyl]-2-cyclohexyl-ethyl}-amide;
94. 5-(3-Fluoro-phenyl)-furan-2-carboxylic acid {1-(S)-[2-(3-chloro-phenylamino)-1-(S)-methyl-ethylcarbamoyl]-2-cyclohexyl-ethyl}-amide;

TABLE I-continued 95. 5-(3-Fluoro-phenyl)-furan-2-carboxylic acid {2-cyclohexyl-1-(S)-[2-(2-fluoro-phenylamino)-1-(S)-methyl-ethylcarbamoyl]-ethyl}-amide;
96. 5-(3-Fluoro-phenyl)-furan-2-carboxylic acid {1-(S)-[2-(3-chloro-2-fluoro-phenylamino)-1-(S)-methyl-ethylcarbamoyl]-2-cyclohexyl-ethyl}-amide;
97. 5-(3-Fluoro-phenyl)-furan-2-carboxylic acid {1-(S)-[2-(5-chloro-2-fluoro-phenylamino)- 1 -(S)-methyl-ethylcarbamoyl]-2-cyclohexyl-ethyl}-amide;
98. 5-(3-Fluoro-phenyl)-furan-2-carboxylic acid {1-(S)-[2-(3-carbamoyl-phenylamino)-1-(S)-methyl-ethylcarbamoyl]-2-cyclohexyl-ethyl}-amide;
99. 5-(3-Fluoro-phenyl)-furan-2-carboxylic acid {2-cyclohexyl-1-(S)-[2-(3-fluoro-phenylamino)-1-(S)-methyl-ethylcarbamoyl]-ethyl}-amide;
100. 5-(3-Fluoro-phenyl)-furan-2-carboxylic acid {1-(S)-[2-(3-cyano-phenylamino)-1-(S)-methyl-ethylcarbamoyl]-2-cyclohexyl-ethyl}-amide;
101. N-{2-cyclohexyl-1-(S)-[2-(5-fluoro-2,3-dihydro-indol-1-yl)-ethylcarbamoyl]-ethyl}-2-(4-hydroxy-phenyl)-propionamide;
102. 4-Cyclohexyl-N-[2-(5-fluoro-2,3-dihydro-indol-1-yl)-ethyl]-2-(S)-(2-(R)-phenyl-propionylamino)-butyramide;
103. 5-(4-Fluoro-phenyl)-furan-2-carboxylic acid {2-cyclohexyl-1-(S)-[1-(S)-methyl-2-(4-trifluoromethoxy-phenylamino)-ethylcarbamoyl]-ethyl}-amide;
104. 5-(4-Fluoro-phenyl)-furan-2-carboxylic acid {2-cyclohexyl-1-(S)-[2-(4-difluoromethoxy-phenylamino)-1-(S)-methyl-ethylcarbamoyl]-ethyl}-amide;
105. 5-(4-Fluoro-phenyl)-furan-2-carboxylic acid {2-cyclohexyl-1-(S)-[2-(4-methoxy-phenylamino)-1-(S)-methyl-ethylcarbamoyl]-ethyl}-amide;
106. 5-(4-Fluoro-phenyl)-furan-2-carboxylic acid {2-cyclohexyl-1-(S)-[2-(3-methanesulfonyl-phenylamino)-1-(S)-methyl-ethylcarbamoyl]-ethyl}-amide;
107. 5-(4-Fluoro-phenyl)-furan-2-carboxylic acid {2-cyclohexyl-1-(S)-[2-(4-methanesulfonyl-phenylamino)-1-(S)-methyl-ethylcarbamoyl]-ethyl}-amide;
108. 3-(3-Fluoro-phenyl)-[1,2,4]oxadiazole-5-carboxylic acid {2-cyclohexyl-1-(S)-[1-(S)-methyl-2-(4-trifluoromethoxy-phenylamino)-ethylcarbamoyl]-ethyl}-amide;
109. 3-(4-Fluoro-phenyl)-[1,2,4]oxadiazole-5-carboxylic acid {2-cyclohexyl-1-(S)-[1-(S)-methyl-2-(4-trifluoromethoxy-phenylamino)-ethylcarbamoyl]-ethyl}-amide;
110. 3-[2-(S)-(3-Cyclohexyl-2-(S)-{[5-(3-fluoro-phenyl)-furan-2-carbonyl]-amino}-propionylamino)-propylamino]-benzoic acid methyl ester;
111. 5-(3-Fluoro-phenyl)-furan-2-carboxylic acid {2-cyclohexyl-1-(S)-[1-(S)-methyl-2-(3-trifluoromethoxy-phenylamino)-ethylcarbamoyl]-ethyl}-amide;
112. 5-(3-Fluoro-phenyl)-furan-2-carboxylic acid {1-(S)-[2-(2-chloro-5-fluoro-phenylamino)-1-(S)-methyl-ethylcarbamoyl]-2-cyclohexylethyl}-amide;
113. 5-(3-Fluoro-phenyl)-furan-2-carboxylic acid {1-(S)-[2-(2-chloro-phenylamino)-1-(S)-methyl-ethylcarbamoyl]-2-cyclohexyl-ethyl}-amide;
114. 5-(3-Fluoro-phenyl)-furan-2-carboxylic acid {2-cyclohexyl-1-(S)-[2-(4-methoxy-2,6-dimethyl-phenylamino)-1-(S)-methyl-ethylcarbamoyl]-ethyl}-amide;
115. 5-(3-Fluoro-phenyl)-furan-2-carboxylic acid {2-cyclohexyl-1-(S)-[2-(4-methoxy-3,5-dimethyl-phenylamino)-1-(S)-methyl-ethylcarbamoyl]-ethyl}-amide;
116. 5-(3-Fluoro-phenyl)-furan-2-carboxylic acid {2-cyclohexyl-1-(S)-[2-(2-methanesulfonyl-phenylamino)-1-(S)-methyl-ethylcarbamoyl]-ethyl}-amide;
117. 5-(3-Fluoro-phenyl)-furan-2-carboxylic acid {2-cyclohexyl-1-(S)-[1-(S)-methyl-2-(4-methylsulfanyl-phenylamino)-ethylcarbamoyl]-ethyl}-amide;
118. 5-(3-Fluoro-phenyl)-furan-2-carboxylic acid {2-cyclohexyl-1-(S)-[1-(S)-methyl-2-(4-methylsulfamoyl-phenylamino)-ethylcarbamoyl]-ethyl}-amide;
119. 5-(3-Fluoro-phenyl)-furan-2-carboxylic acid {2-cyclohexyl-1-(S)-[1-(S)-methyl-2-(4-trifluoromethylsulfanyl-phenylamino)-ethylcarbamoyl]-ethyl}-amide;
120. 5-(3-Fluoro-phenyl)-furan-2-carboxylic acid {2-cyclohexyl-1-(S)-[2-(3-dimethylcarbamoyl-phenylamino)-1-(S)-methyl-ethylcarbamoyl]-ethyl}-amide;
121. 5-(3-Fluoro-phenyl)-furan-2-carboxylic acid {1-(S)-[2-(2-carbamoyl-phenylamino)-I -(S)-methyl-ethylcarbamoyl]-2-cyclohexyl-ethyl}-amide;
122. 5-(3-Fluoro-phenyl)-furan-2-carboxylic acid {2-cyclohexyl-1-(S)-[2-(4-dimethylcarbamoyl-phenylamino)-1-(S)-methyl-ethylcarbamoyl]-ethyl}-amide;
123. 3-Cyclohexyl-2-(S)-(3-methoxy-propionylamino)-N-[1-(S)-methyl-2-(4-trifluoromethoxy-phenylamino)-ethyl]-propionamide;
124. 3-Cyclohexyl-2-(S)-(2-methoxy-acetylamino)-N-[1-(S)-methyl-2-(4-trifluoromethoxy-phenylamino)-ethyl]-propionamide;
125. 5-(3-Fluoro-phenyl)-furan-2-carboxylic acid {2-cyclohexyl-1-(S)-[2-(4-hydroxy-phenylamino)-1-(S)-methyl-ethylcarbamoyl]-ethyl}-amide;
126. 5-(3-Fluoro-phenyl)-furan-2-carboxylic acid {2-cyclohexyl-1-(S)-[2-(4-fluoro-phenylamino)-1-(S)-methyl-ethylcarbamoyl]-ethyl}-amide;
127. 5-(3-Fluoro-phenyl)-furan-2-carboxylic acid {3,3t-dimethyl-1-(S)-[1-(S)-methyl-2-(4-trifluoromethoxy-phenylamino)-ethylcarbamoyl]-butyl}-amide;
128. 5-(3-Fluoro-phenyl)-furan-2-carboxylic acid {1-(S)-[2-(4-difluoromethoxy-phenylamino)-1-(S)-methyl-ethylcarbamoyl]-3,3-dimethyl-butyl}-amide;
129. 5-(3-Fluoro-phenyl)-furan-2-carboxylic acid {1-(S)-[2-(4-methanesulfonyl-phenylamino)-1-(S)-methyl-ethylcarbamoyl]-3,3-dimethyl-butyl}-amide;
130. 5-(3-Fluoro-phenyl)-furan-2-carboxylic acid {1-(S)-[2-(3-methanesulfonyl-phenylamino)-1-(S)-methyl-ethylcarbamoyl]-3,3-dimethyl-butyl}-amide;
131. 5-(3-Fluoro-phenyl)-furan-2-carboxylic acid {1-(S)-[2-(3-carbamoyl-phenylamino)-1-(S)-methyl-ethylcarbamoyl]-3,3-dimethyl-butyl}-amide;
132. 5-(3-Fluoro-phenyl)-furan-2-carboxylic acid {1-(S)-[2-(4-methoxy-phenylamino)-1-(S)-methyl-ethylcarbamoyl]-3,3-dimethyl-butyl}-amide;
133. 5-(3-Fluoro-phenyl)-furan-2-carboxylic acid {2-cyclohexyl-1-(S)-[1-(S)-methyl-2-(5-methyl-isoxazol-3-ylamino)-ethylcarbamoyl]-ethyl}-amide;

TABLE I-continued 134. 5-(3-Fluoro-phenyl)-furan-2-carboxylic acid {1-(S)-[2-(3-acetylamino-phenylamino)-1-(S)-methyl-ethylcarbamoyl]-2-cyclohexyl-ethyl}-amide;
135. Tetrahydropyran-4-carboxylic acid {2-cyclohexyl-1-(S)-[1-(S)-methyl-2-(4-trifluoromethoxy-phenylamino)-ethylcarbamoyl]-ethyl}-amide;
136. 5-(3-Fluoro-phenyl)-furan-2-carboxylic acid (2-cyclohexyl-1-(S)-{1-(S)-methyl-2-[4-(morpholine-4-sulfonyl)-phenylamino]-ethylcarbamoyl}-ethyl)-amide;
137. 5-(3-Fluoro-phenyl)-furan-2-carboxylic acid {2-cyclohexyl-1-(S)-[1-(S)-methyl-2-(3-oxo-1,3-dihydro-isobenzofuran-5-ylamino)-ethylcarbamoyl]-ethyl}-amide;
138. 5-(3-Fluoro-phenyl)-furan-2-carboxylic acid {2-cyclohexyl-1-(S)-[1-(S)-methyl-2-(4-sulfamoyl-phenylamino)-ethylcarbamoyl]-ethyl}-amide;
139. Tetrahydropyran-4-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide;
140. Tetrahydrofuran-3-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide;
141. 1-(3-Fluoro-phenyl)-1H-pyrazole-4-carboxylic acid {2-cyclohexyl-1-(S)-[1-(S)-methyl-2-(4-trifluoromethoxy-phenylamino)-ethylcarbamoyl]-ethyl}-amide;
142. 1-(4-Fluoro-phenyl)-1H-pyrazole-4-carboxylic acid {2-cyclohexyl-1-(S)-[1-(S)-methyl-2-(4-trifluoromethoxy-phenylamino)-ethylcarbamoyl]-ethyl}-amide;
143. 5-Pyridin-3-yl-furan-2-carboxylic acid (2-cyclohexyl-1-(S)-[1-(S)-methyl-2-(4-trifluoromethoxy-phenylamino)-ethylcarbamoyl]-ethyl}-amide;
144. 5-(1-Oxy-pyridin-3-yl)-furan-2-carboxylic acid {2-cyclohexyl-1-(S)-[1-(S)-methyl-2-(4-trifluoromethoxy-phenylamino)-ethylcarbamoyl]-ethyl}-amide;
145. 3-(3-Fluoro-phenyl)-isoxazole-5-carboxylic acid {2-cyclohexyl-1-(S)-[1-(S)-methyl-2-(4-trifluoromethoxy-phenylamino)-ethylcarbamoyl]-ethyl}-amide;
146. 3-(4-Fluoro-phenyl)-isoxazole-5-carboxylic acid {2-cyclohexyl-1-(S)-[1-(S)-methyl-2-(4-trifluoromethoxy-phenylamino)-ethylcarbamoyl]-ethyl}-amide;
147. 5-(3-Fluoro-phenyl)-[1,3,4]oxadiazole-2-carboxylic acid {2-cyclohexyl-1-(S)-[1-(S)-methyl-2-(4-trifluoromethoxy-phenylamino)-ethylcarbamoyl]-ethyl}-amide;
148. N-{2-cyclohexyl-1-(S)-[2-(5-fluoro-2,3-dihydro-indol-1-yl)-ethylcarbamoyl]-ethyl}-2-(R)-phenyl-butyramide;
149. N-{1-(S)-[1-(R)-Benzyloxymethyl-2-(5-fluoro-2,3-dihydro-indol-1-yl)-ethylcarbamoyl]-2-cyclohexyl-ethyl}-3-methoxy-benzamide;
150. N-{2-Cyclohexyl-1-(S)-[2-(5-fluoro-2,3-dihydro-indol-1-yl)-1-(R)-hydroxymethyl-ethylcarbamoyl]-ethyl}-3-methoxy-benzamide;
151. N-{2-Cyclohexyl-1-(S)-[2-(5-fluoro-2,3-dihydro-indol-1-yl)-1-(S)-morpholin-4-ylmethyl-ethylcarbamoyl]-ethyl}-3-methoxy-benzamide;
152. 5-(3-Trifluoromethyl-phenyl)-furan-2-carboxylic acid {1-(S)-[1-(R)-benzyloxymethyl-2-(5-fluoro-2,3-dihydro-indol-1-yl)-ethylcarbamoyl]-2-cyclohexyl-ethyl}-amide;
153. 5-(3-Trifluoromethyl-phenyl)-furan-2-carboxylic acid {2-cyclohexyl-1-(S)-[2-(5-fluoro-2,3-dihydro-indol-1-yl)-1-(R)-hydroxymethyl-ethylcarbamoyl]-ethyl}-amide;
154. {1-(S)-[1-(R)-Benzyloxymethyl-2-(5-fluoro-2,3-dihydro-indol-1-yl)-ethylcarbamoyl]-3,3-dimethyl-butyl}-carbamic acid tert-butyl ester;
155. N-{1-(S)-[1-(R)-Benzyloxymethyl-2-(5-fluoro-2,3-dihydro-indol-1-yl)-ethylcarbamoyl]-3,3-dimethyl-butyl}-3-methoxy-benzamide;
156. N-{1-(S)-[2-(5-Fluoro-2,3-dihydro-indol-1-yl)-1-(R)-hydroxymethyl-ethylcarbamoyl]-3,3-dimethyl-butyl}-3-methoxy-benzamide;
157. {1-(S)-[1-(S)-(5-Fluoro-2,3-dihydro-indol-1-ylmethyl)-3-methanesulfonyl-propylcarbamoyl]-3,3-dimethyl-butyl}-carbamic acid tert-butyl ester;
158. 3-(S)-(2-(S)-Benzyloxycarbonylamino-4,4-dimethyl-pentanoylamino)-4-(5-flUoro-2,3-dihydro-indol-1-yl)-butyric acid tert-butyl ester;
159. 3-(S)-(2-(S)-Benzyloxycarbonylamino-4,4-dimethyl-pentanoylamino)-4-(5-flUoro-2,3-dihydro-indol-1-yl)-butyric acid;
160. 4-(5-Fluoro-2,3-dihydro-indol-1-yl)-3-(S)-[2-(S)-(3-methoxy-benzoylamino)-4,4-dimethyl-pentanoylamino]-butyric acid tert-butyl ester;
161. 3-(S)-[3-Cyclohexyl-2-(S)-(3-methoxy-benzoylamino)-propionylamino]-4-(5-fluoro-2,3-dihydro-indol-1-yl)-butyric acid benzyl ester;
162. 3-(S)-[3-Cyclohexyl-2-(S)-(3-methoxy-benzoylamino)-propionylamino]-4-(5-fluoro-2,3-dihydro-indol-1-yl)-butyric acid;
163. 4-(5-Fluoro-2,3-dihydro-indol-1-yl)-3-(S)-[2-(S)-(3-methoxy-benzoylamino)-4,4-dimethyl-pentanoylamino]-butyric acid ethyl ester;
164. {1-(S)-[2-Cyano-1-(S)-(5-fluoro-2,3-dihydro-indol-1-ylmethyl)-ethylcarbamoyl]-3,3-dimethyl-butyl}-carbamic acid tert-butyl ester;
165. N-{1-(S)-[2-Cyano-1-(S)-(5-fluoro-2,3-dihydro-indol-1-ylmethyl)-ethylcarbamoyl]-3,3-dimethyl-butyl}-3-methoxy-benzamide;
166. N-{1-(S)-[2-(5-Fluoro-2,3-dihydro-indol-1-yl)-1-(S)-(1H-tetrazol-5-ylmethyl)-ethylcarbamoyl]-3,3-dimethyl-butyl}-3-methoxy-benzamide;
167. N-{1-(S)-[5-Amino-1-(S)-(5-fluoro-2,3-dihydro-indol-1-ylmethyl)-pentylcarbamoyl]-3-cyclohexyl-propyl}-3-methoxy-benzamide;
168. 3-(S)-(2-(S)-Benzyloxycarbonylamino-3-cyclohexyl-propionylamino)-4-(5-fluoro-2,3-dihydro-indol-1-yl)-butyric acid benzyl ester;
169. 1-(S)-[1-(R)-Benzyloxymethyl-2-(5-fluoro-2,3-dihydro-indol-1-yl)-ethylcarbamoyl]-2-cyclohexyl-ethyl}-carbamic acid benzyl ester;
170. N-{3-Cyclohexyl-1-(S)-[2-(3,5-dimethoxy-benzyloxy)-1-(R)-(5-fluoro-2,3-dihydro-indol-1-ylmethyl)-ethylcarbamoyl]-propyl}-3-methoxy-benzamide;
171. 4-{2-(R)-[4-Cyclohexyl-2-(S)-(3-methoxy-benzoylamino)-butyrylamino]-3-(S-fluoro-2,3-dihydro-indol-1-yl)-propoxymethyl}-benzoic acid methyl ester;
172. (S,S)-N-{3-Cyclohexyl-1-[2-(5-fluoro-2,3-dihydro-indol-1-yl)-1-(4-hydroxy-benzyl)-ethylcarbamoyl]-propyl}-3-methoxy-benzamide;

TABLE I-continued

173. Tetrahydropyran-4-carboxylic acid {2-cyclohexyl-1-(S)-[2-(5-fluoro-3,3-dimethyl-2,3-dihydro-indol-1-yl)-1-(S)-methyl-ethylcarbamoyl]-ethyl}-amide;
174. {2-Cyclohexyl-1-(S)-[2-(5-fluoro-2,3-dihydro-indol-1-yl)-1-(S)-methyl-ethylcarbamoyl]-ethyl}-carbamic acid benzyl ester;
175. 4-Benzyloxy-N-(R,S)-{[2-(4-amidinophenylamino)-1-(S)-methyl-ethylcarbamoyl]-(2,4-dichloro-phenyl)-methyl}-benzamide;
176. {1-(S)-[2-(5-Fluoro-2,3-dihydro-indol-1-yl)-1-(S)-methyl-ethylcarbamoyl]-3,3-dimethyl-butyl}-carbamic acid benzyl ester;
177. Cyclopropanecarboxylic acid {1-(S)-[2-(5-fluoro-2,3-dihydro-indol-1-yl)-1-(5)-methyl-ethylcarbamoyl]-3,3-dimethyl-butyl}-amide;
178. Pyridazine-4-carboxylic acid {1-(5)-[2-(5-fluoro-2,3-dihydro-indol-1-yl)-1-(5)-methyl-ethylcarbamoyl]-3,3-dimethyl-butyl}-amide;
179. 4,4-Dimethyl-2-(S)-(2-1H-tetrazol-5-yl-acetylamino)-pentanoic acid [2-(5-fluoro-2,3-dihydro-indol-1-yl)-1-(S)-methyl-ethyl]-amide;
180. (2-Cyclohexyl-1-(S)-{1-(S)-methyl-2-[3-(1H-tetrazol-5-yl)-phenylamino]-ethylcarbamoyl}-ethyl)-carbamic acid benzyl ester;
181. (S,S)-2-(3-Chloro-benzenesulfonylamino)-3-cyclohexyl-N-[1-methyl-2-(4-trifluoromethoxy-phenylamino)-ethyl]-propionamide;
182. (S,S)-3-Cyclohexyl-N-[1-methyl-2-(4-trifluoromethoxy-phenylamino)-ethyl]-2-(3-trifluoromethoxy-benzenesulfonylamino)-propionamide;
183. (S,S)-3-Cyclohexyl-N-[1-methyl-2-(4-trifluoromethoxy-phenylamino)-ethyl]-2-(pyridine-3-sulfonylamino)-propionamide;
184. (S,S)-{2-Cyclohexyl-1-[1-methyl-2-(4-trifluoromethoxy-phenylamino)-ethylcarbamoyl]-ethyl}-carbamic acid tetrahydro-pyran-4-yl ester;
185. 3-(R)-{2-Cyclohexyl-1-(S)-[1-(S)-methyl-2-(4-trifluoromethoxy-pheflylamino)-ethylcarbamoyl]-ethylcarbamoyloxy}-pyrrolidine-1-carboxylic acid tert-butyl ester;
186. (S,S)-{2-Cyclohexyl-1-[1-methyl-2-(4-trifluoromethoxy-phenylamino)-ethylcarbamoyl]-ethyl}-carbamic acid 1,1-dioxo-hexahydro-1$\lambda^6$-thiopyran-4-yl ester;
187. {2-Cyclohexyl-1-(S)-[1-(S)-methyl-2-(4-trifluoromethoxy-phenylamino)-ethylcarbamoyl]-ethyl}-carbamic acid pyrrolidin-3-(R)-yl ester;
188. {2-Cyclohexyl-1-(S)-[1-(S)-methyl-2-(4-trifluoromethoxy-phenylamino)-ethylcarbamoyl]-ethyl}-carbamic acid tetrahydrofuran-3-(R)-yl ester;
189. {2-Cyclohexyl-1-(S)-[1-(S)-methyl-2-(4-trifluoromethoxy-phenylamino)-ethylcarbamoyl]-ethyl}-carbamic acid tetrahydrofuran-3-(S)-yl ester;
190. (S,S)-{2-Cyclopentyl-1-[1-methyl-2-(4-trifluoromethoxy-phenylamino)-ethylcarbamoyl]-ethyl}-carbamic acid tetrahydropyran-4-yl ester;
191. (S,S)-{2-Cyclopentyl-1-[1-methyl-2-(4-trifluoromethoxy-phenylamino)-ethylcarbamoyl]-ethyl]-carbamic acid tetrahydrofuran-3-(R)-yl ester;
192. (S,S)-{2-Cyclopentyl-1-[1-methyl-2-(4-trifluoromethoxy-phenylamino)-ethylcarbamoyl]-ethyl}-carbamic acid tetrahydrofuran-3-(S)-yl ester;
193. N-((S)-(2-(5-fluoroindolin-1-yl)ethylcarbamoyl)(cyclohexyl) methyl)-3-methylbenzamide;
194. N-((S)-1-(2-(5-fluoroindolin-1-yl)ethylcarbamoyl)-2-cyclopropylethyl)-5-(3-(trifluoromethyl)phenyl)furan-2-carboxamide
195. N-((S)-1-(2-(5-fluoroindolin-1-yl)ethylcarbamoyl)-2-(2-chlorophenyl)ethyl)-3-methylbenzamide;
196. N-((S)-1-(2-(5-fluoroindolin-1-yl)ethylcarbamoyl)-2-(3-chlorophenyl)ethyl)-5-(3-(trifluoromethyl)phenyl)furan-2-carboxamide;
197. N-((S)-1-(2-(5-fluoroindolin-1-yl)ethylcarbamoyl)-2-(3-chlorophenyl)ethyl)-3-methylbenzamide;
198. N-((S)-1-(2-(5-fluoroindolin-1-yl)ethylcarbamoyl)-2-(4-chlorophenyl)ethyl)-S-(3-(trifluoromethyl)phenyl)furan-2-carboxamide;
199. N-((S)-1-(2-(5-fluoroindolin-1-yl)ethylcarbamoyl)-2-(4-chlorophenyl)ethyl)-3-methylbenzamide;
200. N-((S)-1-(2-(5-fluoroindolin-1-yl)ethylcarbamoyl)-2-cyclopentylethyl)-S-(3-(trifluoromethyl)phenyl)furan-2-carboxamlde
201. (S)-N-{2-Cyclopentyl-1-[2-(5-fluoro-2,3-dihydro-indol-1-yl)-ethylcarbamoyl]-ethyl}-3-methyl-benzamide;
202. N-((S)-1-(2-(5-fluoroindolin-1-yl)ethylcarbamoyl)-3,3-dimethylbutyl)-5-(3-(trifluoromethyl)phenyl)furan-2-carboxamide;
203. N-((S)-1-(2-(5-fluoroindolin-1-yl)ethylcarbamoyl)-3,3-dimethylbutyl)-3-methylbenzamide;
204. N-((S)-1-(2-(5-fluoroindolin-1-yl)ethylcarbamoyl)-3-cyclohexylpropyl)-3-methylbenzamide;
205. N-((S)-1-(2-(5-fluoroindolin-1-yl)ethylcarbamoyl)-2-phenylethyl)-3-methylbenzamide;
206. N-((S)-1-(2-(5-fluoroindolin-1-yl)ethylcarbamoyl)-2-phenylethyl)-5-(3-(trifluoromethyl)phenyl)furan-2-carboxamide
207. N-(R,S)-((3-(benzyloxy)-1-(5-fluoroindolin-1-yl)propan-2-(R)-ylcarbamoyl)(2,4-dichlorophenyl)methyl)furan-2-Carboxamide;
208. N-(R,S)-((3-(5-fluoroindolin-1-yl)-1-hydroxypropan-2-(R)-ylcarbamoyl)(2,4-dichlorophenyl)methyl)-3,4-difluorobenzamide;
209. N-(S)-((3-(5-fluoroindolin-1-yl)-1-hydroxypropan-2-(R)-ylcarbamoyl)(2,4-dichlorophenyl)methyl)furan-2-carboxamide
210. (S,S)-3-Cyclohexyl-2-(2,4-dimethyl-thiazole-5-sulfonylamino)-N-[2-(5-fluoro-2,3-dihydro-indol-1-yl)-1-methyl-ethyl]-propionamide;
211. N-(S)-((3-(benzyloxy)-1-(5-fluoroindolin-1-yl)propan-2-(R)-ylcarbamoyl)(2,4-dichlorophenyl)methyl)-3,4-difluorobenzamide;

TABLE I-continued

212. N-(S)-((3-(5-fluoroindolin-1-yl)-1-hydroxypropan-2-(R)-ylcarbamoyl)(2,4-dichlorophenyl)methyl) furan-2-carboxamide;
213. (R,S)-N-((2-(5-fluoroindolin-1-yl)ethylcarbamoyl)(2,4-dichlorophenyl)methyl)3-methylbenzamide;
214. (S,S)-N-((3-(5-fluoroindolin-1-yl)-1-hydroxypropan-2-ylcarbamoyl)(2,4-dichlorophenyl)methyl)-3,4-difluorobenzamide;
215. (S,S)-{2-Cyclohexyl-1-[2-(5-fluoro-3,3-dimethyl-2,3-dihydro-indol-1-yl)-1-methyl-ethylcarbamoyl]-ethyl}-carbamic acid tetrahydro-pyran-4-yl ester;
216. {2-Cyclohexyl-1-(S)-[2-(5-fluoro-3,3-dimethyl-2,3-dihydro-indol-1-yl)-1-(S)-methyl-ethylcarbamoyl]-ethyl}-carbamic acid (R)-tetrahydrofuran-3-yl ester;
217. (S,S)-{2-Cyclohexyl-1-[2-(5-fluoro-3,3-dimethyl-2,3-dihydro-indol-1-yl)-1-methyl-ethylcarbamoyl]-ethyl}-carbamic acid (S)-tetrahydro-furan-3-yl ester;
218. (S,S)-4-(5-Fluoro-2,3-dihydro-indol-1-yl)-3-[2-(3-methoxy-benzoylamino)-4,4-dimethyl-pentanoylamino]-butyric acid;
219. (S)-3-Cyclohexyl-N-[2-(5-fluoro-2,3-dihydro-indol-1-yl)-ethyl]-2-[3-(5-phenyl-thiophen-2-yl)-ureido]-propionamide;
220. (S)-{2-Cyclohexyl-1-[2-(5-fluoro-2,3-dihydro-indol-1-yl)-ethylcarbamoyl]-ethyl}-carbamic acid benzyl ester
221. (S)-3-Cyclohexyl-2-[3-(3,5-dimethyl-isoxazol-4-yl)-ureido]-N-[2-(5-fluoro-2,3-dihydro-indol-1-yl)-ethyl]-propionamide;
222. (S)-3-Cyclohexyl-N-[2-(5-fluoro-2,3-dihydro-indol-1-yl)-ethyl]-2-(5-methyl-1-phenyl-1H-pyrazole-4-sulfonylamino)-propionamide;
223. (S)-3-Cyclohexyl-N-[2-(5-fluoro-2,3-dihydro-indol-1-yl)-ethyl]-2-(5-isoxazol-3-yl-thiophene-2-sulfonylamino)-propionamide;
224. (S)-2-(4-Bromo-3-chloro-thiophene-2-sulfonylamino)-3-cyclohexyl-N-[2-(5-fluoro-2,3-dihydro-indol-1-yl)-ethyl]-propionamide;
225. (S)-2-(3-Biphenyl-4-yl-ureido)-3-cyclohexyl-N-[2-(5-fluoro-2,3-dihydro-indol-1-yl)-ethyl]-propionamide;
226. (S)-3-Cyclohexyl-N-[2-(5-fluoro-2,3-dihydro-indol-1-yl)-ethyl]-2-(4-phenoxy-benzenesulfonylamino)-propionamide;
227. (S)-2-(5-Chloro-thiophene-2-sulfonylamino)-3-cyclohexyl-N-[2-(5-fluoro-2,3-dihydro-indol-1-yl)-ethyl]-propionamide;
228. (S)-3-Cyclohexyl-N-[2-(5-fluoro-2,3-dihydro-indol-1-yl)-ethyl]-2-(naphthalene-1-sulfonylamino)-propionamide;
229. (S)-3-Cyclohexyl-N-[2-(5-fluoro-2,3-dihydro-indol-1-yl)-ethyl]-2-(4-trifluoromethyl-benzenesulfonylamino)-Propionamide
230. (S)-3-Cyclohexyl-N-[2-(5-fluoro-2,3-dihydro-indol-1-yl)-ethyl]-2-(4-trifluoromethoxy-benzenesulfonylamino)-propionamide;
231. (S)-3-Cyclohexyl-N-[2-(5-fluoro-2,3-dihydro-indol-1-yl)-ethyl]-2-[5-(2-methyl-5-trifluoromethyl-2H-pyrazol-3-yl)-thiophene-2-sulfonylamino]-propionamide;
232. (S)-3-Cyclohexyl-N-[2-(5-fluoro-2,3-dihydro-indol-1-yl)-ethyl]-2-(3-methyl-3H-imidazole-4-sulfonylamino)-propionamide;
233. (S)-3-Cyclohexyl-N-[2-(5-fluoro-2,3-dihydro-indol-1-yl)-ethyl]-2-[3-(5-methyl-[1,3,4]oxadiazol-2-yl)-benzenesulfonylamino]-propionamide;
234. (S)-2-(Benzo[b]thiophene-2-sulfonylamino)-3-cyclohexyl-N-[2-(5-fluoro-2,3-dihydro-indol-1-yl)-ethyl]-propionamide;
235. (S)-3-Cyclohexyl-N-[2-(5-fluoro-2,3-dihydro-indol-1-yl)-ethyl]-2-(thiophene-2-sulfonylamino)-propionamide;
236. (S)-3-Cyclohexyl-N-[2-(5-fluoro-2,3-dihydro-indol-1-yl)-ethyl]-2-[4-(4-fluoro-phenoxy)-benzenesulfonylamino]-propionamide;
237. (S)-3-Cyclohexyl-N-[2-(5-fluoro-2,3-dihydro-indol-1-yl)-ethyl]-2-[5-(2-methyl-thiazol-4-yl)-thiophene-2-sulfonylamino]-propionamide;
238. (S)-3-Cyclohexyl-N-[2-(5-fluoro-2,3-dihydro-indol-1-yl)-ethyl]-2-(4'-methoxy-biphenyl-4-sulfonylamino)-propionamide
239. (S)-3-Cyclohexyl-N-[2-(5-fluoro-2,3-dihydro-indol-1-yl)-ethyl]-2-(4-methoxy-benzenesulfonylamino)-propionamide;
240. (S)-3-Cyclohexyl-2-(4-difluoromethoxy-benzenesulfonylamino)-N-[2-(5-fluoro-2,3-dihydro-indol-1-yl)-ethyl]-propionamide;
241. (S)-2-(5-Chloro-1,3-dimethyl-1H-pyrazole-4-sulfonylamino)-3-cyclohexyl-N-[2-(5-fluoro-2,3-dihydro-indol-1-yl)-ethyl]-propionamide;
242. (S)-3-Cyclohexyl-N-[2-(5-fluoro-2,3-dihydro-indol-1-yl)-ethyl]-2-phenylmethanesulfonylamino-propionamide;
243. (S)-3-Cyclohexyl-N-[2-(5-fluoro-2,3-dihydro-indol-1-yl)-ethyl]-2-(toluene-3-sulfonylamino)-propionamide;
244. (S)-3-Cyclohexyl-N-[2-(5-fluoro-2,3-dihydro-indol-1-yl)-ethyl]-2-[4-(4-methoxy-phenoxy)-benzenesulfonylamino]-propionamide;
245. (S)-3-Cyclohexyl-N-[2-(5-fluoro-2,3-dihydro-indol-1-yl)-ethyl]-2-(3-methoxy-benzenesulfonylamino)-propionamide;
246. (S)-3-Cyclohexyl-N-[2-(5-fluoro-2,3-dihydro-indol-1-yl)-ethyl]-2-(4-oxazol-5-yl-benzenesulfonylamino)-propionamide;
247. 5-(3-Fluoro-phenyl)-furan-2-carboxylic acid {2-cyclohexyl-1-(S)-[1-(S)-methyl-2-(3-methyl-isoxazol-5-ylamino)-ethylcarbamoyl]-ethyl}-amide;
248. (S)-3-Cyclohexyl-N-[2-(5-fluoro-2,3-dihydro-indol-1-yl)-ethyl]-2-(thiophene-3-sulfonylamino)-propionamide;
249. (S)-3-Cyclohexyl-N-[2-(5-fluoro-2,3-dihydro-indol-1-yl)-ethyl]-2-methanesulfonylamino-propionamide;
250. (S,S)-3-Cyclohexyl-N-[2-(5-fluoro-2,3-dihydro-indol-1-yl)-1-methyl-ethyl]-2-(5-oxazol-5-yl-thiophene-3-sulfonylamino)-propionamide;

TABLE I-continued 251. (S,S)-3-Cyclohexyl-N-[2-(5-fluoro-2,3-dihydro-indol-1-yl)-1-methyl-ethyl]-2-(toluene-3-sulfonylamino)-propionamide;
252. (S,S)-3-[4,4-Dimethyl-2-(toluene-3-sulfonylamino)-pentanoylamino]-4-(5-fluoro-2,3-dihydro-indol-1-yl)-butyric acid tert-butyl ester;
253. (S,S)-3-Cyclohexyl-N-[2-(5-fluoro-2,3-dihydro-indol-1-yl)-1-methyl-ethyl]-2-(2-methyl-4-trifluoromethyl-furan-3-sulfonylamino)-propionamide
254. (S,S)-3-Cyclohexyl-N-[2-(5-fluoro-2,3-dihydro-indol-1-yl)-1-methyl-ethyl]-2-(3-trifluoromethoxy-benzenesulfonylamino)-propionamide.
255. (S)-3-Cyclohexyl-N-[2-(5-fluoro-2,3-dihydro-indol-1-yl)-ethyl]-2-(1-methyl-iH-imidazole-4-sulfonylamino)-propionamide;
256. (S)-2-(5-Benzenesulfonyl-thiophene-2-sulfonylamrno)-3-cyclohexy[N-2-(5-fluoro-2,3-dihydro-indol-1-yl)-ethyl]-propionamide;
257. (S)-2-(2-Acetylamino-4-methyl-thiazole-5-sulfonylamino)-3-cyclohexyl-N-[2-(5-fluoro-2,3-dihydro-indol-1-yl)-ethyl]-propionamide;
258. (S)-3-Cyclohexyl-2-(4,5-dichloro-thiophene-2-sulfonylamino)-N-[2-(5-fluoro-2,3-dihydro-indol-1-yl)-ethyl]-propionamide;
259. (S,S)-2-(3-Chloro-benzenesulfonylamino)-3-cyclohexyl-N-[2-(5-fluoro-2,3-dihydro-indol-1-yl)-1-methyl-ethyl]-propionamide;
260. (S,S)-N-{3-Cyclohexyl-1-[1-(5-fluoro-2,3-dihydro-indol-1-ylmethyl)-3-hydroxy-propylcarbamoyl]-propyl}-3-methoxy-benzamide;
261. (S,S)-3-(2-tert-Butoxycarbonylamino-3-cyclohexyl-propionylamino)-4-(5-fluoro-2,3-dihydro-indol-1-yl)-butyric acid benzyl ester;
262. (S,S)-3-[4,4-Dimethyl-2-(toluene-3-sulfonylamino)-pentanoylamino]-4-(5-fluoro-2,3-dihydro-indol-1-yl)-butyric acid;
263. (S,S)-3-Cyclohexyl-2-(3,5-dimethyl-isoxazole-4-sulfonylamino)-N-[2-(5-fluoro-2,3-dihydro-indol-1-yl)-1-methyl-ethyl]-propionamide;
264. (S,S)-2-Benzenesulfonylamino-3-cyclohexyl-N-[2-(5-fluoro-2,3-dihydro-indol-1-yl)-1-methyl-ethyl]-propionamide;
265. (S,S)-4,4-Dimethyl-2-(toluene-3-sulfonylamino)-pentanoic acid [2-(5-fluoro-2,3-dihydro-indol-1-yl)-1-methyl-ethyl]-amide;
266. 5-(3-Fluoro-phenyl)-furan-2-carboxylic acid {1-(S)-[2-(4-benzyloxy-phenylamino)-1-(S)-methyl-ethylcarbamoyl]-2-cyclohexyl-ethyl}-amide;
267. 5-(3-Fluoro-phenyl)-furan-2-carboxylic acid {2-cyclohexyl-1-(S)-[1-(S)-methyl-2-(3-methyl-isothiazol-5-ylamino)-ethylcarbamoyl]-ethyl}-amide;
268. Tetrahydrofuran-2-(R)-carboxylic acid {3,3-dimethyl-1-(S)-[1-(S)-methyl-2-(4-trifluoromethoxy-phenylamino)-ethylcarbamoyl]-butyl}-amide;
269. Tetrahydropyran-4-carboxylic acid {3,3-dimethyl-1-(S)-[1-(S)-methyl-2-(4-trifluoromethoxy-phenylamino)-ethylcarbamoyl]-butyl}-amide;
270. Tetrahydro-pyran-4-carboxylic acid {1-(S)-[2-(5-fluoro-3,3-dimethyl-2,3-dihydro-indol-1-yl)-1-(S)-methyl-ethylcarbamoyl]-3,3-dimethyl-butyl}-amide;
271. Tetrahydro-furan-2-(R)-carboxylic acid {1-(S)-[2-(5-fluoro-3,3-dimethyl-2,3-dihydro-indol-1-yl)-1-(S)-methyl-ethylcarbamoyl]-3,3-dimethyl-butyl}-amide;
272. Tetrahydrofuran-3-(R,S)-carboxylic acid {2-cyclohexyl-1-(S)-[1-(S)-methyl-2-(4-trifluoromethoxy-phenylamino)-ethylcarbamoyl]-ethyl}-amide;
273. Tetrahydrofuran-2-(R)-carboxylic acid {2-cyclohexyl-1-(S)-[2-(5-fluoro-3,3-dimethyl-2,3-dihydro-indol-1-yl)-1-(S)-methyl-ethylcarbamoyl]-ethyl}-amide;
274. Tetrahydrofuran-2-(R)-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide.

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$-$C_4$) alkane carboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example, glycolic, lactic, malic, tartaric or citric acid, such as amino acids, for example, aspartic or glutamic acid, or with organic sulfonic acids, such as ($C_1$-$C_4$)-alkylsuflonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W, X and combinations thereof.

Compounds of the present invention useful for treating cathepsin S dependent conditions, preferably have cathepsin S inhibition constants less than 10 µM. More preferably, compounds of the present invention useful for treating cathepsin S dependent conditions have cathepsin S inhibition constants of less than 1.0 µM. Most preferably, compounds of the present invention useful for treating cathepsin S dependent conditions have cathepsin S inhibition constants of less than 0.1 µM.

In a preferred aspect, compounds of the present invention that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular chronic neuropathic pain (see, WO 03/020287), Alzheimer's disease and certain autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In a preferred aspect, the pharmaceutical composition of the present invention provides a compound according to Formula I.

In one aspect of the present invention, compositions of the present invention that comprise compounds of the present invention and pharmaceutically acceptable excipients, selectively inhibit cathepsin S in the presence of other cathepsin isozymes (e.g. cathepsin K).

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in vitro and in vivo pharmacological tests generally known in the art, and as illustrated herein.

The above cited properties are demonstrable in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. The dosage in vitro may range between about $10^{-3}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et al., *J. Rheumatology* 1993, 20, 1176). The efficacy of the compounds of the present invention for the treatment of osteoarthritis can be determined using models such as, or similar to, the rabbit partial lateral meniscectomy model, as described previously (Colombo et al., *Arth. Rheum.* 1993, 26, 875-886). The efficacy of the compounds in the model can be quantified using histological scoring methods, as described previously (O'Byrne et al., *Inflamm. Res.* 1995, 44, S 177-S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I.

Methods of the present invention useful for treating cathepsin S dependent conditions, preferably use compounds that have cathepsin S inhibition constants less than 10 µM. More preferably, methods of the present invention useful for treating cathepsin S dependent conditions use compounds that have cathepsin S inhibition constants of less than 1.0 µM. Most preferably, methods of the present invention useful for treating cathepsin S dependent conditions use compounds that have cathepsin S inhibition constants of less than 0.1 µM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W, X and combinations thereof.

In a preferred aspect, methods of the present invention use compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

VI. EXAMPLES

A. Compounds

General Procedure. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard.

Preparation 1

Synthesis of 2,2-dimethyl-5-fluoroindoline

Step A

A solution of N-Boc-4-fluoroaniline (9.02 g, 42.7 mmol) in THF (112 mL) was cooled to −60° C. using a cryocool instrument. The solution was treated with 1.7 M t-BuLi in pentane (63 mL, 106.7 mmol) dropwise. After the first equivalent of base was consumed, a yellow solution formed. The reaction was allowed to warm to −20° C. and was stirred at that temperature for 2.5 hours. The reaction was then treated with a solution of methallyl bromide (5.67 g, 42.7 mmol) in THF (35 mL) dropwise and stirred for an additional 1.5 hours at −20° C. The reaction was then quenched by addition of water. After coming to room temperature, the reaction was treated with ethyl acetate and extracted with water and brine, dried over MgSO$_4$ and filtered. The solvent was then removed and the residue was purified on silica gel using a gradient of 0-25% ethyl acetate in hexane to afford 11.3 g (80% yield) of [4-Fluoro-2-(2-methyl-allyl)-phenyl]-carbamic acid tert-butyl ester as a white solid; $^1$H NMR (CDCl$_3$, 400 MHz) δ 1.50 (s, 9H), 1.72 (s, 3H), 3.28 (s, 2H), 4.71 (s, 1H), 4.92 (s, 1H), 6.32-6.50 (m, 1H), 6.86 (dd, 1H, J$_1$=3.0, J$_2$=9.1), 6.93 (ddd, 1H, J$_1$=3.0, J$_2$=8.5, J$_3$=11.5), 7.65-7.82 (m, 1H); HPLC-MS calcd. for C$_{15}$H$_{20}$FNO$_2$ (M+H$^+$-tBu) 210.1, found 210.3.

Step B

A sample of [4-Fluoro-2-(2-methyl-allyl)-phenyl]-carbamic acid tert-butyl ester (1.10 g, 4.14 mmol) was treated with anisole (5 mL), dichloromethane (5 mL) and trifluoroacetic acid (5 mL) and stirred for 4 hours. The solvent was removed and the reaction was transferred to a microwave reaction vial using methanesulfonic acid (3 mL). The reaction was heated to 170° C. for 10 minutes. The reaction was cooled to room temperature and quenched into excess stirring 1 M NaOH. The aqueous phase was extracted twice with ethyl acetate and the combined organics were dried over MgSO$_4$ and filtered. The resulting oil was purified on silica gel using a gradient of 0-70% t-butyl ethyl ether and hexane to afford 450 mg (66% yield) of 2,2-dimethyl-5-fluoroindoline; $^1$H NMR (CDCl$_3$, 400 MHz) δ 1.08 (s, 6H), 2.58 (s, 2H), 6.24 (dd, 1H, J$_1$=4.4, J$_2$=8.4), 6.43-6.48 (m, 1H), 6.53-6.56 (m, 1H); HPLC-MS calcd. for C$_{10}$H$_{12}$FN (M+H$^+$) 166.1, found 166.4.

Preparation 2

Synthesis of 3,3-dimethyl-5-fluoroindoline

According to the procedure described in S. Coulton et al. WO9925709 with the following modifications. N-(4-Fluorophenyl)-N-(2-methyl-allyl)-acetamide (5 grams, 24.12 mmol) was added to a microwave tube with aluminum trichloride (7 grams, 52.4 mmol). The tube was capped and heated to 150° C. for 20 minutes under microwave. The slurry was worked up with water and ethyl acetate, the organic layer was extracted with 3 washes of saturated sodium bicarbonate solution and the organic layer was dried over magnesium sulfate. The solution was then filtered and rotary evaporated to yield pure 1-(5-Fluoro-3,3-dimethyl-2,3-dihydro-indol-1-yl)-ethanone in quantitative yield. This was converted to the free indoline by suspending the entire 5 grams of product in 20 mL of 6 M HCl and heating in a microwave to 200° C. for 10 minutes. The resulting 5-Fluoro-3,3-dimethyl-2,3-dihydro-1H-indole crystallized on cooling as the hydrochloride salt in quantitative yield. This material was identical to the previously reported compound.

Preparation 3

Synthesis of (S)-[1-Cyclopropyl-2-(5-fluoro-3,3-dimethyl-2,3-dihydro-indol-1-yl)-ethyl]-carbamic acid benzyl ester Step A (S)-cyclopropyl glycine was prepared according to a modified procedure from that reported in D. J. Bayston et al. U.S. Pat. No. 6,191,306. A sample of (R)-phenethyl-(S)-cyclopropyl glycine (16.8 g, 76.7 mmol) was treated with THF (200 mL), water (100 mL) and 10% Pd/C (4.76 g). To the stirring mixture was added formic acid (17 mL) and the reaction was stirred overnight. The catalyst was then removed by filtration through a pad of celite and the solvent was removed by rotary evaporation. The material was co-evaporated with methanol several times and dried under vacuum to afford 4.75 g (54% yield) of the desired material as a solid which was used without further purification.

The material from the previous step (4.75 g, 41 mmol) was dissolved in 130 mL of 1 N NaOH and treated with benzyl chloroformate (5.92 g, 49.5 mmol) with vigorous stirring. The reaction was stirred overnight and then extracted with dichloromethane twice. The organics were discarded and the aqueous phase was acidified with conc. HCl and extracted with dichloromethane three times. The combined organics were dried over MgSO$_4$ and the solvent was removed to afford 7.38 g (72% yield) of the (S)-benzyloxycarbonylamino-cyclopropyl-acetic acid as a white solid.

Step B

A solution of (S)-benzyloxycarbonylamino-cyclopropyl-acetic acid (3.2 g, 12.8 mmol) in THF (20 mL) was cooled in an ice/water bath and treated with a 1 M solution of BH$_3$ in THF (16.7 mL, 16.7 mmol). The reaction was stirred for 4 hours and then treated with 1 M HCl until the bubbling ceased. The reaction was stirred overnight and the organic solvent was removed by rotary evaporation. The residue was treated with ethyl acetate and transferred to a separatory funnel. The aqueous phase was discarded and the organics were washed twice with 1 M NaOH, dried over MgSO$_4$ and the solvent was removed. The residue was purified on silica gel using a gradient of 0-100% ethyl acetate in hexane to afford 1.5 g (50% yield) of (S)-(1-Cyclopropyl-2-hydroxyethyl)-carbamic acid benzyl ester as a white solid; $^1$H NMR (CDCl$_3$, 400 MHz) δ 0.26-0.37 (m, 1H), 0.34-0.44 (m, 1H), 0.47-0.61 (m, 2H), 0.83-0.94 (m, 1H), 2.95-3.04 (m, 1H), 3.70 (dd, 1H, J$_1$=5.8, J$_2$=11.1), 3.79-3.88 (m, 1H), 5.00-5.12 (m, 1H), 5.10 (s, 2H), 7.29-7.31 (m, 5H); HPLC-MS calcd. for C$_{13}$H$_{17}$NO$_3$ (M+H$^+$) 236.1, found 236.3.

Step C (S)-[1-Cyclopropyl-2-(5-fluoro-3,3-dimethyl-2,3-dihydro-indol-1-yl)-ethyl]-carbamic acid benzyl ester was prepared in 67% yield an analogous manner to example 22, step A except that the alcohol from the previous step and 1 equivalent of 3,3-dimethyl-5-fluoroindoline (WO 9925709) were used as coupling partners; HPLC-MS calcd. for C$_{23}$H$_{27}$FN$_2$O$_2$ (M+H$^+$) 383.2, found 383.4.

Preparation 4

Synthesis of (S)-[1-Cyclopropyl-2-(5-fluoro-3,3-spirocycloprpyl-indol-1-yl)-ethyl]-carbamic acid benzyl ester Step A A solution of 5-fluoroisatin (5 g, 30.2 mmol) in DMF (60 mL) was cooled in an ice/water bath and treated with sodium hydride (1.44 g, 60.6 mmol) portionwise. The reaction was stirred for 15 minutes after the addition of the last portion and then treated with p-methoxybenzyl chloride (5.32 g, 45.3 mmol) and allowed to stir for 1 hour. The reaction was then quenched by slow addition of excess methanol. After bubbling had stopped, the reaction was poured into water (100 mL) and extracted twice with ethyl acetate. The organics were combined, dried over MgSO$_4$ and the solvent was removed. The residue was purified by silica gel chromatography using a gradient of 0-100% ethyl acetate in hexane to afford 7.1 g (82%) of 5-Fluoro-1-(4-methoxy-benzyl)-1H-indole-2,3-dione; $^1$H NMR (CDCl$_3$, 400 MHz) δ 3.79 (s, 3H), 4.86 (s, 2H), 6.75 (dd, 1H, J$_1$=3.6, J$_2$=8.6), 6.84-6.90 (m, 2H), 7.19 (ddd, 1H, J$_1$=J$_2$=8.6, J$_3$=3.6), 7.22-7.27 (m, 1H), 7.26-7.31 (m, 2H); HPLC-MS calcd. for C$_{16}$H$_{12}$FNO$_3$ (M+H$^+$) 286.1, found 286.3.

Step B

A solution of 5-fluoro-1-(4-methoxy-benzyl)-1H-indole-2,3-dione (7.1 g, 24.9 mmol) in hydrazine hydrate (35 mL) and ethanol (15 mL) was refluxed overnight, diluted with water and extracted twice with ethyl acetate. The combined organics were dried over Na$_2$SO$_4$, filtered and concentrated. The residue was purified by silica gel chromatography using a gradient of 0-100% ethyl acetate in hexane to afford 6.1 g (90%) of 5-fluoro-1-(4-methoxy-benzyl)-1,3-dihydro-indol-2-one; $^1$H NMR (CDCl$_3$, 400 MHz) δ 3.59 (s, 2H), 3.77 (s, 3H), 4.83 (s, 2H), 6.63 (dd, 1H, J$_1$=4.2, J$_2$=8.6), 6.82-6.91 (m, 3H), 6.96-7.01 (m, 1H), 7.19-7.23 (m, 1H), 7.27-7.31 (m, 1H); HPLC-MS calcd. for C$_{16}$H$_{14}$FNO$_2$ (M+H$^+$) 272.1, found 272.3.

Step C

A solution of 5-fluoro-1-(4-methoxy-benzyl)-1,3-dihydro-indol-2-one (6.12 g, 22.6 mmol) in DMF (65 mL) was cooled in an ice/water bath and treated with dibromoethane (6.35 g, 33.8 mmol) followed by sodium hydride (1.09 g, 45 mmol) portionwise. After stirring at 0° C. for 1 hour, the reaction was cooled to −78° C. and treated with excess methanol. After bubbling had stopped, the reaction was poured into water (100 mL) and extracted twice with ethyl acetate. The organics were combined, dried over Na$_2$SO$_4$ and the solvent was removed. The residue was purified by silica gel chromatography using a gradient of 0-100% ethyl acetate in hexane to afford 4.1 g (61%) of 5-fluoro-1-(4-methoxy-benzyl)-siprocyclopropyloxindole; $^1$H NMR (CDCl$_3$, 400 MHz) δ 1.54 (dd, 2H, J$_1$=4.0, J$_2$=7.8), 1.83 (dd, 2H, J$_1$=4.3, J$_2$=8.1), 3.77 (s, 3H), 4.91 (s, 2H), 6.57 (dd, 1H, J$_1$=2.5, J$_2$=8.0), 6.69 (dd, 1H, J$_1$=4.2, J$_2$=8.5), 6.81 (dd, 1H, J$_1$=2.5, J$_2$=9.3), 6.83-6.87 (m, 2H), 7.22-7.25 (m, 2H); HPLC-MS calcd. for C$_{18}$H$_{16}$FNO$_2$ (M+H$^+$) 298.1, found 298.3.

Step D

A solution of 5-fluoro-1-(4-methoxy-benzyl)-siprocyclopropyloxindole (3.38 g, 11.4 mmol) in TFA (20 mL) was stirred at 60° C. overnight. The solvent was then removed and the reaction was diluted with ethyl acetate and washed with saturated aqueous NaHCO$_3$ until the washings were neutral. The organic phase was then washe with brine, dried over Na$_2$SO$_4$ and the solvent was removed. The residue was purified by silica gel chromatography using a gradient of 0-100% ethyl acetate in hexane to afford 1.94 g (96%) of 5-fluoro-siprocyclopropyloxindole; $^1$H NMR (MeOD, 400 MHz) δ 1.76-1.86 (m, 4H), 6.91-6.94 (m, 1H), 7.07-7.11 (m, 2H); HPLC-MS calcd. for C$_{10}$H$_8$FNO (M+H$^+$) 178.2, found 178.3.

Step E

A sample of 5-fluoro-siprocyclopropyloxindole (172 mg, 97 µmol) was cooled in an ice/water bath and treated with a 1.0 M solution of LAH (1.94 ml, 1.9 mmol). The reaction was stirred at room temperature for 15 minutes and then at 50° C. for 3 hours and finally was' cooled back down with an ice/water bath. The reaction was treated with 1 M NaOH (1.9 mL) followed by water (1.9 mL). The reaction was filtered over celite and dried over MgSO$_4$. After filtration, the solvent was removed and the crude material of 5-fluoro-siprocyclopropylindoline was used as the indoline partner to prepare [1-Cyclopropyl-2-(5-fluoro-3,3-spirocycloprpyl-indol-1-yl)-ethyl]-carbamic acid benzyl ester in 62% yield in an analogous manner to example 22, step A; HPLC-MS calcd. for C$_{23}$H$_{25}$FN$_2$O$_2$ (M+H$^+$) 381.2, found 381.4.

In addition, synthesis of other 3,3-spiro-cycloalkylindolines are also described in (1) Jackson, A. H. et al. Tetrahedron (1968), 24(1), 403-13; (2) Jansen, A. B. A. et al. Tetrahedron (1965), 21(6), 1327-31; (3) Bermudez, J. et al. J. Med. Chem. (1990), 33(7), 1929-32; (4) Nishio, T. et al. Helv. Chim. Acta (1990), 73(6), 1719-23; (5) Nishio, T. et al. J. Chem. Soc., Perkin Trans 1 (1991), (1), 141-3; (6) Kucerovy, A. et al. Synth. Commun. (1992), 22(5), 729-33; (7) Kato, M. et al. Chem. Pharm. Bull. (1995), 43(8), 1351-7.

Preparation 5

Synthesis of 4-nitrophenyl tetrahydropyran-4-yl carbonate

To a solution of tetrahydro-4H-pyran-4-ol (408 mg, 102 mmol) and pyridine (632 mg, 19.1 mmol) in 15 mL of CH$_2$Cl$_2$ was added p-nitrophenyl chloroformate (968 mg, 102 mmol). The mixture was stirred at rt for 30 h. Water was added and the organic layer was separated, and washed with 5% aq. citric acid. The organic layer was treated with an aq. solution of ammonia (NH$_4$OH/H$_2$O: ¼ v/v) for 15 min. The organic layer was separated, washed with aq. sodium bicarbonate and brine. After the solvent was removed, the desire product was isolated as a solid. $^1$H NMR (CD$_3$Cl, 400 MHz) δ 1.80 (m, 2H), 2.00 (m, 2H), 3.52 (m, 2H), 3.92 (m, 2H), 4.88 (m, 1H), 7.32 (d, J=7 Hz, 2H), 8.21 (d, J=7 Hz, 2H).

Preparation 6

Synthesis of (S)-2-(4-Methoxy-phenylamino)-1-methyl ethyl amine

Step A

Preparation of (S)-2-(tert-Butoxycarbonylamino)-propionaldehyde.

(S)-(−)-2-(tert-Butoxycarbonylamino)-1-propanol (523 mg, 2.98 mmol, 1.0 equiv.) was dissolved in 45 mL methylene chloride in a 100 mL r.b. flask with a magnetic stir bar. To this clear homogeneous solution, Dess-Martin periodinane (1.523 g, 3.591 mmol, 1.2 equiv.) was added in one part and the cloudy white reaction mixture was allowed to stir at room temperature for 2 h. Thin-layer chromatography monitored the reaction to completion. The reaction mixture was diluted with 100 mL ethyl acetate. Sodium bisulfite solution (2 M, 20 mL) was added to the reaction mixture and the organic layer was separated. The aqueous layer was washed with 3×30 mL EtOAc. The combined organic layers were washed with 50 mL 1 M NaOH, followed by saturated NaCl (30 mL) and dried over MgSO$_4$. Filtration and rotary evaporation produced the desired product as a yellow oil (475 mg, 92% yield, R$_f$=0.63, 1:1 hexanes/ethyl acetate).

Step B

Preparation of [2-(4-methoxy-phenylamino)-(1S)-methyl-ethyl]-carbamic acid tert-butyl ester (S)-2-(tert-Butoxycarbonylamino)-propionaldehyde (473 mg, 2.74 mmol) and p-anisidine (1.031 g, 8.371 mmol, 3.0 equiv.) was dissolved in 45 mL of MeOH at 0° C. in a 100 mL r.b. flask with a magnetic stir bar. Optionally, acetic acid (469 µL, 8.21 mmol, 3.0 equiv.) can be added via syringe to assist in the reaction. To the stirring dark colored solution was added sodium cyanoborohydride (326 mg, 5.82 mmol, 1.89 equiv.). Gas evolution and disappearance of color were observed. The reaction was allowed to slowly warm to room temperature with stirring over 30 minutes and the reaction was monitored by LC/MS. At the completion of the reaction, the mixture was quenched with 1 M NaOH, and extracted 3×50 mL ethyl acetate. The resulting organics were washed with 50 mL saturated NaHCO$_3$, 40 mL saturated NaCl, and dried over MgSO$_4$. Evaporation of ethyl acetate provided 728 mg of a brown oil. Purification by automated ISCO chromatography provided a clear oil of [2-(4-methoxy-phenylamino)-(1S)-methyl-ethyl]-carbamic acid tert-butyl ester (583 mg, 2.079 mmol, 76% yield). HPLC-MS calcd. for C$_{15}$H$_{24}$N$_2$O$_3$ (M+H$^+$) 281.2, found 281.5. $^1$H NMR (CDCl$_3$, 400 MHz) δ 1.21 (d, 6H, J=6.6 Hz), 1.47 (s, 9H), 3.05 (dd, 1H, J=12.2, 7.3 Hz), 3.13 (dd, 1H, J=12.2, 4.6 Hz), 3.76 (s, 3H), 3.93 (broad s, 1H), 4.62 (broad s, 1H), 6.60 (d, 2H, J=6.8 Hz), 6.80 (2H, d, J=6.8 Hz).

Step C

[2-(4-Methoxy-phenylamino)-(1S)-methyl-ethyl]-carbamic acid tert-butyl ester (383 mg, 1.37 mmol) was added to 10 mL of a trifluoroacetic acid solution (10 v/v % in methylene chloride) at room temperature in a 25 mL r.b. flask with a magnetic stirbar. The reaction turns dark purple/black in color after 5 minutes. The reaction is allowed to stir at room temperature until the reaction is judged complete by HPLC/MS. The solvent is removed by evaporation and to provide 2-(4-Methoxy-phenylamino)-(1S)-methyl-ethyl-ammonium trifluoroacetate salt as a brown oil (394 mg, 1.34 mmol, 98% yield) and used directly in the next reaction. HPLC-MS calcd. for C$_{10}$H$_{16}$N$_2$O (M+H$^+$) 181.1, found 181.5.

Preparation 7

(R)-3-Benzyloxy-N$^1$-(4-methoxy-phenyl)-propane-1,2-diamine

Step A

N-Boc-OBn-Serine (750 mg, 2.54 mmol), p-anisidine (344 mg, 2.79 mmol) and HOBt (377 mg, 2.79 mmol) were charged to a 50 mL roundbottom flask and treated with CH$_2$Cl$_2$ (6 mL). The reaction was then treated with EDCI (535 mg, 2.79 mmol) and allowed to stir for 2 hours. The reaction was then diluted with ethyl acetate and extracted twice with water, twice with 1 M HCl and twice with 1 M NaOH. The organics were then dried over MgSO$_4$ and the solvent was removed to afford 450 mg (44%) of a white solid: $^1$H NMR (CDCl$_3$, 400 MHz) δ 1.49 (s, 9H), 3.63-3.72 (m, 1H), 3.81 (s, 3H), 4.00-4.08 (m, 1H), 4.47-4.50 (m, 1H), 4.55-4.70 (m, 2H), 5.45-5.60 (m, 1H), 6.87 (d, 2H, J=8.8), 7.30-7.41 (m, 7H), 8.20-8.33 (m, 1H); HPLC-MS calcd. for C$_{22}$H$_{28}$N$_2$O$_5$ (M+H$^+$) 401.2, found 401.4.

Step B

The product from Step A (400 mg, 1.00 mmol) was added to an ice cold solution of borane (1 M) in THF. The cooling bath was removed and the reaction was allowed to stir for 24 h at which point the excess reagent was quenched using 5% NaHSO$_4$. The reaction was diluted with ethyl acetate and extracted twice with 1 M NaOH. The organics were dried over MgSO$_4$ and the solvent was removed. The resulting residue contained material that was missing the Boc group and some material that still had it (by HPLC-MS). The oil was treated with MeOH (2 mL) and 4 M HCl (2 mL) and stirred for 3 hours. The solvent was then removed and the reaction was partitioned between ethyl acetate and 1 M NaOH. The aqueous phase was extracted twice more with ethyl acetate and the combined organics were dried over MgSO$_4$ and the solvent was removed.

Preparation 8

Synthesis of (S)—N$^1$-(4-trifluoromethoxy-phenyl)-propane-1,2-diamine

Step A (S)-2-(benzylcarbonylamino)-propionaldehyde (S)-2-(benzylcarbonylamino)-propanol (5 g, 23.9 mmol) was dissolved in CH$_2$Cl$_2$ (200 mL) and treated with Dess-Martin periodinane (12.26 g, 1.1 eq). The mixture was stirred for 2 hours, then quenched with sodium thiosulphate, and the solvent removed in vacuo. The residue was then separated between sodium hydroxide (1M, 500 mL) and ethyl acetate (500 mL). The organics were washed with brine, dried (MgSO$_4$) and evaporated in vacuo to yield a clear oil which was used immediately in the next step without further purification.

Step B

[1-(S)-Methyl-2-(4-trifluoromethoxy-phenylamino)-ethyl]-carbamic acid benzyl ester (S)-2-(benzylcarbonylamino)-propionaldehyde was dissolved in methanol (300 mL). Acetic acid (4 mL, 2.9 eq) was added and the mixture treated with 4-trifluoromethoxy aniline (9.6 mL, 3 eq) and stirred for 15 minutes then sodium cyanoborohydride (4.36 g, 2.9 eq) was added with some effervescence. The mixture was stirred for 3 hours, and then the solvent reduced in vacuo. This was then separated between hydrochloric acid (1M, 500 mL×2) and ethyl acetate (500 mL). The organics were washed with sodium bicarbonate (500 mL), brine (500 mL), dried (MgSO$_4$) and evaporated in vacuo to give a clear oil which was purified by silica gel chromatography eluted with a gradient of 0-100% ethyl acetate/hexane.

Step C (S)—N1-(4-Trifluoromethoxy-phenyl)-propane-1,2-diamine

[1-(S)-Methyl-2-(4-trifluoromethoxy-phenylamino)-ethyl]-carbamic acid benzyl ester (23.9 mmol) was dissolved in ethanol (200 mL) then placed under nitrogen. 10% Palladium on carbon was added (0.5 g) and the mixture was stirred under hydrogen (atmospheric pressure) overnight. When reaction was complete, the mixture was filtered through celite. The celite was washed with ethanol (5×50 ml) then evaporated in vacuo to give a brown oil (4.03 g, 17.21 mmol, 72% yield over 3 steps).

Preparation 9

Synthesis of 2,2,-5-trifluoroindoline

Step A

5-Fluoro-1H-indole-2,3-dione (956 mg, 5.79 mmol, 1 eq) was added as a solution in dry DMF to a stirred slurry of sodium hydride (278 mg, 11.6 mmol, 2 eq) in dry DMF drop wise over 15 minutes under an inert atmosphere with adequate pressure release to accommodate $H_2$ evolution. The resulting mixture was stirred for 1 hour and p-methoxybenzyl chloride was added via syringe to the reaction. The solution was then stirred ca 2 hours and worked up by addition of water followed by extraction into ethyl acetate. The organic layer was washed twice with water and then dried over $MgSO_4$. Column chromatography with ethyl acetate/hexane afforded 5-Fluoro-1-(4-methoxy-benzyl)-1H-indole-2,3-dione as a red solid (1.3 g, 80% yield). $^1$H NMR ($CDCl_3$) δ(ppm): 7.3-7.24 (m, 3H), 7.20 (td, J=8.7, 2.7 Hz, 1H), 6.9-6.86 (m, 2H), 6.76 (dd, J=8.6, 3.6 Hz, 1H), 3.81 (s, 2H), 3.78 (s, 3H). LC/MS=286.1 (M+1).

Step B

The product from step A (200 mg, 0.701 mmol, 1 eq) was dissolved in 10 mL of dry DCM and placed under and inert atmosphere. DAST (339 mg, 2.103 mmol, 3 eq) was added via syringe and the reaction was stirred overnight. The reaction was worked up by addition of saturated aqueous sodium bicarbonate and the organic layer was dried over $MgSO_4$, filtered, and rotary evaporated to dryness. The resulting crude material was purified by flash chromatography using ethyl acetate/hexane as a solvent system. $^1$H NMR ($CDCl_3$) δ(ppm): 7.3-7.28 (m, 1H), 7.22 (d, J=8.7 Hz, 2H), 7.09 (td, J=8.7, 1.3 Hz, 1H), 6.87 (d, J=8.7 Hz, 2H), 6.73 (m, 1H), 4.83 (s, 2H), 3.79 (s, 3H). LC/MS=308.1 (M+1).

Step C

The product from step B (1.178 g, 3.83 mmol, 1 eq) was dissolved in 75 mL of dry THF and placed under an inert atmosphere. $LiAlH_4$ (291 mg, 7.66 mmol, 2 eq) was added as a solid under a positive pressure of $N_2$ at −78° C. The reaction was allowed to stir at this temperature for 30 min and then allowed to warm to room temp over a period of 6 hours. The reaction was worked up by addition of water dropwise followed by 4 equivalents of aqueous KOH. The slurry was diluted with 500 mL of water and extracted with 2×200 mL portions of ethyl acetate. The organic layers were combined, dried over $MgSO_4$, filtered, and rotary evaporated to dryness. The resulting crude material was purified by flash chromatography using ethyl acetate/hexane as a solvent system (28%). $^1$H NMR ($CD_3OD$) δ(ppm): 7.21 (d, J=8.8 Hz, 2H), 7.06 (dd, J=8.2, 1.3 Hz, 1H), 6.89 (m, 1H), 6.84 (d, J=8.7 Hz, 2H), 6.77 (dd, J=8.6, 4.3 Hz, 1H), 4.83 (s, 2H), 3.73 (s, 3H), 3.12 (s, 2H). LC/MS=294.1 (M+1).

Step D

The product from step C (50 mg, 0.1704 mmol, 1 eq) was taken up in 1 mL of TFA. The solution was placed in a microwave tube, sealed, and heated to 175° C. for 5 minutes. The resulting black solution was neutralized with saturated sodium bicarbonate and extracted with 2×50 mL portions of ethyl acetate. The organic layers were dried over $MgSO_4$, filtered, and rotary evaporated to dryness. The resulting solid was dissolved in a 50:50 mix of DMSO/MeOH and purified by prep HPLC. Yield 23.8 mg of white solid (81%). $^1$H NMR (DMSO $D_6$) δ (ppm): 10.41 (s, 1H), 7.13 (dd, J=8.6, 2.4 Hz, 1H), 7.01 (td, J=8.6, 2.7 Hz, 1H), 6.8 (dd, J=8.5, 4.5 Hz, 1H), 3.5 (s, 2H).

\* Compounds synthesized according to the procedure described in Example 1.

\# Compounds synthesized according to the procedure described in Example 83.

$ Compounds synthesized according to the procedure described in Example 141.

& Compounds synthesized according to the procedure described in Example 22.

\*\*\* Compounds synthesized according to the procedure described in Example 181.

$$$ Compounds synthesized according to the procedure described in Example 184.

Example 1

N-{cis-2-[2-(4-Methoxy-phenylamino)-ethylcarbamoyl]-cyclohexyl}-3-methyl-benzamide

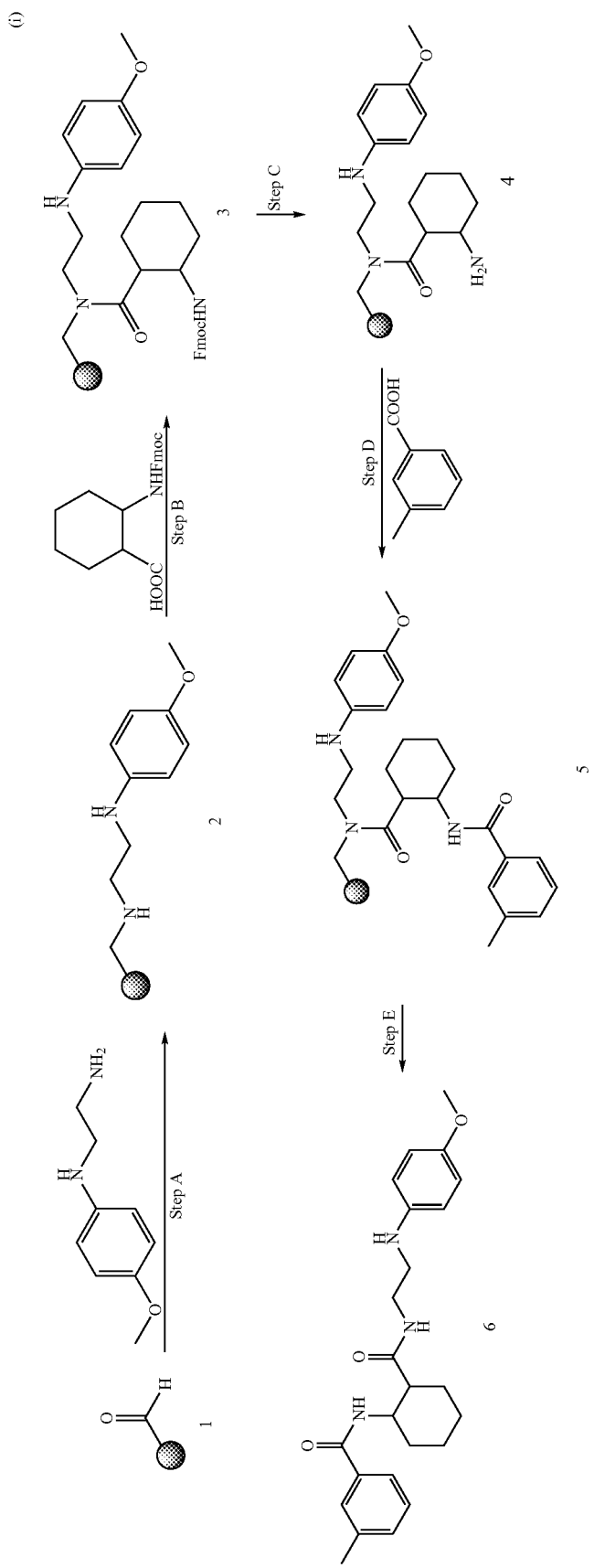

Step A

An aldehyde-functionalized polystyrene resin 1 ("Pal-Resin", 10.30 g @1.05 mmol/g, 10.8 mmol) was swelled in DMF (50 mL) for 10 min. $N^1$-(4-Methoxy-phenyl)-ethane-1,2-diamine (3.59 g, 21.6 mmol, prepared according to the procedures in E. Altmann et al *J. Med. Chem.* 2002, 45, 2352 and references cited therein) in DMF (150 mL) was added followed by acetic acid (5.0 ml, 86.4 mmol) and the mixture was agitated for 90 min at room temperature. Sodium triacetoxyborohydride (6.87 g, 32.4 mmol) was added and the mixture was shaken for 14 hours at room temperature. The reductively aminated resin 2 was then filtered and washed (DMF×3, alternate MeOH/DCM×4, MeCN×3).

Step B

Resin 2 (60 mg, 0.05 mmol) was swelled in DMF (1.5 mL) and a solution of Fmoc-cis-2-amino-1-cyclohexane carboxylic acid (55 mg, 0.15 mmol), HOBt (21 mg, 0.15 mg) and DIC (24 μL, 0.15 mmol) was added. The mixture was shaken for 3 hours at room temperature, then filtered and washed (DMF×5) to yield resin 3.

Step C

Resin 3 (0.05 mmol) was swelled in DMF (1.5 mL) and a solution of 20 v/v % piperidine in DMF (1.5 mL) was added. The mixture was shaken for 30 min at room temperature, then filtered and washed (DMF×5) to yield resin 4.

Step D

Resin 4 (0.05 mmol) was swelled in DMF (1.5 mL) and a solution of m-toluic acid (21 mg, 0.15 mmol), HOBt (21 mg, 0.15 mg) and DIC (24 μL, 0.15 mmol) was added. The mixture was shaken for 3 h at room temperature, then filtered and washed (DMF×3, alternate MeOH/DCM×4, MeCN×3) to yield resin 5.

Step E

To resin 5 (0.05 mmol) was added a solution of trifluoroacetic acid/DCM/H$_2$O in the v/v ratio 45:45:10. The mixture was shaken for 1 h at room temperature and filtered. Step E was repeated once, the filtrates combined and dried in vacuo. Reverse phase HPLC chromatography yielded the title compound 6 (10 mg, 0.025 mmol, 50%) as a white solid. MS calcd. for $C_{24}H_{32}N_3O_3$ (M+H$^+$) 410.24, found 410.2.

Example 2

5-(3-Trifluoromethyl-phenyl)-furan-2-carboxylic acid (S)-{2-cyclohexyl-1-[2-(5-fluoro-2,3-dihydro-indol-1-yl)-ethylcarbamoyl]-ethyl}-amide;* $C_{31}H_{33}F_4N_3O_3$; $^1$H NMR (CDCl$_3$) δ(ppm) 8.07 (m, 1H), 7.85 (m, 2H), 7.48 (m, 3H), 7.10 (m, 2H), 7.00 (m, 2H), 6.73 (m, 1H), 4.52 (m, 1H), 3.76 (m, 2H), 3.65 (m, 2H), 3.42 (m, 2H), 3.14 (m, 2H), 1.63 (m, 7H), 1.34 (m, 1H), 1.14 (m, 3H), 0.87 (m, 2H); LCMS: 572.5 (M+H)$^+$.

Example 3

(S)—N-{1-[2-(5-Fluoro-2,3-dihydro-indol-1-yl)-ethylcarbamoyl]-3-methyl-butyl}-3-methyl-b enzamide

Step A

Preparation of (S)-4-Methyl-2-(3-methyl-benzoylamino)-pentanoic acid. (L)-Leucine (2.54 g, 19.4 mmol) was dissolved in 1 M aqueous NaOH solution. This solution was cooled to 0° C. using an ice/water bath. After initiation of vigorous stirring, m-toluloyl chloride was added dropwise via syringe. The reaction was allowed to come to room temperature overnight. The reaction was then treated with concentrated HCl until the pH was highly acidic. The resulting solid was collected and dissolved in EtOH (30 mL). Water (~20 mL) was added to this mixture and the solution was rotary evaporated at a pressure of 30 mBar until the product solidified. The resulting solid was collected and dried to afford 3.5 g (72%) of product.

Step B

Preparation of (S)—N-[1-(2-Hydroxy-ethylcarbamoyl)-3-methyl-butyl]-3-methyl-benzamide. (S)-4-Methyl-2-(3-methyl-benzoylamino)-pentanoic acid (1 g. 4.0 mmol), ethanolamine (270 mg, 4.4 mmol) and HOBt (596 mg, 4.4 mmol) were treated with DCM (20 mL) followed by EDCI (845 mg, 4.4 mmol). The reaction was allowed to stir for 2 h and then purified directly by silica gel column chromatography using ethyl acetate and hexane to afford the product (350 mg, 30%) as a solid: $^1$H NMR (CDCl$_3$, 400 MHz) δ 0.89-0.99 (m, 6H), 1.67-1.79 (m, 3H), 2.37 (s, 3H), 3.31-3.41 (m, 1H), 3.42-3.52 (m, 1H), 3.61 (dd, 1H, $J_1$=2.7, $J_2$=8.1), 7.24-7.34 (m, 2H), 7.43 (dd, 1H, $J_1$=$J_2$=5.3), 7.57-7.63 (m, 2H); HPLC-MS calcd. for $C_{16}H_{24}N_2O_3$ (M+H$^+$) 292.18, found 292.2.

Step C (S)—N-[1-(2-Hydroxy-ethylcarbamoyl)-3-methyl-butyl]-3-methyl-benzamide (803 mg, 2.75 mmol) was dissolved in DCM (10 mL) and treated with the Dess-Martin periodinane (1.3 g, 5.4 mmol). The reaction was allowed to stir for 2 hours and then diluted with DCM and extracted with 1 M Na$_2$S$_2$O$_3$ solution (1×) and saturated aqueous NaHCO$_3$ solution (1×). The organics were dried and the solvent was removed. The resulting solid was partitioned into lots and used for several reductive aminations as described below:

A 100 mg (0.34 mmol) portion of the material prepared as above along with NaCNBH$_3$ (65 mg, 1.0 mmol) and 5-fluoroindoline (95 mg, 0.69 mmol) were dissolved in DMF (1 mL) and treated with acetic acid (112 mg, 1.9 mmol). Optionally, MeOH may be used as solvent in this reaction. The resulting solution was allowed to stand overnight at room temperature and diluted with ethyl acetate. The organic portion was extracted with aqueous NaHCO$_3$ solution (1×), dried over MgSO$_4$ and evaporated. The resulting oil was purified over silica gel using ethyl acetate and hexane as the solvents to afford the title compound (60.7 mg, 43%) as an oil: $^1$H NMR (CDCl$_3$, 400 MHz) δ 0.92-1.00 (m, 6H), 1.62-1.83 (m, 3H), 2.40 (s, 3H), 2.85-3.00 (m, 2H), 3.10-3.22 (m, 2H), 3.30-3.41 (m, 2H), 3.45-3.58 (m, 2H), 4.62-4.70 (m, 1H), 6.38 (dd, 1H, $J_1$=4.1, $J_2$=8.4), 6.53-6.61 (m, 1H), 6.63-6.75 (m, 2H), 6.77-6.83 (m, 1H), 7.27-7.35 (m, 2H), 7.50-7.57 (m, 2H); HPLC-MS calcd. for $C_{24}H_{30}FN_3O_2$ (M+H$^+$) 412.2, found 412.2.

Example 4

N—(S)-{2-cyclohexyl-1-[2-(5-fluoro-2,3-dihydro-indol-1-yl)-ethylcarbamoyl]-ethyl}-4-phenoxy-benzamide; $C_{32}H_{36}FN_3O_3$; $^1H$ NMR (CDCl$_3$) δ(ppm) 8.04 (m, 1H), 7.66 (m, 2H), 7.30 (m, 2H), 7.11 (m, 3H), 6.95 (m, 6H), 4.50 (m, 1H), 3.75 (m, 2H), 3.63 (m, 2H), 3.39 (m, 2H), 3.12 (m, 2H), 1.61 (m, 7H), 1.31 (m, 1H), 1.09 (m, 3H), 0.87 (m, 2H); LCMS: 530.5 (M+H)$^+$.

Example 5

1-Benzoyl-piperidine-4-carboxylic acid (S)-{2-cyclohexyl-1-[2-(5-fluoro-2,3-dihydro-indol-1-yl)-ethylcarbamoyl]-ethyl}-amide;* $C_{32}H_{41}FN_4O_3$; LCMS: 549.6 (M+H)$^+$

Example 6

(S)-3-Cyclohexyl-N-[2-(5-fluoro-2,3-dihydro-indol-1-yl)-ethyl]-2-[2-(4-methoxy-phenyl)-acetylamino]-propionamide;* $C_{28}H_{36}FN_3O_3$; $^1H$ NMR (CDCl$_3$) δ(ppm) 7.91 (m, 1H), 7.00 (m, 5H), 6.85 (m, 2H), 6.46 (m, 1H), 4.29 (m, 1H), 3.75 (m, 3H), 3.66 (m, 4H), 3.40 (m, 2H), 3.16 (m, 2H), 1.59 (m, 7H), 1.12 (m, 4H), 0.86 (m, 2H); LCMS: 482.5 (M+H)$^+$.

Example 7

(S)—N-{1-[2-(5-Chloro-2,3-dihydro-indol-1-yl)-ethylcarbamoyl]-3-methyl-butyl}-3-methyl-benzamide. The title compound (12 mg, 8%) was prepared in the same manner as Example 3 except that the reductive amination partner in Step C was 5-chloroindoline instead of 5-fluoroindoline: $^1H$ NMR (CDCl$_3$, 400 MHz) δ 0.95 (dd, 6H, $J_1=J_2=4.9$), 1.60-1.80 (m, 3H), 2.40 (s, 3H), 2.84-2.99 (m, 2H), 3.12-3.24 (m, 2H), 3.38 (dd, 1H, $J_1=J_2=8.4$), 3.43-3.55 (m, 2H), 4.62-4.70 (m, 1H), 6.35 (d, 1H, J=8.3), 3.62 (dd, 1H, $J_1=4.6, J_2=8.0$), 6.77-6.84 (m, 1H), 3.94 (dd, 1H, $J_1=2.0, J_2=8.3$), 6.97-7.00 (m, 1H), 7.27-7.35 (m, 2H), 7.50-7.57 (m, 2H); HPLC-MS calcd. for $C_{24}H_{30}FN_3O_2$ (M+H$^+$) 428.2, found 428.2.

Example 8

(S)—N-{3-Cyclohexyl-1-[2-(7-methoxy-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 7-methoxyindoline as starting materials, the title compound was prepared in 30% yield. The final material was purified by reverse phase preparative HPLC Using TFA as a modifier. The final compound is therefore a partial TFA salt and the properties are reported for the material as it appeared after solvent removal: $^1H$ NMR (CDCl$_3$, 400 MHz) δ 0.78-0.92 (m, 2H), 1.05-1.32 (m, 6H), 1.59-1.81 (m, 6H), 1.94-2.05 (m, 1H), 3.10-3.20 (m, 2H), 3.45-3.72 (m, 5H), 3.80 (s, 3H), 3.86 (s, 3H), 4.62 (dd, 1H, $J_1=7.8, J_2=13.7$), 6.78 (d, 1H, $J_1=8.2$), 6.86 (d, 1H, $J_1=7.2$), 7.00-7.08 (m, 2H), 7.18-7.23 (m, 1H), 7.30-7.47 (m, 3H), 7.53-7.62 (m, 1H); HPLC-MS calcd. for $C_{29}H_{39}N_3O_4$ (M+H$^+$) 494.3, found 494.5.

Example 9

Furan-2-carboxylic acid (S)-{2-cyclohexyl-1-[2-(5-fluoro-2,3-dihydro-indol-1-yl)-ethylcarbamoyl]-ethyl}-amide;* $C_{24}H_{30}FN_3O_3$; $^1H$ NMR (CDCl$_3$) δ(ppm) 8.21 (m, 1H), 7.48 (m, 1H), 7.31 (m, 1H), 7.16 (m, 1H), 7.06 (m, 2H), 6.50 (m, 1H), 6.43 (m, 1H), 4.52 (m, 1H), 3.92 (m, 2H), 3.75 (m, 2H), 3.53 (m, 2H), 3.26 (m, 2H), 1.69 (m, 7H), 1.41 (m, 1H), 1.16 (m, 3H), 0.89 (m, 2H); LCMS: 428.5 (M+H)$^+$.

Example 10

(S)—N-{3-Cyclohexyl-1-[2-(6-fluoro-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 6-fluoroindoline as starting materials, the title compound was prepared in 40% yield. The final material was purified by reverse phase preparative HPLC using TFA as a modifier. The final compound is therefore a partial TFA salt and the properties are reported for the material as it appeared after solvent removal: $^1H$ NMR (CDCl$_3$, 400 MHz) δ 0.72-0.86 (m, 2H), 1.03-1.28 (m, 6H), 1.58-1.69 (m, 6H), 1.85-1.96 (m, 1H), 2.89 (dd, 2H, $J_1=J_2=8.1$), 3.19 (dd, 2H, $J_1=J_2=6.0$), 3.43 (dd, 2H, $J_1=J_2=8.4$), 3.37-3.47 (m, 1H), 3.53-3.62 (m, 1H), 3.84 (s, 3H), 4.64 (dd, 1H, $J_1=7.0, J_2=14.1$), 6.16 (d, 1H, J=10.2), 6.26-6.33 (m, 1H), 6.92 (dd, 1H, $J_1=J_2=6.7$), 7.02-7.07 (m, 2H), 7.12-7.19 (m, 2H), 7.26-7.39 (m, 3H); HPLC-MS calcd. for $C_{28}H_{36}FN_3O_3$ (M+H$^+$) 482.3, found 482.5.

Example 11

(S)—N-{3-Cyclohexyl-1-[2-(7-fluoro-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 7-fluoroindoline as starting materials, the title compound was prepared in 40% yield. The final material was purified by reverse phase preparative HPLC using TFA as a modifier. The final compound is therefore a partial TFA salt and the properties are reported for the material as it appeared after solvent removal: $^1H$ NMR (CDCl$_3$, 400 MHz) δ 0.73-0.87 (m, 2H), 1.03-1.28 (m, 6H), 1.58-1.78 (m, 6H), 1.83-1.95 (m, 1H), 3.01 (dd, 2H, $J_1=J_2=8.4$), 3.41-3.50 (m, 4H), 3.55-3.72 (m, 1H), 3.84 (s, 3H), 4.63 (dd, 1H, $J_1=7.1, J_2=14.3$), 6.53-6.68 (m, 2H), 6.78 (dd, 1H, $J_1=8.5, J_2=12.3$), 6.86 (d, 1H, $J_1=7.0$), 7.01-7.08 (m, 2H), 7.20 (d, 1H, $J_1=7.8$), 7.26-7.39 (m, 3H); HPLC-MS calcd. for $C_{28}H_{36}FN_3O_3$ (M+H$^+$) 482.3, found 482.5.

Example 12

(S)—N-{3-Cyclohexyl-1-[2-(5-cyano-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 5-cyanoindoline as starting materials, the title compound was prepared in 20% yield. The final material was purified by reverse phase preparative HPLC using TFA as a modifier. The final compound is therefore a partial TFA salt and the properties are reported for the material as it appeared after solvent removal: $^1H$ NMR (CDCl$_3$, 400 MHz) δ 0.64-0.77 (m, 2H), 0.97-1.15 (m, 6H), 1.49-1.64 (m, 6H), 1.72-1.84 (m, 1H), 2.84-2.92 (m, 2H), 3.16-3.30 (m, 2H), 3.32-3.51 (m, 4H), 3.77 (s, 3H), 4.49 (dd, 1H, $J_1=7.4, J_2=14.4$), 6.24 (d, 1H, $J_1=8.3$), 6.97-7.02 (m, 1H), 7.04-7.07 (m, 1H), 7.09-7.15 (m, 2H), 7.18-7.28 (m, 2H); HPLC-MS calcd. for $C_{29}H_{36}N_4O_3$ (M+H$^+$) 482.3, found 482.5.

Example 13

Furan-3-carboxylic acid (S)-{2-cyclohexyl-1-[2-(5-fluoro-2,3-dihydro-indol-1-yl)-ethylcarbamoyl]-ethyl}-amide; $C_{24}H_{30}FN_3O_3$; $^1$H NMR (CDCl$_3$) δ(ppm) 8.14 (m, 1H), 7.88 (m, 1H), 7.35 (m, 1H), 7.19 (m, 2H), 6.97 (m, 2H), 6.60 (m, 1H), 4.46 (m, 1H), 3.80 (m, 2H), 3.64 (m, 2H), 3.40 (m, 2H), 3.16 (m, 2H), 1.57 (m, 7H), 1.29 (m, 1H), 1.13 (m, 3H), 0.84 (m, 2H); LCMS: 428.5 (M+H)$^+$.

Example 14

Cyclopropanecarboxylic acid (S)-{2-cyclohexyl-1-[2-(5-fluoro-2,3-dihydro-indol-1-yl)-ethylcarbamoyl]-ethyl}-amide;* $C_{23}H_{32}FN_3O_2$; $^1$H NMR (CDCl$_3$) δ(ppm) 7.90 (m, 1H), 7.10 (m, 1H), 6.97 (m, 2H), 6.76 (m, 1H), 4.34 (m, 1H), 3.70 (m, 4H), 3.41 (m, 2H), 3.16 (m, 2H), 1.61 (m, 7H), 1.30 (m, 3H), 1.13 (m, 1H), 0.75 (m, 7H); LCMS:402.5 (M+H)$^+$.

Example 15

(S)—N-{3-Cyclohexyl-1-[2-(4-methoxy-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 4-methoxyindoline as starting materials, the title compound was prepared in 30% yield. The final material was purified by reverse phase preparative HPLC using TFA as a modifier. The final compound is therefore a partial TFA salt and the properties are reported for the material as it appeared after solvent removal: $^1$H NMR (CDCl$_3$, 400 MHz) δ 0.67-0.80 (m, 2H), 0.92-1.21 (m, 6H), 1.46-1.67 (m, 6H), 1.79-1.92 (m, 1H), 2.88 (dd, 1H, $J_1=J_2=8.1$), 3.16-3.21 (m, 2H), 3.41 (dd, 1H, $J_1=J_2=8.1$), 3.51-3.43 (m, 2H), 3.71 (s, 3H), 3.73 (s, 3H), 4.44 (dd, 1H, $J_1=7.1, J_2=13.9$), 6.27 (d, 1H, J=7.9), 6.33 (d, 1H, J=8.2), 6.84-6.78 (m, 1H), 6.91-6.97 (m, 1H), 6.99 (dd, 1H, $J_1=J_2=8.0$), 7.14-7.17 (m, 2H), 7.17-7.27 (m, 3H); HPLC-MS calcd. for $C_{29}H_{39}N_3O_4$ (M+H$^+$) 494.3, found 494.5.

Example 16

(S)—N-{3-Cyclohexyl-1-[2-(5-methoxy-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 5-methoxyindoline as starting materials, the title compound was prepared in 20% yield. The final material was purified by reverse phase preparative HPLC using TFA as a modifier. The final compound is therefore a partial TFA salt and the properties are reported for the material as it appeared after solvent removal: $^1$H NMR (CDCl$_3$, 400 MHz) δ 0.58-0.72 (m, 2H), 0.85-1.10 (m, 6H), 1.37-1.59 (m, 6H), 1.62-1.73 (m, 1H), 2.54-2.67 (m, 2H), 2.85-2.98 (m, 2H), 3.20-3.33 (m, 2H), 3.41 (s, 3H), 3.55-3.70 (m, 2H), 3.64 (s, 3H), 4.34 (dd, 1H, $J_1=7.1, J_2=13.9$), 6.72-6.78 (m, 2H), 6.84-6.90 (m, 2H), 7.06-7.19 (m, 5H); HPLC-MS calcd. for $C_{29}H_{39}N_3O_4$ (M+H$^+$) 494.3, found 494.5.

Example 17

1-(4-Chloro-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;* $C_{31}H_{40}ClFN_4O_4S$; $^1$H NMR (CDCl$_3$) δ(ppm) 8.16 (m, 1H), 7.61 (m, 2H), 7.45 (m, 2H), 7.25 (m, 1H), 7.02 (m, 2H), 6.72 (m, 1H), 4.25 (m, 2H), 3.83 (m, 2H), 3.69 (m, 3H), 3.45 (m, 2H), 3.21 (m, 2H), 2.25 (m, 2H), 2.09 (m, 1H), 1.76 (m, 2H), 1.59 (m, 7H), 1.47 (m, 2H), 1.18 (m, 1H), 1.05 (m, 3H), 0.80 (m, 2H); LCMS: 619.5 (M+H)$^+$.

Example 18

(S)—N-{3-Cyclohexyl-1-[2-(5-fluoro-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 5-fluoroindoline as starting materials, the title compound was prepared in 40% yield. The final material was purified by reverse phase preparative HPLC using TFA as a modifier. The final compound is therefore a partial TFA salt and the properties are reported for the material as it appeared after solvent removal: $^1$H NMR (CDCl$_3$, 400 MHz) δ 0.50-0.65 (m, 2H), 0.79-1.05 (m, 6H), 1.33-1.53 (m, 6H), 1.60-1.74 (m, 1H), 2.70 (dd, 2H, $J_1=J_2=8.1$), 2.94 (dd, 2H, $J_1=J_2=6.0$), 3.15 (dd, 2H, $J_1=J_2=8.1$), 3.20-3.43 (m, 2H), 3.60 (s, 3H), 4.30-4.38 (m, 1H), 6.17-6.23 (m, 1H), 6.45-6.55 (m, 1H), 6.56-6.60 (m, 1H), 6.62-6.74 (m, 2H), 6.78-6.88 (m, 1H), 6.94-7.15 (m, 3H); HPLC-MS calcd. for $C_{28}H_{36}FN_3O_3$ (M+H$^+$) 482.3, found 482.5.

Example 19

(S)—N-{3-Cyclohexyl-1-[2-(5-benzyloxy-2,3-dihydro-indol-1-yl)-ethylcarbamoyl]-propyl}-3-methoxy-benzamide. Following the procedures of Example 3, except using m-anisoyl chloride, (S)-2-amino-4-cyclohexyl-butyric acid, ethanolamine and 5-benzyloxyindoline as starting materials, the title compound was prepared in 10% yield. The final material was purified by reverse phase preparative HPLC using TFA as a modifier. The final compound is therefore a partial TFA salt: HPLC-MS calcd. for $C_{35}H_{43}N_3O_4$ (M+H$^+$) 570.3, found 570.6.

Example 20 and Example 21

N-{1-(S)-[2-(4-Methoxy-phenylamino)-propylcarbamoyl]-3-methyl-butyl}-3-methyl-benzamide and N-{1-(S)-[2-(4-Methoxy-phenylamino)-1-methyl-ethylcarbamoyl]-3-methyl-butyl}-3-methyl-benzamide

Step A

In a flame-dried flask, sodium t-butoxide (1.38 g, 14.4 mmol), BINAP (0.897 g, 1.44 mmol) and Pd$_2$dba$_3$ (0.443 g, 0.484 mmol) were treated with anhydrous dioxane (10 mL) followed by 4-bromoanisole (1.49 g, 7.99 mmol) and 1,2-diaminopropane (0.671 g, 9.06 mmol). The flask was sealed with a 3-way stopper and immersed into a 90° C. pre-heated oil bath and allowed to stir overnight. The reaction flask was cooled to rt. Dioxane was removed prior to extraction. The concentrated mixture was diluted with ethyl acetate and extracted with water (2×). The organics were extracted with 1 M NaOH (2×) followed by 1 M HCl (2×). The aqueous layer was collected and treated with NaOH pellets until the pH was highly basic. The aqueous portion was once again extracted with ethyl acetate. The organics were collected, dried over MgSO$_4$ and concentrated. The resulting material was used for the next acylation step in the synthesis without purification.

Step B

The material from the Step A (117 mg, 0.650 mmol) was dissolved with DMF followed by the addition of (S)-4-Methyl-2-(3-methyl-benzoylamino)-pentanoic acid (128 mg, 0.510 mmol, prepared according to Example 3, Step A), HATU (277 mg, 0.73 mmol) and DIPEA (210 mg, 1.62 mmol). The reaction was allowed to stir at rt overnight. The mixture was diluted with ethyl acetate and extracted with water followed by 1 M HCl. The organics were collected, dried over $MgSO_4$ and concentrated. The final material was purified by reverse phase preparative HPLC using TFA as a modifier. The final compound is therefore a partial TFA salt and the properties are reported for the material as it appeared after solvent removal. The data are reported for the diastereomeric mixtures.

The first material to come off was Example 20, N-{1-(S)-[2-(4-Methoxy-phenylamino)-propylcarbamoyl]-3-methyl-butyl}-3-methyl-benzamide (10%): $^1$H NMR ($CDCl_3$, 400 MHz) δ 0.85-1.02 (m, 6H), 1.02-1.35 (m, 3H), 1.65-1.82 (m, 3H), 2.37 and 2.38 (s's, 3H), 3.40-3.58 (m, 2H), 3.63-3.80 (m, 1H), 3.79 (s, 3H), 4.42-4.54 (m, 1H), 4.60-5.30 (m, 2H), 6.79-6.88 (m, 2H), 6.93-7.07 (m, 2H), 7.23-7.38 (m, 3H), 7.41-7.59 (m, 2H); HPLC-MS calcd. for $C_{24}H_{33}N_3O_3$ (M+H$^+$) 412.3, found 412.2.

The second material to come off (in 2 peaks that were combined) was Example 21, N-{1-(S)-[2-(4-Methoxy-phenylamino)-1-methyl-ethylcarbamoyl]-3-methyl-butyl}-3-methyl-benzamide (10%): $^1$H NMR ($CDCl_3$, 400 MHz) δ 0.85-1.00 (m, 6H), 1.27-1.30 (m, 3H), 1.62-1.80 (m, 3H), 2.36 and 2.37 (s's, 3H), 3.09-3.18 (m, 2H), 3.71 and 3.74 (s's, 3H), 3.71-3.92 (m, 1H), 4.13-4.28 (m, 1H), 4.53-4.64 (m, 1H), 6.57-6.92 (m, 6H), 7.27-7.33 (m, 2H), 7.49-7.62 (m, 2H); HPLC-MS calcd. for $C_{24}H_{33}N_3O_3$ (M+H$^+$) 412.3, found 412.2. The identity of Example 21 was further confirmed by comparing its NMR spectrum with those of Examples 22 and 23.

Example 22

N-{1-(S)-[2-(4-Methoxy-phenylamino)-1-(S)-methyl-ethylcarbamoyl]-3-methyl-butyl}-3-methyl-benzamide Step A Preparation of (S)-2-(tert-Butoxycarbonyl-1-amino)-1-propionaldehyde (S)-(−)-2-(tert-Butoxycarbonyl-1-amino)-1-propanol (523 mg, 2.98 mmol, 1.0 equiv.) was dissolved in 45 mL methylene chloride in a 100 mL r.b. flask with a magnetic stir bar. To this clear homogeneous solution, Dess-Martin periodinane (1.523 g, 3.591, 1.2 equiv.) was added in one part and the cloudy white solution reaction was allowed to stir at room temperature for 2 h. Thin-layer chromatography monitored the reaction to completion. The reaction mixture was diluted with 100 mL ethyl acetate. Sodium bisulfate solution (2 M, 20 mL) was added to the reaction mixture and the organic layer was separated. The aqueous layer was washed with 3×30 mL EtOAc. The combined organic layers were washed with 50 mL 1 M NaOH, followed by saturated NaCl (30 mL) and dried over $MgSO_4$. Filtration and rotary evaporation produced the desired product as a yellow oil (475 mg, 92% yield, $R_f$=0.63, 1:1 hexanes/ethyl acetate).

Step B

Preparation of [2-(4-Methoxy-phenylamino)-(1S)-methyl-ethyl]-carbamic acid tert-butyl ester. (S)-2-(tert-Butoxycarbonyl-1-amino)-1-propionaldehyde (473 mg, 2.74 mmol) and p-anisidine (1.031 g, 8.371 mmol, 3.0 equiv.) was dissolved in 45 mL of MeOH at 0° C. in a 100 mL r.b. flask with a magnetic stir bar. Optionally, acetic acid (469 μL, 8.21 mmol, 3.0 equiv.) can be added via syringe to assist in the reaction. To the stirring dark colored solution was added sodium cyanoborohydride (326 mg, 5.82 mmol, 1.89 equiv.). Gas evolution and disappearance of color were observed. The reaction was allowed to slowly warm to room temperature with stirring over 30 minutes and the reaction was monitored by LC/MS. At the completion of the reaction, the mixture was quenched with 1 M NaOH, and extracted 3×50 mL ethyl acetate. The resulting organics were washed with 50 mL saturated $NaHCO_3$, 40 mL saturated NaCl, and dried over $MgSO_4$. Evaporation of ethyl acetate provided 728 mg of a brown oil. Purification by automated ISCO chromatography provided a clear oil of [2-(4-Methoxy-phenylamino)-(1S)-methyl-ethyl]-carbamic acid tert-butyl ester (583 mg, 2.079 mmol, 76% yield). HPLC-MS calcd. for $C_{15}H_{24}N_2O_3$ (M+H$^+$) 281.2, found 281.5. $^1$H NMR ($CDCl_3$, 400 MHz) δ 1.21 (d, 6H, J=6.6 Hz), 1.47 (s, 9H), 3.05 (dd, 1H, J=12.2, 7.3 Hz), 3.13 (dd, 1H, J=12.2, 4.6 Hz), 3.76 (s, 3H), 3.93 (broad s, 1H), 4.62 (broad s, 1H), 6.60 (d, 2H, J=6.8 Hz), 6.80 (2H, d, J=6.8 Hz).

Step C

[2-(4-Methoxy-phenylamino)-(1S)-methyl-ethyl]-carbamic acid tert-butyl ester (383 mg, 1.37 mmol) was added to 10 mL of a trifluoroacetic acid solution (10 v/v % in methylene chloride) at room temperature in a 25 mL r.b. flask with a magnetic stirbar. The reaction turns dark purple/black in color after 5 minutes. The reaction is allowed to stir at room temperature until the reaction is judged complete by HPLC/MS. The solvent is removed by evaporation and to provide 2-(4-Methoxy-phenylamino)-(1S)-methyl-ethyl-ammonium; trifluoro-acetate salt as a brown oil (394 mg, 1.34 mmol, 98% yield) and used directly in the next reaction. HPLC-MS calcd. for $C_{10}H_{16}N_2O$ (M+H$^+$) 181.1, found 181.5.

Step D 2-(4-Methoxy-phenylamino)-(1S)-methyl-ethyl-ammonium trifluoro-acetate salt (253 mg, 0.860, 1.0 equiv.), 4-Methyl-(2S)-(3-methyl-benzoylamino)-pentanoic acid (Example 3, step A, 212 mg, 0.850 mmol, 1.0 equiv.), HATU (327 mg, 0.866 mmol, 1.0 equiv.), and $CH_2Cl_2$ (15 mL) were combined in a 50 mL r.b. flask with a magnetic stir-bar. The resulting cloudy white solution reaction was allowed to stir at room temperature for 20 minutes, upon which DIPEA (450 μL, 2.583 mmol, 3.0 equiv.) was added via syringe. The reaction mixture turned dark yellow in color. The resulting solution was allowed to stir at room temperature for 3 h. When the reaction was complete by LC/MS, it was extracted with 35 mL water, washed the organic layer with 10 mL saturated NaCl and dried over $MgSO_4$. After evaporation of solvent, the crude mixture was purified by ISCO normal phase separation to provide (37 mg, 0.090 mmol, 10% yield) of a white solid. $^1$H NMR ($CDCl_3$, 400 MHz) δ 0.95 (m, 6H), 1.16 (d, 3H, J=6.8 Hz), 1.72 (m, 3H), 2.36 (s, 3H), 3.14 (d, 2H, J=6.2 Hz), 3.75 (s, 3H), 4.19 (m, 1H), 4.75 (m, 1H), 6.60 (d, 1H, J=8.8 Hz), 6.77 (d, 1H, J=8.8 Hz), 6.77-6.84 (m, 1H), 7.01 (m, 1H), 7.30 (m, 1H), 7.59 (m, 1H); HPLC-MS calcd. for $C_{24}H_{33}N_3O_3$ (M+H$^+$) 412.3, found 412.5.

Example 23

N-{1-(S)-[2-(4-Methoxy-phenylamino)-1-(R)-methyl-ethylcarbamoyl]-3-methyl-butyl}-3-methyl-benzamide. Following the procedures of Example 22, except it uses (R)-(+)-2-(tert-Butoxycarbonyl-1-amino)-1-propanol as the starting material in step A, the title compound was prepared: HPLC-MS calcd. for $C_{24}H_{33}N_3O_3$ (M+H$^+$) 412.3, found 412.5.

Example 24

1H-Indole-2-carboxylic acid {3-cyclohexyl-(1S)-[2-(4-methoxy-phenylamino)-(1S)-methyl-ethylcarbamoyl]-propyl}-amide. The title compound was prepared following the procedures of Example 22, except that in step D it uses 4-cyclohexyl-(2S)-[(1H-indole-2-carbonyl)-amino]-butyric acid instead of Methyl-(2S)-(3-methyl-benzoylamino)-pentanoic acid. The final compound is isolated as a mixture of diastereomers in a 1.5:1 ratio. HPLC-MS calcd. for $C_{29}H_{38}N_4O_3$ (M+H$^+$) 491.3, found 491.5. $^1$H NMR (CDCl$_3$, 400 MHz) δ 0.55-1.38 (m, 16H), 1.53-1.71 (m, 2H), 2.89 (m, 2H), 3.49 (s, 3H), 4.03 (m, 1H), 4.41 (m, 1H), 6.35-7.17 (m, 9H), 7.40 (1H, m), 9.48 (s, 1H) 4-Cyclohexyl-(2S)-[(1H-indole-2-carbonyl)-amino]-butyric acid is made by the following procedure: (+)-Ethyl-(S)-2-amino-4-cyclohexylbutyrate hydrochloride (1.643 g, 6.577 mmol, 1.0 equiv.), 2-indolecarboxylic acid (1.166 g, 7.235 mmol, 1.1 equiv.), HATU (2.750 g, 7.232 mmol, 1.1 equiv.), and CH$_2$Cl$_2$ (80 mL) were combined in a 100 mL r.b. flask with a magnetic stir-bar. The resulting cloudy white solution reaction was allowed to stir at room temperature for 20 minutes, upon which DIPEA (5.8 mL, 33.29 mmol, 4.6 equiv.) was added via syringe. The reaction mixture turned dark yellow in color. The resulting solution was allowed to stir at rt for 3 h. When the reaction was complete by LC/MS, it was extracted with 100 mL water, washed the organic layer with 50 mL saturated NaCl and dried over MgSO$_4$. After evaporation of solvent, the crude mixture was purified by ISCO normal phase separation to provide (2.161 g, 6.062 mmol, 92% yield) of 4-cyclohexyl-(2S)-[(1H-indole-2-carbonyl)-amino]-butyric acid ethyl ester as a clear liquid. HPLC-MS calcd. for $C_{21}H_{28}N_2O_3$ (M+H$^+$) 357.5, found 357.5.

4-Cyclohexyl-(2S)-[(1H-indole-2-carbonyl)-amino]-butyric acid ethyl ester (2.27 g, 6.37 mmol, 1.0 equiv.) was dissolved in 40 mL MeOH and 20 mL H$_2$O in a 100 mL r.b. flask containing a magnetic stir-bar at 0° C. Lithium hydroxide (188 mg, 7.849 mmol, 1.2 equiv.) is added in one-part. The reaction is allowed to slowly warm and the reaction is monitored to completion by LC/MS. Extraction of the clear reaction solution with 4×75 mL ethyl acetate, dried over MgSO$_4$ and evaporation provides (2.07 g, 6.30 mmol, 99% yield) of a off-white solid of 4-Ccyclohexyl-2-[(1H-indole-2-carbonyl)-amino]-butyric acid. HPLC-MS calcd. for $C_{19}H_{24}N_2O_3$ (M+H$^+$) 328.3, found 329.5.

Example 25

1H-Indole-2-carboxylic acid {3-cyclohexyl-(1S)-[2-(4-methoxy-phenylamino)-(1R)-methyl-ethylcarbamoyl]-propyl}-amide. Following the procedures of Example 22, except using 4-cyclohexyl-(2S)-[(1H-indole-2-carbonyl)-amino]-butyric acid (see Example 24) and (R)-(+)-2-(tert-butoxycarbonyl-1-amino)-1-propanol as starting materials, the title compound was prepared. HPLC-MS calcd. for $C_{29}H_{38}N_4O_3$ (M+H$^+$) 491.3, found 491.5.

Example 26

N-{2-Cyclohexyl-(1S)-[2-(4-methoxy-phenylamino)-(1R)-methyl-ethylcarbamoyl]-ethyl}-3-methoxy-benzamide. Following the procedures of Example 22, except using m-anisoyl chloride, 3-cyclohexyl-L-alanine and (R)-(+)-2-(tert-butoxycarbonyl-1-amino)-1-propanol as starting materials, the title compound was prepared. The final product was isolated as a 1.2:1 mixture of diastereomers. HPLC-MS calcd. for $C_{27}H_{37}N_3O_4$ (M+H$^+$) 468.3, found 468.5. $^1$H NMR (CDCl$_3$, 400 MHz) δ 0.88-1.71 (m, 14H), 3.19-3.23 (m, 2H), 3.70 (s, 6H), 4.11-4.25 (m, 2H), 4.35-4.42 (m, 1H), 4.41 (m, 1H), 6.79-7.33 (m, 7H), 7.91-8.02 (1H, m).

Example 27

5-(3-Trifluoromethyl-phenyl)-furan-2-carboxylic acid {3-cyclohexyl-(1S)-[2-(4-methoxy-phenylamino)-(1S)-methyl-ethylcarbamoyl]-propyl}-amide. Following the procedures of Example 24, except using 5-(3-trifluoromethyl-phenyl)-furan-2-carboxylic acid and (S)-2-amino-4-cyclohexyl-butyric acid as starting materials, the title compound was prepared. HPLC-MS calcd. for $C_{32}H_{38}F_3N_3O_4$ (M+H$^+$) 586.3, found 586.5. $^1$H NMR (CDCl$_3$, 400 MHz) δ 0.78-1.64 (m, 16H), 1.72-1.88 (m, 2H), 3.19-3.23 (m, 2H), 3.63-3.74 (m, 4H), 4.14 (m, 1H), 6.67-7.81 (m, 10H), 8.24 (m, 2H).

Example 28

N-{(1S)-[2-(5-Fluoro-2,3-dihydro-indol-1-yl)-1,1-dimethyl-ethylcarbamoyl]-2-phenyl-ethyl}-3-methyl-benzamide

Step A 2-(3-Methyl-benzoylamino)-3-phenyl-propionic acid was prepared according to the procedure of Example 3, Step A, except using (L)-phenylalanine instead of (L)-leucine.

Step B

Synthesis of N-[1-(2-hydroxy-1,1-dimethyl-ethylcarbamoyl)-(2S)-phenyl-ethyl]-3-methyl-benzamide. 2-(3-Methyl-benzoylamino)-3-phenyl-propionic acid (1.087 g, 3.866 mmol, 1.05 equiv.) and Bis(2-oxo-3-oxazolidinyl)phosphonic chloride (BOP-Cl, 930 mg, 3.65 mmol, 1.0 equiv.) was dissolved in CH$_2$Cl$_2$ at 0° C. To the resulting white suspension was added was added a 2 mL CH$_2$Cl$_2$ of 2-amino-2-methyl-propan-1-ol (364 mg, 4.08 mmol, 1.11 equiv.) and triethylamine (500 μL, 3.59 mmol, 1.0 equiv) were added via syringe. To the resulting solution, slow addition of triethylamine (500 μL, 3.59 mmol, 1.0 equiv) in 2 mL CH$_2$Cl$_2$ was added by addition funnel over a 2 h period. The resulting solution was allowed to warm overnight and the reaction was monitored by LC/MS. The reaction was worked up by quenching with water (20 mL) and addition of 4M HCl until reaction reaches pH 1. The organic layer was separated and the aqueous layer was washed 3×35 mL ethyl acetate. The combined organic extracts were washed with saturated NaHCO$_3$ (20 mL), saturated NaCl (30 mL) and dried over MgSO$_4$. After rotary evaporation 325 mg of crude material was obtained. Automated ISCO chromatography was performed and 171 mg (0.4827 mmol, 13.2% isolated yield) of a clear oil was obtained (R$_f$=0.43 in 1:1 hexane:ethyl acetate). HPLC-MS calcd. for $C_{21}H_{26}N_2O_3$ (M+H$^+$) 355.2, found 355.5. $^1$H NMR (CDCl$_3$, 400 MHz) δ 1.22 (s, 6H), 2.03 (s, 1H), 2.40 (s, 3H), 3.32-3.06 (m, 2H), 3.62 (d, 1H, J=11.1 Hz), 3.46 (d, 1H, J=11.1 Hz), 4.75 (m, 1H), 7.23-7.58 (m, 9H), 8.23 (m, 1H).

Step C

Following the procedures of Example 3, Step C, N-[1-(2-Hydroxy-1,1-dimethyl-ethylcarbamoyl)-(2S)-phenyl-ethyl]-3-methyl-benzamide was converted to the title compound. HPLC-MS calcd. for $C_{29}H_{32}FN_3O_2$ (M+Ht) 474.2, found 474.6. $^1$H NMR (CDCl$_3$, 400 MHz) δ 1.21 (s, 3H), 1.29 (s, 3H), 2.31 (s, 3H), 2.83-3.00 (m, 4H), 3.16-3.31 (m, 4H), 4.66 (broad s, 1H), 6.60-7.47 (m, 11H).

Example 29

Tetrahydrofuran-2-(S)-carboxylic acid {2-cyclohexyl-1-(S)-[1-(S)-methyl-2-(4-trifluoromethoxy-phenylamino)-ethylcarbamoyl]-ethyl}-amide.* $C_{24}H_{34}F_3N_3O_4$; LCMS: 486.4 (M+H)$^+$.

Example 30

Tetrahydrofuran-2-(R)-carboxylic acid {2-cyclohexyl-1-(S)-[1-(S)-methyl-2-(4-trifluoromethoxy-phenylamino)-ethylcarbamoyl]-ethyl}1-amide.* $C_{24}H_{34}F_3N_3O_4$; LCMS: 486.4 (M+H)$^+$.

Example 31 and Example 32

N-{1-(S)-[1-(4-Methoxy-phenyl)-piperidin-3-(S)-ylcarbamoyl]-3-methyl-butyl}-3-methyl-benzamide and N-{1-(S)-[1-(4-Methoxy-phenyl)-piperidin-3-(R)-ylcarbamoyl]-3-methyl-butyl}-3-methyl-benzamide.

Step A

N,N-Diethylnipecotamide (2.00 g, 10.8 mmol), 4-bromoanisole (2.44 g, 13.0 mmol), Pd$_2$ dba$_3$ (149 mg, 0.16 mmol), 2-(di-t-butylphosphino)biphenyl (194 mg, 0.65 mmol) and THF (11 mL) were charged to a 100 mL round-bottom flask with a threaded top capable of being sealed. Then, t-BuOK (1.70 g, 15.9 mmol) was added in one portion and the flask was sealed. The flask got hot and after 15 min a gel formed. After overnight stirring, the reaction was partitioned between ethyl acetate and water and the aqueous layer was discarded. The organic layer was then extracted twice with 5% KHSO$_4$ and discarded. The acidic aqueous layer was made basic with solid KOH pellets, extracted twice with ethyl acetate and discarded. The final organics were then dried over MgSO$_4$ and the solvent was removed to yield 1.8 g (57%) of solid. HPLC-MS calcd. for $C_{17}H_{26}N_2O_2$ (M+H$^+$) 291.2, found 291.2.

Step B

The product from Step A (1.3 g, 4.5 mmol) was treated with 6 M HCl (20 mL) in a sealed reaction vessel and heated to 90° C. for 3 days. The reaction was cooled to room temperature and the solvent was removed. Analysis of the mixture by HPLC-MS indicated that the reaction was roughly half done. The reaction was diluted with water and filtered. The aqueous solution was then made basic with solid KOH and extracted twice with ethyl acetate and organics were discarded. The aqueous solution was then brought to pH 5 with 1 M HCl and extracted with ethyl acetate. The organics from the last extraction were dried over MgSO$_4$ and the solvent was removed to yield 500 mg (47%) of solid: $^1$H NMR (CDCl$_3$, 400 MHz) δ 1.72-1.87 (m, 2H), 1.84-2.03 (m, 2H), 2.13 (s, 1H), 2.76-2.89 (m, 1H), 2.87-3.00 (m, 1H), 3.05-3.26 (m, 2H), 3.30-3.45 (m, 2H), 6.80-6.90 (m, 1H), 7.00-7.10 (m, 2H), 10.75-10.95 (m, 2H).

Step C

The product from Step B (440 mg, 1.87 mmol) was suspended in tBuOH and treated with diphenylphosphoryl azide (618 mg, 2.24 mmol) followed by triethylamine (454 mg, 4.49 mmol). The reaction was then refluxed overnight and the solvent was removed. The reaction was partitioned between ethyl acetate and water and the water was discarded. The organics were extracted with 1 M NaOH twice and water twice. The solvent was removed and the reaction was treated with MeOH. After being allowed to crystallize overnight, the solid was filtered off and the mother liquor was rotary evaporated and purified by silica gel column chromatography using a linear gradient of ethyl acetate and hexane to afford the product the Boc protected piperidine amine as a solid (120 mg, 21%): $^1$H NMR (CDCl$_3$, 400 MHz) δ 1.48 (s, 9H), 1.50-1.70 (m, 1H), 1.65-1.91 (m, 3H), 2.80-3.10 (m, 3H), 3.21 (d, 1H, J=10.8), 3.78 (s, 1H), 3.83-3.93 (m, 1H), 4.94-5.10 (m, 1H), 6.84 (d, 1H, J=9.0), 6.92 (d, 1H, J=9.0); HPLC-MS calcd. for $C_{17}H_{26}N_2O_3$ (M+H$^+$) 307.2, found 307.2.

Step D

The material from Step C (60 mg, 200/mol) was charged to a 25 mL round bottom flask and treated with MeOH (1 mL) and 4 M HCl in dioxane (1 mL). After 4 h, the solvent was removed and the reaction was dried on the high vacuum overnight. The resulting material was treated with (S)-4-Methyl-2-(3-methyl-benzoylamino)-pentanoic acid (59 mg, 240 μmol, prepared according to Example 3, Step A) and HATU (96 mg, 250 μmol) and dissolved in DMF (2 mL). The resulting solution was treated with DIPEA (126 mg, 980 μmol) and allowed to stir for 6 hours. The reaction was diluted with ethyl acetate and extracted with water twice and 1 M NaOH twice, dried over MgSO$_4$ and rotary evaporated. The resulting oil was chromatographed over silica gel using ethyl acetate and hexane as solvents. The two diastereomers of the product were separated and were arbitrarily assigned the chirality about the piperidine carbon.

The faster eluting compound (16.6 mg, 19%) was assigned as Example 31: $^1$H NMR (CDCl$_3$, 400 MHz) δ 0.95-1.05 (m, 6H), 1.64-1.90 (m, 8H), 2.39 (s, 3H), 2.89-2.98 (m, 2H), 3.03-3.11 (m, 1H), 3.14 (dd, 1H, J$_1$=2.8, J$_2$=11.8), 3.77 (s, 3H), 4.13-4.22 (m, 1H), 4.67-4.76 (m, 1H), 6.70 (d, 1H, J=8.1), 6.76 (d, 1H, J=7.6), 6.78-6.83 (m, 2H), 6.85-6.91 (m, 2H), 7.29-7.34 (m, 2H), 7.54-7.62 (m, 2H). The slower eluting compound (18.3 mg, 21.5%) was assigned as Example 32: $^1$H NMR (CDCl$_3$, 400 MHz) δ 0.95-1.04 (m, 6H), 1.56-1.90 (m, 8H), 2.40 (s, 3H), 2.90-2.98 (m, 2H), 3.02-3.12 (m, 1H), 3.20 (dd, 1H, J$_1$=2.8, J$_2$=11.6), 3.79 (s, 3H), 4.13-4.21 (m, 1H), 4.63-4.72 (m, 1H), 6.71 (d, 1H, J=8.1), 6.74 (d, 1H, J=7.6), 6.82-6.86 (m, 2H), 6.88-6.94 (m, 2H), 7.29-7.34 (m, 2H), 7.57-7.63 (m, 2H).

Example 33

N-{1-(S)-[cis-2-(4-Methoxy-phenylamino)-cyclohexyl-carbamoyl]-3-methyl-butyl}-3-methyl-benzamide. The title compound was prepared according to the procedures of Examples 20 and 21, except that cis-diaminocyclohexane was used in the Step A. The final material was purified by reverse phase preparative HPLC using TFA as a modifier. The final compound is therefore a partial TFA salt and the properties are reported for the material as it appeared after solvent removal (20%): $^1$H NMR (CDCl$_3$, 400 MHz) δ 0.91 (d, 3H, J=6.1), 0.95 (d, 3H, J=6.2), 1.21-1.35 (m, 1H), 1.35-1.48 (m, 1H), 1.51-1.97 (m, 9H), 2.29 (s, 3H), 3.71-3.80 (m, 1H), 3.80 (s, 3H), 4.36-4.61 (m, 2H), 6.83-6.91 (m, 2H), 7.18-7.31 (m, 2H), 7.38-7.53 (m, 4H), 7.63-7.78 (m, 1H), 8.33-8.41 (m, 1H), 8.80-9.50 (m, 2H).

Example 34

N-{1-(S)-[trans-2-(4-Methoxy-phenylamino)-cyclohexylcarbamoyl]-3-methyl-butyl}-3-methyl-benzamide. The title compound was prepared according to the procedures of Examples 20 and 21, except that trans-diaminocyclohexane was used in the Step A. The final material was purified by reverse phase preparative HPLC using TFA as a modifier. The final compound is therefore a partial TFA salt and the properties are reported for the material as it appeared after solvent removal (20%): $^1$H NMR (CDCl$_3$, 400 MHz) δ 0.85-1.05 (m, 6H), 1.05-1.41 (m, 3H), 1.43-1.51 (m, 1H), 1.60-1.96 (m, 7H), 2.32 (s, 3H), 3.81 (s, 3H), 3.70-3.95 (m, 2H), 4.24-4.33 (m, 1H), 6.88 (d, 1H, J=8.6), 7.22-7.39 (m, 4H), 7.51-7.59 (m, 2H), 7.74-7.85 (m, 1H), 8.68-8.80 (m, 1H), 9.30-9.90 (m, 2H).

Example 35

N-{1-(S)-[1-(R)-Benzyloxymethyl-2-(4-methoxy-phenylamino)-ethylcarbamoyl]-3-methyl-butyl}-3-methyl-benzamide Step A N-Boc-OBn-Serine (750 mg, 2.54 mmol), p-anisidine (344 mg, 2.79 mmol) and HOBt (377 mg, 2.79 mmol) were charged to a 50 mL roundbottom flask and treated with DCM (6 mL). The reaction was then treated with EDCI (535 mg, 2.79 mmol) and allowed to stir for 2 hours. The reaction was then diluted with ethyl acetate and extracted twice with water, twice with 1 M HCl and twice with 1 M NaOH. The organics were then dried over MgSO$_4$ and the solvent was removed to afford 450 mg (44%) of a white solid: $^1$H NMR (CDCl$_3$, 400 MHz) δ 1.49 (s, 9H), 3.63-3.72 (m, 1H), 3.81 (s, 3H), 4.00-4.08 (m, 1H), 4.47-4.50 (m, 1H), 4.55-4.70 (m, 2H), 5.45-5.60 (m, 1H), 6.87 (d, 2H, J=8.8), 7.30-7.41 (m, 7H), 8.20-8.33 (m, 1H); HPLC-MS calcd. for C$_{22}$H$_{28}$N$_2$O$_5$ (M+H$^+$) 401.2, found 401.4.

Step B

The product from Step A (400 mg, 1.00 mmol) was added to an ice cold solution of borane (1 M) in THF. The cooling bath was removed and the reaction was allowed to stir for 24 h at which point the excess reagent was quenched using 5% NaHSO$_4$. The reaction was diluted with ethyl acetate and extracted twice with 1 M NaOH. The organics were dried over MgSO$_4$ and the solvent was removed. The resulting residue contained material that was missing the Boc group and some material that still had it (by HPLC-MS). The oil was treated with MeOH (2 mL) and 4 M HCl (2 mL) and stirred for 3 hours. The solvent was then removed and the reaction was partitioned between ethyl acetate and 1 M NaOH. The aqueous phase was extracted twice more with ethyl acetate and the combined organics were dried over MgSO$_4$ and the solvent was removed. The residue was treated with (S)-4-Methyl-2-(3-methyl-benzoylamino)-pentanoic acid (249 mg, 1 mmol, obtained from Example 3, Step A), HOBt (148 mg, 1.1 mmol) and DCM (5 mL). The reaction was then treated with EDCI (211 mg, 1.1 mmol) and allowed to stir for 3 hours. The reaction was then diluted with ethyl acetate and extracted with 1 M NaOH twice. The combined organics were dried over MgSO$_4$ and the solvent was removed. The residue was purified by silica gel column chromatography using ethyl acetate and hexane as solvents to afford a white solid (100 mg, 19%). The material is most likely partially racemized at the leucine so the data are reported for the major species: $^1$H NMR (CDCl$_3$, 400 MHz) δ 0.90-1.02 (m, 6H), 1.62-1.79 (m, 3H), 2.38 (s, 3H), 3.24-3.38 (m, 2H), 3.51 (dd, 1H, J$_1$=J$_2$=5.3), 3.61-3.65 (m, 1H), 3.75 (s, 3H), 3.70-3.87 (m, 1H), 4.24-4.37 (m, 1H), 4.68-4.78 (m, 2H), 6.59 (d, 2H, J$_1$=8.5), 6.77 (d, 2H, J$_1$=8.4), 6.89 (d, 2H, J$_1$=8.0), 7.26-7.40 (m, 6H), 7.58-7.66 (m, 2H); HPLC-MS calcd. for C$_{31}$H$_{39}$N$_3$O$_4$ (M+H$^+$) 518.3, found 518.3.

Example 36

N—(S)-{[1-(R)-Benzyloxymethyl-2-(5-fluoro-2,3-dihydro-indol-1-yl)-ethylcarbamoyl]-phenyl-methyl}-3-methoxy-benzamide. Following the procedures of Example 22, except using N-Boc-OBn-serinol, 5-fluoroindoline, (L)-phenylglycine and anisoyl chloride as starting materials, the title compound was prepared. The chiral center on the phenylglycine completely racemized during the reaction so the data are reported for the 50-50 diastereomeric mixture (60% yield): $^1$H NMR (CDCl$_3$, 400 MHz) δ 2.75-2.82 (m, 1H), 2.86-2.93 (m, 1H), 2.96 (dd, 0.5H, J$_1$=7.3, J$_2$=13.7), 3.07 (dd, 0.5H, J$_1$=6.0, J$_2$=13.8), 3.12-3.18 (m, 2H), 3.32-3.42 (m, 1.5H), 3.55 (dd, 0.5H, J$_1$=4.5, J$_2$=9.3), 3.69-3.56 (m, 1H), 3.82 (s, 3H), 4.23-4.34 (m, 1H), 4.36 (dd, 1H, J$_1$=11.9, J$_2$=21.2), 4.52 (dd, 1H, J=11.9, J$_2$=18.7), 5.58 (d, 1H, J=6.3), 6.13 (d, 0.5H, J=8.3), 6.12-6.28 (m, 2H), 6.41 (dd, 0.5H, J$_1$=4.0, J$_2$=8.5), 6.11-6.82 (m, 2H), 7.04 (d, 1H, J=7.9), 7.12-7.17 (m, 1H), 7.25-7.47 (m, 11H), 7.54 (dd, 1H, J$_1$=6.5, J$_2$=11.2); HPLC-MS calcd. for C$_{34}$H$_{34}$FN$_3$O$_4$ (M+H$^+$) 568.3, found 568.3.

Example 37

N-[1-(S)-[1-(R)-Benzyloxymethyl-2-(5-fluoro-2,3-dihydro-indol-1-yl)-ethylcarbamoyl]-2-(4-fluoro-phenyl)-ethyl]-3-methoxy-benzamide. Following the procedures of Example 22, except using N-Boc-OBn-serinol, 5-fluoroindoline, (L)-4-fluoropheylalanine and anisoyl chloride as starting materials, the title compound was prepared. The chiral center on the 4-fluorophnylalanine partially racemized during the reaction and the data are reported for the major diastereomer (30% yield): $^1$H NMR (CDCl$_3$, 400 MHz) δ 2.85-3.24 (m, 6H), 3.24-3.47 (m, 3H), 3.53-3.64 (m, 1H), 3.81 (s, 3H), 4.14-4.22 (m, 1H), 4.37-4.49 (m, 2H), 4.75 (dd, 1H, J$_1$=7.2, J$_2$=14.0), 6.08-6.17 (m, 1H), 6.38-6.43 (m, 1H), 6.67-6.86 (m, 2H), 6.85-6.95 (m, 2H), 7.00-7.06 (m, 1H), 7.14-7.33 (m, 11H); HPLC-MS calcd. for C$_{35}$H$_{35}$F$_2$N$_3$O$_4$ (M+H$^+$) 600.3, found 600.5.

Example 38

N-{1-(S)-[(2-Benzyloxy-1-(R)-(5-fluoro-2,3-dihydro-indol-1-ylmethyl)-ethylcarbamoyl]-3-cyclohexyl-propyl}-3-methoxy-benzamide. Following the procedures of Example 22, except using 5-fluoroindoline, m-anisoyl chloride, (R)-(+)-3-benzyloxy-2-(tert-butoxycarbonylamino)-1-propanol and (S)-2-amino-4-cyclohexyl-butyric acid as starting materials, the title compound was prepared as a mixture of two diastereomers. HPLC-MS calcd. for $C_{36}H_{44}FN_3O_4$ (M+H$^+$) 602.3, found 602.5.

Example 39 and Example 40

N-{3-Cyclohexyl-1-(S)-[2-(5-fluoro-2,3-dihydro-indol-1-yl)-1-(R)-hydroxymethyl-ethylcarbamoyl]-propyl}-3-methoxy-benzamide and N-{3-Cyclohexyl-1-(R)-[(S)-2-(5-fluoro-2,3-dihydro-indol-1-yl)-1-(R)-hydroxymethyl-ethylcarbamoyl]-propyl}-3-methoxy-benzamide. The title compound of Example 38 (492 mg, 818 μmol) and 10% Pd/C (20 mg) were treated with MeOH (3.5 mL) and 4 M HCl in dioxane (0.5 mL). The atmosphere in the reaction was then exchanged for hydrogen and the reaction was stirred under hydrogen for 1 h. The atmosphere in the reaction was then exchanged back to nitrogen and the reaction was filtered through a plug of celite and the solvent was removed. The reaction was diluted with DCM and extracted with saturated aqueous NaHCO$_3$ solution. The organics were dried over MgSO$_4$ and the solvent was removed. The residue was purified by silica gel column chromatography using ethyl acetate and hexane as solvents to afford 2 products. The faster running material (Example 39) was present in much less abundance than the slower material (Example 40) and was assigned as being the diastereomer that was racemized during the coupling step. The yields and data are as follows:

Example 39

(80 mg, 18% yield); $^1$H NMR (CDCl$_3$, 400 MHz) δ 0.71-0.84 (m, 2H), 0.98-1.22 (m, 6H), 1.51-1.65 (m, 5H), 1.62-1.75 (m, 1H), 1.85-1.96 (m, 1H), 2.80-2.89 (m, 2H), 3.01-3.09 (m, 1H), 3.12-3.22 (m, 1H), 3.20-3.32 (m, 1H), 3.36-3.44 (m, 1H), 3.58-3.76 (m, 2H), 3.76 (s, 3H), 4.06-4.14 (m, 1H), 4.52 (dd, 1H, $J_1$=7.5, $J_2$=13.7), 6.39-6.47 (m, 1H), 6.61-6.68 (m, 1H), 6.68-6.81 (m, 2H), 6.89-7.02 (m, 2H), 7.18-7.28 (m, 3H); HPLC-MS calcd. for $C_{29}H_{38}FN_3O_4$ (M+H$^+$) 512.3, found 512.5.

Example 40

(270 mg, 65% yield); $^1$H NMR (CDCl$_3$, 400 MHz) δ 0.61-0.77 (m, 2H), 0.93-1.20 (m, 6H), 1.47-1.60 (m, 5H), 1.61-1.73 (m, 1H), 1.77-1.89 (m, 1H), 2.78-2.81 (m, 2H), 3.02 (dd, 1H, $J_1$=6.5, $J_2$=13.5), 3.15-3.29 (m, 2H), 3.40-3.50 (m, 1H), 3.62-3.75 (m, 2H), 3.75 (s, 3H), 4.09-4.18 (m, 1H), 4.53 (dd, 1H, $J_1$=7.0, $J_2$=13.8), 6.36-6.42 (m, 1H), 6.61-6.68 (m, 1H), 6.69-6.74 (m, 1H), 6.93-6.99 (m, 2H), 7.02-7.12 (m, 1H), 7.20-7.27 (m, 3H); HPLC-MS calcd. for $C_{29}H_{38}FN_3O_4$ (M+H$^+$) 512.3, found 512.5.

Example 41

1H-Indole-2-carboxylic acid {(1S)-[2-benzyloxy-(1R)-(5-fluoro-2,3-dihydro-indol-1-ylmethyl)-ethylcarbamoyl]-3-cyclohexyl-propyl}-amide. Following the procedures of Example 22, except using 5-fluoroindoline, 2-indolecarboxylic acid, (R)-(+)-3-benzyloxy-2-(tert-butoxycarbonylamino)-1-propanol and (S)-2-amino-4-cyclohexyl-butyric acid as starting materials, the title compound was prepared. The final compound was isolated as a 5:1 mixture of diastereomers. HPLC-MS calcd. for $C_{37}H_{43}FN_4O_3$ (M+H) 611.3, found 611.6. $^1$H NMR (CDCl$_3$, 400 MHz) δ 0.47-1.36 (m, 13H), 1.47-1.67 (m, 2H), 2.89 (broad s, 2H), 3.34-3.59 (m, 6H), 4.01 (m, 2H), 4.41 (m, 2H), 6.35-7.41 (m, 10H), 9.61 (broad s, 1H).

Example 42

(S,S)-5-(5-Fluoro-2,3-dihydro-indol-1-yl)-4-[4-methyl-2-(3-methyl-benzoylamino)-pentanoylamino]-pentanoic acid benzyl ester. N-Boc-(L)-glutamic acid-6-benzyl ester (2.00 g, 5.93 mmol) was dissolved in THF (5 mL) and cooled to ice bath temperature and treated with a 1 M solution of borane in THF (12 mL, 12 mmol). After 1.5 hours of stirring while cold, the reaction was cautiously quenched with MeOH followed by a solution of 5% KHSO$_4$ in water. The reaction was then diluted with ethyl acetate and extracted 4 times with 1 M NaOH solution. The organics were dried over MgSO$_4$ and the solvent was removed. The residue was purified by silica gel column chromatography using ethyl acetate and hexane as solvents to afford a white solid (900 mg, 47%); HPLC-MS calcd. for $C_{17}H_{25}NO_5$ (M+H$^+$) 324.2, found 324.2. Following the procedures of Example 22, this material was converted to the title compound (80% overall yield): $^1$H NMR (CDCl$_3$, 400 MHz) δ 0.84-0.94 (m, 6H), 1.57-1.72 (m, 3H), 1.72-1.88 (m, 1H), 2.02-2.13 (m, 1H), 2.36 (s, 3H), 2.41-2.50 (m, 2H), 2.86-3.04 (m, 2H), 3.16 (dd, 1H, $J_1$=6.6, $J_2$=12.8), 3.26-3.38 (m, 1H), 3.47 (dd, 1H, $J_1$=7.8, $J_2$=15.9), 4.13-4.27 (m, 1H), 4.63-4.72 (m, 1H), 5.06 (s, 2H), 6.31-6.37 (m, 2H), 6.69 (dd, 1H, $J_1$=$J_2$=8.9), 6.79 (d, 1H, J=8.0), 6.86 (d, 1H, J=7.9), 6.98 (d, 1H, J=8.3), 7.24-7.39 (m, 6H), 7.52-7.60 (m, 2H); HPLC-MS calcd. for $C_{34}H_{40}FN_3O_4$ (M+H$^+$) 574.3, found 574.5.

Example 43

(S,S)-5-(5-Fluoro-2,3-dihydro-indol-1-yl)-4-[4-methyl-2-(3-methyl-benzoylamino)-pentanoylamino]-pentanoic acid. The title compound of Example 42 (200 mg, 0.348 mmol) and 10% Pd/C were treated with MeOH (2 mL) and the atmosphere in the reaction was switched to hydrogen. After stirring overnight, the atmosphere in the reaction was switched back to nitrogen and the reaction was filtered through celite. Removal of solvent and drying afforded a white solid (168 mg, 94); HPLC-MS calcd. for $C_{27}H_{34}FN_3O_4$ (M+H$^+$) 484.3, found 484.4.

Example 44

(S,S)—N-{1-[3-Carbamoyl-1-(5-fluoro-2,3-dihydro-indol-1-ylmethyl)-propylcarbamoyl]-3-methyl-butyl}-3-methyl-benzamide. The title compound of Example 43 (30 mg, 61 μmol) was treated with dioxane (2 mL) and concentrated ammonia (0.2 mL). HATU (35 mg, 92 μmol) was added and the reaction was stirred overnight. Another portion of HATU (80 mg, 210 μmol) was added and the reaction was stirred for an additional 3 hours. The reaction was then diluted with ethyl acetate and extracted once with 1 M NaOH solution. The organics were dried over MgSO$_4$ and the solvent was removed. The residue was purified by silica gel column chromatography using DCM and methanol as solvents to afford the title compound (25 mg, 84%); $^1$H NMR (CDCl$_3$, 400 MHz) δ 0.90 (s, 3H), 0.91 (s, 3H), 0.88-0.99 (m, 1H), 1.58-1.80 (m, 4H), 1.97-2.12 (m, 2H), 2.23-2.30 (m, 2H), 2.37 (s, 3H), 2.82 (s, 2H), 2.85-3.04 (m, 3H), 3.15 (dd, 1H, $J_1$=6.5, $J_2$=13.6), 3.34 (dd, 1H, $J_1$=8.4, $J_2$=16.9), 3.48 (dd, 1H, $J_1$=8.1, $J_2$=16.0), 4.12-4.21 (m, 1H), 4.40-4.72 (m, 1H), 5.86 (s, 1H), 6.32-6.47 (m, 2H), 6.72 (dd, 1H, $J_1$=$J_2$=8.4), 6.79 (d, 1H, J=7.4), 6.94 (d, 1H, J=7.6), 7.06 (d, 1H, J=8.4), 7.23-7.36 (m, 2H), 7.52-7.61 (m, 2H); HPLC-MS calcd. for $C_{27}H_{35}FN_4O_3$ (M+H$^+$) 483.3, found 483.5.

Example 45

(S,S)—N-{1-[1-(5-Fluoro-2,3-dihydro-indol-1-ylmethyl)-3-ureido-propylcarbamoyl]-3-methyl-butyl}-3-methyl-benzamide. The title compound of Example 43 (58.8 mg, 121 µmol) was treated with tBuOH (2 mL), diphenylphosphoryl azide (70 mg, 254 µmol) and triethylamine (60 mg, 592 mmol). The reaction was heated at 90° C. for 3 hours and cooled to rt. HPLC-MS analysis indicated that the Curtius rearrangement had occurred, but that the intermediate isocyanate had been hydrolyzed to the carbamic acid and activated as the azide rather than being intercepted by the alcohol. The solvent was removed and the reaction was extractively worked up with ethyl acetate and water, dried over $MgSO_4$ and rotary evaporated. The residue was treated with concentrated ammonia and allowed to stir overnight. The reaction was again extractively worked up and then chromatographed on silica gel using DCM an MeOH as eluent to afford the title material (12 mg, 20%); $^1H$ NMR ($CDCl_3$, 400 MHz) δ 0.88 (d, 3H, J=6.3), 0.91 (d, 3H, J=6.3), 1.55-1.80 (m, 4H), 1.85-1.95 (m, 1H), 2.37 (s, 3H), 2.90-3.03 (m, 3H), 3.06-3.26 (m, 2H), 3.37 (dd, 1H, $J_1$=8.7, $J_2$=17.1), 3.48-3.61 (m, 2H), 4.01-4.26 (m, 1H), 4.26-4.38 (m, 1H), 4.50 (dd, 1H, $J_1$=7.7, $J_2$=15.0), 6.00-6.20 (m, 1H), 6.49 (dd, 1H, $J_1$=4.0, $J_2$=8.4), 6.74 (ddd, 1H, $J_1$=2.5, $J_2$=$J_3$=8.9), 6.78-6.83 (m, 1H), 7.16-7.20 (m, 1H), 7.23-7.37 (m, 3H), 7.50-7.57 (m, 2H).

Example 46

(S,S)-3-[4-Cyclohexyl-2-(3-methoxy-benzoylamino)-butyrylamino]-4-(5-fluoro-2,3-dihydro-indol-1-yl)-butyric acid benzyl ester. Following the procedures of Example 42, the title compound was prepared (82% overall yield); HPLC-MS calcd. for $C_{37}H_{44}FN_3O_5$ (M+H$^+$) 630.3, found 630.5.

Example 47

(S,S)-3-[4-Cyclohexyl-2-(3-methoxy-benzoylamino)-butyrylamino]-4-(5-fluoro-2,3-dihydro-indol-1-yl)-butyric acid. The title compound of Example 46 (300 mg, 0.476 mmol) was treated with 10% Pd/C (40 mg), MeOH (5 mL) and THF (5 mL). The atmosphere in the reaction was exchanged for hydrogen and the reaction was allowed to stir for 1 h under a balloon of hydrogen. The atmosphere was then exchanged back to nitrogen, the reaction was filtered through a pad of celite and the solvent was removed to afford 244 mg (95%) of a crystalline solid; $^1H$ NMR (DMSO, 400 MHz) δ 0.55-0.88 (m, 2H), 1.00-1.22 (m, 7H), 2.93 (dd, 1H, $J_1$=5.8, $J_2$=13.6), 3.11 (dd, 1H, $J_1$=7.6, $J_2$=13.7), 3.25 (dd, 1H, $J_1$=8.7, $J_2$=17.5), 3.34 (s, 3H), 3.41-3.50 (m, 1H), 3.81 (s, 3H), 4.30-4.41 (m, 1H), 6.71-6.79 (m, 1H), 6.85-6.89 (m, 1H), 7.07-7.12 (m, 1H), 7.37 (dd, 1H, $J_1$=$J_2$=7.8), 7.40-7.48 (m, 2H), 7.98 (d, 1H, J=8.6), 8.32 (d, 1H, J=8.1); HPLC-MS calcd. for $C_{30}H_{38}FN_3O_5$ (M+H) 483.3, found 483.5.

Example 48

(S,S)—N-{1-[1-Benzyl-2-(5-fluoro-2,3-dihydro-indol-1-yl)-ethylcarbamoyl]-3-cyclohexyl-propyl}-3-methoxy-benzamide. Following the procedures of Example 22, except using N-Boc-(L)-phenylalaminol, the title compound was prepared. The final material was purified by preparative HPLC using TFA as a modifier. The final compound is therefore a partial TFA salt and the properties are reported for the material as it appeared after solvent removal. (40% overall yield); $^1H$ NMR ($CDCl_3$, 400 MHz) δ 0.60-0.78 (m, 2H), 0.82-1.15 (m, 6H), 1.33-1.94 (m, 9H), 2.63-3.52 (m, 5H), 3.75-3.81 (m, 3H), 4.01-4.54 (m, 3H), 6.26-6.36 (m, 1H), 6.41-6.46 (m, 0.5H), 6.56-6.88 (m, 2H), 6.96-7.33 (m, 11H); HPLC-MS calcd. for $C_{35}H_{42}FN_3O_3$ (M+H$^+$) 572.3, found 572.5.

Example 49

(S,S)—N-{3-Cyclohexyl-1-[1-(5-fluoro-2,3-dihydro-indol-1-ylmethyl)-3-methyl-butylcarbamoyl]-propyl}-3-methoxy-benzamide. Following the procedures of Example 22, except using N-Boc-(L)-leucinol, the title compound was prepared. The final material was purified by preparative HPLC using TFA as a modifier. The final compound is therefore a partial TFA salt and the properties are reported for the material as it appeared after solvent removal (40% overall yield); $^1H$ NMR ($CDCl_3$, 400 MHz) δ 0.64-0.88 (m, 8H), 0.95-1.24 (m, 6H), 1.25-1.45 (m, 2H), 1.45-1.88 (m, 10H), 2.86-3.57 (m, 3H), 3.76-3.81 (m, 3H), 3.94-4.48 (m, 3H), 6.20-6.37 (m, 1H), 6.49-6.90 (m, 2H), 6.96-7.18 (m, 2H) 7.21-7.33 (m, 3H); HPLC-MS calcd. for $C_{32}H_{44}FN_3O_3$ (M+H$^+$) 538.3, found 538.5.

Example 50

(S,S)—N-{3-Cyclohexyl-1-[1-(5-fluoro-2,3-dihydro-indol-1-ylmethyl)-2-methyl-propylcarbamoyl]-propyl}-3-methoxy-benzamide. Following the procedures of Example 22, except using N-Boc-(L)-valinol, the title compound was prepared. The final material was purified by reverse phase preparative HPLC using TFA as a modifier. The final compound is therefore a partial TFA salt and the properties are reported for the material as it appeared after solvent removal (40% overall yield); $^1H$ NMR ($CDCl_3$, 400 MHz) δ 0.53-0.82 (m, 2H), 0.84-1.22 (m, 11H), 1.39-1.63 (m, 6H), 1.70-1.97 (m, 2H), 2.87-2.97 (m, 2H), 3.04-3.20 (m, 1H), 3.35-3.54 (m, 1H), 3.75-3.81 (m, 3H), 3.98-4.20 (m, 2H), 4.40-4.60 (m, 1H) 6.17-6.38 (m, 1H), 6.48-6.74 (m, 2H), 6.75-6.88 (m, 1H), 6.94-7.18 (m, 3H), 7.20-7.30 (m, 3H); HPLC-MS calcd. for $C_{31}H_{42}FN_3O_3$ (M+H$^+$) 524.3, found 524.5.

Example 51

(S,S)—N-{3-Cyclohexyl-1-[2-(5-fluoro-2,3-dihydro-indol-1-yl)-1-phenyl-ethylcarbamoyl]-propyl}-3-methoxy-benzamide. Following the procedures of Example 22, except using N-Boc-(L)-phenylglycinol, the title compound was prepared. The final material was purified by reverse phase preparative HPLC using TFA as a modifier. The final compound is therefore a partial TFA salt and the properties are reported for the material as it appeared after solvent removal (40% overall yield); $^1H$ NMR ($CDCl_3$, 400 MHz) δ 0.62-0.77 (m, 2H), 0.94-1.20 (m, 6H), 1.42-1.77 (m, 8H), 1.81-1.93 (m, 1H), 2.79-2.81 (m, 1H), 3.09-3.20 (m, 1H), 3.32-3.47 (m, 1H), 3.69-3.81 (m, 3H), 4.36-4.65 (m, 1H), 5.13-5.35 (m, 1H) 6.26-6.36 (m, 1H), 6.57-6.87 (m, 4H), 6.73-6.99 (m, 1H), 7.06-7.35 (m, 8H); HPLC-MS calcd. for $C_{34}H_{40}FN_3O_3$ (M+H$^+$) 558.3, found 558.5.

Example 52

(S,S)—N-{3-Cyclohexyl-1-[1-(5-fluoro-2,3-dihydro-indol-1-ylmethyl)-3-morpholin-4-yl-propylcarbamoyl]-propyl}-3-methoxy-benzamide The title compound was prepared following the procedure described in Example 151. $^1H$ NMR (MeOD, 400 MHz) δ 0.65-0.81 (m, 2H), 0.85-0.99 (m, 1H), 1.03-1.34 (m, 11H), 1.52-1.81 (m, 9H), 1.81-1.98 (m, 2H), 2.15-2.25 (m, 1H), 2.85-2.98 (m, 2H), 2.99 (dd, 1H, $J_1$=4.9, $J_2$=13.7), 3.10-3.47 (m, 11H), 3.53-3.63 (m, 2H), 3.86 (s, 3H), 3.62-3.90 (m, 5H), 3.93-4.03 (m, 1H), 4.05-4.14 (m, 1H), 4.22-4.35 (m, 2H), 4.45-4.55 (m, 1H), 6.51 (dd, 1H, $J_1$=4.1, $J_2$=8.6), 6.75 (ddd, 1H, J=2.5, $J_2$=$J_3$=8.9), 6.83 (dd, 1H, J=2.5, $J_2$=8.4), 7.09-7.14 (m, 2H), 7.36-7.45 (m, 4H); HPLC-MS calcd. for $C_{34}H_{47}FN_4O_4$ (M+H$^+$) 595.4, found 595.5.

Example 53

N-{1-(S)-[2-(R)-Benzyloxy-1-(R)-(5-fluoro-2,3-dihydro-indol-1-ylmethyl)-propylcarbamoyl]-3-cyclohexyl-propyl}-3-methoxy-benzamide. Following the procedures of Example 22, except using N-Boc-O-Bn-ether-(L)-threoninol, the title compound was prepared. The final material was purified by preparative HPLC using TFA as a modifier. The final compound is therefore a partial TFA salt and the properties are reported for the material as it appeared after solvent removal (40% overall yield); $^1$H NMR (CDCl$_3$, 400 MHz) δ 0.60-0.85 (m, 3H), 0.85-1.25 (m, 9H), 1.44-1.85 (m, 8H), 2.80-3.29 (m, 2H), 2.94-3.08 (m, 2H), 3.17-3.25 (m, 1H), 3.28-3.38 (m, 2H), 3.75-3.80 (m, 3H), 4.04-4.13 (m, 1H), 4.20-4.32 (m, 2H) 4.47-4.65 (m, 3H), 6.18-6.48 (m, 2H), 6.58-6.91 (m, 3H), 6.95-7.03 (m, 1H), 7.09-7.41 (m, 8H); HPLC-MS calcd. for $C_{37}H_{46}FN_3O_4$ (M+H$^+$) 616.3, found 616.5.

Example 54

N-{1-(R)-[1-(R)-Benzylsulfanylmethyl-2-(5-fluoro-2,3-dihydro-indol-1-yl)-ethylcarbamoyl-3-cyclohexyl-propyl}-3-methoxy-benzamide. Following the procedures of Example 22, except using N-Boc-S-Bn-(L)-cystinol, the title compound was prepared. The final material was purified by preparative HPLC using TFA as a modifier. (20% overall yield); HPLC-MS calcd. for $C_{36}H_{44}F3O_3S$ (M+H$^+$) 618.3, found 618.5.

Example 55

(S,S)-[5-[4-Cyclohexyl-2-(3-methoxy-benzoylamino)-butyrylamino]-6-(5-fluoro-2,3-dihydro-indol-1-yl)-hexyl]-carbamic acid benzyl ester. Following the procedures of Example 22, except using N-Boc-N-Cbz-(L)-lysinol, the title compound was prepared. The final material was purified by reverse phase preparative HPLC using TFA as a modifier. The final compound is therefore a partial TFA salt and the properties are reported for the material as it appeared after solvent removal (40% overall yield); $^1$H NMR (CDCl$_3$, 400 MHz) δ 0.58-0.83 (m, 2H), 0.93-1.22 (m, 7H), 1.22-1.95 (m, 16H), 2.76-3.48 (m, 8H), 3.72-3.79 (m, 3H), 4.00-4.23 (m, 2H), 4.42-4.55 (m, 1H), 4.80-5.08 (m, 3H), 6.23-6.45 (m, 2H), 6.30-7.12 (m, 5H) 7.17-7.30 (m, 8H); HPLC-MS calcd. for $C_{40}H_{51}FN_4O_5$ (M+H$^+$) 687.4, found 687.5.

Example 56

1-(6-Chloro-pyridazin-3-yl)-piperidine-4-carboxylic acid (S)-{2-cyclohexyl-1-[2-(5-fluoro-2,3-dihydro-indol-1-yl)-ethylcarbamoyl]-ethyl}-amide;* $C_{29}H_{38}ClFN_6O_2$; $^1$H NMR (CDCl$_3$) δ(ppm) 7.97 (m, 1H), 7.27 (m, 1H), 7.18 (m, 1H), 7.09 (m, 1H), 6.95 (m, 3H), 4.22 (m, 3H), 3.77 (m, 2H), 3.61 (m, 2H), 3.41 (m, 2H), 3.10 (m, 4H), 2.66 (m, 1H), 1.89 (m, 2H), 1.72 (m, 2H), 1.60 (m, 7H), 1.09 (m, 4H), 0.81 (m, 2H); LCMS: 557.5 (M+H)$^+$.

Example 57

1-(4-Methoxy-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;*

$^1$H NMR (CDCl$_3$) δ(ppm) 7.99 (m, 1H), 7.60 (m, 2H), 7.17 (m, 1H), 6.97 (m, 4H), 6.62 (d, J=6.4 Hz, 1H), 4.24 (m, 1H), 3.80 (s, 3H), 3.77 (m, 1H), 3.64 (m, 4H), 3.40 (m, 2H), 3.17 (m, 2H), 2.18 (m, 2H), 2.04 (m, 1H), 1.74 (m, 2H), 1.60 (m, 9H), 1.44 (m, 1H), 1.17 (m, 1H), 1.05 (m, 3H), 0.80 (m, 2H); LCMS: 615.5 (M+H)$^+$.

Example 58

1-Benzenesulfonyl-piperidine-4-carboxylic acid (S)-{2-cyclohexyl-1-[2-(5-fluoro-2,3-dihydro-indol-1-yl)-ethylcarbamoyl]-ethyl}-amide;* $C_{31}H_{41}FN_4O_4S$; $^1$H NMR (CDCl$_3$) δ(ppm) 7.95 (m, 1H), 7.66 (m, 3H), 7.51 (m, 3H), 7.13 (m, 1H), 6.97 (m, 1H), 6.58 (m, 1H), 4.24 (m, 1H), 3.72 (m, 4H), 3.61 (m, 2H), 3.39 (m, 2H), 3.16 (m, 2H), 2.20 (m, 2H), 2.11 (m, 1H), 1.68 (m, 2H), 1.58 (m, 9H), 1.17 (m, 1H), 1.04 (m, 3H), 0.80 (m, 2H); LCMS: 585.5 (M+H)$^+$.

Example 59

N-{2-cyclohexyl-1-(S)-[2-(5-fluoro-2,3-dihydro-indol-1-yl)-ethylcarbamoyl]-ethyl}-2-(2-fluoro-biphenyl-4-yl)-propionamide; $C_{34}H_{39}F_2N_3O_2$; LCMS: 560.6 (M+H)$^+$.

Example 60

N-{2-cyclohexyl-1-(S)-[2-(5-fluoro-2,3-dihydro-indol-1-yl)-ethylcarbamoyl]-ethyl}-2-p-tolyl-propionamide;* $C_{29}H_{38}FN_3O_2$; LCMS: 480.5 (M+H)$^+$

Example 61

N-{2-cyclohexyl-1-(S)-[2-(5-fluoro-2,3-dihydro-indol-1-yl)-ethylcarbamoyl]-ethyl}-2-o-tolyl-propionamide; $C_{29}H_{38}FN_3O_2$; LCMS: 480.5 (M+H)$^+$

Example 62

N-{2-cyclohexyl-1-(S)-[2-(5-fluoro-2,3-dihydro-indol-1-yl)-ethylcarbamoyl]-ethyl}-2-(4-fluoro-phenyl)-propionamide; $C_{28}H_{35}F_2N_3O_2$; LCMS: 484.5 (M+H)$^+$.

Example 63

1-Methyl-1H-imidazole-4-carboxylic acid (S)-{2-cyclohexyl-1-[2-(5-fluoro-2,3-dihydro-indol-1-yl)-ethylcarbamoyl]-ethyl}-amide;* $C_{24}H_{32}FN_5O_2$; $^1$H NMR (CD$_3$OD) δ(ppm) 8.63 (s, 1H), 7.86 (s, 1H), 6.70 (m, 1H), 6.60 (m, 1H), 6.36 (m, 1H), 4.46 (m, 1H), 3.83 (s, 3H), 3.31 (m, 4H), 3.08 (m, 2H), 2.83 (m, 2H), 1.56 (m, 7H), 1.25 (m, 1H), 1.07 (m, 3H), 0.81 (m, 2H); LCMS: 442.5 (M+H)$^+$.

Example 64

2-(4-Chloro-phenyl)-N-{2-cyclohexyl-1-(S)-[2-(5-fluoro-2,3-dihydro-indol-1-yl)-ethylcarbamoyl]-ethyl}-propionamide;* $C_{28}H_{35}ClFN_3O_2$; LCMS:(M+H) 500.4 (35ClM+H)$^+$, 502.5 (37ClM+H)$^+$.

Example 65

1-Benzyl-5-oxo-pyrrolidine-3-carboxylic acid (S)-{2-cyclohexyl-1-[2-(5-fluoro-2,3-dihydro-indol-1-yl)-ethylcarbamoyl]-ethyl}-amide;* $C_{31}H_{39}FN_4O_3$; LCMS: 535.5 (M+H)$^+$.

Example 66

1-(4-Fluoro-benzenesulfonyl)-piperidine-4-carboxylic acid (S)-{2-cyclohexyl-1-[2-(5-fluoro-2,3-dihydro-indol-1-yl)-ethylcarbamoyl]-ethyl}-amide;* $C_{31}H_{40}F_2N_4O_4S$; $^1$H NMR (CD$_3$OD) δ(ppm) 7.84 (m, 2H), 7.35 (m, 2H), 6.91 (m, 1H), 6.85 (m, 1H), 6.74 (m, 1H), 4.31 (m, 1H), 3.72 (m, 2H), 3.55 (m, 2H), 3.47 (m, 2H), 3.31 (m, 2H), 3.26 (m, 2H), 3.03 (m, 2H), 2.35 (m, 2H), 2.19 (m, 1H), 1.79 (m, 3H), 1.67 (m, 6H), 1.51 (m, 2H), 1.28 (m, 2H), 1.15 (m, 3H), 0.89 (m, 2H); LCMS: 603.5 (M+H)$^+$.

Example 67

N—(S)-{2-cyclohexyl-1-[2-(5-fluoro-2,3-dihydro-indol-1-yl)-ethylcarbamoyl]-ethyl}-4-(piperidin-4-yloxy)-benzamide; $C_{31}H_{41}FN_4O_3$; LCMS: 537.5 (M+H)$^+$.

Example 68

N—(S)-{2-cyclohexyl-1-[2-(5-fluoro-2,3-dihydro-indol-1-yl)-ethylcarbamoyl]-ethyl}-4-(1-methanesulfonyl-piperidin-4-yloxy)-benzamide;* $C_{32}H_{43}FN_4O_5S$; $^1$H NMR (CD$_3$OD) δ(ppm) 7.81 (m, 2H), 6.98 (m, 2H), 6.92 (m, 1H), 6.82 (m, 2H), 4.57 (m, 1H), 3.52 (m, 6H), 3.29 (m, 5H), 3.03 (m, 2H), 2.87 (s, 3H), 2.07 (m, 2H), 1.91 (m, 2H), 1.79 (m, 2H), 1.69 (m, 5H), 1.40 (m, 1H), 1.20 (m, 3H), 0.97 (m, 2H); LCMS: 615.5 (M+H)$^+$.

Example 69

4-(1-Acetyl-piperidin-4-yloxy)-N—(S)-{2-cyclohexyl-1-[2-(5-fluoro-2,3-dihydro-indol-1-yl)-ethylcarbamoyl]-ethyl}-benzamide;* $C_{33}H_{43}FN_4O_4$; $^1$H NMR (CD$_3$OD) δ(ppm) 7.81 (m, 2H), 7.01 (m, 2H), 6.93 (m, 1H), 6.82 (m, 1H), 6.75 (m, 1H), 4.74 (m, 1H), 4.58 (m, 1H), 3.79 (m, 2H), 3.54 (m, 6H), 3.30 (m, 2H), 3.01 (m, 2H), 2.13 (s, 3H), 2.00 (m, 2H), 1.69 (m, 9H), 1.40 (m, 1H), 1.19 (m, 3H), 0.95 (m, 2H); LCMS: 579.5 (M+H)$^+$.

Example 70

N-{2-cyclohexyl-1-(S)-[2-(5-fluoro-2,3-dihydro-indol-1-yl)-ethylcarbamoyl]-ethyl}-2-(R)-phenyl-propionamide;* $C_{28}H_{36}FN_3O_2$; $^1$H NMR (CD$_3$OD) δ(ppm) 7.27 (m, 5H), 6.94 (m, 1H), 6.82 (m, 1H), 6.82 (m, 1H), 6.67 (m, 1H), 4.33 (m, 1H), 3.72 (m, 1H), 3.36 (m, 4H), 2.94 (m, 2H), 1.69 (m, 5H), 1.55 (m, 2H), 1.44 (d, J=7.2 Hz, 3H), 1.17 (m, 4H), 0.93 (m, 2H); LCMS: 466.5 (M+H)$^+$.

Example 71

N—(S)-{2-cyclohexyl-1-[2-(5-fluoro-2,3-dihydro-indol-1-yl)-ethylcarbamoyl]-ethyl}-3-methyl-benzamide;* $C_{27}H_{34}FN_3O_2$; $^1$H NMR (CD$_3$OD) δ(ppm) 7.61 (m, 2H), 7.34 (m, 2H), 6.87 (m, 1H), 6.78 (m, 1H), 6.67 (m, 1H), 4.58 (m, 1H), 3.49 (m, 4H), 3.26 (m, 2H), 2.97 (m, 2H), 2.38 (s, 3H), 1.68 (m, 7H), 1.39 (m, 1H), 1.17 (m, 3H), 0.95 (m, 2H); LCMS: 452.5 (M+H)$^+$.

Example 72

5-Methanesulfonyl-thiophene-2-carboxylic acid (S)-{2-cyclohexyl-1-[2-(5-fluoro-2,3-dihydro-indol-1-yl)-ethylcarbamoyl]-ethyl}-amide;* $C_{25}H_{32}FN_3O_4S_2$; $^1$H NMR (CD$_3$OD) δ(ppm) 7.70 (m, 1H), 7.62 (m, 1H), 6.76 (m, 1H), 6.66 (m, 1H), 6.52 (m, 1H), 4.45 (m, 1H), 3.38 (m, 4H), 3.19 (m, 5H), 2.88 (m, 2H), 1.63 (m, 7H), 1.28 (m, 1H), 1.08 (m, 3H), 0.85 (m, 2H); LCMS: 522.5 (M+H)$^+$.

Example 73

5-Oxo-1-thiophen-2-ylmethyl-pyrrolidine-3-carboxylic acid (S)-{2-cyclohexyl-1-[2-(5-fluoro-2,3-dihydro-indol-1-yl)-ethylcarbamoyl]-ethyl}-amide; $^1$H NMR (CD$_3$OD) δ(ppm) 7.34 (m, 1H), 7.01 (m, 2H), 6.97 (m, 1H), 6.91 (m, 1H), 6.80 (m, 1H), 6.67 (m, 1H), 4.59 (m, 2H), 4.31 (m, 1H), 3.47 (m, 7H), 3.23 (m, 3H), 2.99 (m, 2H), 2.62 (m, 2H), 1.68 (m, 3H), 1.52 (m, 2H), 1.17 (m, 5H), 0.92 (m, 2H); LCMS: 541.5 (M+H)$^+$.

Example 74

1-Furan-2-ylmethyl-5-oxo-pyrrolidine-3-carboxylic acid (S)-{2-cyclohexyl-1-[2-(5-fluoro-2,3-dihydro-indol-1-yl)-ethylcarbamoyl]-ethyl}-amide;* $C_{29}H_{37}FN_4O_4$; $^1$H NMR (CD$_3$OD) δ(ppm) 7.34 (s, 1H), 6.79 (m, 1H), 6.68 (m, 1H), 6.50 (m, 1H), 6.23 (m, 2H), 4.33 (m, 1H), 4.27 (m, 2H), 3.37 (m, 7H), 3.21 (m, 3H), 2.87 (m, 2H), 2.50 (m, 2H), 1.57 (m, 3H), 1.43 (m, 2H), 1.06 (m, 5H), 0.81 (m, 2H); LCMS: 525.5 (M+H)$^+$.

Example 75

5-Phenyl-furan-2-carboxylic acid (S)-{2-cyclohexyl-1-[2-(5-fluoro-2,3-dihydro-indol-1-yl)-ethylcarbamoyl]-ethyl}-amide;* $C_{30}H_{34}FN_3O_3$; LCMS: 504.5 (M+H)$^+$.

Example 76

2-Phenyl-thiazole-4-carboxylic acid (S)-{2-cyclohexyl-1-[2-(5-fluoro-2,3-dihydro-indol-1-yl)-ethylcarbamoyl]-ethyl}-amide;* $C_{29}H_{33}FN_4O_2S$; LCMS: 521.5 (M+H)$^+$.

Example 77

1-Methanesulfonyl-piperidine-4-carboxylic acid (S)-{2-cyclohexyl-1-[2-(5-fluoro-2,3-dihydro-indol-1-yl)-ethylcarbamoyl]-ethyl}1-amide;* $C_{26}H_{39}FN_4O_4S$; LCMS: 523.5 (M+H)$^+$.

Example 78

5-Methyl-2-trifluoromethyl-furan-3-carboxylic acid (S)-{2-cyclohexyl-1-[2-(5-fluoro-2,3-dihydro-indol-1-yl)-ethylcarbamoyl]-ethyl}-amide;* $C_{26}H_{31}F_4N_3O_3$; $^1$H NMR (CD$_3$OD) δ(ppm) 6.86 (m, 1H), 6.77 (m, 1H), 6.62 (m, 1H), 6.41 (m, 1H), 4.50 (m, 1H), 3.48 (m, 4H), 3.24 (m, 2H), 2.99 (m, 2H), 2.34 (s, 3H), 1.64 (m, 7H), 1.35 (m, 1H), 1.17 (m, 3H), 0.92 (m, 2H); LCMS: 510.5 (M+H)$^+$.

Example 79

N—(S)-{2-cyclohexyl-1-[2-(5-fluoro-2,3-dihydro-indol-1-yl)-ethylcarbamoyl]-ethyl}-4-(methanesulfonylamino-methyl)-benzamide; $C_{28}H_{37}FN_4O_4S$; $^1$H NMR (CD$_3$OD) δ(ppm) 7.82 (m, 2H), 7.47 (m, 2H), 6.85 (m, 1H), 6.76 (m, 1H), 6.62 (m, 1H), 4.59 (m, 1H), 4.31 (s, 2H), 3.48 (m, 4H), 3.22 (m, 2H), 2.95 (m, 2H), 2.89 (s, 3H), 1.68 (m, 7H), 1.39 (m, 1H), 1.18 (m, 3H), 0.94 (m, 2H); LCMS: 545.5 (M+H)+.

Example 80

N—(S)-{2-cyclohexyl-1-[2-(5-fluoro-2,3-dihydro-indol-1-yl)-ethylcarbamoyl]-ethyl}-3-methanesulfonyl-benzamide; $C_{27}H_{34}FN_3O_4S$; 1H NMR (CD3OD) δ(ppm) 8.41 (m, 1H), 8.12 (m, 2H), 7.72 (m, 1H), 6.87 (m, 1H), 6.77 (m, 1H), 6.65 (m, 1H), 4.60 (m, 1H), 3.50 (m, 4H), 3.27 (m, 2H), 3.16 (s, 3H), 2.98 (m, 2H), 1.70 (m, 7H), 1.39 (m, 1H), 1.18 (m, 3H), 0.95 (m, 2H); LCMS: 516.5 (M+H)+.

Example 81

N—(S)-{2-cyclohexyl-1-[2-(5-fluoro-2,3-dihydro-indol-1-yl)-ethylcarbamoyl]-ethyl}-4-methanesulfonylamino-benzamide; $C_{27}H_{35}FN_4O_4S$; 1H NMR (CD3OD) δ(ppm) 7.81 (d, J=8.0 Hz, 2H), 7.28 (d, J=8.0 Hz, 2H), 6.90 (m, 1H), 6.79 (m, 1H), 6.71 (m, 1H), 4.58 (m, 1H), 3.52 (m, 4H), 3.28 (m, 2H), 3.02 (s, 3H), 2.98 (m, 2H), 1.68 (m, 7H), 1.38 (m, 1H), 1.18 (m, 3H), 0.95 (m, 2H); LCMS: 531.5 (M+H)+.

Example 82

5-Phenyl-thiophene-2-carboxylic acid (S)-{2-cyclohexyl-1-[2-(5-fluoro-2,3-dihydro-indol-1-yl)-ethylcarbamoyl]-ethyl}-amide; $C_{30}H_{34}FN_3O_2S$; 1H NMR (CD3OD) δ(ppm) 7.75 (m, 1H), 7.67 (m, 2H), 7.40 (m, 4H), 6.88 (m, 1H), 6.80 (m, 1H), 6.70 (m, 1H), 4.56 (m, 1H), 3.52 (m, 4H), 3.28 (m, 2H), 2.98 (m, 2H), 1.71 (m, 7H), 1.41 (m, 1H), 1.19 (m, 3H), 0.94 (m, 2H); LCMS: 521.5 (M+H)+.

Example 83

5-(3-Fluoro-phenyl)-furan-2-carboxylic acid {2-cyclohexyl-1-(S)-[1-(S)-methyl-2-(4-trifluoromethoxy-phenylamino)-ethylcarbamoyl]-ethyl}-amide;

The title compound was prepared according to the following scheme.

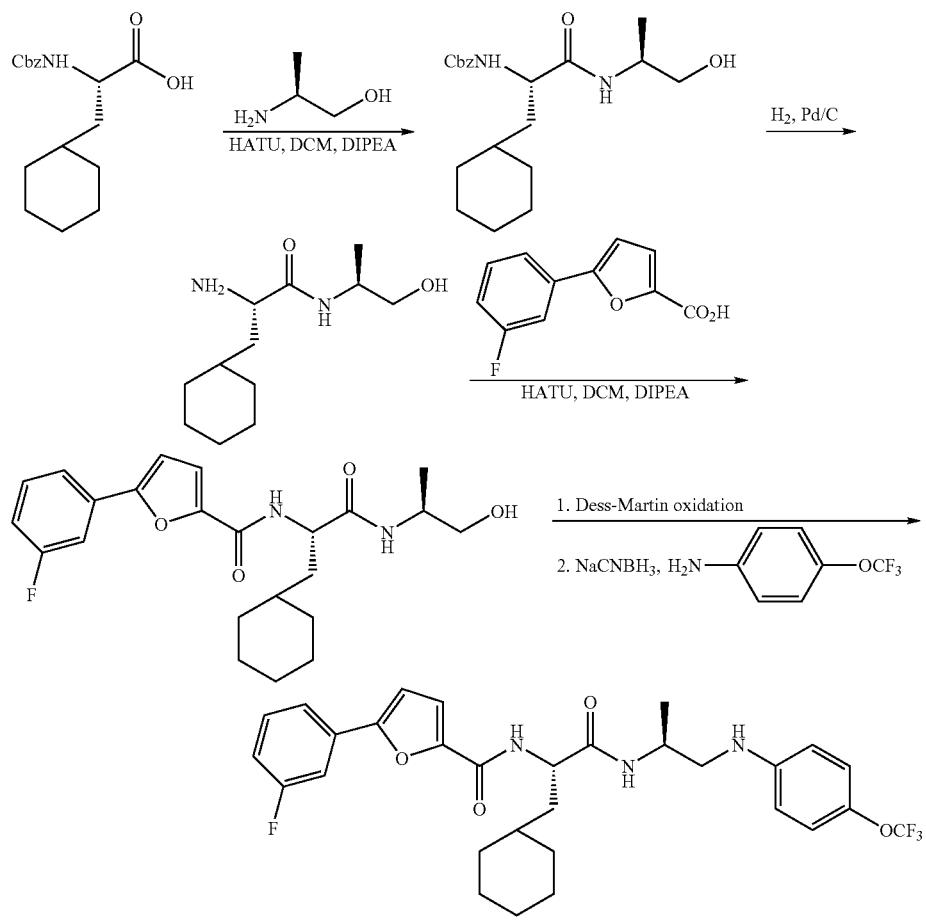

$C_{30}H_{33}F_4N_3O_4$; 1H NMR (CDCl3) δ(ppm) 7.51 (m, 1H), 7.41 (m, 1H), 7.32 (m, 2H), 7.08 (m, 7H), 6.67 (m, 1H), 4.44 (m, 1H), 4.17 (m, 1H), 3.45 (m, 1H), 3.23 (m, 1H), 1.65 (m, 7H), 1.26 (m, 4H), 1.08 (m, 3H), 0.98 (m, 2H); LCMS: 576.4 (M+H)+.

Example 84

5-(3-Fluoro-phenyl)-furan-2-carboxylic acid {2-cyclohexyl-1-(S)-[2-(4-difluoromethoxy-phenylamino)-1-(S)-methyl-ethylcarbamoyl]-ethyl}-amide;#

$C_{30}H_{34}F_3N_3O_4$; $^1H$ NMR ($CDCl_3$) δ(ppm) 8.28 (m, 1H), 7.40 (m, 1H), 7.32 (m, 1H), 7.22 (m, 1H), 7.06 (m, 7H), 6.67 (m, 1H), 6.41 (t, J=72 Hz, 1H), 4.38 (m, 1H), 4.15 (m, 1H), 3.54 (m, 1H), 3.26 (m, 1H), 1.63 (m, 7H), 1.31 (m, 1H), 1.28 (d, J=8.0 Hz, 3H), 1.10 (m, 3H), 0.89 (m, 2H); LCMS: 558.2 $(M+H)^+$.

Example 85

5-(3-Fluoro-phenyl)-furan-2-carboxylic acid {1-(S)-[2-(benzo[1,3]dioxol-5-ylamino)-1-(S)-methyl-ethylcarbamoyl]-2-cyclohexyl-ethyl}-amide;# $C_{30}H_{34}FN_3O_5$; $^1H$ NMR ($CDCl_3$) δ(ppm) 8.12 (m, 1H), 7.40 (m, 1H), 7.31 (m, 2H), 7.03 (m, 3H), 6.89 (m, 2H), 6.74 (m, 2H), 5.94 (s, 2H), 4.30 (m, 1H), 4.11 (m, 1H), 3.60 (m, 1H), 3.26 (m, 1H), 1.68 (m, 7H), 1.32 (m, 4H), 1.16 (m, 3H), 0.93 (m, 2H); LCMS: 536.4 $(M+H)^+$.

Example 86

5-(3-Fluoro-phenyl)-furan-2-carboxylic acid {2-cyclohexyl-1-(S)-[2-(4-methoxy-phenylamino)-1-(S)-methyl-ethylcarbamoyl]-ethyl}-amide;# $C_{30}H_{36}FN_3O_4$; $^1H$ NMR ($CDCl_3$) δ(ppm) 8.12 (m, 1H), 7.40 (m, 1H), 7.30 (m, 4H), 7.01 (m, 3H), 6.84 (m, 2H), 6.63 (d, J=4.0 Hz, 2H), 4.32 (m, 1H), 4.15 (m, 1H), 3.73 (s, 3H), 3.63 (m, 1H), 3.26 (m, 1H), 1.63 (m, 7H), 1.32 (m, 4H), 1.14 (m, 3H), 0.88 (m, 2H); LCMS: 522.4 $(M+H)^+$.

Example 87

5-(3-Fluoro-phenyl)-furan-2-carboxylic acid {2-cyclohexyl-1-(S)-[2-(3,5-difluoro-phenylamino)-1-(S)-methyl-ethylcarbamoyl]-ethyl}-amide;# $C_{29}H_{32}F_3N_3O_3$; $^1H$ NMR ($CDCl_3$) δ(ppm) 7.49 (m, 1H), 7.40 (m, 3H), 7.15 (m, 1H), 6.98 (m, 1H), 6.85 (m, 1H), 6.70 (m, 1H), 6.09 (m, 3H), 4.59 (m, 1H), 4.15 (m, 1H), 3.13 (m, 2H), 1.60 (m, 7H), 1.24 (m, 4H), 1.05 (m, 3H), 0.86 (m, 2H); LCMS: 528.4 $(M+H)^+$.

Example 88

5-(3-Fluoro-phenyl)-furan-2-carboxylic acid {2-cyclohexyl-1-(S)-[2-(3-methanesulfonyl-phenylamino)-1-(S)-methyl-ethylcarbamoyl]-ethyl}-amide;# $C_{30}H_{36}FN_3O_5S$; $^1H$ NMR ($CDCl_3$) δ(ppm) 7.50 (m, 1H), 7.28 (m, 4H), 7.19 (m, 1H), 7.20 (m, 1H), 7.12 (m, 1H), 6.91 (m, 3H), 6.71 (m, 1H), 4.58 (m, 1H), 4.18 (m, 1H), 3.22 (m, 2H), 2.98 (s, 3H), 1.57 (m, 7H), 1.22 (m, 4H), 1.05 (m, 3H), 0.86 (m, 2H); LCMS: 570.4 $(M+H)^+$.

Example 89

5-(3-Fluoro-phenyl)-furan-2-carboxylic acid {2-cyclohexyl-1-(S)-[2-(4-methanesulfonyl-phenylamino)-1-(S)-methyl-ethylcarbamoyl]-ethyl}-amide;# $C_{30}H_{36}FN_3O_5S$; $^1H$ NMR ($CDCl_3$) δ(ppm) 7.62 (m, 2H), 7.47 (m, 1H), 7.34 (m, 3H), 7.18 (m, 1H), 7.00 (m, 1H), 6.88 (m, 1H), 6.71 (m, 1H), 6.58 (m, 2H), 4.59 (m, 1H), 4.20 (m, 1H), 3.19 (m, 2H), 2.93 (s, 3H), 1.59 (m, 7H), 1.22 (m, 4H), 1.03 (m, 3H), 0.86 (m, 2H); LCMS: 570.4 $(M+H)^+$.

Example 90

5-(3-Fluoro-phenyl)-furan-2-carboxylic acid {2-cyclohexyl-1-(S)-[2-(2,3-difluoro-phenylamino)-1-(S)-methyl-ethylcarbamoyl]-ethyl}-amide;# $C_{29}H_{32}F_3N_3O_3$; $^1H$ NMR ($CDCl_3$) δ(ppm) 7.46 (m, 1H), 7.34 (m, 2H), 7.19 (m, 1H), 7.10 (m, 1H), 6.98 (m, 1H), 6.81 (m, 1H), 6.70 (m, 1H), 6.45 (m, 3H), 4.58 (m, 1H), 4.19 (m, 1H), 3.18 (d, J=4.0 Hz, 2H), 1.60 (m, 7H), 1.22 (m, 4H), 1.05 (m, 3H), 0.86 (m, 2H); LCMS: 528.4 $(M+H)^+$.

Example 91

5-(3-Fluoro-phenyl)-furan-2-carboxylic acid {2-cyclohexyl-1-(S)-[2-(2,5-difluoro-phenylamino)-1-(S)-methyl-ethylcarbamoyl]-ethyl-}-amide;# $C_{29}H_{32}F_3N_3O_3$; $^1H$ NMR ($CDCl_3$) δ(ppm) 7.48 (m, 1H), 7.35 (m, 3H), 7.19 (m, 1H), 6.99 (m, 1H), 6.70 (m, 3H), 6.38 (m, 1H), 6.20 (m, 1H), 4.63 (m, 1H), 4.19 (m, 1H), 3.14 (m, 2H), 1.59 (m, 7H), 1.20 (m, 4H), 1.04 (m, 3H), 0.83 (m, 2H); LCMS: 528.4 $(M+H)^+$.

Example 92

5-(3-Fluoro-phenyl)-furan-2-carboxylic acid {2-cyclohexyl-1-(S)-[2-(2,6-difluoro-phenylamino)-1-(S)-methyl-ethylcarbamoyl]-ethyl}-amide;# $C_{29}H_{32}F_3N_3O_3$; $^1H$ NMR ($CDCl_3$) δ(ppm) 7.51 (m, 1H), 7.40 (m, 2H), 7.32 (m, 1H), 7.17 (m, 1H), 6.95 (m, 1H), 6.72 (m, 5H), 4.64 (m, 1H), 4.11 (m, 1H), 3.40 (m, 1H), 3.25 (m, 1H), 1.60 (m, 7H), 1.31 (m, 1H), 1.14 (m, 6H), 0.86 (m, 2H); LCMS: 528.4 $(M+H)^+$.

Example 93

5-(3-Fluoro-phenyl)-furan-2-carboxylic acid {1-(S)-[2-(4-cyano-phenylamino)-1-(S)-methyl-ethylcarbamoyl]-2-cyclohexyl-ethyl}-amide;# $C_{30}H_{33}FN_4O_3$; $^1H$ NMR ($CDCl_3$) δ(ppm) 7.44 (m, 1H), 7.33 (m, 4H), 7.13 (d, J=3.6 Hz, 1H), 6.98 (m, 1H), 6.70 (d, J=3.6 Hz, 1H), 6.64 (m, 1H), 6.51 (d, J=8.8 Hz, 2H), 4.55 (m, 1H), 4.17 (m, 1H), 3.15 (m, 2H), 1.58 (m, 7H), 1.21 (m, 1H), 1.18 (d, J=6.8 Hz, 3H), 1.02 (m, 3H), 0.84 (m, 2H); LCMS: 517.4 $(M+H)^+$.

Example 94

5-(3-Fluoro-phenyl)-furan-2-carboxylic acid {1-(S)-[2-(3-chloro-phenylamino)-1-(S)-methyl-ethylcarbamoyl]-2-cyclohexyl-ethyl}1-amide;# $C_{29}H_{33}FClN_3O_3$; $^1H$ NMR ($CDCl_3$) δ(ppm) 7.42 (m, 1H), 7.33 (m, 2H), 7.10 (m, 4H), 6.96 (m, 1H), 6.72 (m, 2H), 6.67 (m, 2H), 4.48 (m, 1H), 4.14 (m, 1H), 3.17 (m, 2H), 1.61 (m, 7H), 1.40 (m, 1H), 1.20 (d, J=6.8 Hz, 3H), 1.08 (m, 3H), 0.88 (m, 2H); LCMS: 526.3 $(M+H)^+$.

Example 95

5-(3-Fluoro-phenyl)-furan-2-carboxylic acid {2-cyclohexyl-1-(S)-[2-(2-fluoro-phenylamino)-1-(S)-methyl-ethylcarbamoyl]-ethyl}-amide;# $C_{29}H_{33}F_2N_3O_3$; $^1H$ NMR ($CDCl_3$) δ(ppm) 7.44 (m, 1H), 7.33 (m, 2H), 7.11 (d, J=3.6 Hz, 1H), 6.93 (m, 4H), 6.74 (m, 1H), 6.67 (d, J=3.6 Hz, 1H), 6.53 (m, 2H), 4.58 (m, 1H), 4.18 (m, 1H), 3.19 (m, 2H), 1.60 (m, 7H), 1.31 (m, 1H), 1.18 (d, J=6.8 Hz, 3H), 1.06 (m, 3H), 0.86 (m, 2H); LCMS: 510.4 $(M+H)^+$.

Example 96

5-(3-Fluoro-phenyl)-furan-2-carboxylic acid {1-(S)-[2-(3-chloro-2-fluoro-phenylamino)-1-(S)-methyl-ethylcarbamoyl]-2-cyclohexyl-ethyl}-amide;# $C_{29}H_{32}ClF_2N_3O_3$; $^1H$ NMR ($CDCl_3$) δ(ppm) 7.45 (m, 1H), 7.31 (m, 3H), 7.13 (d, J=3.6 Hz, 1H), 6.98 (m, 1H), 6.83 (m, 1H), 6.69 (d, J=3.6 Hz, 1H), 6.58 (m, 3H), 4.60 (m, 1H), 4.17 (m, 1H), 3.17 (m, 2H), 1.58 (m, 7H), 1.31 (m, 1H), 1.17 (d, J=6.8 Hz, 3H), 1.05 (m, 3H), 0.85 (m, 2H); LCMS: 544.4 (M+H)+.

Example 97

5-(3-Fluoro-phenyl)-furan-2-carboxylic acid {1-(S)-[2-(5-chloro-2-fluoro-phenylamino)-1-(S)-methyl-ethylcarbamoyl]-2-cyclohexyl-ethyl}-amide;# $C_{29}H_{32}ClF_2N_3O_3$; 1H NMR (CDCl$_3$) δ(ppm) 7.43 (m, 1H), 7.34 (m, 2H), 7.11 (d, J=3.6 Hz, 1H), 7.0 (m, 2H), 6.75 (m, 1H), 6.68 (d, J=3.6 Hz, 1H), 6.59 (m, 2H), 6.48 (m, 1H), 4.60 (m, 1H), 4.19 (m, 1H), 3.11 (m, 2H), 1.56 (m, 7H), 1.29 (m, 1H), 1.17 (d, J=3.6 Hz, 3H), 1.02 (m, 3H), 0.84 (m, 2H); LCMS: 544.3 (M+H)+.

Example 98

5-(3-Fluoro-phenyl)-furan-2-carboxylic acid {1-(S)-[2-(3-carbamoyl-phenylamino)-1-(S)-methyl-ethylcarbamoyl]-2-cyclohexyl-ethyl}-amide;# $C_{30}H_{35}FN_4O_4$; 1H NMR (CDCl$_3$) δ(ppm) 7.46 (m, 1H), 7.25 (m, 5H), 7.11 (m, 2H), 6.94 (m, 4H), 6.67 (d, J=4.0 Hz, 1H), 4.52 (m, 1H), 4.52 (m, 1H), 4.18 (m, 1H), 3.35 (m, 1H), 3.12 (m, 1H), 1.58 (m, 7H), 1.33 (m, 1H), 1.17 (d, J=6.8 Hz, 3H), 1.06 (m, 3H), 0.85 (m, 2H); LCMS: 535.4 (M+H)+.

Example 99

5-(3-Fluoro-phenyl)-furan-2-carboxylic acid {2-cyclohexyl-1-(S)-[2-(3-fluoro-phenylamino)-1-(S)-methyl-ethylcarbamoyl]-ethyl}-amide;# $C_{29}H_{33}F_2N_3O_3$; 1H NMR (CDCl$_3$) δ(ppm) 7.42 (m, 1H), 7.33 (m, 2H), 7.09 (m, 2H), 6.99 (m, 2H), 6.89 (m, 1H), 6.67 (d, J=3.6 Hz, 1H), 6.45 (m, 3H), 4.51 (m, 1H), 4.14 (m, 1H), 3.17 (m, 2H), 1.61 (m, 7H), 1.31 (m, 1H), 1.19 (d, J=6.8 Hz, 3H), 1.04 (m, 3H), 0.87 (m, 2H); LCMS: 510.4 (M+H)+.

Example 100

5-(3-Fluoro-phenyl)-furan-2-carboxylic acid {1-(S)-[2-(3-cyano-phenylamino)-1-(S)-methyl-ethylcarbamoyl]-2-cyclohexyl-ethyl}-amide;# $C_{30}H_{33}FN_4O_3$; 1H NMR (CDCl$_3$) δ(ppm) 7.44 (m, 1H), 7.34 (m, 2H), 7.13 (m, 2H), 6.99 (m, 2H), 6.91 (m, 1H), 6.77 (m, 2H), 6.70 (d, J=3.6 Hz, 1H), 6.63 (m, 1H), 4.54 (m, 1H), 4.17 (m, 1H), 3.13 (m, 2H), 1.59 (m, 7H), 1.28 (m, 1H), 1.19 (d, J=6.8 Hz, 3H), 1.03 (m, 3H), 0.86 (m, 2H); LCMS: 517.4 (M+H)+.

Example 101

N-{2-cyclohexyl-1-(S)-[2-(5-fluoro-2,3-dihydro-indol-1-yl)-ethylcarbamoyl]-ethyl}-2-(4-hydroxy-phenyl)-propionamide; $C_{28}H_{36}FN_3O_3$; 1H NMR (CD$_3$OD) δ(ppm) 7.02 (m, 2H), 6.83 (m, 2H), 6.61 (m, 3H), 4.19 (m, 1H), 3.43 (m, 4H), 3.21 (m, 1H), 3.16 (m, 1H), 2.89 (m, 3H), 1.60 (m, 2H), 1.45 (m, 5H), 1.26 (m, 3H), 0.70 (m, 6H); LCMS: 482.5 (M+H)+.

Example 102

4-Cyclohexyl-N-[2-(5-fluoro-2,3-dihydro-indol-1-yl)-ethyl]-2-(S)-(2-(R)-phenyl-propionylamino)-butyramide;* $C_{29}H_{38}FN_3O_2$; 1H NMR(CH$_3$CD) δ(ppm) 7.17 (m, 5H), 6.62 (m, 2H), 6.26 (m, 1H), 4.11 (m, 1H), 3.62 (m, 1H), 3.25 (m, 1H), 3.20 (m, 3H), 3.16 (m, 1H), 2.92 (m, 2H), 2.76 (m, 2H), 1.82 (m, 1H), 1.52 (m, 5H), 1.34 (d, J=8.0 Hz, 4H), 1.06 (m, 6H), 0.67 (m, 2H); LCMS: 480.4 (M+H)+.

Example 103

5-(4-Fluoro-phenyl)-furan-2-carboxylic acid {2-cyclohexyl-1-(S)-[1-(S)-methyl-2-(4-trifluoromethoxy-phenylamino)-ethylcarbamoyl]-ethyl}-amide;# $C_{30}H_{33}F_4N_3O_4$; 1H NMR (CDCl$_3$) δ(ppm) 7.62 (m, 2H), 7.07 (m, 3H), 6.97 (d, J=8.4 Hz, 2H), 6.83 (m, 1H), 6.69 (m, 1H), 6.60 (m, 3H), 4.55 (m, 1H), 4.16 (m, 1H), 3.13 (m, 2H), 1.61 (m, 7H), 1.33 (m, 1H), 1.18 (d, J=6.8 Hz, 3H), 1.04 (m, 3H), 0.86 (m, 2H); LCMS: 576.5 (M+H)+.

Example 104

5-(4-Fluoro-phenyl)-furan-2-carboxylic acid {2-cyclohexyl-1-(S)-[2-(4-difluoromethoxy-phenylamino)-1-(S)-methyl-ethylcarbamoyl]-ethyl}-amide;# $C_{30}H_{34}F_3N_3O_4$; 1H NMR (CDCl$_3$) δ(ppm) 7.60 (m, 2H), 7.06 (m, 3H), 6.90 (m, 3H), 6.61 (m, 3H), 6.30 (t, J=74 Hz, 1H), 4.84 (m, 1H), 4.57 (m, 1H), 4.15 (m, 1H), 3.15 (m, 2H), 1.62 (m, 7H), 1.33 (m, 1H), 1.16 (d, J=6.8 Hz, 3H), 1.05 (m, 3H), 0.88 (m, 2H); LCMS: 558.2 (M+H)+.

Example 105

5-(4-Fluoro-phenyl)-furan-2-carboxylic acid {2-cyclohexyl-1-(S)-[2-(4-methoxy-phenylamino)-1-(S)-methyl-ethylcarbamoyl]-ethyl}-amide;# 1H NMR (CDCl$_3$) δ(ppm) 8.27 (m, 1H), 7.56 (m, 2H), 7.30 (m, 3H), 6.99 (m, 3H), 6.78 (m, 2H), 6.51 (d, J=3.2, 1H), 4.26 (m, 1H), 3.68 (m, 1H), 3.63 (s, 3H), 3.60 (m, 1H), 3.21 (m, 1H), 1.59 (m, 7H), 1.24 (m, 4H), 1.05 (m, 3H), 0.82 (m, 2H); LCMS: 522.2 (M+H)+.

Example 106

5-(4-Fluoro-phenyl)-furan-2-carboxylic acid {2-cyclohexyl-1-(S)-[2-(3-methanesulfonyl-phenylamino)-1-(S)-methyl-ethylcarbamoyl]-ethyl}-amide;# $C_{30}H_{36}FN_3O_5S$; 1H NMR (CDCl$_3$) δ(ppm) 7.61 (m, 2H), 7.20 (m, 1H), 7.06 (m, 5H), 6.79 (M, 3H), 6.60 (d, J=3.2 Hz, 1H), 4.58 (m, 1H), 4.17 (m, 1H), 3.15 (m, 2H), 2.95 (s, 3H), 1.60 (m, 7H), 1.27 (m, 1H), 1.15 (d, J=6.8 Hz, 3H), 1.00 (m, 3H), 0.82 (m, 2H); LCMS: 570.5 (M+H)+.

Example 107

5-(4-Fluoro-phenyl)-furan-2-carboxylic acid {2-cyclohexyl-1-(S)-[2-(4-methanesulfonyl-phenylamino)-1-(S)-methyl-ethylcarbamoyl]-ethyl}-amide;# $C_{30}H_{36}FN_3O_5S$; 1H NMR (CDCl$_3$) δ(ppm) 7.62 (m, 4H), 7.08 (m, 3H), 6.61 (m, 2H), 6.55 (m, 3H), 4.57 (m, 1H), 4.19 (m, 1H), 3.15 (m, 2H), 2.91 (s, 3H), 1.63 (m, 7H), 1.28 (m, 1H), 1.76 (d, J=6.8 Hz, 3H), 1.04 (m, 3H), 0.85 (m, 2H); LCMS: 570.5 (M+H)+.

Example 108

3-(3-Fluoro-phenyl)-[1,2,4]oxadiazole-5-carboxylic acid {2-cyclohexyl-1-(S)-[1-(S)-methyl-2-(4-trifluoromethoxy-phenylamino)-ethylcarbamoyl]-ethyl}-amide; $C_{28}H_{31}F_4N_5O_4$; 1H NMR (CDCl$_3$) δ(ppm) 7.82 (d, J=8.0 Hz, 1H), 7.72 (m, 2H), 7.39 (m, 1H), 7.15 (m, 4H), 6.99 (m, 2H), 4.52 (m, 1H), 4.21 (m, 1H), 3.40 (m, 1H), 3.22 (m, 1H), 1.64 (m, 7H), 1.29 (m, 4H), 1.08 (m, 3H), 0.89 (m, 2H); LCMS: 578.5 (M+H)+.

Example 109

3-(4-Fluoro-phenyl)-[1,2,4]oxadiazole-5-carboxylic acid {2-cyclohexyl-1-(S)-[1-(S)-methyl-2-(4-trifluoromethoxy-phenylamino)-ethylcarbamoyl]-ethyl}-amide; $^1$H NMR (CDCl$_3$) δ(ppm) 8.04 (m, 2H), 7.65 (d, J=8.0 Hz, 1H), 7.08 (m, 4H), 6.75 (d, J=8.0 Hz, 2H), 6.62 (m, 1H), 4.55 (m, 1H), 4.20 (m, 1H), 3.21 (m, 2H), 1.63 (m, 7H), 1.23 (m, 4H), 1.05 (m, 3H), 0.85 (m, 2H); LCMS: 578.5 (M+H)$^+$.

Example 110

3-[2-(S)-(3-Cyclohexyl-2-(S)-{[5-(3-fluoro-phenyl)-furan-2-carbonyl]-amino}-propionylamino)-propylamino]-benzoic acid methyl ester;$^\#$ C$_{31}$H$_{36}$FN$_3$O$_5$; $^1$H NMR (CDCl$_3$) δ(ppm) 7.80 (m, 2H), 7.44 (m, 1H), 7.33 (m, 2H), 7.13 (m, 1H), 6.99 (m, 2H), 6.69 (m, 1H), 6.55 (m, 3H), 4.55 (m, 1H), 4.20 (m, 1H), 3.78 (s, 3H), 3.21 (m, 2H), 1.56 (m, 7H), 1.27 (m, 1H), 1.20 (d, J=6.8 Hz, 3H), 1.04 (m, 3H), 0.84 (m, 2H); LCMS: 550.4 (M+H)$^+$.

Example 111

5-(3-Fluoro-phenyl)-furan-2-carboxylic acid {2-cyclohexyl-1-(S)-[1-(S)-methyl-2-(3-trifluoromethoxy-phenylamino)-ethylcarbamoyl]-ethyl}-amide;$^\#$ C$_{30}$H$_{33}$F$_4$N$_3$O$_4$; $^1$H NMR (CDCl$_3$) δ(ppm) 7.44 (m, 1H), 7.34 (m, 2H), 7.12 (m, 2H), 6.98 (m, 2H), 6.69 (m, 2H), 6.57 (m, 2H), 6.48 (s, 1H), 4.53 (m, 1H), 4.19 (m, 1H), 1.61 (m, 7H), 1.24 (m, 1H), 1.21 (d, J=6.8 Hz, 3H), 1.04 (m, 3H), 0.88 (m, 2H); LCMS: 576.4 (M+H)$^+$.

Example 112

5-(3-Fluoro-phenyl)-furan-2-carboxylic acid {1-(S)-[2-(2-chloro-5-fluoro-phenylamino)-1-(S)-methyl-ethylcarbamoyl]-2-cyclohexyl-ethyl}-amide;$^\#$ C$_{29}$H$_{32}$ClF$_2$N$_3$O$_3$; $^1$H NMR (CDCl$_3$) δ(ppm) 7.45 (m, 1H), 7.35 (m, 2H), 7.09 (m, 3H), 6.99 (m, 1H), 6.69 (m, 1H), 6.56 (m, 1H), 6.34 (m, 1H), 6.26 (m, 1H), 4.62 (m, 1H), 4.25 (m, 1H), 3.12 (m, 2H), 1.63 (m, 7H), 1.25 (m, 1H), 1.20 (d, J=6.8 Hz, 3H), 1.03 (m, 3H), 0.85 (m, 2H); LCMS: 544.3 (M+H)$^+$.

Example 113

5-(3-Fluoro-phenyl)-furan-2-carboxylic acid {1-(S)-[2-(2-chloro-phenylamino)-1-(S)-methyl-ethylcarbamoyl]-2-cyclohexyl-ethyl}-amide;$^\#$ C$_{29}$H$_{33}$CWFN$_3$O$_3$; $^1$H NMR (CDCl$_3$) δ(ppm) 7.47 (m, 1H), 7.32 (m, 3H), 7.17 (m, 1H), 7.16 (m, 1H), 7.14 (m, 1H), 6.96 (m, 1H), 6.68 (m, 3H), 6.59 (m, 1H), 4.63 (m, 1H), 4.25 (m, 1H), 3.20 (d, J=6.4 Hz, 2H), 1.60 (m, 7H), 1.26 (m, 1H), 1.20 (d, J=6.8 Hz, 3H), 1.03 (m, 3H), 0.86 (m, 2H); LCMS: 526.3 (M+H)$^+$.

Example 114

5-(3-Fluoro-phenyl)-furan-2-carboxylic acid {2-cyclohexyl-1-(S)-[2-(4-methoxy-2,6-dimethyl-phenylamino)-1-(S)-methyl-ethylcarbamoyl]-ethyl}-amide;$^\#$ C$_{32}$H$_{40}$FN$_3$O$_4$; $^1$H NMR (CDCl$_3$) δ(ppm) 9.09 (s, 1H), 7.41 (m, 1H), 7.32 (m, 2H), 7.01 (m, 3H), 6.64 (m, 1H), 6.55 (s, 2H), 4.27 (m, 1H), 3.71 (s, 3H), 3.37 (m, 2H), 2.40 (s, 6H), 1.76 (m, 7H), 1.38 (m, 4H), 1.20 (m, 3H), 0.81 (m, 2H); LCMS: 550.4 (M+H)$^+$.

Example 115

5-(3-Fluoro-phenyl)-furan-2-carboxylic acid {2-cyclohexyl-1-(S)-[2-(4-methoxy-3,5-dimethyl-phenylamino)-1-(S)-methyl-ethylcarbamoyl]-ethyl}-amide;$^\#$ C$_{32}$H$_{40}$FN$_3$O$_4$; $^1$H NMR (CDCl$_3$) δ(ppm) 7.41 (m, 1H), 7.32 (m, 3H), 7.11 (m, 1H), 7.06 (s, 2H), 6.99 (m, 2H), 6.65 (m, 1H), 4.30 (m, 1H), 4.16 (m, 1H), 3.68 (m, 1H), 3.64 (s, 3H), 3.30 (m, 1H), 2.20 (s, 6H), 1.67 (m, 7H), 1.33 (m, 4H), 1.17 (m, 3H), 0.91 (m, 2H); LCMS: 550.4 (M+H)$^+$.

Example 116

5-(3-Fluoro-phenyl)-furan-2-carboxylic acid {2-cyclohexyl-1-(S)-[2-(2-methanesulfonyl-phenylamino)-1-(S)-methyl-ethylcarbamoyl]-ethyl}-amide;$^\#$ C$_{30}$H$_{36}$FN$_3$O$_5$S; $^1$H NMR (CDCl$_3$) δ(ppm) 7.68 (m, 1H), 7.49 (M, 1H), 7.38 (m, 4H), 7.15 (d, J=3.6 Hz, 1H), 6.99 (m, 1H), 6.84 (d, J=8.4 Hz, 1H), 6.71 (m, 3H), 4.65 (m, 1H), 4.20 (m, 1H), 3.31 (m, 1H): 3.17 (m, 1H), 2.97 (s, 3H), 1.63 (7H), 1.31 (m, 1H), 1.20 (d, J=6.8 Hz, 3H), 1.08 (m, 3H), 0.91 (m, 2H); LCMS: 570.3 (M+H)$^+$.

Example 117

5-(3-Fluoro-phenyl)-furan-2-carboxylic acid {2-cyclohexyl-1-(S)-[1-(S)-methyl-2-(4-methylsulfanyl-phenylamino)-ethylcarbamoyl]-ethyl}-amide;$^\#$ C$_{30}$H$_{36}$FN$_3$O$_3$S; $^1$H NMR (CDCl$_3$) δ(ppm) 7.52 (m, 1H), 7.41 (d, J=8.0 Hz, 1H), 7.33 (m, 2H), 7.17 (s, 2H), 7.05 (m, 5H), 6.66 (d, J=3.6 Hz, 1H), 4.39 (m, 1H), 4.16 (m, 1H), 3.45 (m, 1H), 3.22 (m, 1H), 2.38 (s, 3H), 1.66 (m, 7H), 1.32 (m, 1H), 1.27 (d, J=7.2 Hz, 3H), 1.09 (m, 3H), 0.89 (m, 2H); LCMS: 538.4 (M+H)$^+$.

Example 118

5-(3-Fluoro-phenyl)-furan-2-carboxylic acid {2-cyclohexyl-1-(S)-[1-(S)-methyl-2-(4-methylsulfamoyl-phenylamino)-ethylcarbamoyl]-ethyl}-amide;$^\#$ C$_{30}$H$_{37}$FN$_4$O$_5$S; $^1$H NMR (CDCl$_3$) δ(ppm) 7.54 (m, 2H), 7.44 (m, 2H), 7.34 (m, 2H), 7.13 (m, 1H), 6.96 (m, 2H), 6.69 (m, 2H), 6.53 (m, 2H), 4.59 (m, 1H), 4.19 (m, 1H), 3.16 (m, 2H), 2.53 (s, 3H), 1.60 (m, 7H), 1.28 (m, 1H), 1.19 (d, J=7.2 Hz, 3H), 1.02 (m, 3H), 0.86 (m, 2H); LCMS: 585.3 (M+H)$^+$.

Example 119

5-(3-Fluoro-phenyl)-furan-2-carboxylic acid {2-cyclohexyl-1-(S)-[1-(S)-methyl-2-(4-trifluoromethylsulfanyl-phenylamino)-ethylcarbamoyl]-ethyl}-amide;$^\#$ C$_{30}$H$_{33}$F$_4$N$_3$O$_3$S; $^1$H NMR (CDCl$_3$) δ(ppm) 7.46 (m, 1H), 7.37 (m, 4H), 7.12 (d, J=3.6 Hz, 1H), 7.03 (m, 2H), 6.69 (d, J=3.6 Hz, 1H), 6.63 (m, 3H), 4.58 (m, 1H), 4.19 (m, 1H), 3.19 (m, 2H), 1.55 (m, 7H), 1.27 (m, 1H), 1.20 (d, J=6.8 Hz, 3H), 1.02 (m, 3H), 0.84 (m, 2H); LCMS: 592.3 (M+H)$^+$.

Example 120

5-(3-Fluoro-phenyl)-furan-2-carboxylic acid {2-cyclohexyl-1-(S)-[2-(3-dimethylcarbamoyl-phenylamino)-1-(S)-methyl-ethylcarbamoyl]-ethyl}-amide;$^\#$ C$_{32}$H$_{39}$FN$_4$O$_4$; $^1$H NMR (CDCl$_3$) δ(ppm) 7.43 (m, 1H), 7.32 (m, 2H), 7.16 (m, 1H), 7.10 (m, 3H), 6.98 (m, 1H), 6.79 (m, 2H), 6.80 (d, J=7.2 Hz, 1H), 6.68 (d, J=3.6 Hz, 1H), 4.46 (m, 1H), 4.13 (m, 1H), 3.26 (m, 1H), 3.19 (m, 1H), 3.04 (s, 3H), 2.92 (s, 3H), 1.61 (m, 7H), 1.31 (m, 1H), 1.21 (d, J=6.8 Hz, 3H), 1.08 (m, 3H), 0.88 (m, 2H); LCMS: 563.4 (M+H)$^+$.

Example 121

5-(3-Fluoro-phenyl)-furan-2-carboxylic acid {1-(S)-[2-(2-carbamoyl-phenylamino)-1-(S)-methyl-ethylcarbamoyl]-2-cyclohexyl-ethyl}-amide;[#] $C_{30}H_{35}FN_4O_4$; $^1$H NMR (CDCl$_3$) δ(ppm) 7.46 (m, 1H), 7.31 (m, 4H), 7.13 (m, 2H), 6.96 (m, 1H), 6.83 (m, 1H), 6.69 (m, 2H), 6.59 (m, 2H), 6.12 (s, 1H), 4.62 (m, 1H), 4.19 (m, 1H), 3.30 (m, 1H), 3.17 (m, 1H), 1.59 (m, 7H), 1.31 (m, 1H), 1.19 (d, J=7.8 Hz, 3H), 1.06 (m, 3H), 0.84 (m, 2H); LCMS: 535.4 (M+H)$^+$.

Example 122

5-(3-Fluoro-phenyl)-furan-2-carboxylic acid {2-cyclohexyl-1-(S)-[2-(4-dimethylcarbamoyl-phenylamino)-1-(S)-methyl-ethylcarbamoyl]-ethyl}-amide;[#] $C_{32}H_{39}FN_4O_4$; $^1$H NMR (CDCl$_3$) δ(ppm) 7.44 (d, J=8.0 Hz, 1H), 7.34 (m, 2H), 7.25 (d, J=8.8 Hz, 2H), 7.12 (d, i=3.6 Hz, 1H), 6.96 (m, 2H), 6.79 (m, 1H), 6.67 (m, 3H), 4.53 (m, 1H), 4.16 (m, 1H), 3.18 (m, 2H), 3.01 (s, 6H), 1.63 (m, 7H), 1.30 (m, 1H), 1.20 (d, J=6.8 Hz, 3H), 1.06 (m, 3H), 0.88 (m, 2H); LCMS: 563.4 (M+H)$^+$.

Example 123

3-Cyclohexyl-2-(S)-(3-methoxy-propionylamino)-N-[1-(S)-methyl-2-(4-trifluoromethoxy-phenylamino)-ethyl]-propionamide.* $C_{23}H_{34}F_3N_3O_4$; LCMS: 474.5 (M+H)$^+$.

Example 124

3-Cyclohexyl-2-(S)-(2-methoxy-acetylamino)-N-[1-(S)-methyl-2-(4-trifluoromethoxy-phenylamino)-ethyl]-propionamide.* $C_{22}H_{32}F_3N_3O_4$; LCMS: 460.5 (M+H)$^+$.

Example 125

5-(3-Fluoro-phenyl)-furan-2-carboxylic acid {2-cyclohexyl-1-(S)-[2-(4-hydroxy-phenylamino)-1-(S)-methyl-ethylcarbamoyl]-ethyl}-amide.[#] $C_{29}H_{34}FN_3O_4$; LCMS: 508.4 (M+H)$^+$.

Example 126

5-(3-Fluoro-phenyl)-furan-2-carboxylic acid {2-cyclohexyl-1-(S)-[2-(4-fluoro-phenylamino)-1-(S)-methyl-ethylcarbamoyl]-ethyl}-amide;[#] $C_{29}H_{33}F_2N_3O_3$; $^1$H NMR (CDCl$_3$) δ(ppm) 8.14 (d, J=7.2, 1H), 7.41 (m, 3H), 7.32 (m, 2H), 7.08 (m, 3H), 6.99 (m, 2H), 6.65 (d, J=3.6 Hz, 1H), 4.30 (m, 1H), 4.13 (m, 1H), 3.71 (m, 1H), 3.31 (m, 1H), 1.67 (m, 7H), 1.40 (m, 1H), 1.32 (d, J=6.8 Hz, 3H), 1.14 (m, 3H), 0.91 (m, 2H); LCMS: 510.4 (M+H)$^+$.

Example 127

5-(3-Fluoro-phenyl)-furan-2-carboxylic acid {3,3-dimethyl-1-(S)-[1-(S)-methyl-2-(4-trifluoromethoxy-phenylamino)-ethylcarbamoyl]-butyl}-amide;[#] $C_{28}H_{31}F_4N_3O_4$; $^1$H NMR (CDCl$_3$) δ(ppm) 7.40 (m, 1H), 7.32 (m, 2H), 7.07 (m, 5H), 6.86 (m, 3H), 6.68 (d, J=3.6 Hz, 1H), 4.44 (m, 1H), 4.14 (m, 1H), 3.31 (m, 1H), 3.18 (m, 1H), 1.91 (m, 1H), 1.63 (m, 1H), 1.22 (d, J=6.8 Hz, 3H), 0.94 (s, 9H); LCMS: 550.4 (M+H)$^+$.

Example 128

5-(3-Fluoro-phenyl)-furan-2-carboxylic acid {1-(S)-[2-(4-difluoromethoxy-phenylamino)-1-(S)-methyl-ethylcarbamoyl]-3,3-dimethyl-butyl}-amide;[#] $C_{28}H_{32}F_3N_3O_4$; $^1$H NMR (CDCl$_3$) δ(ppm) 7.38 (m, 1H), 7.31 (m, 3H), 7.05 (m, 1H), 6.99 (m, 5H), 6.89 (m, 1H), 6.68 (m, 1H), 6.37 (t, J=74 Hz, 1H), 4.41 (m, 1H), 4.12 (m, 1H), 3.39 (m, 1H), 3.20 (m, 1H), 1.92 (m, 1H), 1.65 (m, 1H), 1.25 (d, J=6.8 Hz, 3H), 0.95 (s, 9H); LCMS: 532.4 (M+H)$^+$.

Example 129

5-(3-Fluoro-phenyl)-furan-2-carboxylic acid {1-(S)-[2-(4-methanesulfonyl-phenylamino)-1-(S)-methyl-ethylcarbamoyl]-3,3-dimethyl-butyl}-amide;[#] $C_{28}H_{34}FN_3O_5S$; $^1$H NMR (CDCl$_3$) δ(ppm) 7.61 (m, 2H), 7.46 (m, 1H), 7.34 (m, 2H), 7.17 (m, 2H), 6.99 (m, 1H), 6.76 (m, 1H), 6.72 (d, J=3.6 Hz, 1H), 6.56 (d, 8.0 Hz, 2H), 4.56 (m, 1H), 4.16 (m, 1H), 3.19 (d, 8.0 Hz, 2H), 2.93 (s, 3H), 1.89 (m, 1H), 1.60 (m, 1H), 1.20 (d, J=6.8 Hz, 3H), 0.90 (s, 9H); LCMS: 544.3 (M+H)$^+$.

Example 130

5-(3-Fluoro-phenyl)-furan-2-carboxylic acid {1-(S)-[2-(3-methanesulfonyl-phenylamino)-1-(S)-methyl-ethylcarbamoyl]-3,3-dimethyl-butyl}-amide;[#] $C_{28}H_{34}FN_3O_5S$; $^1$H NMR (CDCl$_3$) δ(ppm) 7.50 (m, 1H), 7.29 (m, 4H), 7.17 (m, 2H), 7.12 (m, 1H), 6.99 (m, 2H), 6.87 (m, 1H), 6.71 (m, 1H), 4.55 (m, 1H), 4.15 (m, 1H), 3.22 (m, 2H), 2.98 (s, 3H), 1.84 (m, 1H), 1.62 (m, 1H), 1.21 (d, J=6.8 Hz, 3H), 0.90 (s, 9H); LCMS: 544.3 (M+H)$^+$.

Example 131

5-(3-Fluoro-phenyl)-furan-2-carboxylic acid {1-(S)-[2-(3-carbamoyl-phenylamino)-1-(S)-methyl-ethylcarbamoyl]-3,3-dimethyl-butyl}-amide;[#] $C_{28}H_{33}FN_4O_4$; $^1$H NMR (CDCl$_3$) δ(ppm) 7.67 (s, 1H), 7.61 (m, 1H), 7.48 (m, 1H), 7.40 (m, 1H), 7.33 (m, 3H), 7.14 (m, 4H), 6.99 (m, 1H), 6.68 (d, J=3.6 Hz, 1H), 4.44 (m, 1H), 4.21 (m, 1H), 3.51 (m, 1H), 3.18 (m, 1H), 1.87 (m, 1H), 1.67 (m, 1H), 1.22 (d, J=8.0 Hz, 3H), 0.99 (s, 9H); LCMS: 509.4 (M+H)$^+$.

Example 132

5-(3-Fluoro-phenyl)-furan-2-carboxylic acid {1-(S)-[2-(4-methoxy-phenylamino)-1-(S)-methyl-ethylcarbamoyl]-3,3-dimethyl-butyl}-amide;[#] $C_{28}H_{34}FN_3O_4$; $^1$H NMR (CDCl$_3$) δ(ppm) 8.33 (m, 1H), 7.37 (m, 5H), 7.04 (m, 1H), 6.99 (m, 2H), 6.87 (m, 2H), 6.63 (d, J=3.6 Hz, 1H), 4.28 (m, 1H), 4.17 (m, 1H), 3.75 (s, 3H), 3.63 (m, 1H), 3.29 (m, 1H), 1.88 (m, 1H), 1.72 (m, 1H), 1.31 (d, J=8.0 Hz, 3H), 0.99 (s, 9H); LCMS: 496.4 (M+H)$^+$.

Example 133

5-(3-Fluoro-phenyl)-furan-2-carboxylic acid {2-cyclohexyl-1-(S)-[1-(S)-methyl-2-(5-methyl-isoxazol-3-ylamino)-ethylcarbamoyl]-ethyl}-amide;[#] $C_{27}H_{33}FN_4O_4$; $^1$H NMR (CDCl$_3$) δ(ppm) 7.47 (m, 1H), 7.44 (m, 2H), 7.14 (m, 1H), 6.93 (m, 2H), 6.80 (m, 1H), 6.69 (m, 1H), 5.51 (s, 1H), 4.57 (m, 1H), 4.09 (m, 1H), 3.23 (m, 2H), 2.20 (s, 3H), 1.73 (m, 1H), 1.58 (m, 6H), 1.30 (m, 1H), 1.16 (m, 6H), 0.86 (m, 2H); LCMS: 497.5 (M+H)$^+$.

Example 134

5-(3-Fluoro-phenyl)-furan-2-carboxylic acid {1-(S)-[2-(3-acetylamino-phenylamino)-1-(S)-methyl-ethylcarbamoyl]-2-cyclohexyl-ethyl}-amide;# $C_{31}H_{37}FN_4O_4$; $^1$H NMR (CDCl$_3$) δ(ppm) 7.92 (s, 1H), 7.61 (m, 1H), 7.31 (m, 5H), 7.10 (m, 3H), 6.98 (m, 1H), 6.82 (m, 1H), 6.66 (d, J=3.6 Hz, 1H), 4.43 (m, 1H), 4.12 (m, 1H), 3.48 (m, 1H), 3.25 (m, 1H), 2.08 (s, 3H), 1.58 (m, 7H), 1.36 (m, 1H), 1.14 (m, 6H), 0.89 (m, 2H); LCMS: 549.5 (M+H)$^+$.

Example 135

Tetrahydropyran-4-carboxylic acid {2-cyclohexyl-1-(S)-[1-(S)-methyl-2-(4-trifluoromethoxy-phenylamino)-ethylcarbamoyl]-ethyl}-amide.* $C_{25}H_{36}F_3N_3O_4$; LCMS: 500.4 (M+H)$^+$.

Example 136

5-(3-Fluoro-phenyl)-furan-2-carboxylic acid (2-cyclohexyl-1-(S)-{1-(S)-methyl-2-[4-(morpholine-4-sulfonyl)-phenylamino]-ethylcarbamoyl}-ethyl)-amide;# $C_{33}H_{41}FN_4O_6S$; $^1$H NMR (CDCl$_3$) δ(ppm) 7.48 (m, 3H), 7.35 (m, 3H), 7.16 (d, J=3.6 Hz, 1H), 7.00 (m, 1H), 6.78 (m, 1H), 6.72 (d, J=3.6 Hz, 1H), 6.58 (m, 2H), 4.60 (m, 1H), 4.21 (m, 1H), 3.67 (m, 4H), 3.19 (d, J=6.4 Hz, 2H), 2.89 (m, 4H), 1.63 (m, 7H), 1.28 (m, 1H), 1.22 (d, J=6.8 Hz, 3H), 1.03 (m, 3H), 0.87 (m, 2H); LCMS: 641.5 (M+H)$^+$.

Example 137

5-(3-Fluoro-phenyl)-furan-2-carboxylic acid {2-cyclohexyl-1-(S)-[1-(S)-methyl-2-(3-oxo-1,3-dihydro-isobenzofuran-5-ylamino)-ethylcarbamoyl]-ethyl}-amide;# $C_{31}H_{34}FN_3O_5$; $^1$H NMR (CDCl$_3$) δ(ppm) 7.45 (m, 1H), 7.35 (m, 2H), 7.22 (m, 2H), 7.15 (d, J=4.0 Hz, 1H), 7.10 (m, 1H), 7.02 (m, 2H), 6.93 (m, 1H), 6.71 (d, J=4.0 Hz, 1H), 5.15 (s, 2H), 4.56 (m, 1H), 4.20 (m, 1H), 3.24 (m, 2H), 1.59 (m, 7H), 1.29 (m, 1H), 1.22 (d, J=6.8 Hz, 3H), 1.04 (m, 3H), 0.85 (m, 2H); LCMS: 548.5 (M+H)$^+$.

Example 138

5-(3-Fluoro-phenyl)-furan-2-carboxylic acid {2-cyclohexyl-1-(S)-[1-(S)-methyl-2-(4-sulfamoyl-phenylamino)-ethylcarbamoyl]-ethyl}-amide;# $C_{29}H_{35}FN_4O_5S$; $^1$H NMR (CDCl$_3$) δ(ppm) 7.60 (m, 3H), 7.50 (m, 1H), 7.39 (m, 1H), 7.32 (m, 1H), 7.16 (m, 2H), 6.98 (m, 1H), 6.70 (d, J=3.6 Hz, 1H), 6.54 (d, J=8.8 Hz, 2H), 4.64 (m, 1H), 4.17 (m, 1H), 3.20 (m, 2H), 1.24 (m, 7H), 1.22 (m, 4H), 1.02 (m, 3H), 0.84 (m, 2H); 571.5 (M+H)$^+$.

Example 139

Tetrahydropyran-4-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide.$^\$$ $C_{28}H_{42}FN_3O_3$; LCMS: 488.5 (M+H)$^+$.

Example 140

Tetrahydrofuran-3-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide.$^\$$ $C_{27}H_{40}FN_3O_3$; LCMS: 474.5 (M+H)$^+$.

Example 141

1-(3-Fluoro-phenyl)-1H-pyrazole-4-carboxylic acid {2-cyclohexyl-1-(S)-[1-(S)-methyl-2-(4-trifluoromethoxy-phenylamino)-ethylcarbamoyl]-ethyl}-amide; The title compound was prepared following the procedures described in example 181, except in step E, HATU mediated amide coupling with 1-(3-Fluoro-phenyl)-1H-pyrazole-4-carboxylic acid was conducted. $C_{29}H_{33}F_4N_5O_3$; $^1$H NMR (CD$_3$OD) δ(ppm) 8.67 (s, 1H), 8.05 (s, 1H), 7.52 (m, 2H), 7.43 (m, 1H), 7.03 (m, 1H), 6.87 (d, J=8.8 Hz, 2H), 7.52 (m, 2H), 7.43 (m, 1H), 4.05 (m, 1H), 3.05 (m, 2H), 1.58 (m, 7H), 1.32 (m, 1H), 1.10 (m, 6H), 0.84 (m, 2H); LCMS: 576.5 (M+H)$^+$.

Example 142

1-(4-Fluoro-phenyl)-1H-pyrazole-4-carboxylic acid {2-cyclohexyl-1-(S)-[1-(S)-methyl-2-(4-trifluoromethoxy-phenylamino)-ethylcarbamoyl]-ethyl}-amide;$^\$$ $C_{29}H_{33}F_4N_5O_3$; $^1$H NMR (CD$_3$OD) δ(ppm) 8.56 (s, 1H), 8.04 (s, 1H), 7.68 (m, 2H), 7.17 (m, 2H), 6.88 (d, J=8.8 Hz, 2H), 6.57 (m, 2H), 4.47 (m, 1H), 4.04 (m, 1H), 3.05 (m, 2H), 1.57 (m, 7H), 1.30 (m, 1H), 1.08 (m, 6H), 0.85 (m, 2H); LCMS: 576.5 (M+H)$^+$.

Example 143

5-Pyridin-3-yl-furan-2-carboxylic acid {2-cyclohexyl-1-(S)-[1-(S)-methyl-2-(4-trifluoromethoxy-phenylamino)-ethylcarbamoyl]-ethyl}-amide;$^\$$ $C_{29}H_{33}F_3N_4O_4$; $^1$H NMR (CDCl$_3$) δ(ppm) 9.18 (s, 1H), 8.58 (d, J=4.8 Hz, 1H), 8.42 (d, J=4.0 Hz, 1H), 7.71 (m, 1H), 7.61 (d, J=7.2 Hz, 1H), 7.32 (d, J=7.6 Hz, 1H), 7.13 (d, J=3.6 Hz, 1H), 7.04 (m, 2H), 6.92 (m, 3H), 4.52 (m, 1H), 4.20 (m, 1H), 3.33 (m, 1H), 3.19 (m, 1H), 1.66 (m, 7H), 1.30 (m, 1H), 1.22 (d, J=6.8 Hz, 3H), 1.07 (m, 3H), 0.87 (m, 2H); LCMS: 559.5 (M+H)$^+$.

Example 144

5-(1-Oxy-pyridin-3-yl)-furan-2-carboxylic acid {2-cyclohexyl-1-(S)-[1-(S)-methyl-2-(4-trifluoromethoxy-phenylamino)-ethylcarbamoyl]-ethyl}-amide;$^\$$ $C_{29}H_{33}F_3N_4O_5$; $^1$H NMR (CDCl$_3$) δ(ppm) 9.27 (s, 1H), 8.26 (d, J=6.4 Hz, 1H), 7.81 (d, J=8.0 Hz, 1H), 7.48 (m, 1H), 7.34 (m, 1H), 7.13 (d, J=3.6 Hz, 1H), 6.98 (m, 2H), 6.89 (d, J=4.0 Hz, 1H), 6.71 (m, 3H), 4.50 (m, 1H), 4.17 (m, 1H), 3.18 (m, 2H), 1.65 (m, 7H), 1.30 (m, 1H), 1.21 (d, J=6.8 Hz, 3H), 1.06 (m, 3H), 0.86 (m, 2H); LCMS: 575.5 (M+H)$^+$.

Example 145

3-(3-Fluoro-phenyl)-isoxazole-5-carboxylic acid {2-cyclohexyl-1-(S)-[1-(S)-methyl-2-(4-trifluoromethoxy-phenylamino)-ethylcarbamoyl]-ethyl}-amide;$^\$$ $C_{29}H_{32}F_4N_4O_4$; $^1$H NMR (CDCl$_3$) δ(ppm) 7.48 (m, 3H), 7.14 (m, 2H), 7.10 (s, 1H), 7.06 (m, 2H), 6.83 (m, 2H), 6.76 (m, 1H), 4.46 (m, 1H), 4.19 (m, 1H), 3.30 (m, 1H), 3.19 (m, 1H), 1.65 (m, 7H), 1.33 (m, 1H), 1.24 (d, J=6.8 Hz, 3H), 1.09 (m, 3H), 0.89 (m, 2H); LCMS: 577.5 (M+H)$^+$.

Example 146

3-(4-Fluoro-phenyl)-isoxazole-5-carboxylic acid {2-cyclohexyl-1-(S)-[1-(S)-methyl-2-(4-trifluoromethoxy-phenylamino)-ethylcarbamoyl]-ethyl}-amide;$^\$$ $C_{29}H_{32}F_4N_4O_4$; $^1$H NMR (CDCl$_3$) δ(ppm) 7.72 (m, 2H), 7.08 (m, 6H), 6.95 (m, 3H), 4.44 (m, 1H), 4.19 (m, 1H), 3.36 (m, 1H), 3.21 (m, 1H), 1.65 (m, 7H), 1.33 (m, 1H), 1.25 (d, J=6.8 Hz, 3H), 1.11 (m, 3H), 0.89 (m, 2H); LCMS: 577.5 $(M+H)^+$.

Example 147

5-(3-Fluoro-phenyl)-[1,3,4]oxadiazole-2-carboxylic acid {2-cyclohexyl-1-(S)-[1-(S)-methyl-2-(4-trifluoromethoxy-phenylamino)-ethylcarbamoyl]-ethyl}-amide; $C_{28}H_{31}F_4N_5O_4$; $^1$H NMR ($CDCl_3$) δ(ppm) 7.83 (d, J=8.0 Hz, 1H), 7.76 (m, 2H), 7.44 (m, 2H), 7.07 (m, 2H), 6.90 (m, 3H), 4.51 (m, 1H), 4.19 (m, 1H), 3.33 (m, 1H), 3.20 (m, 1H), 1.66 (m, 7H), 1.33 (m, 1H), 1.23 (d, J=6.8 Hz, 3H), 1.07 (m, 3H), 0.90 (m, 2H); LCMS: 578.5 $(M+H)^+$.

Example 148

N-{2-cyclohexyl-1-(S)-[2-(5-fluoro-2,3-dihydro-indol-1-yl)-ethylcarbamoyl]-ethyl}-2-(R)-phenyl-butyramide; $C_{28}H_{31}F_4N_5O_4$; $^1$H NMR($CH_3CD$) δ(ppm) 7.24 (m, 2H), 7.16 (m, 2H), 7.10 (m, 1H), 6.68 (m, 1H), 6.59 (m, 1H), 6.24 (m, 1H), 4.31 (m, 1H), 3.34 (m, 1H), 3.14 (m, 4H), 2.88 (m, 2H), 2.74 (m, 2H), 1.91 (m, 1H), 1.62 (m, 7H), 1.42 (m, 2H), 1.22 (m, 1H), 1.07 (m, 3H), 0.81 (m, 5H); LCMS: 480.6 $(M+H)^+$.

Example 149

N-{1-(S)-[1-(R)-Benzyloxymethyl-2-(5-fluoro-2,3-dihydro-indol-1-yl)-ethylcarbamoyl]-2-cyclohexyl-ethyl}-3-methoxy-benzamide.

Step A

Following the procedures of Example 22, except using N-Boc-OBn-serinol, 5-fluoroindoline (1 eq) and Boc-cyclohexylalanine as starting materials, {1-(S)-[1-(R)-Benzyloxymethyl-2-(5-fluoro-2,3-dihydro-indol-1-yl)-ethylcarbamoyl]-2-cyclohexyl-ethyl}-carbamic acid tert-butyl ester was prepared in 40% overall yield.

Step B

A sample of {1-(S)-[1-(R)-Benzyloxymethyl-2-(5-fluoro-2,3-dihydro-indol-1-yl)-ethylcarbamoyl]-2-cyclohexyl-ethyl}-carbamic acid tert-butyl ester (210 mg, 0.34 mmol) was treated with a mixture of trifluoroacetic acid, dichloromethane and water (45:45:10) and allowed to age for 2 hours. The solvent was then removed by rotary evaporation. The resulting oil was treated with m-anisic acid (75 mg, 0.49 mmol), HATU (187 mg, 0.49 mmol) and dichloromethane (2 mL). The reaction was then treated with diisopropylethylamine (245 mg, 1.9 mmol) and stirred for 2 hours. The reaction was diluted with ethyl acetate, extracted with saturated aqueous $NaHCO_3$ twice, dried over $MgSO_4$ and the solvent was removed. The resulting oil was purified over silica gel using a gradient of 0 to 100% ethyl acetate in hexane to afford 195 mg (87%) of the title material; $^1$H NMR ($CDCl_3$, 400 MHz) δ 0.84-1.03 (m, 2H), 1.06-1.22 (m, 3H), 1.32-1.45 (m, 1H), 1.58-1.87 (m, 7H), 2.92 (dd, 1H, $J_1$=$J_2$=8.2), 3.13-3.25 (m, 2H), 3.31-3.46 (m, 2H), 3.54 (dd, 1H, $J_1$=54.2, $J_2$=9.4), 3.68 (dd, 1H, $J_1$=2.4, $J_2$=9.3), 3.84 (s, 3H), 4.26-4.36 (m, 1H), 4.53 (dd, 2H, $J_1$=11.8, $J_2$=26.0), 4.65-4.74 (m, 1H), 6.46 (dd, 1H, $J_1$=4.1, $J_2$=8.4), 6.46 (d, 1H, J=8.3), 6.69-6.83 (m, 2H), 7.02-7.09 (m, 1H), 7.27-7.39 (m, 7H); HPLC-MS calcd. for $C_{35}H_{42}FN_3O_4$ $(M+H^+)$ 587.3, found 587.5.

Example 150

N-{2-Cyclohexyl-1-(S)-[2-(5-fluoro-2,3-dihydro-indol-1-yl)-1-(R)-hydroxymethyl-ethylcarbamoyl]-ethyl}-3-methoxy-benzamide This material was prepared in 71% yield using an identical procedure to example 40; $^1$H NMR ($CDCl_3$, 400 MHz) δ 0.70-0.85 (m, 2H), 0.93-1.07 (m, 3H), 1.22-1.35 (m, 1H), 1.44-1.68 (m, 7H), 2.72-2.88 (m, 2H), 2.96 (dd, 1H, $J_1$=6.9, $J_2$=13.5), 3.10 (dd, 1H, $J_1$=7.5, $J_2$=13.5), 3.20 (q, 1H, J=8.6), 3.32-3.41 (m, 1H), 3.58 (dd, 2H, $J_1$=4.9, $J_2$=11.4), 3.65-3.74 (m, 1H), 3.71 (s, 3H), 4.09-4.19 (m, 1H), 4.52-4.60 (m, 1H), 6.23 (dd, 1H, $J_1$=4.2, $J_2$=8.6), 6.56 (ddd, 1H, $J_1$=2.6, $J_2$=$J_3$=9.0), 6.66-6.71 (m, 1H), 6.92-6.97 (m, 1H), 7.08 (d, 1H, J=7.8), 7.16-7.25 (m, 3H), 7.31 (d, 1H, J=8.2); HPLC-MS calcd. for $C_{28}H_{36}FN_3O_4$ $(M+H^+)$ 498.3, found 498.5.

Example 151

N-{2-Cyclohexyl-1-(S)-[2-(5-fluoro-2,3-dihydro-indol-1-yl)-1-(S)-morpholin-4-ylmethyl-ethylcarbamoyl]-ethyl}-3-methoxy-benzamide A solution of the title compound of example 150 (21 mg, 43 μmol) in dichloromethane (1 mL) was treated with triethylamine (43 mg, 0.43 mmol) and cooled in an ice/water bath. The reaction mixture was then treated with methanesulfonyl chloride (9.8 mg, 85 μmol) and stirred for 1 hour. The reaction was then treated with saturated aqueous $NaHCO_3$ (2 mL) and stirred for 1 hour. The aqueous phase was extracted a total of 3 times with dichloromethane and the combined organic layers were dried over $MgSO_4$ and the solvent was removed. The resulting oil was dissolved in morpholine (2 mL) and heated to 55° C. for 1 hour. The solvent was removed and the reaction was dissolved in ethyl acetate and extracted twice with 1 M aqueous NaOH. The organics were dried over $MgSO_4$ and the solvent was removed. The resulting oil was purified over silica gel using a gradient of 0-100% ethyl acetate in hexane with a 10 minute elution using pure ethyl acetate afterward to afford 4.2 mg (17%) of the title material as an oil; $^1$H NMR ($CDCl_3$, 400 MHz) δ 0.82-1.06 (m, 2H), 1.12-1.31 (m, 4H), 1.31-1.43 (m, 1H), 1.59-1.86 (m, 8H), 2.31-2.60 (m, 8H), 2.90-2.99 (m, 2H), 3.14 (dd, 1H, $J_1$=5.8, $J_2$=13.9), 3.27 (dd, 1H, $J_1$=5.0, $J_2$=14.0), 3.37 (dd, 1H, $J_1$=8.5, $J_2$=17.1), 3.48 (dd, 1H, $J_1$=8.1, $J_2$=16.3), 3.58-3.78 (m, 2H), 3.71 (dd, 1H, $J_1$=$J_2$=4.6), 4.21-4.30 (m, 1H), 4.61-4.71 (m, 1H), 6.15 (dd, 1H, $J_1$=4.2, $J_2$=8.4), 6.46-6.60 (m, 1H), 6.72-6.78 (m, 1H), 6.78-6.82 (m, 1H), 7.05-7.10 (m, 1H), 7.27-7.38 (m, 3H); HPLC-MS calcd. for $C_{32}H_{43}FN_4O_4$ $(M+H^+)$ 567.3, found 567.5.

Example 152

5-(3-Trifluoromethyl-phenyl)-furan-2-carboxylic acid {1-(S)-[1-(R)-benzyloxymethyl-2-(5-fluoro-2,3-dihydro-indol-1-yl)-ethylcarbamoyl]-2-cyclohexyl-ethyl}-amide This material was prepared in 92% yield from {1-(S)-[1-(R)-Benzyloxymethyl-2-(5-fluoro-2,3-dihydro-indol-1-yl)-ethylcarbamoyl]-2-cyclohexyl-ethyl}-carbamic acid tert-butyl ester (example 149, step A) using a protocol analogous to example 149, step B; HPLC-MS calcd. for $C_{39}H_{41}F_4N_3O_4$ $(M+H^+)$ 692.3, found 692.4.

Example 153

5-(3-Trifluoromethyl-phenyl)-furan-2-carboxylic acid {2-cyclohexyl-1-(S)-[2-(5-fluoro-2,3-dihydro-indol-1-yl)-1-(R)-hydroxymethyl-ethylcarbamoyl]-ethyl}-amide This material was prepared in 71% yield using an identical procedure to example 40; HPLC-MS calcd. for $C_{32}H_{35}F_4N_3O_4$ (M+H$^+$) 602.3, found 602.4.

Example 154

{1-(S)-[1-(R)-Benzyloxymethyl-2-(5-fluoro-2,3-dihydro-indol-1-yl)-ethylcarbamoyl]-3,3-dimethyl-butyl}-carbamic acid tert-butyl ester Following the procedures of example 22, except using N-Boc-OBn-serinol, 5-fluoroindoline and Boc-cyclohexylalanine as starting materials, the title compound was prepared in 40% overall yield; $^1$H NMR (CDCl$_3$, 400 MHz) δ 0.93 (s, 9H), 1.29-1.38 (m, 1H), 1.41 (s, 9H), 1.86 (dd, 1H, $J_1$=3.7, $J_2$=14.5), 2.90 (dd, 2H, $J_1$=$J_2$=8.3), 3.14 (d, 2H, J=7.1), 3.35 (dd, 2H, $J_1$=$J_2$=8.4), 3.50 (dd, 1H, $J_1$=4.3, $J_2$=9.3), 3.68 (dd, 1H, $J_1$=2.8, $J_2$=9.3), 4.05-4.13 (m, 1H), 4.18-4.27 (m, 1H), 4.53 (dd, 2H, J=11.9, $J_2$=24.4), 4.73-4.79 (m, 1H), 6.45 (dd, 1H, $J_1$=4.2, $J_2$=8.5), 6.53 (d, 1H, J=8.4), 6.68-6.74 (m, 1H), 6.75-6.79 (m, 1H), 7.28-7.39 (m, 5H); HPLC-MS calcd. for $C_{30}H_{42}FN_3O_4$ (M+H$^+$) 528.3, found 528.6.

Example 155

N-{1-(S)-[1-(R)-Benzyloxymethyl-2-(5-fluoro-2,3-dihydro-indol-1-yl)-ethylcarbamoyl]-3,3-dimethyl-butyl}-3-methoxy-benzamide This material was prepared in an analogous fashion to example 149, step B in 95% yield; $^1$H NMR (CDCl$_3$, 400 MHz) δ 0.96 (s, 9H), 1.62 (dd, 1H, $J_1$=8.5, $J_2$=14.5), 1.90 (dd, 1H, $J_1$=4.1, $J_2$=14.5), 2.88 (dd, 1H, $J_1$=$J_2$=8.3), 3.15-3.18 (m, 1H), 3.28-3.41 (m, 2H), 3.48 (dd, 1H, $J_1$=4.4, $J_2$=9.4), 3.64 (dd, 1H, $J_1$=3.1, $J_2$=9.4), 3.79 (s, 3H), 4.19-4.30 (m, 1H), 4.49 (dd, 1H, $J_1$=11.8, $J_2$=28.9), 4.68 (ddd, 1H, $J_1$=4.1, $J_2$=8.5, $J_3$=12.5), 6.43 (dd, 1H, $J_1$=4.2, $J_2$=8.5), 6.67-6.78 (m, 4H), 6.98-7.05 (m, 1H), 7.25-7.32 (m, 7H), 7.33-7.35 (m, 1H); HPLC-MS calcd. for $C_{33}H_{40}FN_3O_4$ (M+H$^+$) 562.3, found 562.5.

Example 156

N-{1-(S)-[2-(5-Fluoro-2,3-dihydro-indol-1-yl)-1-(R)-hydroxymethyl-ethylcarbamoyl]-3,3-dimethyl-butyl}-3-methoxy-benzamide This material was prepared in 71% yield using an identical procedure to example 40; $^1$H NMR (CDCl$_3$, 400 MHz) δ 0.74 (s, 9H), 1.41 (dd, 1H, $J_1$=8.3, $J_2$=14.5), 1.70 (dd, 1H, $J_1$=4.4, $J_2$=14.5), 2.57-2.72 (m, 2H), 2.85 (dd, 1H, $J_1$=6.8, $J_2$=13.6), 3.02 (dd, 1H, $J_1$=7.7, $J_2$=13.6), 3.07 (dd, 1H, $J_1$=8.7, $J_2$=17.4), 3.17-3.26 (m, 1H), 3.48 (dd, 1H, $J_1$=4.5, $J_2$=11.4), 3.55 (dd, 1H, $J_1$=3.4, $J_2$=11.4), 3.60 (s, 3H), 3.88-3.98 (m, 1H), 4.43 (ddd, 1H, $J_1$=4.3, $J_2$=8.1, $J_3$=12.3), 6.16 (dd, 1H, $J_1$=4.1, $J_2$=8.5), 6.41 (d, 1H, J=7.7), 6.48 (ddd, 1H, $J_1$=2.6, $J_2$=$J_3$=9.0), 6.52-6.56 (m, 1H), 6.75-6.79 (m, 1H), 6.78-6.84 (m, 1H), 6.98-7.10 (m, 3H); HPLC-MS calcd. for $C_{26}H_{34}FN_3O_4$ (M+H$^+$) 472.3, found 472.5.

Example 157

{1-(S)-[1-(S)-(5-Fluoro-2,3-dihydro-indol-1-ylmethyl)-3-methanesulfonyl-propylcarbamoyl]-3,3-dimethyl-butyl}-carbamic acid tert-butyl ester

Step A

A solution of (L)-N-Boc-methioninol (700 mg, 3.0 mmol) in dichloromethane (20 mL) was cooled in an ice/water bath and treated with solid 77% mCPBA (1.40 g, 6.25 mmol). After 1 hour of stirring, an additional 300 mg of mCPBA was added and the reaction was stirred an additional hour and was then judged to be complete by HPLC-MS analysis. The reaction was filtered and the solvent was removed by rotary evaporation. The residue was treated with water (30 mL) and 5 g of Na$_2$S$_2$O$_3$. The aqueous phase was made basic with NaHCO$_3$ and water was removed by rotary evaporation until some salts started precipitating. The aqueous phase was then exracted with dichloromethane 4 times and discarded. The combined organic extracts were dried over MgSO$_4$ and the solvent was removed to afford 795 mg (86%) of the corresponding sulfone as a white solid; $^1$H NMR (CDCl$_3$, 400 MHz) a 1.38 (s, 9H), 1.89-2.11 (m, 2H), 2.52-2.67 (m, 1H), 2.88 (s, 3H), 3.08 (dd, 2H, $J_1$=$J_2$=8.0), 3.54-3.72 (m, 3H), 4.98 (d, 1H, J=8.4); HPLC-MS calcd. for $C_{10}H_{21}NO_5S$ (M+Na$^+$) 562.3, found 562.5.

Step B

[1-(S)-(5-Fluoro-2,3-dihydro-indol-1-ylmethyl)-3-methanesulfonyl-propyl]-carbamic acid tert-butyl ester was prepared in 72% yield an analogous manner to example 22, step A, except that the sulfone from the previous step and 1 equivalent of 5-fluoroindoline were used as coupling partners; $^1$H NMR (CDCl$_3$, 400 MHz) δ 1.56 (s, 9H), 2.01-2.16 (m, 1H), 2.32-2.43 (m, 1H), 3.06 (s, 3H), 3.07 (dd, 1H, $J_1$=$J_2$=4.0), 3.13-3.23 (m, 2H), 3.23-3.34 (m, 2H), 3.95-4.06 (m, 1H), 4.70-4.79 (m, 1H), 6.48 (dd, 1H, $J_1$=4.1, $J_2$=8.5), 6.84-6.92 (m, 1H), 6.93-6.97 (m, 1H); HPLC-MS calcd. for $C_{18}H_{27}FN_2O_4S$ (M+H$^+$) 387.2, found 387.4.

Steps C and D

These transformations were performed in 76% yield in an analogous fashion to Example 22 steps C and D; $^1$H NMR (CDCl$_3$, 400 MHz) δ 0.81 (s, 9H), 0.75-0.86 (m, 1H), 1.25 (dd, 1H, $J_1$=8.6, $J_2$=14.4), 1.29 (s, 9H), 1.69 (dd, 1H, $J_1$=3.5, $J_2$=14.4), 1.84-1.96 (m, 1H), 2.09-2.22 (m, 1H), 2.82 (s, 3H), 2.78-2.87 (m, 2H), 2.94 (dd, 1H, $J_1$=6.4, $J_2$=13.9), 2.97-3.08 (m, 3H), 3.20-3.33 (m, 2H), 3.86 (ddd, 1H, $J_1$=3.8, $J_2$=8.1, $J_3$=12.0), 4.06-4.15 (m, 1H), 4.59-4.67 (m, 1H), 6.17-6.25 (m, 1H), 6.25 (dd, 1H, $J_1$=4.1, $J_2$=8.5), 8.58-8.66 (m, 1H), 8.67-8.71 (m, 1H); HPLC-MS calcd. for $C_{25}H_{40}FN_3O_5S$ (M+H$^+$) 514.3, found 514.5.

Example 158

3-(S)-(2-(S)-Benzyloxycarbonylamino-4,4-dimethyl-pentanoylamino)-4-(5-fluoro-2,3-dihydro-indol-1-yl)-butyric acid tert-butyl ester

Step A 3-(S)-Benzyloxycarbonylamino-4-(5-fluoro-2,3-dihydro-indol-1-yl)-butyric acid tert-butyl ester was prepared in 71% yield an analogous manner to example 22, step A except that N-Cbz-γ-O-tBu-aspartinol and 1 equivalent of 5-Fluoroindoline were used as coupling partners; HPLC-MS calcd. for $C_{124}H_{29}FN_2O_4$ (M+H$^+$) 429.2, found 429.4.

Step B

A sample of the product of step A (1.3 g, 3.0 mmol) was treated with 20% Pd(OH)$_2$ on carbon (260 mg) and methanol (2 mL). The atmosphere in the reaction was exchanged for hydrogen by sparging the solution with a long needle for 3 minutes and the reaction was stirred under 1 atmosphere of hydrogen for 2 hours. The atmosphere was exchanged back to nitrogen by again sparging the solution with a long needle for 3 minutes. The reaction mixture was filtered through celite and the solvent was removed. The resulting oil was treated with Cbz-tBu-ala DCHA salt (1.8 g, 3.7 mmol), HATU (1.4 g, 3.8 mmol) and DMF (2 mL). The reaction was then treated with diisopropylethylamine (1.2 g, 9.2 mmol) and stirred overnight. The reaction was diluted with ethyl acetate and extracted with water twice and 1 M NaOH once. The organics were then dried over MgSO$_4$ and the solvent was removed. The residue was purified over silica gel using a gradient of 0 to 100% ethyl acetate in hexane to afford 1.3 g (77%) of the title material as a solid; $^1$H NMR (CDCl$_3$, 400 MHz) δ 0.92 (s, 9H), 1.39 (dd, 1H, J$_1$=5.8, J$_2$=14.4), 1.44 (s, 9H), 1.82 (dd, 1H, J$_1$=3.7, J$_2$=14.5), 2.51 (dd, 1H, J$_1$=5.5, J$_2$=16.2), 2.61 (dd, 1H, J$_1$=4.7, J$_2$=16.3), 2.92 (dd, 1H, J$_1$=J$_2$=8.2), 3.07 (dd, 1H, J$_1$=7.4, J$_2$=13.6), 3.17 (dd, 1H, J$_1$=6.0, J$_2$=13.8), 3.28-3.47 (m, 2H), 4.09-4.17 (m, 1H), 4.33-4.43 (m, 1H), 4.98-5.13 (m, 3H), 6.40 (dd, 1H, J$_1$=4.0, J$_2$=8.4), 6.69-6.84 (m, 3H), 7.26-7.37 (m, 5H); HPLC-MS calcd. for $C_{31}H_{42}FN_3O_5$ (M+H$^+$) 556.3, found 556.5.

Example 159

3-(S)-(2-(S)-Benzyloxycarbonylamino-4,4-dimethyl-pentanoylamino)-4-(5-fluoro-2,3-dihydro-indol-1-yl)-butyric acid The title compound of example 158 (46 mg, 83 μmol) was dissolved in a mixture of TFA, dichloromethane and water in a ratio of 45:45:10 (1 mL) and stirred overnight. The solvent was removed and the reaction was lyophilized to afford 58.1 mg (114% of theory) of material that likely had some water or multiple TFA salts included; $^1$H NMR (MeOD, 400 MHz) δ 0.91 (s, 9H), 1.49 (dd, 1H, J$_1$=9.3, J$_2$=14.4), 1.67 (dd, 1H, J$_1$=3.1, J$_2$=14.5), 2.63 (d, 1H, J=6.5), 2.98 (dd, 1H, J$_1$=J$_2$=8.1), 3.17 (dd, 1H, J$_1$=5.5, J$_2$=13.6), 3.26-3.34 (m, 1H), 3.47 (dd, 1H, J$_1$=8.6, J$_2$=17.3), 3.58 (dd, 1H, J$_1$=8.4, J$_2$=16.6), 4.13 (dd, 1H, J$_1$=3.0, J$_2$=9.3), 4.46-4.55 (m, 1H), 4.98-5.11 (m, 2H), 6.68 (dd, 1H, J$_1$=4.1, J$_2$=8.6), 6.77-6.84 (m, 1H), 6.86-6.91 (m, 1H), 7.24-7:33 (m, 5H); HPLC-MS calcd. for $C_{27}H_{34}FN_3O_5$ (M+H$^+$) 500.2, found 500.5.

Example 160

4-(5-Fluoro-2,3-dihydro-indol-1-yl)-3-(S)-[2-(S)-(3-methoxy-benzoylamino)-4,4-dimethyl-pentanoylamino]-butyric acid tert-butyl ester This material was prepared in 92% yield in an analogous fashion to example 158 except that 3-(S)-(2-(S)-Benzyloxycarbonylamino-4,4-dimethyl-pentanoylamino)-4-(5-fluoro-2,3-dihydro-indol-1-yl)-butyric acid tert-butyl ester was deprotected and m-anisic acid was used as the acid; $^1$H NMR (CDCl$_3$, 400 MHz) δ 0.95 (s, 9H), 1.40 (s, 9H), 1.57 (dd, 1H, J$_1$=8.5, J$_2$=14.5), 1.88 (dd, 1H, J$_1$=4.0, J$_2$=14.5), 2.51 (dd, 1H, J$_1$=5.9, J$_2$=16.3), 2.61 (dd, 1H, J$_1$=5.1, J$_2$=16.3), 2.81-2.96 (m, 2H), 3.07 (dd, 1H, J$_1$=7.4, J$_2$=13.8), 3.22 (dd, 1H, J$_1$=6.5, J$_2$=13.8), 3.34 (dd, 1H, J$_1$=8.5, J$_2$=17.1), 3.44 (dd, 1H, J=8.6, J$_2$=16.3), 3.82 (s, 3H), 4.34-4.43 (m, 1H), 4.64 (ddd, 1H, J=4.0, J$_2$=J$_3$=8.5), 6.39 (dd, 1H, J=4.1, J$_3$=8.5), 6.57 (d, 1H, J=8.4), 6.66-6.75 (m, 1H), 6.73-6.78 (m, 1H), 6.97 (d, 1H, J=8.5), 6.98-7.04 (m, 1H), 7.23-7.33 (m, 3H); HPLC-MS calcd. for $C_{31}H_{42}FN_3O_5$ (M+H$^+$) 556.3, found 556.5.

Example 161

3-(S)-[3-Cyclohexyl-2-(S)-(3-methoxy-benzoylamino)-propionylamino]-4-(5-fluoro-2,3-dihydro-indol-1-yl)-butyric acid benzyl ester This material was prepared in 47% yield using an identical procedure to example 149; $^1$H NMR (CDCl$_3$, 400 MHz) δ 0.66-0.87 (m, 2H), 0.94-1.07 (m, 3H), 1.13-1.27 (m, 1H), 1.37-1.69 (m, 8H), 2.55 (dd, 1H, J$_1$=5.6, J$_2$=16.4), 2.62 (dd, 1H, J$_1$=5.0, J$_2$=16.4), 2.76 (dd, 1H, J$_1$=J$_2$=8.3), 2.94 (dd, 1H, J$_1$=7.4, J$_2$=13.7), 3.08 (dd, 1H, J$_1$=6.7, J$_2$=13.7), 3.26 (dd, 1H, J$_1$=8.4, J$_2$=16.5), 3.70 (s, 3H), 4.32-4.40 (m, 1H), 4.44-4.52 (m, 1H), 4.93 (s, 2H), 6.18 (dd, 1H, J$_1$=4.1, J$_2$=8.6), 6.34 (d, 1H, J=8.1), 6.55 (ddd, 1H, J$_1$=2.5, J$_2$=8.8, J$_3$=11.3), 6.61-6.66 (m, 1H), 6.67 (d, 1H, J=8.6), 6.39 (dddd, 1H, J$_1$=1.0, J$_2$=2.6, J$_2$=8.1, J$_2$=9.1), 7.12-7.23 (m, 3H); HPLC-MS calcd. for $C_{36}H_{42}FN_3O_5$ (M+H$^+$) 616.3, found 616.5.

Example 162

3-(S)-[3-Cyclohexyl-2-(S)-(3-methoxy-benzoylamino)-propionylamino]-4-(5-fluoro-2,3-dihydro-indol-1-yl)-butyric acid The title compound of example 161 (242 mg, 0.40 mmol) was treated with 20% Pd(OH)$_2$ on carbon (50 mg) and methanol (5 mL). The atmosphere in the reaction was exchanged for hydrogen by sparging the solution with a long needle for 3 minutes and the reaction was stirred under 1 atmosphere of hydrogen for 2.5 hours. The atmosphere was exchanged back to nitrogen by again sparging the solution with a long needle for 3 minutes. The reaction was filtered through celite and the solvent was removed to afford 150 mg (72%) of the title compound as a solid. The material was made into the mesylate salt in quantitative yield by treating an ether solution with stoichiometric methanesulfonic acid and the data are given for the salt; $^1$H NMR (DMSO-d$_6$, 400 MHz) δ 0.90-1.04 (m, 2H), 1.16-1.32 (m, 4H), 1.35-1.46 (m, 1H), 1.62-1.84 (m, 7H), 2.64-2.71 (m, 1H), 2.69 (s, 3H), 2.81 (dd, 1H, J$_1$=7.4, J$_2$=16.8), 3.44-3.51 (m, 1H), 3.80 (s, 3H), 3.82-3.94 (m, 2H), 4.09-4.18 (m, 1H), 4.47 (dd, 1H, J$_1$=6.7, J$_2$=8.8), 4.51-4.60 (m, 1H), 7.05-7.13 (m, 2H), 7.18-7.23 (m, 1H), 7.28-7.34 (m, 2H), 7.34-7.37 (m, 2H); HPLC-MS calcd. for $C_{29}H_{36}FN_3O_5$ (M+H$^+$) 526.3, found 526.5.

Example 163

4-(5-Fluoro-2,3-dihydro-indol-1-yl)-3-(S)-[2-(S)-(3-methoxy-benzoylamino)-4,4-dimethyl-pentanoylamino]-butyric acid ethyl ester The title compound of example 218 (75 mg, 0.15 mmol) was treated with triethylorthoformate (270 mg, 1.8 mmol), ethanol (2 mL) and camphorsulfonic acid (53 mg, 0.23 mmol) and stirred overnight. The reaction was then diluted with ethyl acetate and extracted with saturated aqueous $NaHCO_3$. The organic layer was then dried over $MgSO_4$ and the solvent was removed. The resulting oil was purified over silica gel using a gradient of 0-100% ethyl acetate in hexane to afford 35 mg (44%) of the title compound as a solid; HPLC-MS calcd. for $C_{29}H_{38}FN_3O_5$ (M+H$^+$) 528.3, found 528.5.

Example 164

{1-(S)-[2-Cyano-1-(S)-(5-fluoro-2,3-dihydro-indol-1-ylmethyl)-ethylcarbamoyl]-3,3-dimethyl-butyl}-carbamic acid tert-butyl ester Step A A solution of N-Boc cyanoalanine (2 g, 9.3 mmol) in THF (30 mL) was cooled in an ice/NaCl bath to –10° C. and treated with triethylamine (0.94 g, 9.3 mmol) followed by dropwise addition of isobutyl chloroformate (1.35 g, 9.9 mmol). The reaction mixture was stirred for 4 minutes at –10° C. and filtered through a coarse scintered glass funnel. Meanwhile, in another flask, a solution of $NaBH_4$ (0.71 g, 19 mmol) in water (10 mL) was prepared and cooled in an ice/water bath. The filtered solution of the mixed anhydride was added dropwise to the cold $NaBH_4$ solution and the resulting mixture was stirred for 2 hours. The THF was removed on the rotary evaporator and the reaction was acidified with 5% $NaHSO_4$ solution to pH 3 and diluted with ethyl acetate and water. The organics were extracted twice with aqueous $NaHCO_3$ and dried over $MgSO_4$. The solvent was removed to afford 1.2 g (64%) of (S)-(2-Cyano-1-hydroxymethyl-ethyl)-carbamic acid tert-butyl ester; $^1$H NMR (CDCl$_3$, 400 MHz) δ 1.45 (s, 9H), 2.09-2.17 (m, 1H), 2.73 (d, 1H, J=6.0), 3.76 (dd, 1H, $J_1$=4.7, $J_2$=10.8), 3.80-3.86 (m, 1H), 3.91-3.99 (m, 1H), 4.98-5.07 (m, 1H).

Step B (S)-[2-Cyano-1-(5-fluoro-2,3-dihydro-indol-1-ylmethyl)-ethyl]-carbamic acid tert-butyl ester was prepared in 27% yield an analogous manner to example 22 step A, except that the nitrile from the previous step and 1 equivalent of 5-Fluoroindoline were used as coupling partners; HPLC-MS calcd. for $C_{17}H_{22}FN_3O_2$ (M+H$^+$) 320.2, found 320.4.

Steps C and D

These transformations were performed in 48% yield in an analogous fashion to Example 22 steps C and D; HPLC-MS calcd. for $C_{24}H_{35}FN_4O_3$ (M+H$^+$) 447.3, found 447.5.

Example 165

N-{1-(S)-[2-Cyano-1-(S)-(5-fluoro-2,3-dihydro-indol-1-ylmethyl)-ethylcarbamoyl]-3,3-dimethyl-butyl}-3-methoxy-benzamide This material was prepared in 25% yield using an identical procedure to example 149 step B; HPLC-MS calcd. for $C_{27}H_{33}FN_4O_3$ (M+H$^+$) 481.3, found 481.5.

Example 166

N-{1-(S)-[2-(5-Fluoro-2,3-dihydro-indol-1-yl)-1-(S)-(1H-tetrazol-5-ylmethyl)-ethylcarbamoyl]-3,3-dimethyl-butyl}-3-methoxy-benzamide The title compound of example 165 (50 mg, 0.10 mmol) in THF (1 mL) was treated with tributyltin azide (55 mg, 0.17 mmol) and sealed in a gastight vial. The reaction was stirred for 3 days and the solvent was removed. The residue was purified by preperative HPLC to afford 10 mg (20%) of the title material; HPLC-MS calcd. for $C_{27}H_{34}FN_7O_3$ (M+H$^+$) 524.3, found 524.5.

Example 167

N-{1-(S)-[5-Amino-1-(S)-(5-fluoro-2,3-dihydro-indol-1-ylmethyl)-pentylcarbamoyl]-3-cyclohexyl-propyl}-3-methoxy-benzanide.[&]

HPLC-MS calcd. for $C_{32}H_{45}FN_4O_3$ (M+H$^+$) 553.4, found 553.6.

Example 168

3-(S)-(2-(S)-Benzyloxycarbonylamino-3-cyclohexyl-propionylamino)-4-(5-fluoro-2,3-dihydro-indol-1-yl)-butyric acid benzyl ester.[&]

$^1$H NMR (CDCl$_3$, 400 MHz) δ 0.80-0.95 (m, 2H), 1.11-1.18 (m, 3H), 1.26-1.32 (m, 1H), 1.37-1.44 (m, 1H), 1.55-1.75 (m, 6H), 2.59-2.76 (m, 2H), 2.89 (t, 2H, $J_1$=8.0 Hz), 3.03-3.09 (m, 1H), 3.15-3.20 (m, 1H), 3.27-3.42 (m, 2H), 4.13-4.19 (m, 1H), 4.48-4.50 (m, 1H), 5.04-5.19 (m, 4H), 6.30-6.33 (m, 1H), 6.67-6.72 (m, 1H), 6.76-6.79 (m, 2H), 7.30-7.38 (m, 9H); HPLC-MS calcd. for $C_{36}H_{42}FN_3O_5$ (M+H$^+$) 616.3, found 616.5.

Example 169

1-(S)-[1-(R)-Benzyloxymethyl-2-(5-fluoro-2,3-dihydro-indol-1-yl)-ethylcarbamoyl]-2-cyclohexyl-ethyl}-carbamic acid benzyl ester.[&]

$^1$H NMR (CDCl$_3$, 400 MHz) δ 0.83-0.98 (m, 2H), 1.09-1.24 (m, 3H), 1.26-1.35 (m, 1H), 1.40-1.51 (m, 1H), 1.55-1.75 (m, 6H), 2.93 (t, 2H, J=7.6 Hz), 3.13-3.26 (m, 1H), 3.34-3.43 (m, 1H), 3.51-3.53 (m, 1H), 3.67 (d, 1H, J=7.6 Hz), 4.15-4.20 (m, 1H), 4.27-4.30 (m, 1H), 4.43-4.56 (m, 2H), 5.03-5.18 (m, 4H), 6.51-6.57 (m, 1H), 6.73-6.81 (m, 1H), 6.94-6.98 (m, 1H), 7.27-7.39 (m, 10H); HPLC-MS calcd. for $C_{35}H_{42}FN_3O_4$ (M+H$^+$) 588.3, found 588.5.

Example 170

N-{3-Cyclohexyl-1-(S)-[2-(3,5-dimethoxy-benzyloxy)-1-(R)-(5-fluoro-2,3-dihydro-indol-1-ylmethyl)-ethylcarbamoyl]-propyl}-3-methoxy-benzamide.[&]

$^1$H NMR (CDCl$_3$, 400 MHz) δ 0.74-0.93 (m, 2H), 1.11-1.81 (m, 10H), 1.84-2.01 (m, 3H), 2.41-2.50 (m, 1H), 2.62-2.73 (m, 3H), 3.04-3.16 (m, 2H), 3.55 (s, 3H), 3.66 (broad s, 5H), 3.79 (s, 3H), 4.42-4.55 (m, 4H), 6.01 (s, 2H), 6.45 (s, 1H), 6.88-7.28 (m, 7H) HPLC-MS calcd. for $C_{38}H_{48}FN_3O_6$ (M+H$^+$) 662.4, found 662.6.

Example 171

4-{2-(R)-[4-Cyclohexyl-2-(S)-(3-methoxy-benzoylamino)-butyrylamino]-3-(5-fluoro-2,3-dihydro-indol-1-yl)-propoxymethyl}-benzoic acid methyl ester.<sup>&</sup>

$^1$H NMR (CDCl$_3$, 400 MHz) δ 0.82-0.88 (m, 2H), 1.17-1.25 (m, 3H), 1.62-1.75 (m, 10H), 3.27-3.81 (m, 4H), 3.84 (s, 3H), 3.93 (s, 3H), 4.23-4.36 (m, 2H), 4.51-4.56 (m, 4H), 6.42 (d, 1H, J=2.8 Hz), 6.57-6.61 (m, 1H), 6.92-6.96 (m, 1H), 7.03-7.09 (m, 1H), 7.22-7.45 (m, 5H), 8.00 (d, 2H, J=8.4 Hz), HPLC-MS calcd. for C$_{38}$H$_{46}$FN$_3$O$_6$ (M+H$^+$) 660.3, found 660.6.

Example 172

(S,S)—N-{3-Cyclohexyl-1-[2-(5-fluoro-2,3-dihydro-indol-1-yl)-1-(4-hydroxy-benzyl)-ethylcarbamoyl]-propyl}-3-methoxy-benzamide.<sup>&</sup>

HPLC-MS calcd. for C$_{35}$H$_{42}$FN$_3$O$_4$ (M+H$^+$) 588.3, found 588.5.

Example 173

Tetrahydropyran-4-carboxylic acid {2-cyclohexyl-1-(S)-[2-(5-fluoro-3,3-dimethyl-2,3-dihydro-indol-1-yl)-1-(S)-methyl-ethylcarbamoyl]-ethyl}-amide.<sup>$</sup>

C$_{28}$H$_{42}$FN$_3$O$_3$; LCMS: 486.6 (M+H)$^+$.

Example 174

{2-Cyclohexyl-1-(S)-[2-(5-fluoro-2,3-dihydro-indol-1-yl)-1-(S)-methyl-ethylcarbamoyl]-ethyl}-carbamic acid benzyl ester.<sup>&</sup>

$^1$H NMR (CD$_3$OD, 400 MHz) δ 0.69-0.80 (m, 2H), 1.00-1.10 (m, 5H), 1.10 (d, 3H, J=6.8 Hz), 2.75-2.81 (m, 3H), 3.00-3.05 (m, 1H), 3.13 (q, 1H, J=8.8 Hz), 3.39 (dd, 1H, J=15.2, 8.4 Hz), 3.90-4.12 (m, 2H), 4.89-4.91 (m, 2H), 6.28-6.35 (m, 1H), 6.58-6.32 (m, 1H), 6.68 (d, 1H, J=8.0 Hz), 7.18-7.24 (m, 5H). HPLC-MS calcd. for C$_{28}$H$_{36}$FN$_3$O$_3$ (M+H$^+$) 482.3, found 482.5.

Example 175

4-Benzyloxy-N—(R,S)—{[2-(4-amidinophenylamino)-1-(S)-methyl-ethylcarbamoyl]-(2,4-dichloro-phenyl)-methyl}-benzamide.<sup>&</sup>

HPLC-MS calcd. for C$_{32}$H$_{31}$Cl$_2$N$_5$O$_3$ (M+H$^+$) 604.2, found 604.4.

Example 176

{1-(S)-[2-(5-Fluoro-2,3-dihydro-indol-1-yl)-1-(S)-methyl-ethylcarbamoyl]-3,3-dimethyl-butyl}-carbamic acid benzyl ester.<sup>$</sup>

HPLC-MS calcd. for C$_{26}$H$_{34}$FN$_3$O$_3$ (M+H$^+$) 456.3, found 456.5.

Example 177

Cyclopropanecarboxylic acid {1-(S)-[2-(5-fluoro-2,3-dihydro-indol-1-yl)-1-(S)-methyl-ethylcarbamoyl]-3,3-dimethyl-butyl}-amide.<sup>$</sup>

HPLC-MS calcd. for C$_{22}$H$_{32}$FN$_3$O$_2$ (M+H$^+$) 390.2, found 390.5.

Example 178

Pyridazine-4-carboxylic acid {1-(S)-[2-(5-fluoro-2,3-dihydro-indol-1-yl)-1-(S)-methyl-ethylcarbamoyl]-3,3-dimethyl-butyl}-amide.<sup>$</sup>

HPLC-MS calcd. for C$_{23}$H$_{30}$FN$_5$O$_2$ (M+H$^+$) 428.2, found 428.5.

Example 179

4,4-Dimethyl-2-(S)-(2-1H-tetrazol-5-yl-acetylamino)-pentanoic acid [2-(5-fluoro-2,3-dihydro-indol-1-yl)-1-(S)-methyl-ethyl]-amide.<sup>$</sup>

HPLC-MS calcd. for C$_{21}$H$_{30}$FN$_7$O$_2$ (M+H$^+$) 432.2, found 432.5.

Example 180

(2-Cyclohexyl-1-(S)-{1-(S)-methyl-2-[3-(1H-tetrazol-5-yl)-phenylamino]-ethylcarbamoyl}-ethyl)-carbamic acid benzyl ester.<sup>$</sup>

HPLC-MS calcd. for C$_{27}$H$_{35}$N$_7$O$_3$ (M+H$^+$) 506.3, found 506.5.

Example 181

(S,S)-2-(3-Chloro-benzenesulfonylamino)-3-cyclohexyl-N-[1-methyl-2-(4-trifluoromethoxy-phenylamino)-ethyl]-propionamide

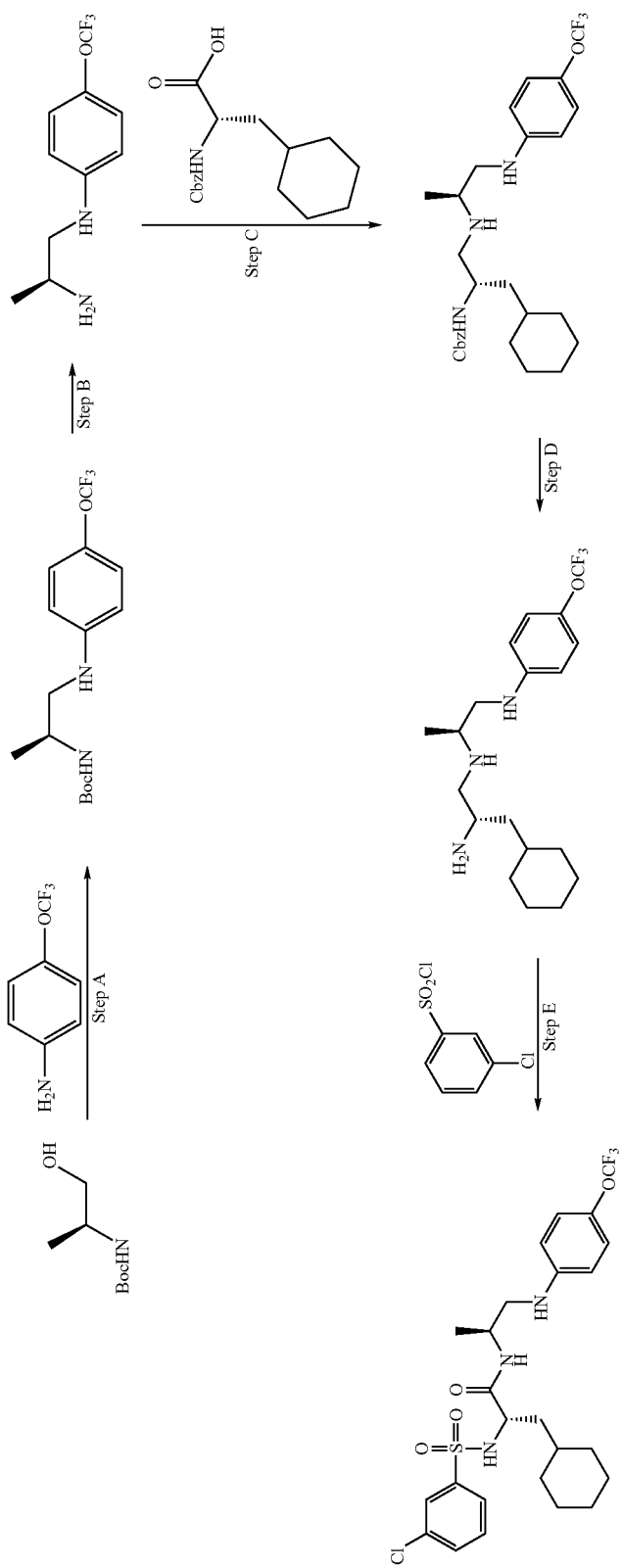

Step A (S)-[1-Methyl-2-(4-trifluoromethoxy-phenylamino)-ethyl]-carbamic acid tert-butyl ester was produced as follows: S—N-Boc-Alinol (259 mg, 1.47 mmol) and Dess-Martin periodane (748 mg, 1.76 mmol) were dissolved in 25 mL of dry DCM and stirred for 1 hour. The resulting slurry was partitioned with $Na_2S_2O_3$ and sodium bicarbonate, washed with brine, dried over magnesium sulfate and dried down to a white solid. The resulting aldehyde was treated with a methanol solution of 4-trifluoromethoxyaniline (260 mg, 1.47 mmol), $NaCNBH_3$ (179 mg, 2.94 mmol), and acetic acid (353 mg, 5.88 mmol) sequentially. The resulting solution was stirred for 1 hour, stripped to dryness, taken up in ethyl acetate and washed with sodium bicarbonate. The organic layer was then dried over magnesium sulfate, stripped down and purified by column chromatography, yield 418 mg (85%).

Step B

S—N-(4-Trifluoromethoxy-phenyl)-propane-1,2-diamine was prepared as follows: [1-Methyl-2-(4-trifluoromethoxy-phenylamino)-ethyl]-carbamic acid tert-butyl ester was dissolved in 50% TFA/DCM for 3 hours. The reaction was worked up by stripping off the volatiles and ethyl acetate was added. The organic layer was then washed with sodium bicarbonate, dried over magnesium sulfate and stripped to dryness. The resulting compound was then purified by flash chromatography.

Step C (S,S)-{2-Cyclohexyl-1-[1-methyl-2-(4-trifluoromethoxy-phenylamino)-ethylcarbamoyl]-ethyl}-carbamic acid benzyl ester: (S)—N-(4-trifluoromethoxy-phenyl)-propane-1,2-diamine (76.7 mg, 0.328 mmol), (S)-2-benzyloxycarbonylamino-3-cyclohexyl-propionic acid (100 mg, 0.328 mmol) and HATU (125 mg, 0.328 mmol) were added to a round bottom flask with 20 mL of dry DCM. DIPEA (127 mg, 0.982 mmol) was added dropwise over three minutes with vigorous stirring. The resulting slurry was stirred for 1.5 hours. The solution was then washed with sodium bicarbonate, the organic layer was separated and partially concentrated and the concentrate was purified by flash chromatography. Yield 138 mg, 81%.

Step D (S,S)-2-Amino-3-cyclohexyl-N-[1-methyl-2-(4-trifluoromethoxy-phenylamino)-ethyl]-propionamide: The product from step C (138 mg, 0.265 mmol) and 5 mol % of 10% palladium on carbon (14 mg) was dissolved in 20 mL of methanol and purged with nitrogen. Balloon pressure of hydrogen was added and the resulting slurry was stirred for 5 hours. The septum was removed and the slurry was filtered through celite and concentrated. Yield 98 mg, quantitative.

Step E

The product from step D (15.4 mg, 39.7 μmol) was added to a flask with DMAP (14.5 mg, 0.119 mmol) and dry DMF (0.5 mL). 3-Chloro-benzenesulfonyl chloride (8.37 mg, 39.7 μmol) was added as a solution in 0.5 mL of dry DMF dropwise over 3 minutes. The resulting solution was stirred for 12 hours and the volatiles were stripped off. The solids were taken up in methanol and purified by prep HPLC. Yield 15 mg, 67%. $^1$H NMR ($CDCl_3$) δ(ppm): 7.9 (s, 1H), 7.75 (d, J=7.9 Hz, 1H), 7.6 (d, J=8 Hz, 1H), 7.5 (t, J=7.9 Hz, 1H), 7.05 (d, J=8.3 Hz, 2H), 6.6 (d, J=8.9 Hz, 2H), 6.15 (s, 1H), 5.1 (s, 1H), 4.1 (m, 1H), 3.65 (m, 1H), 3.25 (dd J=4.7, 12.9 Hz, 1H), 3.1 (dd J=7.5, 12.7 Hz, 1H), 1.6 (m, 7H), 1.4 (m, 1H), 1.3 (m, 1H), 1.2 (d, J=8.4 Hz, 3H), 1.07 (m, 3H), 0.65 (m, 1H). $C_{25}H_{31}CWF_3N_3O_4S$: LC/MS=562.2 (M+1).

Example 182

(S,S)-3-Cyclohexyl-N-[1-methyl-2-(4-trifluoromethoxy-phenylamino)-ethyl]-2-(3-trifluoromethoxy-benzenesulfonylamino)-propionamide; $C_{26}H_{31}F_6N_3O_5S$: LC/MS: 612.19 $(M+1)^+$.***

Example 183

(S,S)-3-Cyclohexyl-N-[1-methyl-2-(4-trifluoromethoxy-phenylamino)-ethyl]-2-(pyridine-3-sulfonylamino)-propionamide; $C_{24}H_{31}F_3N_4O_4S$: LC/MS: 529.20 $(M+1)^+$.***

Example 184

(S,S)-{2-Cyclohexyl-1-[1-methyl-2-(4-trifluoromethoxy-phenylamino)-ethylcarbamoyl]-ethyl}-carbamic acid tetrahydro-pyran-4-yl ester

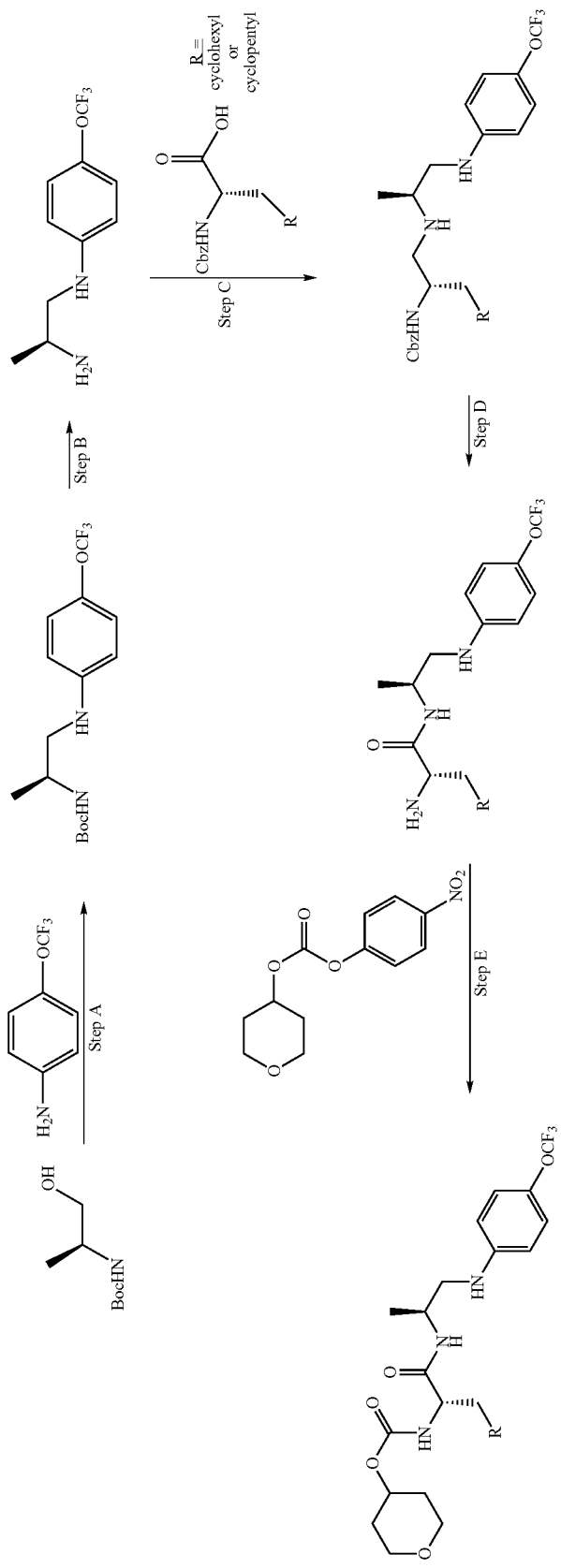

The conjugate from step D, (S,S)-2-amino-3-cyclohexyl-N-[1-methyl-2-(4-trifluoromethoxy-phenylamino)-ethyl]-propionamide was prepared according to Example 181, steps A-D.

Step E

The conjugate from step D (25.4 mg, 65.5 µmol) and 4-nitrophenyl tetrahydropyran-4-yl carbonate (19.3 mg, 72.1 mmol) were placed in a vial and 1.0 mL of dry DMF was added through a septum by syringe. DIPEA (25.4 mg, 196.5 µmol) was added by syringe and the reaction was stirred overnight. The solution was diluted with methanol and purified by prep HPLC, yield 21 mg (62%). $^1$H NMR (CDCl$_3$) δ(ppm): 7.04 (d, J=8.0 Hz, 2H); 6.66 (d, J=8.0 Hz, 2H); 6.1 (s, 1H); 5.15 (s, 1H); 4.80 (m, 1H); 4.27 (q, J=6.5 Hz, 1H); 4.1 (q, J=9.0 Hz, 1H); 3.88 (m, 2H); 3.48 (m, 2H); 3.18 (m, 2H); 1.85 (m, 2H); 1.66 (m, 9H); 1.48 (m, 1H); 1.27 (d, J=6.8 Hz, 3H); 1.13 (m, 3H). $C_{25}H_{36}F_3N_3O_5$: LC/MS=516.26 (M+1)$^+$.

Example 185

3-(R)-{2-Cyclohexyl-1-(S)-[1-(S)-methyl-2-(4-trifluoromethoxy-phenylamino)-ethylcarbamoyl]-ethylcarbamoyloxy}-pyrrolidine-1-carboxylic acid tert-butyl ester: $C_{29}H_{43}F_3N_4O_6$; LC/MS: 601.31 (M+1)$^+$.$^{\$\$\$}$ Example 186

(S,S)-{2-Cyclohexyl-1-[1-methyl-2-(4-trifluoromethoxy-phenylamino)-ethylcarbamoyl]-ethyl}-carbamic acid 1,1-dioxo-hexahydro-1λ$^6$-thiopyran-4-yl ester: $C_{25}H_{36}F_3N_3O_6S$; LC/MS: 564.23 (M+1)$^+$.$^{\$\$\$}$ Example 187

{2-Cyclohexyl-1-(S)-[1-(S)-methyl-2-(4-trifluoromethoxy-phenylamino)-ethylcarbamoyl]-ethyl}-carbamic acid pyrrolidin-3-(R)-yl ester: $C_{24}H_{35}F_3N_4O_4$; LC/MS: 501.26 (M+1)$^+$.$^{\$\$\$}$ Example 188

{2-Cyclohexyl-1-(S)-[1-(S)-methyl-2-(4-trifluoromethoxy-phenylamino)-ethylcarbamoyl]-ethyl}-carbamic acid tetrahydrofuran-3-(R)-yl ester: $C_{24}H_{34}F_3N_3O_5$; LC/MS: 502.25 (M+1)$^+$.$^{\$\$\$}$ Example 189

{2-Cyclohexyl-1-(S)-[1-(S)-methyl-2-(4-trifluoromethoxy-phenylamino)-ethylcarbamoyl]-ethyl}-carbamic acid tetrahydrofuran-3-(S)-yl ester: $C_{24}H_{34}F_3N_3O_5$; LC/MS: 502.25 (M+1)$^+$.$^{\$\$\$}$ Example 190

(S,S)-{2-Cyclopentyl-1-[1-methyl-2-(4-trifluoromethoxy-phenylamino)-ethylcarbamoyl]-ethyl}-carbamic acid tetrahydropyran-4-yl ester: $C_{24}H_{34}F_3N_3O_5$; LC/MS: 502.25 (M+1)$^+$.$^{\$\$\$}$ Example 191

(S,S)-{2-Cyclopentyl-1-[1-methyl-2-(4-trifluoromethoxy-phenylamino)-ethylcarbamoyl]-ethyl}-carbamic acid tetrahydrofuran-3-(R)-yl ester: $C_{23}H_{32}F_3N_3O_5$; LC/MS: 488.23 (M+1)$^+$.$^{\$\$\$}$ Example 192

(S,S)-{2-Cyclopentyl-1-[1-methyl-2-(4-trifluoromethoxy-phenylamino)-ethylcarbamoyl]-ethyl}-carbamic acid tetrahydrofuran-3-(S)-yl ester: $C_{23}H_{32}F_3N_3O_5$; LC/MS: 488.23 (M+1)$^+$.$^{\$\$\$}$ Example 193

N—((S)-(2-(5-fluoroindolin-1-yl)ethylcarbamoyl)(cyclohexyl)methyl)-3-methylbenzamide.*

LC/MS for $C_{26}H_{32}FN_3O_2$ 438.5 (M+H$^+$).

Example 194

N—((S)-1-(2-(5-fluoroindolin-1-yl)ethylcarbamoyl)-2-cyclopropylethyl)-5-(3-(trifluoromethyl)phenyl)furan-2-carboxamide LC/MS for $C_{28}H_{27}F_4N_3O_3$ 530.4 (M+H$^+$).

Example 195

N—((S)-1-(2-(5-fluoroindolin-1-yl)ethylcarbamoyl)-2-(2-chlorophenyl)ethyl)-3-methylbenzamide.*

LC/MS for $C_{27}H_{27}ClFN_3O_2$ 480.4 (M+H$^+$).

Example 196

N—((S)-1-(2-(5-fluoroindolin-1-yl)ethylcarbamoyl)-2-(3-chlorophenyl)ethyl)-5-(3-(trifluoromethyl)phenyl)furan-2-carboxamide.*

LC/MS for $C_{31}H_{26}ClF_4N_3O_3$ 600.4 (M+H$^+$).

Example 197

N—((S)-1-(2-(5-fluoroindolin-1-yl)ethylcarbamoyl)-2-(3-chlorophenyl)ethyl)-3-methylbenzamide.*

LC/MS for $C_{27}H_{27}ClFN_3O_2$ 480.4 (M+H$^+$).

Example 198

N—((S)-1-(2-(5-fluoroindolin-1-yl)ethylcarbamoyl)-2-(4-chlorophenyl)ethyl)-5-(3-(trifluoromethyl)phenyl)furan-2-carboxamide.*

LC/MS for $C_{31}H_{26}ClF_4N_3O_3$ 600.4 (M+H$^+$).

Example 199

N—((S)-1-(2-(5-fluoroindolin-1-yl)ethylcarbamoyl)-2-(4-chlorophenyl)ethyl)-3-methylbenzamide.*

LC/MS for $C_{27}H_{27}ClFN_3O_2$ 480.4 (M+H$^+$).

Example 200

N—((S)-1-(2-(5-fluoroindolin-1-yl)ethylcarbamoyl)-
2-cyclopentylethyl)-5-(3-(trifluoromethyl)phenyl)
furan-2-carboxamide.*

LC/MS for $C_{30}H_{31}F_4N_3O_3$ 558.5 (M+H$^+$).

Example 201

(S)—N-{2-Cyclopentyl-1-[2-(5-fluoro-2,3-dihydro-
indol-1-yl)-ethylcarbamoyl]-ethyl}-3-methyl-benza-
mide.*

LC/MS for $C_{26}H_{32}FN_3O_2$ 438.5 (M+H$^+$).

Example 202

N—((S)-1-(2-(5-fluoroindolin-1-yl)ethylcarbamoyl)-
3,3-dimethylbutyl)-5-(3-(trifluoromethyl)phenyl)
furan-2-carboxamide.*

LC/MS for $C_{29}H_{31}F_4N_3O_3$ 546.4 (M+H$^+$).

Example 203

N—((S)-1-(2-(5-fluoroindolin-1-yl)ethylcarbamoyl)-
3,3-dimethylbutyl)-3-methylbenzamide.*

LC/MS for $C_{25}H_{32}FN_3O_2$ 426.5 (M+H$^+$).

Example 204

N—((S)-1-(2-(5-fluoroindolin-1-yl)ethylcarbamoyl)-
3-cyclohexylpropyl)-3-methylbenzamide.*

LC/MS for $C_{2-8}H_{36}FN_3O_2$ 466.5 (M+H$^+$).

Example 205

N—((S)-1-(2-(5-fluoroindolin-1-yl)ethylcarbamoyl)-
2-phenylethyl)-3-methylbenzamide.*

LC/MS for $C_{27}H_{28}FN_3O_2$ 446.5 (M+H$^+$).

Example 206

N—((S)-1-(2-(5-fluoroindolin-1-yl)ethylcarbamoyl)-
2-phenylethyl)-5-(3-(trifluoromethyl)phenyl)furan-2-
carboxamide.*

LC/MS for $C_{31}H_{27}F_4N_3O_3$ 566.4 (M+H$^+$).

Example 207

N—(R,S)-((3-(benzyloxy)-1-(5-fluoroindolin-1-yl)
propan-2-(R)-ylcarbamoyl)(2,4-dichlorophenyl)me-
thyl)furan-2-carboxamide.&

LC/MS for $C_{31}H_{28}Cl_2FN_3O_4$ 596.4 (M+H$^+$).

Example 208

N—(R,S)-((3-(5-fluoroindolin-1-yl)-1-hydroxypro-
pan-2-(R)-ylcarbamoyl)(2,4-dichlorophenyl)methyl)-
3,4-difluorobenzamide.&

LC/MS for $C_{26}H_{22}Cl_2F_3N_3O_3$ 552.3 (M+H$^+$).

Example 209

N—(S)-((3-(5-fluoroindolin-1-yl)-1-hydroxypropan-
2-(R)-ylcarbamoyl)(2,4-dichlorophenyl)methyl)fu-
ran-2-carboxamide.&

LC/MS for $C_{24}H_{22}Cl_2FN_3O_4$ 506.3 (M+H$^+$).

Example 210

(S,S)-3-Cyclohexyl-2-(2,4-dimethyl-thiazole-5-sul-
fonylamino)-N-[2-(5-fluoro-2,3-dihydro-indol-1-yl)-
1-methyl-ethyl]-propionamide.***

LC/MS for $C_{25}H_{35}FN_4O_3S_2$ 523.5 (M+H$^+$).

Example 211

N—(S)-((3-(benzyloxy)-1-(5-fluoroindolin-1-yl)
propan-2-(R)-ylcarbamoyl)(2,4-dichlorophenyl)me-
thyl)-3,4-difluorobenzamide.&

LC/MS for $C_{33}H_{28}Cl_2F_3N_3O_3$ 642.4 (M+H$^+$).

Example 212

N—(S)-((3-(5-fluoroindolin-1-yl)-1-hydroxypropan-
2-(R)-ylcarbamoyl)(2,4-dichlorophenyl)methyl)fu-
ran-2-carboxamide.&

LC/MS for $C_{24}H_{22}Cl_2FN_3O_4$ 506.4 (M+H$^+$).

Example 213

(R,S)—N-((2-(5-fluoroindolin-1-yl)ethylcarbamoyl)
(2,4-dichlorophenyl)methyl)-3-methylbenzamide.*

LC/MS for $C_{26}H_{24}Cl_2FN_3O_2$ 500.3 (M+H$^+$).

Example 214

(S,S)—N-((3-(5-fluoroindolin-1-yl)-1-hydroxypro-
pan-2-ylcarbamoyl)(2,4-dichlorophenyl)methyl)-3,4-
difluorobenzamide.&

LC/MS for $C_{26}H_{22}Cl_2F_3N_3O_3$ 552.3 (M+H$^+$).

Example 215

(S,S)-{2-Cyclohexyl-1-[2-(5-fluoro-3,3-dimethyl-2,3-di-
hydro-indol-1-yl)-1-methyl-ethylcarbamoyl]-ethyl}-car-
bamic acid tetrahydro-pyran-4-yl ester. $^1$H NMR (CDCl$_3$)
δ(ppm): 6.7 (m, 2H), 6.4 (s, 1H), 6.05 (s, 1H), 5.07 (d, J=8.3
Hz, 1H), 4.78 (s, 1H), 4.2 (s, 1H), 4.1 (s, 1H), 3.88 (m, 2H),
3.51 (m, 2H), 3.24 (m, 1H), 3.13 (m, 2H), 2.95 (m, 1H), 1.89

(m, 7H), 1.76 (m, 1H), 1.7 (m, 7H), 1.3 (m, 10H), 1.13 (m, 3H), 0.89 (m, 2H). $C_{28}H_{42}FN_3O_4$: LC/MS=504.2 (M+1)$^+$.$^{\$\$\$}$

Example 216

{2-Cyclohexyl-1-(S)-[2-(5-fluoro-3,3-dimethyl-2,3-dihydro-indol-1-yl)-1-(S)-methyl-ethylcarbamoyl]-ethyl}-carbamic acid (R)-tetrahydrofuran-3-yl ester. $C_{27}H_{40}FN_3O_4$: LC/MS: 490.3 (M+1)$^+$.$^{\$\$\$}$

Example 217

(S,S)-{2-Cyclohexyl-1-[2-(5-fluoro-3,3-dimethyl-2,3-dihydro-indol-1-yl)-1-methyl-ethylcarbamoyl]-ethyl}-carbamic acid (S)-tetrahydro-furan-3-yl ester. $C_{27}H_{40}FN_3O_4$: LC/MS: 490.3 (M+1)$^+$.$^{\$\$\$}$

Example 218

(S,S)-4-(5-Fluoro-2,3-dihydro-indol-1-yl)-3-[2-(3-methoxy-benzoylamino)-4,4-dimethyl-pentanoylamino]-butyric acid The title compound of example 160 (80 mg, 0.14 mmol) was dissolved in a mixture of TFA, dichloromethane and water in a ratio of 45:45:10 (1 mL) and stirred overnight. The solvent was removed and the reaction was partitioned between water and dichloromethane. The aqueous layer was extracted with dichloromethane 3 times and the combined organics were dried over $MgSO_4$ and the solvent was removed to afford 72 mg (100%) of the title compound as a solid; $^1H$ NMR (MeOD, 400 MHz) δ 0.94 (s, 9H), 1.70 (d, 1H, J=1.1), 2.62 (d, 1H, J=6.5), 2.79-2.93 (m, 2H), 3.06 (dd, 1H, $J_1$=6.0, $J_2$=13.7), 3.19 (dd, 1H, $J_1$=7.7, $J_2$=13.7), 3.45 (dd, 1H, $J_1$=8.6, $J_2$=15.9), 4.42-4.52 (m, 1H), 4.59-4.67 (m, 1H), 6.43 (dd, 1H, $J_1$=4.2, $J_2$=8.5), 6.62-6.68 (m, 1H), 6.72-6.78 (m, 1H), 7.05-7.08 (m, 1H), 7.29-7.38 (m, 3H), 7.96 (d, 1H, J=8.6), 8.37 (d, 1H, J=8.2); HPLC-MS calcd. for $C_{27}H_{34}FN_3O_5$ (M+H$^+$) 500.2, found 500.5.

Example 219

(S)-3-Cyclohexyl-N-[2-(5-fluoro-2,3-dihydro-indol-1-yl)-ethyl]-2-[3-(5-phenyl-thiophen-2-yl)-ureido]-propionamide LC/MS for $C_{30}H_{35}FN_4O_2S$ 535.5 (M+H$^+$).

Example 220

(S)-3-Cyclohexyl-2-[3-(3,5-dimethyl-isoxazol-4-yl)-ureido]-N-[2-(5-fluoro-2,3-dihydro-indol-1-yl)-ethyl]-propionamide LC/MS for $C_{25}H_{34}FN_5O_3$ 472.5 (M+H$^+$).

Example 221

(S)-3-Cyclohexyl-N-[2-(5-fluoro-2,3-dihydro-indol-1-yl)-ethyl]-2-(5-methyl-1-phenyl-1H-pyrazole-4-sulfonylamino)-propionamide.***

LC/MS for $C_{29}H_{36}FN_5O_3S$ 554.5 (M+H$^+$).

Example 222

(S)-3-Cyclohexyl-N-[2-(5-fluoro-2,3-dihydro-indol-1-yl)-ethyl]-2-(5-isoxazol-3-yl-thiophene-2-sulfonylamino)-propionamide.***

LC/MS for $C_{26}H_{31}FN_4O_4S_2$ 547.4 (M+H$^+$).

Example 223

(S)-{2-Cyclohexyl-1-[2-(5-fluoro-2,3-dihydro-indol-1-yl)-ethylcarbamoyl]-ethyl}-carbamic acid benzyl ester LC/MS for $C_{27}H_{34}FN_3O_3$ 468.4 (M+H$^+$).

Example 224

(S)-2-(4-Bromo-3-chloro-thiophene-2-sulfonylamino)-3-cyclohexyl-N-[2-(5-fluoro-2,3-dihydro-indol-1-yl)-ethyl]-propionamide.***

LC/MS for $C_{23}H_{28}BrClFN_3O_3S_2$ 594.3 (M+H$^+$).

Example 225

(S)-2-(3-Biphenyl-4-yl-ureido)-3-cyclohexyl-N-[2-(5-fluoro-2,3-dihydro-indol-1-yl)-ethyl]-propionamide LC/MS for $C_{32}H_{37}FN_4O_2$ 529.5 (M+H$^+$).

Example 226

(S)-3-Cyclohexyl-N-[2-(5-fluoro-2,3-dihydro-indol-1-yl)-ethyl]-2-(4-phenoxy-benzenesulfonylamino)-propionamide.***

LC/MS for $C_{31}H_{36}FN_3O_4S$ 566.5 (M+H$^+$).

Example 227

(S)-2-(5-Chloro-thiophene-2-sulfonylamino)-3-cyclohexyl-N-[2-(5-fluoro-2,3-dihydro-indol-1-yl)-ethyl]-propionamide.***

LC/MS for $C_{23}H_{29}ClFN_3O_3S_2$ 514.4 (M+H$^+$).

Example 228

(S)-3-Cyclohexyl-N-[2-(5-fluoro-2,3-dihydro-indol-1-yl)-ethyl]-2-(naphthalene-1-sulfonylamino)-propionamide.***

LC/MS for $C_{29}H_{34}FN_3O_3S$ 524.5 (M+H$^+$).

Example 229

(S)-3-Cyclohexyl-N-[2-(5-fluoro-2,3-dihydro-indol-1-yl)-ethyl]-2-(4-trifluoromethyl-benzenesulfonylamino)-propionamide.***

LC/MS for $C_{26}H_{31}F_4N_3O_3S$ 542.4 (M+H$^+$).

Example 230

(S)-3-Cyclohexyl-N-[2-(5-fluoro-2,3-dihydro-indol-1-yl)-ethyl]-2-(4-trifluoromethoxy-benzenesulfonylamino)-propionamide.***

LC/MS for $C_{26}H_{31}F_4N_3O_4S$ 558.4 (M+H$^+$).

Example 231

(S)-3-Cyclohexyl-N-[2-(5-fluoro-2,3-dihydro-indol-1-yl)-ethyl]-2-[5-(2-methyl-5-trifluoromethyl-2H-pyrazol-3-yl)-thiophene-2-sulfonylamino]-propionamide.***

LC/MS for $C_{28}H_{33}F_4N_5O_3S_2$ 628.4 (M+H$^+$).

Example 232

(S)-3-Cyclohexyl-N-[2-(5-fluoro-2,3-dihydro-indol-1-yl)-ethyl]-2-(3-methyl-3H-imidazole-4-sulfonylamino)-propionamide.***

LC/MS for $C_{23}H_{32}FN_5O_3S$ 478.5 (M+H$^+$).

Example 233

(S)-3-Cyclohexyl-N-[2-(5-fluoro-2,3-dihydro-indol-1-yl)-ethyl]-2-[3-(5-methyl-[1,3,4]oxadiazol-2-yl)-benzenesulfonylamino]-propionamide.***

LC/MS for $C_{28}H_{34}FN_5O_4S$ 556.5 (M+H$^+$).

Example 234

(S)-2-(Benzo[b]thiophene-2-sulfonylamino)-3-cyclohexyl-N-[2-(5-fluoro-2,3-dihydro-indol-1-yl)-ethyl]-propionamide.***

LC/MS for $C_{27}H_{32}FN_3O_3S_2$ 530.4 (M+H$^+$).

Example 235

(S)-3-Cyclohexyl-N-[2-(5-fluoro-2,3-dihydro-indol-1-yl)-ethyl]-2-(thiophene-2-sulfonylamino)-propionamide.***

LC/MS for $C_{23}H_{30}FN_3O_3S_2$ 480.4 (M+H$^+$).

Example 236

(S)-3-Cyclohexyl-N-[2-(5-fluoro-2,3-dihydro-indol-1-yl)-ethyl]-2-[4-(4-fluoro-phenoxy)-benzenesulfonylamino]-propionamide.***

LC/MS for $C_{31}H_{35}F_2N_3O_4S$ 584.5 (M+H$^+$).

Example 237

(S)-3-Cyclohexyl-N-[2-(5-fluoro-2,3-dihydro-indol-1-yl)-ethyl]-2-[5-(2-methyl-thiazol-4-yl)-thiophene-2-sulfonylamino]-propionamide.***

LC/MS for $C_{27}H_{33}FN_4O_3S_3$ 577.4 (M+H$^+$).

Example 238

(S)-3-Cyclohexyl-N-[2-(5-fluoro-2,3-dihydro-indol-1-yl)-ethyl]-2-(4'-methoxy-biphenyl-4-sulfonylamino)-propionamide.***

LC/MS for $C_{32}H_{38}FN_3O_4S$ 580.5 (M+H$^+$).

Example 239

(S)-3-Cyclohexyl-N-[2-(5-fluoro-2,3-dihydro-indol-1-yl)-ethyl]-2-(4-methoxy-benzenesulfonylamino)-propionamide.***

LC/MS for $C_{26}H_{34}FN_3O_4S$ 504.5 (M+H$^+$).

Example 240

(S)-3-Cyclohexyl-2-(4-difluoromethoxy-benzenesulfonylamino)-N-[2-(5-fluoro-2,3-dihydro-indol-1-yl)-ethyl]-propionamide.***

LC/MS for $C_{26}H_{32}F_3N_3O_4S$ 540.5 (M+H$^+$).

Example 241

(S)-2-(5-Chloro-1,3-dimethyl-1H-pyrazole-4-sulfonylamino)-3-cyclohexyl-N-[2-(5-fluoro-2,3-dihydro-indol-1-yl)-ethyl]-propionamide.***

LC/MS for $C_{24}H_{33}ClFN_5O_3S$ 526.5 (M+H$^+$).

Example 242

(S)-3-Cyclohexyl-N-[2-(5-fluoro-2,3-dihydro-indol-1-yl)-ethyl]-2-phenylmethanesulfonylamino-propionamide.***

LC/MS for $C_{26}H_{34}FN_3O_3S$ 488.5 (M+H$^+$).

Example 243

(S)-3-Cyclohexyl-N-[2-(5-fluoro-2,3-dihydro-indol-1-yl)-ethyl]-2-(toluene-3-sulfonylamino)-propionamide.***

LC/MS for $C_{26}H_{34}FN_3O_3S$ 488.5 (M+H$^+$).

Example 244

(S)-3-Cyclohexyl-N-[2-(5-fluoro-2,3-dihydro-indol-1-yl)-ethyl]-2-[4-(4-methoxy-phenoxy)-benzenesulfonylamino]-propionamide.***

LC/MS for $C_{32}H_{38}FN_3O_5S$ 596.4 (M+H$^+$).

Example 245

(S)-3-Cyclohexyl-N-[2-(5-fluoro-2,3-dihydro-indol-1-yl)-ethyl]-2-(3-methoxy-benzenesulfonylamino)-propionamide.***

LC/MS for $C_{26}H_{34}FN_3O_4S$ 504.5 (M+H$^+$).

Example 246

(S)-3-Cyclohexyl-N-[2-(5-fluoro-2,3-dihydro-indol-1-yl)-ethyl]-2-(4-oxazol-5-yl-benzenesulfonylamino)-propionamide.***

LC/MS for $C_{28}H_{33}FN_4O_4S$ 541.5 (M+H$^+$).

Example 247

5-(3-Fluoro-phenyl)-furan-2-carboxylic acid {2-cyclohexyl-1-(S)-[1-(S)-methyl-2-(3-methyl-isoxazol-5-ylamino)-ethylcarbamoyl]-ethyl}-amide.# $C_{27}H_{33}FN_4O_4$; LCMS: 497.5 (M+H)$^+$.

Example 248

(S)-3-Cyclohexyl-N-[2-(5-fluoro-2,3-dihydro-indol-1-yl)-ethyl]-2-(thiophene-3-sulfonylamino)-propionamide.***

LC/MS for $C_{23}H_{30}FN_3O_3S_2$ 480.5 (M+H$^+$).

Example 249

(S)-3-Cyclohexyl-N-[2-(5-fluoro-2,3-dihydro-indol-1-yl)-ethyl]-2-methanesulfonylamino-propionamide.***

LC/MS for $C_{20}H_{30}FN_3O_3S$ 412.5 (M+H$^+$).

Example 250

(S,S)-3-Cyclohexyl-N-[2-(5-fluoro-2,3-dihydro-indol-1-yl)-1-methyl-ethyl]-2-(5-oxazol-5-yl-thiophene-3-sulfonylamino)-propionamide.***

LC/MS for $C_{27}H_{33}FN_4O_4S_2$ 561.5 (M+H$^+$).

Example 251

(S,S)-3-Cyclohexyl-N-[2-(5-fluoro-2,3-dihydro-indol-1-yl)-1-methyl-ethyl]-2-(toluene-3-sulfonylamino)-propionamide.***

LC/MS for $C_{27}H_{36}FN_3O_3S$ 502.5 (M+H$^+$).

Example 252

(S,S)-3-[4,4-Dimethyl-2-(toluene-3-sulfonylamino)-pentanoylamino]-4-(5-fluoro-2,3-dihydro-indol-1-yl)-butyric acid tert-butyl ester.***

LC/MS for $C_{30}H_{42}FN_3O_5S$ 576.5 (M+H$^+$).

Example 253

(S,S)-3-Cyclohexyl-N-[2-(5-fluoro-2,3-dihydro-indol-1-yl)-1-methyl-ethyl]-2-(2-methyl-4-trifluoromethyl-furan-3-sulfonylamino)-propionamide.***

LC/MS for $C_{26}H_{33}F_4N_3O_4S$ 560.5 (M+H$^+$).

Example 254

(S,S)-3-Cyclohexyl-N-[2-(5-fluoro-2,3-dihydro-indol-1-yl)-1-methyl-ethyl]-2-(3-trifluoromethoxy-benzenesulfonylamino)-propionamide.***

LC/MS for $C_{27}H_{33}F_4N_3O_4S$ 572.4 (M+H$^+$).

Example 255

(S)-3-Cyclohexyl-N-[2-(5-fluoro-2,3-dihydro-indol-1-yl)-ethyl]-2-(1-methyl-1H-imidazole-4-sulfonylamino)-propionamide.***

LC/MS for $C_{23}H_{32}FN_5O_3S$ 478.5 (M+H$^+$).

Example 256

(S)-2-(5-Benzenesulfonyl-thiophene-2-sulfonylamino)-3-cyclohexyl-N-[2-(5-fluoro-2,3-dihydro-indol-1-yl)-ethyl]-propionamide.***

LC/MS for $C_{29}H_{34}FN_3O_5S_3$ 620.4 (M+H$^+$).

Example 257

(S)-2-(2-Acetylamino-4-methyl-thiazole-5-sulfonylamino)-3-cyclohexyl-N-[2-(5-fluoro-2,3-dihydro-indol-1-yl)-ethyl]-propionamide.***

LC/MS for $C_{25}H_{34}FN_5O_4S_2$ 552.5 (M+H$^+$).

Example 258

(S)-3-Cyclohexyl-2-(4,5-dichloro-thiophene-2-sulfonylamino)-N-[2-(5-fluoro-2,3-dihydro-indol-1-yl)-ethyl]-propionamide.***

LC/MS for $C_{23}H_{28}Cl_2FN_3O_3S_2$ 548.4 (M+H$^+$).

Example 259

(S,S)-2-(3-Chloro-benzenesulfonylamino)-3-cyclohexyl-N-[2-(5-fluoro-2,3-dihydro-indol-1-yl)-1-methyl-ethyl]-propionamide.***

LC/MS for $C_{26}H_{33}ClFN_3O_3S$ 522.4 (M+H$^+$).

Example 260

(S,S)—N-{3-Cyclohexyl-1-[1-(5-fluoro-2,3-dihydro-indol-1-ylmethyl)-3-hydroxy-propylcarbamoyl]-propyl}-3-methoxy-benzamide.***

A sample of the title compound of example 47 (114 mg, 0.21 mmol) in THF (5 mL) was cooled in an ice/water bath and treated with triethylamine (21 mg, 0.21 mmol) followed by isobutyl chloroformate. After stirring for 25 minutes, the solution was transferred to a precooled (ice/water bath) stirring solution of excess NaBH$_4$ in water (5 mL). After stirring for 1 hour, the solution was quenched by addition of excess 1 M HCl at 0° C. The reaction was diluted with ethyl acetate and extracted with 1 M NaOH solution. The organics were dried over MgSO$_4$ and the solvent was removed. The residue was purified on silica gel using a gradient of 0 to 100% ethyl acetate in hexane to afford 57 mg (51%) of the title material as a solid; $^1$H NMR (CDCl$_3$, 400 MHz) δ 0.65-0.82 (m, 2H), 1.00-1.25 (m, 6H), 1.47-1.66 (m, 6H), 1.66-1.78 (m, 2H), 1.82-1.97 (m, 2H), 2.88-2.95 (m, 2H), 3.01 (dd, 1H, $J_1$=5.6, $J_2$=13.7), 3.21 (dd, 1H, $J_1$=7.7, $J_2$=13.7), 3.29 (dd, 1H, $J_1$=8.7, $J_2$=17.3), 3.44-3.52 (m, 1H), 3.55-3.68 (m, 2H), 3.83 (s, 3H), 4.31-4.41 (m, 1H), 4.64 (dd, 1H, $J_1$=6.9, $J_2$=14.1), 6.34 (dd, 1H, $J_1$=4.1, $J_2$=8.6), 6.568 (ddd, 1H, $J_1$=2.5, $J_2$=$J_3$=8.9), 6.79 (dd, 1H, $J_1$=2.4, $J_2$=8.3), 7.03-7.08 (m, 1H), 7.15 (d, 1H, J=7.7), 7.22 (d, 1H, J=8.8), 7.29-7.35 (m, 3H); HPLC-MS calcd. for C$_{30}$H$_{40}$FN$_3$O$_4$ (M+H$^+$) 526.3, found 526.5.

Example 261

(S,S)-3-(2-tert-Butoxycarbonylamino-3-cyclohexyl-propionylamino)-4-(5-fluoro-2,3-dihydro-indol-1-yl)-butyric acid benzyl ester Following the procedures of Example 22, except using N-Boc-γ-OBn-aspartinol, 5-fluoroindoline (1 eq) and Boc-cyclohexylalanine as starting materials, the title compound was prepared in 15% overall yield; HPLC-MS calcd. for C$_{33}$H$_{44}$FN$_3$O$_5$ (M+H$^+$) 582.3, found 582.5.

Example 262

(S,S)-3-[4,4-Dimethyl-2-(toluene-3-sulfonylamino)-pentanoylamino]-4-(5-fluoro-2,3-dihydro-indol-1-yl)-butyric acid.***

LC/MS for C$_{26}$H$_{34}$FN$_3$O$_5$S 520.4 (M+H$^+$).

Example 263

(S,S)-3-Cyclohexyl-2-(3,5-dimethyl-isoxazole-4-sulfonylamino)-N-[2-(5-fluoro-2,3-dihydro-indol-1-yl)-1-methyl-ethyl]-propionamide.***

LC/MS for C$_{25}$H$_{35}$FN$_4$O$_4$S 507.4 (M+H$^+$).

Example 264

(S,S)-2-Benzenesulfonylamino-3-cyclohexyl-N-[2-(5-fluoro-2,3-dihydro-indol-1-yl)-1-methyl-ethyl]-propionamide.***

LC/MS for C$_{26}$H$_{34}$FN$_3$O$_3$S 488.5 (M+H$^+$).

Example 265

(S,S)-4,4-Dimethyl-2-(toluene-3-sulfonylamino)-pentanoic acid [2-(5-fluoro-2,3-dihydro-indol-1-yl)-1-methyl-ethyl]-amide.***

LC/MS for C$_{25}$H$_{34}$FN$_3$O$_3$S 476.5 (M+H$^+$).

Example 266

5-(3-Fluoro-phenyl)-furan-2-carboxylic acid {1-(S)-[2-(4-benzyloxy-phenylamino)-1-(S)-methyl-ethylcarbamoyl]-2-cyclohexyl-ethyl}-amide.# C$_{36}$H$_{40}$FN$_3$O$_4$; LCMS:598.6 (M+H$^+$).

Example 267

5-(3-Fluoro-phenyl)-furan-2-carboxylic acid {2-cyclohexyl-1-(S)-[1-(S)-methyl-2-(3-methyl-isothiazol-5-ylamino)-ethylcarbamoyl]-ethyl}-amide.# C$_{27}$H$_{33}$FN$_4$O$_3$S; LCMS: 513.5 (M+H$^+$).

Example 268

Tetrahydrofuran-2-(R)-carboxylic acid {3,3-dimethyl-1-(S)-[1-(S)-methyl-2-(4-trifluoromethoxy-phenylamino)-ethylcarbamoyl]-butyl}-amide.$ C$_{22}$H$_{32}$F$_3$N$_3$O$_4$; $^1$H NMR (CDCl$_3$) δ(ppm) 7.02 (m, 2H); 6.70 (m, 2H); 4.42 (m, 1H); 4.24 (m, 1H); 4.00 (m, 2H); 3.84 (m, 1H); 3.30 (m, 2H); 2.18 (m, 1H); 1.87 (m, 3H); 1.61 (m, 3H); 1.20 (d, J=6.8 Hz, 2H); 0.93 (s, 9H). LCMS: 460.4 (M+H$^+$).

Example 269

Tetrahydropyran-4-carboxylic acid {3,3-dimethyl-1-(S)-[1-(S)-methyl-2-(4-trifluoromethoxy-phenylamino)-ethylcarbamoyl]-butyl}-amide;$ C$_{23}$H$_{34}$F$_3$N$_3$O$_4$; $^1$H NMR (CDCl$_3$) δ(ppm) 7.03 (m, 2H); 6.72 (m, 2H); 4.38 (m, 1H); 4.18 (m, 1H); 3.93 (m, 2H); 3.40 (m, 2H); 3.30 (m, 2H); 2.48 (m, 1H); 1.66 (m, 6H); 1.20 (d, J=6.8 Hz, 3H); 0.93 (s, 9H). LCMS: 474.5 (M+H$^+$).

Example 270

Tetrahydro-pyran-4-carboxylic acid {1-(S)-[2-(5-fluoro-3,3-dimethyl-2,3-dihydro-indol-1-yl)-1-(S)-methyl-ethylcarbamoyl]-3,3-dimethyl-butyl}-amide.$ C$_{26}$H$_{40}$FN$_3$O$_3$; $^1$H NMR (CDCl$_3$) δ(ppm) 6.67 (m, 2H); 6.50 (m, 1H); 6.33 (m, 1H); 6.22 (m, 1H); 4.35 (m, 1H); 4.09 (m, 1H); 3.90 (m, 2H); 3.31 (m, 2H); 3.15 (m, 1H); 3.01 (m, 2H); 2.83 (dd, 1H); 2.26 (m, 1H); 1.68 (m, 5H); 1.45 (m, 1H); 1.20 (m, 6H); 1.0 (d, J=6.8 Hz, 3H); 0.81 (s, 9H) LCMS: 462.5 (M+H$^+$).

Example 271

Tetrahydro-furan-2-(R)-carboxylic acid {1-(S)-[2-(5-fluoro-3,3-dimethyl-2,3-dihydro-indol-1-yl)-1-(S)-methyl-ethylcarbamoyl]-3,3-dimethyl-butyl}-amide.$ C$_{26}$H$_{40}$FN$_3$O$_3$; $^1$H NMR (CDCl$_3$) δ(ppm) 6.88 (m, 1H); 6.68 (m, 2H); 6.33 (m, 1H); 6.22 (m, 1H); 4.25 (m, 2H); 4.15 (m, 1H); 3.89 (m, 1H); 3.77 (m, 1H); 3.15 (m, 1H); 3.04 (m, 2H); 2.85 (dd, 1H); 2.17 (m, 1H); 1.82 (m, 4H); 1.38 (dd, 1H); 1.20 (m, 6H); 1.11 (d, J=6.8 Hz, 3H); 0.82 (s, 9H) LCMS: 448.6 (M+H$^+$).

Example 272

Tetrahydrofuran-3-(R,S)-carboxylic acid {2-cyclohexyl-1-(S)-[1-(S)-methyl-2-(4-trifluoromethoxy-phenylamino)-ethylcarbamoyl]-ethyl}-amide.$ C$_{24}$H$_{34}$F$_3$N$_3$O$_4$; LCMS: 486.5 (M+H$^+$).

Example 273

Tetrahydrofuran-2-(R)-carboxylic acid {2-cyclohexyl-1-(S)-[2-(5-fluoro-3,3-dimethyl-2,3-dihydro-indol-1-yl)-1-(S)-methyl-ethylcarbamoyl]-ethyl}-amide.$ C$_{27}$H$_{40}$FN$_3$O$_3$; LCMS: 474.5 (M+H$^+$).

Example 274

Tetrahydrofuran-2-(R)-carboxylic acid {2-cyclohexyl-1-(S)-[2-(5-fluoro-2,2-dimethyl-2,3-dihydro-indol-1-yl)-1-(S)-methyl-ethylcarbamoyl]-ethyl}-amide.$^\$$ $C_{27}H_{40}FN_3O_3$; LCMS: 474.5 (M+H)$^+$.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 μl in 384-well microtiter plates. Cathepsin S, at a final concentration of 0.3-3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 μl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE II

Assay Data for Inhibitors of Cathepsin

| Compound | $K_i$ Cat. S[a] |
|---|---|
| 1 | + |
| 2 | +++ |
| 3 | ++ |
| 4 | +++ |
| 5 | ++ |
| 6 | ++ |
| 7 | ++ |

TABLE II-continued

Assay Data for Inhibitors of Cathepsin

| Compound | $K_i$ Cat. S[a] |
|---|---|
| 8 | + |
| 9 | +++ |
| 10 | + |
| 11 | + |
| 12 | + |
| 13 | +++ |
| 14 | +++ |
| 15 | + |
| 16 | + |
| 17 | ++ |
| 18 | + |
| 19 | + |
| 20 | + |
| 21 | +++ |
| 22 | +++ |
| 23 | ++ |
| 24 | ++ |
| 25 | + |
| 26 | +++ |
| 27 | +++ |
| 28 | + |
| 29 | +++ |
| 30 | +++ |
| 31 | + |
| 32 | + |
| 33 | ++ |
| 34 | ++ |
| 35 | +++ |
| 36 | +++ |
| 37 | +++ |
| 38 | +++ |
| 39 | +++ |
| 40 | + |
| 41 | +++ |
| 42 | +++ |
| 43 | +++ |
| 44 | +++ |
| 45 | ++ |
| 46 | ++ |
| 47 | +++ |
| 48 | ++ |
| 49 | +++ |
| 50 | +++ |
| 51 | + |
| 52 | ++ |
| 53 | +++ |
| 54 | ++ |
| 55 | ++ |
| 56 | ++ |
| 57 | ++ |
| 58 | ++ |
| 59 | +++ |
| 60 | +++ |
| 61 | +++ |
| 62 | ++ |
| 63 | ++ |
| 64 | +++ |
| 65 | ++ |
| 66 | ++ |
| 67 | ++ |
| 68 | ++ |
| 69 | ++ |
| 70 | +++ |
| 71 | +++ |
| 72 | +++ |
| 73 | +++ |
| 74 | ++ |
| 75 | +++ |
| 76 | +++ |
| 77 | ++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | +++ |
| 90 | +++ |
| 91 | +++ |
| 92 | +++ |
| 93 | ++ |
| 94 | +++ |
| 95 | +++ |
| 96 | ++ |
| 97 | ++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | ++ |
| 111 | +++ |
| 112 | ++ |
| 113 | +++ |
| 114 | +++ |
| 115 | +++ |
| 116 | +++ |
| 117 | +++ |
| 118 | +++ |
| 119 | +++ |
| 120 | +++ |
| 121 | ++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | ++ |
| 134 | +++ |
| 135 | +++ |
| 136 | ++ |
| 137 | +++ |
| 138 | ++ |
| 139 | +++ |
| 140 | +++ |
| 141 | +++ |
| 142 | +++ |
| 143 | +++ |
| 144 | +++ |
| 145 | ++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |

TABLE II-continued

Assay Data for Inhibitors of Cathepsin

| Compound | $K_i$ Cat. S[a] |
|---|---|
| 156 | +++ |
| 157 | +++ |
| 158 | ++ |
| 159 | ++ |
| 160 | +++ |
| 161 | +++ |
| 162 | +++ |
| 163 | +++ |
| 164 | ++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | ++ |
| 176 | +++ |
| 177 | +++ |
| 178 | +++ |
| 179 | ++ |
| 180 | ++ |
| 181 | +++ |
| 182 | +++ |
| 183 | +++ |
| 184 | +++ |
| 185 | ++ |
| 186 | +++ |
| 187 | + |
| 188 | +++ |
| 189 | +++ |
| 190 | +++ |
| 191 | +++ |
| 192 | +++ |
| 193 | ++ |
| 194 | ++ |
| 195 | ++ |
| 196 | ++ |
| 197 | ++ |
| 198 | ++ |
| 199 | +++ |
| 200 | +++ |
| 201 | +++ |
| 202 | +++ |
| 203 | +++ |
| 204 | ++ |
| 205 | ++ |
| 206 | ++ |
| 207 | +++ |
| 208 | +++ |
| 209 | +++ |
| 210 | +++ |
| 211 | +++ |
| 212 | ++ |
| 213 | ++ |
| 214 | ++ |
| 215 | +++ |
| 216 | +++ |
| 217 | +++ |
| 218 | +++ |
| 219 | + |
| 220 | ++ |
| 221 | ++ |
| 222 | ++ |
| 223 | ++ |
| 224 | ++ |
| 225 | ++ |
| 226 | +++ |
| 227 | +++ |
| 228 | ++ |
| 229 | ++ |
| 230 | ++ |
| 231 | +++ |
| 232 | + |
| 233 | +++ |
| 234 | ++ |
| 235 | ++ |
| 236 | ++ |
| 237 | +++ |
| 238 | +++ |
| 239 | ++ |
| 240 | ++ |
| 241 | ++ |
| 242 | + |
| 243 | +++ |
| 244 | +++ |
| 245 | ++ |
| 246 | +++ |
| 247 | ++ |
| 248 | ++ |
| 249 | + |
| 250 | +++ |
| 251 | +++ |
| 252 | ++ |
| 253 | +++ |
| 254 | +++ |
| 255 | ++ |
| 256 | ++ |
| 257 | +++ |
| 258 | ++ |
| 259 | +++ |
| 260 | ++ |
| 261 | − |
| 262 | +++ |
| 263 | +++ |
| 264 | +++ |
| 265 | +++ |
| 266 | +++ |
| 267 | ++ |
| 268 | + |
| 269 | ++ |
| 270 | ++ |
| 271 | + |
| 272 | +++ |
| 273 | +++ |
| 274 | ++ |

[a]Cathepsin S inhibition constant for compounds of Formula I: +, <10 μM; ++, <1.0 μM; +++, <0.1 μM.

TABLE III

Assay Data for Inhibitors of Cathepsin S showing selectivity over other Cathepsin isoenzymes

| Compound | $K_i$ Cat. S[a] | Ki Cat. K[b] | Ki Cat. L[c] | Ki Cat. B[d] |
|---|---|---|---|---|
| 21 | +++ | +++ | +++ | − |
| 31 | + | + | ++ | − |
| 41 | +++ | − | ++ | ++ |
| 51 | + | − | − | − |
| 61 | +++ | − | +++ | − |
| 71 | +++ | + | +++ | − |
| 81 | +++ | + | + | − |
| 91 | +++ | + | ++ | + |
| 101 | +++ | − | + | − |
| 110 | ++ | + | + | − |
| 121 | ++ | + | + | + |
| 131 | +++ | ++ | − | − |
| 141 | +++ | − | + | − |
| 151 | +++ | + | +++ | − |
| 171 | +++ | − | + | − |

TABLE III-continued

Assay Data for Inhibitors of Cathepsin S showing selectivity over other Cathepsin isoenzymes

| Compound | $K_i$ Cat. S[a] | Ki Cat. K[b] | Ki Cat. L[c] | Ki Cat. B[d] |
|---|---|---|---|---|
| 181 | +++ | − | + | − |
| 191 | +++ | + | − | − |
| 201 | +++ | + | ++ | − |
| 211 | +++ | − | + | − |
| 221 | ++ | − | − | − |
| 231 | +++ | − | − | − |
| 241 | ++ | − | + | − |
| 251 | +++ | − | + | − |

[a]Cathepsin S inhibition constant for compounds of Formula I: +, <10 μM; ++, <1.0 μM; +++, <0.1 μM.
[b]Cathepsin K inhibition constant for compounds of Formula I: +, <10 μM; ++, <1.0 μM; +++, <0.1 μM; −, >10 μM.
[c]Cathepsin L inhibition constant for compounds of Formula I: +, <10 μM; ++, <1.0 μM; +++, <0.1 μM; −, >10 μM.
[d]Cathepsin B inhibition constant for compounds of Formula I: +, <10 μM; ++, <1.0 μM; +++, <0.1 μM; −, >10 μM.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A compound of Formula

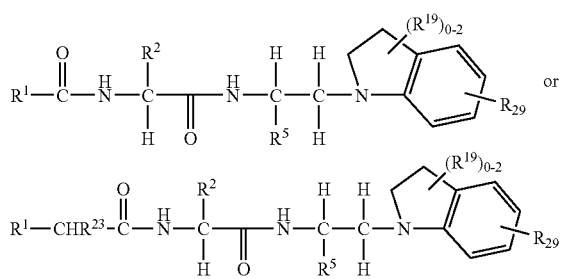

or a pharmaceutically acceptable salt thereof, wherein:

$R^1$ is $C_6$-$C_{10}$ aryl substituted with 0-3 $R^{1a}$, or a $C_3$-$C_8$ cycloalkyl substituted with 0-2 $R^{1b}$, wherein said $C_3$-$C_8$ cycloalkyl is saturated or unsaturated;

each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, $S(=O)CH_3$, $S(=O)_2R^{10}$, $NR^{11}R^{12}$, acetyl, $C(=O)OR^{13}$, $C(=O)NR^{13}R^{14}$, $S(=O)_2NR^{13}R^{14}$, phenyl substituted with 0-3 $R^{15}$, and a $C_1$-$C_4$ alkyl substituted with 0-2 $R^{16}$;

each $R^{1b}$ is independently a member selected from the group consisting of H, OH, F, Cl, acetyl, =O, $C_1$-$C_6$ alkyl, $C_1$-$C_6$ alkoxy, $CF_3$ and $OCF_3$;

$R^2$ is a member selected from the group consisting of a phenyl substituted with 0-3 $R^{15}$, a $C_1$-$C_6$ alkyl substituted with 0-2 $R^{2a}$, a $C_2$-$C_6$ alkenyl, a $C_2$-$C_6$ alkynyl, a $C_3$-$C_7$ cycloalkyl substituted with 0-2 $R^{19}$, and a $C_7$-$C_{11}$ bicycloalkyl substituted with 0-2 $R^{19}$;

each $R^{2a}$ is independently a member selected from the group consisting of a $C_6$-$C_{10}$ aryl substituted with 0-3 $R^{15}$, a $C_3$-$C_8$ cycloalkyl substituted with 0-2 $R^{19}$, and a $C_7$-$C_{11}$ bicycloalkyl substituted with 0-2 $R^{19}$;

$R^5$ is a member selected from the group consisting of H, $C_3$-$C_7$ cycloalkyl, $C_2$-$C_6$ alkenyl, $C_2$-$C_6$ alkyne, phenyl substituted with 0-2 $R^{15}$; and a $C_1$-$C_6$ alkyl substituted with 0-2 $R^{18}$;

each $R^{10}$ is independently a member selected from the group consisting of H, $C_3$-$C_7$ cycloalkyl, a $C_1$-$C_3$ perfluoroalkyl, a $C_1$-$C_4$ alkyl substituted with 0-1 $R^{25}$, and a phenyl substituted with 0-3 $R^{15}$;

each $R^{11}$ is independently a member selected from the group consisting of H, $^tBOC$, Cbz, $C_3$-$C_8$ cycloalkyl, ($C_1$-$C_6$ alkyl)-C(=O)—, ($C_1$-$C_6$ alkyl)-S(=O)$_2$— and a $C_1$-$C_6$ alkyl;

each of $R^{12}$, $R^{13}$ and $R^{14}$ is independently a member selected from the group consisting of H and $C_1$-$C_4$ alkyl;

each $R^{15}$ is independently a member selected from the group consisting of H, OH, F, Cl, Br, I, CN, $NO_2$, $COOR_{13}$, $C(=O)NR^{13}R^{14}$, $S(=O)_2NR^3R^4$, acetyl, —$SCH_3$, —$S(=O)CH_3$, —$S(=O)_2CH_3$, $NR^{26}R^{27}$, $C_1$-$C_6$ alkoxy, $C_1$-$C_3$ perfluoroalkyl, $C_1$-$C_3$ perfluoroalkoxy and a $C_1$-$C_6$ alkyl;

each $R^{16}$ is independently a member selected from the group consisting of H, OH, $COOR^{13}$, $C(=O)NR^{13}R^{14}$, $S(=O)_2NR^{13}R^{14}$, acetyl, —$SCH_3$, —$S(=O)CH_3$, —$S(=O)_2CH_3$, $C_1$-$C_6$ alkoxy, $NR^{26}R^{27}$, and a phenyl substituted with 0-3 $R^{15}$;

each $R^{18}$ is independently a member selected from the group consisting of H, OH, F, Cl, CN, $NO_2$, $C(=O)OR^{30}$, $C(=O)NR^{13}R^{14}$, $NR^{11}R^{12}$, a $C_1$-$C_3$ perfluoroalkyl, a $C_1$-$C_3$ perfluoroalkoxy, a phenyl substituted with 0-3 $R^{15}$; and $C_3$-$C_8$ cycloalkyl;

each $R^{19}$ is independently a member selected from the group consisting of $C_1$-$C_4$ alkyl, F, Cl, $C_1$-$C_4$ alkoxy, $CF_3$ and $OCF_3$;

$R^{23}$ is a bond, H, F, OH, $C_1$-$C_4$ alkyl, and $C_1$-$C_3$ alkylhydroxy;

each $R^{25}$ is independently a member selected from the group consisting of H, $C_3$-$C_7$ cycloalkyl, and a phenyl substituted with 0-3 $R^{15}$;

each $R^{26}$ is independently a member selected from the group consisting of H, $C_1$-$C_4$ alkyl, ($C_1$-$C_4$ alkyl)-C(=O)— and ($C_1$-$C_4$ alkyl)-S(=O)$_2$—;

each $R^{27}$ is independently a member selected from the group consisting of H and $C_1$-$C_4$ alkyl;

each $R^{28}$ is independently a member selected from the group consisting of H, a $C_1$-$C_6$ alkyl, $C_3$-$C_8$ cycloalkyl, a phenyl substituted with 0-3 $R^{15}$, and a benzyl substituted with 0-2 $R^{15}$;

each $R^{29}$ is independently a member selected from the group consisting of H, F, Cl, Br, I, CN, $NO_2$, $OR^{28}$, $SR^{28}$, $S(=O)R^{28}$, $S(=O)_2R^{28}$, $S(=O)_2NR^{13}R^{14}$, $NR^{26}R^{27}$, acetyl, $C(=O)NR^{13}R^{14}$, $C(=O)OR^{13}$, $C_1$-$C_6$alkyl, $OCHF_2$, $SCF_3$, $OCF_3$, and —$C(=NH)NH_2$; and each $R^{30}$ is independently a member selected from the group consisting of H, $C_3$-$C_7$ cycloalkyl, $C_1$-$C_4$ alkyl substituted with 0-1 $R^{25}$, and a phenyl substituted with 0-3 $R^{15}$.

2. The compound of claim 1, wherein $R^1$ is phenyl substituted with 0-3 $R_{1a}$.

3. The compound of claim 1, wherein said compound is of the formula:

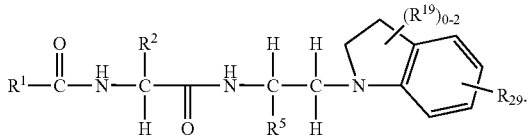

4. The compound of claim 3 wherein:

$R_1$ is $C_3$-$C_8$ cycloalkyl substituted with 0-2 $R_{1b}$, wherein said $C_3$-$C_8$ cycloalkyl is saturated or unsaturated; and $R^2$ is a member selected from the group consisting of a phenyl substituted with 0-3 $R^{15}$, a $C_1$-$C_6$ alkyl substituted with 0-2 $R^{2a}$, and a $C_3$-$C_7$ cycloalkyl substituted with 0-2 $R^{19}$.

5. The compound of claim 3, wherein:

$R^2$ is a member selected from the group consisting of a $C_1$-$C_2$ alkyl substituted with 1 $R^{2a}$, and $C_1$-$C_6$ alkyl;

each $R^{2a}$ is independently a member selected from the group consisting of a phenyl substituted with 0-3 $R^{15}$, and a $C_3$-$C_5$ cycloalkyl substituted with 0-2 $R^{19}$;

$R^5$ is a member selected from the group consisting of H, $C_3$-$C_7$ cycloalkyl; and a $C_1$-$C_6$ alkyl substituted with 0-1 $R^{18}$; and each $R^{18}$ is independently a member selected from the group consisting of H, OH, F, Cl, CN, C(=O)$OR^{30}$, C(=O)$NR^{13}R^{14}$, $NR^{11}R^{12}$, a phenyl substituted with 0-3 $R^{15}$, and $C_3$-$C_8$ cycloalkyl.

6. The compound of claim 1, wherein said compound is of the formula:

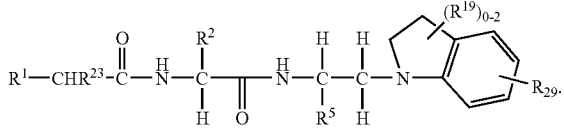

7. The compound of claim 6 wherein:

$R^1$ is $C_6$-$C_{10}$ aryl substituted with 0-3 $R^{1a}$; and each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, S(=O)$CH_3$, S(=O)$_2R^{10}$, $NR^{11}R_{12}$, acetyl, C(=O)$OR^{13}$, C(=O)$NR^{13}R^{14}$, S(=O)$_2NR^{13}R^{14}$, phenyl substituted with 0-3 $R^5$, and a $C_1$-$C_4$ alkyl substituted with 0-2 $R^{16}$.

8. The compound of claim 6, wherein:

$R^2$ is a member selected from the group consisting of a $C_1$-$C_2$ alkyl substituted with 1 $R^{2a}$, and $C_1$-$C_6$ alkyl;

each $R^{2a}$ is independently a member selected from the group consisting of a phenyl substituted with 0-3 $R^{15}$, and a $C_3$-$C_8$ cycloalkyl substituted with 0-2 $R^{19}$; and $R^5$ is a member selected from the group consisting of H, $C_3$-$C_7$ cycloalkyl; and a $C_1$-$C_6$ alkyl.

9. The compound of claim 3 wherein:

$R^1$ is $C_6$-$C_{10}$ aryl substituted with 0-3 $R^{1a}$;

each $R^{1a}$ is independently a member selected from the group consisting of H, $C_1$-$C_3$ perfluoroalkyl, $C_3$-$C_7$ cycloalkyl, F, Cl, Br, CN, $NO_2$, $OR^{10}$, $SCH_3$, S(=O)$CH_3$, S(=O)$_2R^{10}$, $NR^{11}R^{12}$, acetyl, C(=O)$OR^{13}$, C(=O)$NR^{13}R^{14}$, S(=O)$_2NR^{13}R^{14}$, phenyl substituted with 0-3 $R^{15}$; and a $C_1$-$C_4$ alkyl substituted with 0-2 $R^{16}$;

$R^2$ is a member selected from the group consisting of a phenyl substituted with 0-3 $R^{15}$; a $C_1$-$C_2$ alkyl substituted with 1 $R^{2a}$, and a $C_3$-$C_7$ cycloalkyl substituted with 0-2 $R^{19}$; and each $R^{2a}$ is independently a member selected from the group consisting of a $C_6$-$C_{10}$ aryl substituted with 0-3 $R^{15}$; a $C_3$-$C_8$ cycloalkyl substituted with 0-2 $R^{19}$; and a $C_7$-$C_{11}$ bicycloalkyl substituted with 0-2 $R^{19}$.

10. A pharmaceutical composition comprising the compound of claim 3 and a pharmaceutically acceptable excipient.

11. The compound of claim 1, selected from the group consisting of:

(S)—N-{1-[2-(5-Fluoro-2,3-dihydro-indol-1-yl)-ethyl-carbamoyl]-3-methyl-butyl}-3-methyl-benzamide;

N—(S)-{2-cyclohexyl-1-[2-(5-fluoro-2,3-dihydro-indol-1-yl)-ethylcarbamoyl]-ethyl}-4-phenoxy-benzamide;

(S)-3-Cyclohexyl-N-[2-(5-fluoro-2,3-dihydro-indol-1-yl)-ethyl]-2-[2-(4-methoxy-phenyl)-acetylamino]-propionamide;

(S)—N-{1-[2-(5-Chloro-2,3-dihydro-indol-1-yl)-ethyl-carbamoyl]-3-methyl-butyl}-3-methyl-benzamide;

(S)—N-{3-Cyclohexyl-1-[2-(7-methoxy-2,3-dihydro-indol-1-yl)-ethylcarbamoyl]-propyl)-3-methoxy-benzamide;

(S)—N-{3-Cyclohexyl-1-[2-(6-fluoro-2,3-dihydro-indol-1-yl)-ethylcarbamoyl]-propyl}-3-methoxy-benzamide;

(S)—N-{3-Cyclohexyl-1-[2-(7-fluoro-2,3-dihydro-indol-1-yl)-ethylcarbamoyl]-propyl}-3-methoxy-benzamide;

(S)—N-{3-Cyclohexyl-1-[2-(5-cyano-2,3-dihydro-indol-1-yl)-ethylcarbamoyl]-propyl}-3-methoxy-benzamide;

Cyclopropanecarboxylic acid (S)-{2-cyclohexyl-1-[2-(5-fluoro-2,3-dihydro-indol-1-yl)-ethylcarbamoyl]-ethyl}-amide;

(S)—N-{3-Cyclohexyl-1-[2-(4-methoxy-2,3-dihydro-indol-1-yl)-ethylcarbamoyl]-propyl}-3-methoxy-benzamide;

(S)—N-{3-Cyclohexyl-1-[2-(5-methoxy-2,3-dihydro-indol-1-yl)-ethylcarbamoyl]-propyl}-3-methoxy-benzamide;

(S)—N-{3-Cyclohexyl-1-[2-(5-fluoro-2,3-dihydro-indol-1-yl)-ethylcarbamoyl]-propyl}-3-methoxy-benzamide;

(S)—N-{3-Cyclohexyl-1-[2-(5-benzyloxy-2,3-dihydro-indol-1-yl)-ethylcarbamoyl]-propyl}-3-methoxy-benzamide;

N-{3-Cyclohexyl-1-(S)-[2-(5-fluoro-2,3-dihydro-indol-1-yl)-1-(R)-hydroxymethyl-ethylcarbamoyl]-propyl}-3-methoxy-benzamide;

N— 13-Cyclohexyl-1-(R)-[(S)-2-(5-fluoro-2,3-dihydro-indol-1-yl)-1-(R)-hydroxymethyl-ethylcarbamoyl]-propyl}-3-methoxy-benzamide;

(S,S)-5-(5-Fluoro-2,3-dihydro-indol-1-yl)-4-[4-methyl-2-(3-methyl-benzoylamino)-pentanoylamino]-pentanoic acid benzyl ester;

(S,S)-5-(5-Fluoro-2,3-dihydro-indol-1-yl)-4-[4-methyl-2-(3-methyl-benzoylamino)-pentanoylamino]-pentanoic acid;

(S,S)—N-{1-[3-Carbamoyl-1-(5-fluoro-2,3-dihydro-indol-1-ylmethyl)-propylcarbamoyl]-3-methyl-butyl}-3-methyl-benzamide;

(S,S)-3-[4-Cyclohexyl-2-(3-methoxy-benzoylamino)-butyrylamino]-4-(5-fluoro-2,3-dihydro-indol-1-yl)-butyric acid benzyl ester;

(S,S)-3-[4-Cyclohexyl-2-(3-methoxy-benzoylamino)-butyrylamino]-4-(5-fluoro-2,3-dihydro-indol-1-yl)-butyric acid;

(S,S)—N-{1-[1-Benzyl-2-(5-fluoro-2,3-dihydro-indol-1-yl)-ethylcarbamoyl]-3-cyclohexyl-propyl}-3-methoxy-benzamide;

(S,S)—N-{3-Cyclohexyl-1-[1-(5-fluoro-2,3-dihydro-indol-1-ylmethyl)-3-methyl-butylcarbamoyl]-propyl}-3-methoxy-benzamide;

(S,S)—N-{3-Cyclohexyl-1-[1-(5-fluoro-2,3-dihydro-indol-1-ylmethyl)-2-methyl-propylcarbamoyl]-propyl}-3-methoxy-benzamide;

(S,S)—N-{3-Cyclohexyl-1-[2-(5-fluoro-2,3-dihydro-indol-1-yl)-1-phenyl-ethylcarbamoyl]-propyl}-3-methoxy-benzamide;

N-{2-cyclohexyl-1-(S)-[2-(5-fluoro-2,3-dihydro-indol-1-yl)-ethylcarbamoyl]-ethyl}-2-(2-fluoro-biphenyl-4-yl)-propionamide;

N-{2-cyclohexyl-1-(S)-[2-(5-fluoro-2,3-dihydro-indol-1-yl)-ethylcarbamoyl]-ethyl}-2-p-tolyl-propionamide;

N-{2-cyclohexyl-1-(S)-[2-(5-fluoro-2,3-dihydro-indol-1-yl)-ethylcarbamoyl]-ethyl}-2-o-tolyl-propionamide;

N-{2-cyclohexyl-1-(S)-[2-(5-fluoro-2,3-dihydro-indol-1-yl)-ethylcarbamoyl]-ethyl}-2-(4-fluoro-phenyl)-propionamide;

2-(4-Chloro-phenyl)-N-{2-cyclohexyl-1-(S)-[2-(5-fluoro-2,3-dihydro-indol-1-yl)-ethylcarbamoyl]-ethyl}-propionamide;

N-{2-cyclohexyl-1-(S)-[2-(5-fluoro-2,3-dihydro-indol-1-yl)-ethylcarbamoyl]-ethyl}-2-(R)-phenyl-propionamide;

N—(S)-{2-cyclohexyl-1-[2-(5-fluoro-2,3-dihydro-indol-1-yl)-ethylcarbamoyl]-ethyl}-3-methyl-benzamide;

N—(S)-{2-cyclohexyl-1-[2-(5-fluoro-2,3-dihydro-indol-1-yl)-ethylcarbamoyl]-ethyl}-4-(methanesulfonylamino-methyl)-benzamide;

N—(S)-{2-cyclohexyl-1-[2-(5-fluoro-2,3-dihydro-indol-1-yl)-ethylcarbamoyl]-ethyl}-3-methanesulfonyl-benzamide;

N—(S)-{2-cyclohexyl-1-[2-(5-fluoro-2,3-dihydro-indol-1-yl)-ethylcarbamoyl]-ethyl}-4-methanesulfonylamino-benzamide;

N-{2-cyclohexyl-1-(S)-[2-(5-fluoro-2,3-dihydro-indol-1-yl)-ethylcarbamoyl]-ethyl}-2-(4-hydroxy-phenyl)-propionamide;

4-Cyclohexyl-N-[2-(5-fluoro-2,3-dihydro-indol-1-yl)-ethyl]-2-(S)-(2-(R)-phenyl-propionylamino)-butyramide;

N-{2-cyclohexyl-1-(S)-[2-(5-fluoro-2,3-dihydro-indol-1-yl)-ethylcarbamoyl]-ethyl}-2-(R)-phenyl-butyramide;

N-{2-Cyclohexyl-1-(S)-[2-(5-fluoro-2,3-dihydro-indol-1-yl)-1-(R)-hydroxymethyl-ethylcarbamoyl]-ethyl}-3-methoxy-benzamide;

N-{1-(S)-[2-(5-Fluoro-2,3-dihydro-indol-1-yl)-1-(R)-hydroxymethyl-ethylcarbamoyl]-3,3-dimethyl-butyl}-3-methoxy-benzamide;

4-(5-Fluoro-2,3-dihydro-indol-1-yl)-3-(S)-[2-(S)-(3-methoxy-benzoylamino)-4,4-dimethyl-pentanoylamino]-butyric acid tert-butyl ester;

3-(S)-[3-Cyclohexyl-2-(S)-(3-methoxy-benzoylamino)-propionylamino]-4-(5-fluoro-2,3-dihydro-indol-1-yl)-butyric acid benzyl ester;

3-(S)-[3-Cyclohexyl-2-(S)-(3-methoxy-benzoylamino)-propionylamino]-4-(5-fluoro-2,3-dihydro-indol-1-yl)-butyric acid;

4-(5-Fluoro-2,3-dihydro-indol-1-yl)-3-(S)-[2-(S)-(3-methoxy-benzoylamino)-4,4-dimethyl-pentanoylamino]-butyric acid ethyl ester;

N-{1-(S)-[2-Cyano-1-(S)-(5-fluoro-2,3-dihydro-indol-1-ylmethyl)-ethylcarbamoyl]-3,3-dimethyl-butyl}-3-methoxy-benzamide;

N-{1-(S)-[5-Amino-1-(S)-(5-fluoro-2,3-dihydro-indol-1-ylmethyl)-pentylcarbamoyl]-3-cyclohexyl-propyl}-3-methoxy-benzamide;

(S,S)—N-{3-Cyclohexyl-1-[2-(5-fluoro-2,3-dihydro-indol-1-yl)-1-(4-hydroxy-benzyl)-ethylcarbamoyl]-propyl}-3-methoxy-benzamide;

Cyclopropanecarboxylic acid {1-(S)-[2-(5-fluoro-2,3-dihydro-indol-1-yl)-1-(S)-methyl-ethylcarbamoyl]-3,3-dimethyl-butyl}-amide;

N—((S)-(2-(5-fluoroindolin-1-yl)ethylcarbamoyl)(cyclohexyl)methyl)-3-methylbenzamide;

N—((S)-1-(2-(5-fluoroindolin-1-yl)ethylcarbamoyl)-2-(2-chlorophenyl)ethyl)-3-methylbenzamide;

N—((S)-1-(2-(5-fluoroindolin-1-yl)ethylcarbamoyl)-2-(3-chlorophenyl)ethyl)-3-methylbenzamide;

N—((S)-1-(2-(5-fluoroindolin-1-yl)ethylcarbamoyl)-2-(4-chlorophenyl)ethyl)-3-methylbenzamide;

(S)—N-{2-Cyclopentyl-1-[2-(5-fluoro-2,3-dihydro-indol-1-yl)-ethylcarbamoyl]-ethyl}-3-methyl-benzamide;

N—((S)-1-(2-(5-fluoroindolin-1-yl)ethylcarbamoyl)-3,3-dimethylbutyl)-3-methylbenzamide;

N—((S)-1-(2-(5-fluoroindolin-1-yl)ethylcarbamoyl)-3-cyclohexylpropyl)-3-methylbenzamide;

N—((S)-1-(2-(5-fluoroindolin-1-yl)ethylcarbamoyl)-2-phenylethyl)-3-methylbenzamide;

N—(R,S)-((3-(5-fluoroindolin-1-yl)-1-hydroxypropan-2-(R)-ylcarbamoyl)(2,4-dichlorophenyl)methyl)-3,4-difluorobenzamide;

(R,S)—N-((2-(5-fluoroindolin-1-yl)ethylcarbamoyl)(2,4-dichlorophenyl)methyl)-3-methylbenzamide;

(S,S)—N-((3-(5-fluoroindolin-1-yl)-1-hydroxypropan-2-ylcarbamoyl)(2,4-dichlorophenyl)methyl)-3,4-difluorobenzamide;

(S,S)-4-(5-Fluoro-2,3-dihydro-indol-1-yl)-3-[2-(3-methoxy-benzoylamino)-4,4-dimethyl-pentanoylamino]-butyric acid; and (S,S)—N-{3-Cyclohexyl-1-[1-(5-fluoro-2,3-dihydro-indol-1-ylmethyl)-3-hydroxy-propylcarbamoyl]-propyl}-3-methoxy-benzamide.

12. A pharmaceutical composition comprising the compound of claim 11 and a pharmaceutically acceptable excipient.

13. A pharmaceutical composition comprising the compound of claim 6, and a pharmaceutically acceptable excipient.

14. N-{(1S)-[2-(5-Fluoro-2,3-dihydro-indol-1-yl)-1,1-dimethyl-ethylcarbamoyl]-2-phenyl-ethyl}-3-methyl-benzamide.

15. The compound of claim 14, and a pharmaceutically acceptable excipient.

* * * * *